(12) United States Patent
Pellini et al.

(10) Patent No.: US 12,087,453 B2
(45) Date of Patent: *Sep. 10, 2024

(54) SYSTEM AND METHOD FOR OUTCOME TRACKING AND ANALYSIS

(71) Applicant: Foundation Medicine, Inc., Cambridge, MA (US)

(72) Inventors: Michael Pellini, Dana Point, CA (US); Gary Palmer, Waltham, MA (US); Mary Patricia Lancelotta, Somerville, MA (US); Matthew J. Hawryluk, Newton, MA (US); Vincent A. Miller, West Orange, NJ (US)

(73) Assignee: Foundation Medicine, Inc., Boston, MA (US)

( * ) Notice: Subject to any disclaimer, the term of this patent is extended or adjusted under 35 U.S.C. 154(b) by 142 days.

This patent is subject to a terminal disclaimer.

(21) Appl. No.: 17/885,412

(22) Filed: Aug. 10, 2022

(65) Prior Publication Data
US 2022/0399131 A1 Dec. 15, 2022

Related U.S. Application Data

(63) Continuation of application No. 16/579,496, filed on Sep. 23, 2019, now Pat. No. 11,450,438, which is a (Continued)

(51) Int. Cl.
*G16H 70/60* (2018.01)
*G16B 30/00* (2019.01)
(Continued)

(52) U.S. Cl.
CPC ............ *G16H 70/60* (2018.01); *G16B 30/00* (2019.02); *G16H 10/20* (2018.01); *G16H 10/60* (2018.01);
(Continued)

(58) Field of Classification Search
CPC ........ G16H 70/60; G16H 10/60; G16H 15/00; G16H 50/20; G16H 20/10; G16H 10/20; G16B 30/00
(Continued)

(56) References Cited

U.S. PATENT DOCUMENTS 5,920,871 A 7/1999 Marci et al.
6,246,975 B1 6/2001 Rivonelli et al.
(Continued)

FOREIGN PATENT DOCUMENTS

KR 20110097889 A 8/2011
WO WO-2012059839 A2 5/2012
WO WO-2014107549 A2 7/2014

OTHER PUBLICATIONS

[No Author Listed] "Graph Database—Wikipedia" Dec. 7, 2014; Retrieved from the internet on Jun. 26, 2018; en.wikipedia.org/w/index.php?title=Graph_database&oldid=637006716, 5 pages.
(Continued)

*Primary Examiner* — Michael Tomaszewski
(74) *Attorney, Agent, or Firm* — MORRISON & FOERSTER LLP

(57) ABSTRACT

Provided are systems and methods for capturing outcome information associated with various cancer treatments. The system facilitates capture and analysis of cancer treatment information and associated outcome information. The treatment and outcome information can include genomic analysis and information on treatment of different cancers. The system can store and analyze any one or more of: tumor type, genomic alterations (e.g., genes and associated alterations, gene sequence mutations, alterations, amplifications, deletions, etc.), and treatment data (including, for example, treatments targeted to specific genes and/or genomic alterations). Users of the outcome system can supply and use the treatment and outcome information to facilitate diagnosis
(Continued)

and therapy decisions. User interfaces within the system can be configured to allow users to easily locate outcome information associated with particular treatments of tumors having certain genomic alterations.

20 Claims, 101 Drawing Sheets

Related U.S. Application Data continuation of application No. 14/146,742, filed on Jan. 3, 2014, now abandoned.

(60) Provisional application No. 61/749,291, filed on Jan. 5, 2013, provisional application No. 61/749,288, filed on Jan. 5, 2013.

(51) Int. Cl.
*G16H 10/20* (2018.01)
*G16H 10/60* (2018.01)
*G16H 15/00* (2018.01)
*G16H 20/10* (2018.01)
*G16H 50/20* (2018.01)

(52) U.S. Cl.
CPC ............. *G16H 15/00* (2018.01); *G16H 20/10* (2018.01); *G16H 50/20* (2018.01)

(58) Field of Classification Search
USPC ......................................................... 705/2–3
See application file for complete search history.

(56) References Cited

U.S. PATENT DOCUMENTS

| | | | |
|---|---|---|---|
| 6,283,761 B1 | 9/2001 | Joao | |
| 6,458,080 B1* | 10/2002 | Brown | G16H 40/67 |
| | | | 600/300 |
| 6,527,712 B1* | 3/2003 | Brown | G16H 10/20 |
| | | | 128/923 |
| 6,640,211 B1 | 10/2003 | Holden | |
| 6,912,492 B1 | 6/2005 | Johnson et al. | |
| 7,024,369 B1* | 4/2006 | Brown | G16H 20/70 |
| | | | 600/513 |
| 7,353,238 B1* | 4/2008 | Gliklich | G16H 40/20 |
| 10,885,807 B1* | 1/2021 | Lavi | G09B 7/00 |
| 11,158,068 B2 | 10/2021 | Oami et al. | |
| 11,158,425 B2 | 10/2021 | de Deus et al. | |
| 11,450,438 B2* | 9/2022 | Pellini | G16B 30/00 |
| 11,896,596 B2* | 2/2024 | Paik | A61K 31/519 |
| 2002/0026331 A1 | 2/2002 | Case | |
| 2002/0052761 A1* | 5/2002 | Fey | G06Q 10/10 |
| | | | 705/2 |
| 2003/0046114 A1* | 3/2003 | Davies | G16Z 99/00 |
| | | | 705/3 |
| 2003/0113756 A1* | 6/2003 | Mertz | G16H 10/40 |
| | | | 435/6.1 |
| 2004/0078236 A1* | 4/2004 | Stoodley | G16H 70/20 |
| | | | 705/2 |
| 2004/0142371 A1 | 7/2004 | Milosavljevic et al. | |
| 2005/0026117 A1* | 2/2005 | Judson | G16H 70/40 |
| | | | 434/154 |
| 2005/0261941 A1* | 11/2005 | Scarlat | G16H 10/60 |
| | | | 705/3 |
| 2006/0004526 A1* | 1/2006 | Hadd | G16B 20/20 |
| | | | 435/6.12 |
| 2008/0161661 A1* | 7/2008 | Gizewski | A61B 5/0064 |
| | | | 600/306 |
| 2008/0201172 A1* | 8/2008 | McNamar | G16H 10/60 |
| | | | 600/300 |
| 2009/0080734 A1* | 3/2009 | Moriya | G16H 30/40 |
| | | | 382/128 |
| 2009/0222286 A1* | 9/2009 | Elsholz | G16H 10/60 |
| | | | 707/999.1 |
| 2009/0287503 A1* | 11/2009 | Angell | G16H 10/20 |
| | | | 705/3 |
| 2010/0070293 A1* | 3/2010 | Brown | G16H 50/20 |
| | | | 705/2 |
| 2010/0125462 A1* | 5/2010 | Aggarwal | G16H 20/40 |
| | | | 705/2 |
| 2010/0131293 A1* | 5/2010 | Linthicum | G16H 10/60 |
| | | | 715/838 |
| 2010/0138199 A1* | 6/2010 | Soto | G16H 50/20 |
| | | | 703/2 |
| 2010/0191100 A1* | 7/2010 | Anderson | G06T 7/246 |
| | | | 600/424 |
| 2010/0198619 A1* | 8/2010 | Whelchel | G16H 40/20 |
| | | | 705/3 |
| 2010/0218132 A1* | 8/2010 | Soni | G16H 40/63 |
| | | | 709/219 |
| 2011/0112860 A1* | 5/2011 | Kehr | G16H 20/10 |
| | | | 705/2 |
| 2011/0276347 A1* | 11/2011 | Dalton | G16H 10/60 |
| | | | 705/3 |
| 2012/0157340 A1* | 6/2012 | Cesano | G01N 33/5041 |
| | | | 435/7.1 |
| 2013/0096948 A1* | 4/2013 | Parkinson | C12Q 1/6883 |
| | | | 705/3 |
| 2013/0226612 A1* | 8/2013 | Carmeli | G06Q 10/04 |
| | | | 705/2 |
| 2014/0336943 A1 | 11/2014 | Pellini et al. | |
| 2014/0337052 A1* | 11/2014 | Pellini | G16H 15/00 |
| | | | 705/3 |
| 2015/0046180 A1* | 2/2015 | Futscher de Deus | G16H 10/40 |
| | | | 705/2 |
| 2015/0046191 A1* | 2/2015 | Futscher de Deus | G16H 10/60 |
| | | | 705/3 |
| 2015/0100341 A1* | 4/2015 | Pecora | G16H 40/20 |
| | | | 705/2 |
| 2015/0112705 A1* | 4/2015 | Neville | G16H 50/30 |
| | | | 705/2 |
| 2015/0127385 A1* | 5/2015 | Pecora | G16H 50/20 |
| | | | 705/3 |
| 2016/0103973 A1* | 4/2016 | Singal | G16H 50/20 |
| | | | 705/3 |
| 2016/0270717 A1* | 9/2016 | Luna | A61B 5/743 |
| 2016/0350491 A1* | 12/2016 | Pecora | G06Q 30/0201 |
| 2016/0350492 A1* | 12/2016 | Pecora | G16H 50/20 |
| 2016/0350495 A1* | 12/2016 | Pecora | G06Q 10/0637 |
| 2017/0076046 A1* | 3/2017 | Barnes | G06F 16/951 |
| 2017/0365182 A1* | 12/2017 | Lavi | G09B 19/0092 |
| 2018/0174688 A1* | 6/2018 | Pecora | G06F 16/9535 |
| 2019/0172584 A1* | 6/2019 | Athey | G16H 50/70 |
| 2019/0392924 A1* | 12/2019 | Bettencourt-Silva | |
| | | | G16H 50/70 |
| 2020/0020430 A1 | 1/2020 | de Deus et al. | |
| 2020/0020452 A1 | 1/2020 | de Deus et al. | |
| 2020/0211679 A1* | 7/2020 | Pellini | G16H 70/60 |
| 2020/0258601 A1* | 8/2020 | Lau | G16H 50/20 |
| 2020/0294668 A1 | 9/2020 | Pellini et al. | |
| 2021/0090694 A1* | 3/2021 | Colley | G16H 15/00 |
| 2021/0233664 A1* | 7/2021 | Colley | G16H 50/70 |
| 2022/0028512 A1* | 1/2022 | Kohn | G16H 70/20 |

OTHER PUBLICATIONS

Barabasi et al "Network medicine: a network-based approach to human disease" Nature Reviews Genetics (2011) vol. 12 No. 1 pp. 56-68.

Bebek et al, "Network biology methods integrating biological data for translational science" Briefings in Bioinformatics (2012) vol. 13, No. 4 pp. 446-459.

Chun et al., "A network perspective on unraveling the role of TRP channels in biology and disease" Pflugers Archiv—European Journal of Physiology (2014) vol. 446 No. 2 pp. 173-182.

European Supplementary Search Report for European Application No. 14735224.9 dated Jul. 6, 2016, 8 pages.

(56) References Cited

OTHER PUBLICATIONS

Extended European Search Report and Opinion for European Application No. 15833420.1 dated Mar. 15, 2018, 12 pages.
Extended European Search Report and Opinion for European Application No. 15871055.8 dated Jul. 27, 2018, 11 pages.
Extended European Search Report and Opinion for European Application No. 20201144.1 dated Mar. 30, 2021, 11 pages.
Haga et al., "Developing patient-friendly genetic and genomic test reports formats to promote patient engagement and understanding" Genome Medicine (2014) vol. 6 No. 58 pp. 1-11.
International Search Report for PCT/US2014/010124; mailed May 8, 2014, 3 pages.
International Search Report for PCT/US2014/010125; Jun. 24, 2014, 5 pages.
International Search Report for PCT/US2015/045859; mailed Nov. 24, 2015, 4 pages.
International Search Report for PCT/US2015/066325 mailed Apr. 7, 2016, 3 pages.
Written Opinion of the International Searching Authority for PCT/US2015/045859 dated Nov. 24, 2015, 11 pages.
Written Opinion of the International Searching Authority for PCT/US2015/066325 mailed Apr. 7, 2016, 6 pages.
Yilmaz et al., (2009). "Gene-disease relationship discovery based on model-driven data integration and database view definition," Bioinformatics, 25(2):230-236.
Business Wire, (1999). "LabDat Announces Patient Access to Clinical Laboratory Reports," Business Wire, 2 pages.
Caulfield, (1999). "Gene Testing In The Biotech Century: Are Physicians Ready?" Canadian Medical Association Journal, 161(9):1122-1124.
Connor, (1998). "NHS Urged to Plan for New Genetic Tests," The Independent, p. 7, 2 pages.

\* cited by examiner

702 → Test Information

711

Patient Name: Keil, Jesse

Specimen ID: SAMPLE

Additional Recipient: N/A

Date of Collection: 12/31/1969

Date of Birth: 12/31/1969

Client: Sample Case

Specimen Received: 10/12/2012

Collection Method:

Gender: Male

FMI Client #: -1

Report Date: 12/31/1969

Specimen Type: Slide

FMI-Case #: TFRAAAAK

Ordering Physician: Hammond, Heather

Specimen Site: Not Provided

Medical Record #: SAMPLE

Pathologist:

Diagnosis: Prostate acinar adenocarcinoma

704 → Test Results

6 Genomic Alterations: Prostate acinar adenocarcinoma

| ERBB3 amplification | 1 Therapy 2 Trials | — 712 | CCND1 amplification | 0 Therapies 3 Trials | CDK4 amplification | 0 Therapies 3 Trials |
| MDM2 amplification | 0 Therapies 2 Trials | — 714 | MYC amplification | 0 Therapies 2 Trials | NKX2-1 amplification | 0 Therapies 0 Trials |

716, 717, 706, 708

Note: Genomic alterations detected may be associated with activity of certain FDA approved drugs; however the agents listed in this report may have varied clinical evidences in the

*FIG. 7A*

● 6 Genomic Alterations Interpretaions

| Gene | Alteration | Interpretation |
|---|---|---|
| ERBB3 | amplification — 732 | ERBB3 encodes Erbb3 (also known ... therapies in several cancer types. |
| CCND1 | amplification | CCND1 encodes Cyclin D1, which ... investigation in clinical trials. |
| CDK4 | amplification | CDK4 encodes cyclin-dependent ... tumor with CDK4 amplification |

All Patients > Keil, Jesse Report > ERBB3: amplification Alt...

ERBB3: amplification Alteration in Prostate acinar carcinoma

Updated December 31, 1969

| Gene | Alteration | Interpretation |

ERBB3 amplification     ERBB3 encodes Erbb3 (also known as Her3) a member of the epidermal growth factor receptor (Egfr) family. While local amplification of ERBB3 is relatively rare in most cancer types, two studies report amplification of the chromosomal region (12q13) containing ERBB3 in prostate cancer; one study of 16 prostate adenocarcinoma samples found amplification in 56% of cases (Sattler et al., 1999: 10221562, Glinsky et al., 2003: 14580688). Focal ERBB3 amplification in prostate cancer has not been reported in The cBio Cancer Genomics Portal or in CONAN: Copy Number Analysis (http://www.cbioportal.org Oct 2012, http://www.sanger.ac.uk/cgi-bin/genetics/CGP/conan/search.cgi. Oct 2012) Pertuzumab, a humanized monoclonal antibody that interferes with Erb2 and Erb3 heterodimerization, has been recently approved for use in metastatic ERBB2-amplified breast cancer (baselga et al., 2012: 22149875). A Phase 2 study of pertuzumab in men with castration-resistant prostate cancer resulted in prolonged survival (Agus et al., 2007: 17308272). Clinical trials of pertuzumab are ongoing. There are several anti-Erbb3 antibodies that are currently being tested in clinical trials. MM-121, one such monoclonal antibody directed specifically against Erb3, has been observed to have activity in preclinical studies in both ovarian cancer and pancreatic cancer (Sheng et al., 2010:20227043, Liles et al., 2011: 21782199) MM-121 and other anti-Erbb3 antibodies such as AV-203 and U3-1287 are being actively tested as single agents and in combination with other therapies in several cancer types ■ Related Therapies 1
▲ Related Trials 2
● Related References 7

Go Back

*FIG. 7E*

All Patients > Keil, Jesse Report > ERBB3: amplification Alt...

ERBB3: amplification Alteration in Prostate acinar carcinoma

Updated December 31, 1969

| Gene | Alteration | Interpretation |
|---|---|---|
| ERBB3 | amplification | ERBB3 encodes Erbb3 (also known as Her3) a member of the epidermal growth factor receptor (Egfr) family. While local amplification of ERBB3 is relatively rare in most cancer types, two studies report amplification of the chromosomal region (12q10) containing ERBB3 in prostrate cancer; one study of 16 prostate adenocarcinoma samples found amplification in 56% of cases (Sattler et al., 1999: 10221562, Glinsky et al., 2003: 14580688). Focal ERBB3 amplification in prostate cancer has not been reported in The cBio Cancer Genomics Portal or in CONAN: Copy Number Analysis (http://www.cbioportal.org Oct 2012, http://www.sanger.ac.uk/cgi-bin/genetics/CGP/conan/search.cgi. Oct 2012) Pertuzumab, a humanized monoclonal antibody that interferes with Erb2 and Erb3 heterodimerization, has been recently approved for use in metastatic ERBB2-amplified breast cancer (baselga et al., 2012; 22149875). A Phase 2 study of pertuzumab in men with castration-resistant prostate cancer resulted in prolonged survival (Agus et al. 2007; 17308272). Clinical trials of pertuzumab are ongoing. There are several anti-Erb3 antibodies that are currently being tested in clinical trials. MM-121, one such monoclonal antibody directed specifically against Erb3, has been observed to have activity in preclinical studies in both ovarian cancer and pancreatic cancer (Sheng et al., 2010:20227043, Liles et al., 2011: 21782199) MM-121 and other anti-Erb3 antibodies such as AV-203 and U3-1287 are being actively tested as single agents and in combination with other therapies in several cancer types |

734 — ■ Related Therapies 1 ▼ — 740
  Perjeta — 742
736 — ▲ Related Trials 2 ▼
  NCT01447225 — 744
  NCT01603979 — 746
● Related References 7 ▼
  17308272 ⎫
  22149875 ⎪
  14580688 ⎪
  21792199 ⎬ — 748
  10221562 ⎪
  20227043 ⎪
  15571795 ⎭
  — 738

Go Back

FIG. 7F

Associated Information

- 718 — ● 6 Genomic Alteration Interpretations
- 720 — ■ 1 Therapy
- 722 — ▲ 9 Clinical Trials
- 724 — ⬟ 69 References Reference 788 — Agus DB, Sweeney CJ, Morris MJ, et al. (2007) Efficacy and safety of single-agent pertuzumab (rhuMAb 2C4), a human epidermal growth factor receptor dimerization inhibitor, in castration-resistant prostate cancer after progression from taxane-base therapy. J Clin Oncol 25(6):675-81 — 798
View External Link — 796

790 — Arango D, Corner GA, Wadler S, et al. (2001) c-myc/p53 interaction determines sensitivity of human colon carcinoma cells to 5-fluorouracil in vitro and in vivo. Cancer Res 61(12):4910-5
View External Link 792 — Barletta JA, Perner S, Iafrate AJ, et al. (2009) Clinical significance of TTF-1 protein expression and TFF-1 gene amplification in lung adenocarcinoma. J Cell Mol Med 13(8B):1977-86
View External Link 794 — Baselga J, Cortes J, Kim SB, et al. (2012) Pertuzumab plus trastuzumab plus docetaxel for metastatic breast cancer N Engl J Med 366(2):109-19
View External Link

FIG. 7K

Client Name FM Test Portal — J. Thomas ▼ Feedback Contact Us

Patient > Michael Thomas > Trial NCT01306543

Michael Thomas | Report 06.16.11 | Updates | 11.12.11 ✕

Test Information

| | | | |
|---|---|---|---|
| Sex: Male | Client: New England Oncology | Primary Tumor Site: Lung | Collection Method: Resection |
| DOB: 08.02.11 | FMI Client No. FM34834879 | Specimen Site: Pubis | Specimen Received: 09.14.11 |
| SSN: 548-98-6532 | Treating Physician Thomas, John | Diagnosis: Metastatic Carcinoma | Date Reported: 10.23.11 |
| Medical Record: 349XJF87JS | Additional Recipient N/A | Diagnosis Date: 03.22.10 | Submitting Pathologist: Jones, Leslie |
| Requisition No.: 2345345 | Cancer Non Small Cell Lung Cancer | Specimen Collected: 09.12.11 | |

Test Results

6 Genomic Alterations: Non Small Cell Lung Cancer

| EGFR L858R Mutation | TP53 R248L — 2 Therapies / 3 Trials / 12 References | RB1 Deletion, exons 12-21 |

| STK11 Whole Gene Deletion | GENE Vivamus luctus urna sed | GENE Pes cribus nonum publiciaet abem o etrum |

2 Selected genes with no alterations:
KRAS wildtype, ALK

3 Genomic alterations with no associated trials or therapies at time of test
Gene, Description; Gene, Description; Gene, Description

*FIG. 8A*

Associated Information ─ 800

○ 8 updates since last report view    View updates timeline >
○ Genomic alterations interpretations    [∧]

| Gene | Alteration | Interpretation | References ▼ |
|---|---|---|---|
| EGFR | L858R Mutation | In the metastatic setting, EGFR mutations are strong predictors of efficacy for the EGFR tyrosine kinase inhibitors (TKI) erlotinib (Tarceva) | 6 |
| STK11 | Whole gene therapy | TP53 is the most frequently mutated known gene in NSCLC. Targeted therapies for p53 mutated lung tumors are in development and include vaccination and immuna stimulation. Mutations have also been associated with a lack of response to cisplatin-based, induction chemotherapy. In contrast of the improved overall survival in patients with the normal genotype. | 3 |
| TP53 | R248L | TP53 is the most frequently mutated known gene in NSCLC. Targeted therapies for p53 mutated lung tumors are in development and include vaccination and immuna stimulation. Mutations have also been associated with a lack of response to cisplatin-based, induction chemotherapy. In contrast of the improved overall survival in patients with the normal genotype. | 3 |
| GENE | Alteration | In the metastatic setting, EGFR mutations are strong predictors of efficacy for the EGFR tyrosine kinase inhibitors (TKI), erlotinib (Tarceva) | 4 |
| GENE | Alteration | In the metastatic setting, EGFR mutations are strong predictors of efficacy for the EGFR tyrosine kinase inhibitors (TKI), erlotinib (Tarceva) | 4 |

☐ 5   Therapies With Clinical Benefit    ⤒
△ 2   Clinical Trials                     ⤒
◇ 32  References                          ⤒

802 ─ [Updates (8)]
       803

*Fig. 8B*

| Client Name FM Test Portal | J Thomas ▾ Feedback Contact Us |

Patients > Michael Thomas  *806*  Print

Michael Thomas | Report 06.16.11 | Updates 11.12.11

◯ Updates Timeline (Last Updated 11.12.11)

*808*

*810*  *812*  *814*  *816*

Show Updated for: [Interpretations] [Therapies] [Trials] [References]

● Interpretation for Alteration X in GENE has been added as new therapies, trials, and references have been added to associated information lists.  11.12.11
Hide Interpretation

| Gene | Alteration | Interpretation |
| GENE | Alteration | In the metastatic setting EGFR mutations are strong predictors of efficacy for the EGFR tyrosine kinase inhibitors (TKI) erlotinib (Tarceva) |

■ The reference "Mineverem porrum sincips aepudionsed que venecaborepe nonsed ma volorest. quate et vol imi,veliat" supporting evidence of clinical benefit has been added for Sunitinib (Sutent)  11.12.11
Show reference listing ● Interpretation for Alteration X in GENE has been edited  11.10.11

▲ NCT ID: NCT00940225 (Study of Cabozantinib (XL184) has been added as trial with associated benefit for Alteration X in GENE.  11.10.11
Show trial listing ● Interpretation for Alteration X in GENE has been edited to include citation for new reference.  11.10.11

◆ Interpretation for Alteration X in GENE has been edited to delete citation for removed reference.  11.10.11

*809*

■ The reference "Mineverem porrum sincips aepudionsed que venecaborepe nonsed ma volorest. quate et vol imi,veliat" supporting evidence of clinical benefit has been added for Sunitinib (Sutent)  11.12.11
Show reference listing ● Interpretation for Alteration X in GENE has been edited  11.10.11

▲ NCT ID: NCT00940225 (Study of Cabozantinib (XL184) has been added as trial with associated benefit for Alteration X in GENE.  11.10.11
Show that listing ● Interpretation for Alteration X in GENE has been edited to include citation for new reference.  11.10.11

◆ Interpretation for Alteration X in GENE has been edited to delete citation for removed reference.  11.10.11

⌄ More Updates ⌄

● Genomic alteration interpretations
■ 5  Therapies With Clinical Benefit
▲ 2  Clinical Trials
◆ 32 References

Client Name FM Test Portal     J Thomas   Feedback   Contact Us

Patients > Michael Thomas > Report > EGFR: L858R    View Therapy Details   Print

EGFR: L858R Alteration
Updated November 12, 2011

Interpretation
In the Metastatic setting, EGFR mutations are strong predictors of efficacy for the EGFR tyrosine kinase inhibitors (TKI), erlotinib (Tarceva).

Frequency
* Approximately 10% of all NSCLC in the USA
* Approximately 35% of all NSCLC in Asia

Overview
EGFR (Epidermal Growth Factor Receptor) belongs to a class of proteins called receptor tyrosine kinases. In response to signals from the environment, EGFR passes biochemical messages to the cell that stimulates it to grow and divide. The presence of an EGFR abnormality (mutation, amplification, or overexpression) can result in an overabundance or overactivity of EGFR protein, which can lead to excessive proliferation.

Relevance to Targeted Therapies
Laboratory and clinical trial data has demonstrated that NSCLC tumors which contain certain EGFR mutations (eg. exon 19 deletion) (Bell et al., 2005; Lynch et al., 2004; Paez et al., 2004; Pao et al., 2004) or amplification (Hirsch et al., 2008; Hirsch et al., 2006) may have a better response to EGFR inhibitors than to conventional chemotherapy, although the effect on overall survival is modest (Mok et al., 2009; Russell et al., 2009; Tsao et al., 2005). Based on accumulated evidence, the American Society for Clinical Oncology (ASCO) has issued a Provisional Clinical Opinion recommending EGFR mutational analysis for NSCLC patients to predict benefit from EGFR inhibitors (Keedy et al., 2011)

Some patients exhibit resistance to EGFR inhibition, resistance has sometimes been associated with insertions in exon 20, the T790M mutation in EGFR, amplification of the gene c-MET, and mutations in PIK3CA (Engelman et al., 2007; Greulich et al., 2005; Kwak et al., 2005; Ludovini et al., 2011; Sos et al., 2009; Thomas et al., 2005) Irreversible EGFR inhibitors, such as BIBW 2992 (Afatinib) or PF-299804, may be effective in tumors that are resistant to EGFR inhibitors (Janne et al., 2011) Mutations in K-ras have been associated with poor response to small molecule EGFR inhibitors, such as erlotinib and gefitinib, but do not appear to have a predictive role for the efficacy of antibodies such as cetuximab in NSCLC (Mack et al., 2009; O'Byrne et al., 2009; Pao et al., 2005) Mutations in K-ras have been found to be mutually exclusive with EGFR mutations in NSCLC (Shigematsu et al., 2005)

Related Therapies (1)
Erlotinib (Cagrelsa)

Related Trials (1)
NCT01306045

Related References (19)
Bell et al., 2005
Engelman et al., 2007
Greulich et al., 2005
Hirsch et al., 2008
Hirsch et al., 2006
Kwak et al., 2005
Ludovini et al., 2011
Lynch et al., 2004
Mack et al., 2009
Mok et al., 2009

Interpretation History Update

*FIG. 8D*

Client Name FM Test Portal     J. Thomas   Alerts (2)   Support   Feedback

Patients > Michael Thomas
Michael Thomas     Print|Share

| Report of Record 06.15.2011 | Information Updates (11.12.11) |

Updated timelines (Updated 11.12.11)    Hide Filters

View Filters — 820    822    824    818
Show: [All update categories ▼]   Show: [All update types ▼]   Show: [Updates since last login ▼]    Reset

- ◆ Interpretation for Alteration X in GENE has been added as new therapies, trials and references have been added to associated information lists.
  11.01.11

| GENE | Alteration | Interpretation | | |
|------|-----------|----------------|---|---|
| GENE | Alteration | In the metastatic setting, EGFR mutations are strong predictors of efficacy for the EGFR tyrosine kinase inhibitors (TKI) erlotinib (Tarceva) | 5 | 11.01.11 |

- ◆ Interpretaion for Alteration X in GENE has been removed as no therapies, trials, and references are included in associared information lists.
  11.01.11
- ◆ Interpretation for Alteration X in GENE has been edited.
  11.01.11
- ◆ ■ Interpretaion for Alternate X in GENE has been edited to include citation for new reference.
  11.01.11
- ◆ ■ Interpretaion for Alternate X in GENE has been edited to delete citation for removed reference.
  11.01.11
- ● Therapy (Therapy) has been added to list of therapies associated with clinical benefit for Alteration X.
  11.01.11
- ● Therapy (Therapy) has been removed from list of therapies associated with clinical benefits for Alteration X.
  11.01.11
- ● Sunitinib (Sutent) has lost FDA approval for treating small cell lung cancer with Alteration X and Alteration X.
  11.01.11
- ● Sunitinib (Sutent) has lost FDA approval for treating small cell lung cancer in clinical trials.
  11.01.11
- ● ■ The reference "Minverem porrum sincips aepudionsed que venecaborepe nonsed ma volorest, quate quare et vel imi, vellat" supports evidence of clinical benefit has been added for Sunitinib (Sutent)
  11.01.11
- ● ■ The reference "Minverem que venecaborepe ninsed ma volorest, quate quam et vel imi, vellat" supporting evidence of clinical benefit has been disproved and removed for Sunitinib (Sutent)
  11.01.11
- ▲ NCT ID: NCT00940225 (Study of Cabozantinib (XL184) has been added as trial with associated benefit for Alteration X in GENE
  11.01.11
- ▲ NCT ID: NCT00940225 (Study of Cabozantinib (XL184) has been removed as trial with associated benefit for Alteration X in GENE
  11.01.11
- ▲ NCT ID: NCT00940225 (Study of Cabozantinib (XL184) in Adults With Advanced Malignancies) is now closed to participants.
  11.01.11
- ▲ NCT ID: NCT00940225 (Study of Cabozantinib (XL184) in Adults With Advanced Malignancies) is now recruiting
  11.01.11

823 { (bracket grouping the items above)

View older updates

*FIG. 8E*

Associated Information

800

◯ 8 updates since last report view          View updates timeline ⟩  ☑

◯ Genomic alterations interpretations

| Gene | Alteration | Interpretation | References ▼ |
|---|---|---|---|
| EGFR | L858R Mutation | In the metastatic setting, EGFR mutations are strong predictors of efficacy for the EGFR tyrosine kinase inhibitors (TKI) erlotinib (Tarceva) | 6 |
| STK11 | Whole gene therapy | TP53 is the most frequently mutated known gene in NSCLC. Targeted therapies for p53 mutated lung tumors are in development and include vaccination and immuna stimulation. Mutations have also been associated with a lack of response to cisplatin-based, induction chemotherapy. In contrast of the improved overall survival in patients with the normal genotype. | 3 |
| TP53 | R248L | TP53 is the most frequently mutated known gene in NSCLC. Targeted therapies for p53 mutated lung tumors are in development and include vaccination and immuna stimulation. Mutations have also been associated with a lack of response to cisplatin-based, induction chemotherapy. In contrast of the improved overall survival in patients with the normal genotype. | 3 |
| GENE | Alteration | In the metastatic setting, EGFR mutations are strong predictors of efficacy for the EGFR tyrosine kinase inhibitors (TKI), erlotinib (Tarceva) | 4 |
| GENE | Alteration | In the metastatic setting, EGFR mutations are strong predictors of efficacy for the EGFR tyrosine kinase inhibitors (TKI), erlotinib (Tarceva) | 4 |

802

☐ 5   Therapies With Clinical Benefit                                 ↗
△ 2   Clinical Trials                                                 ↗
◇ 32  References                                                      ↗

Updates (8) | 803

FIG. 8F

| | | Patient Name<br>Kell, Jesse | | Report Date<br>31 December 1969 | | Diagnosis<br>Prostate acinar adenocarcinoma |
|---|---|---|---|---|---|---|
| Date of Birth | 31 December 1969 | Client | | Sample Case | Hammond, Heather | Not Given |
| Gender | Male | Physician | | Specimen Received | Not Given | Not Provided |
| FMI Case # | TRFAAAAAK | Additional Recipient | | Specimen Site | -1 | 31 December 1969 |
| Medical Record # | Sample | FMI Client # | | Specimen Date | Not Given | Slide |
| Block ID | Sample | Pathologist | | Specimen Type | | |

↗ 902

ABOUT THE TEST:
FoundationOne is a next-generation sequencing (NGS) based assay which identifies genomic alterations within hundreds of cancer-related genes.

↗ 904

PATIENT RESULTS

| 6 genomic alterations | pg-2 |
| 1 therapy associated with potential clinical benefit | pg-3 |
| 0 therapies associated with lack of response | pg-3 |
| 9 clinical trials | pg-4 |

TUMOR TYPE: PROSTATE ACINAR
ADENOCARCINOMA

Genomic Alterations Identified
ERBB3 amplification
CCND1 amplification
CDK4 amplification
MDM2 amplification
MYC amplification
NKX2-1 amplification → To Fig. 9B

THERAPEUTIC IMPLICATIONS

| Genomic Alterations Detected | FDA Approved Therapies (in patient tumor type) | FDA Approved Therapies (in another tumor type) | Potential Clinical Trials |
|---|---|---|---|
| ERBB3 amplification | None | Pertuzumab | Yes, see clinical trials section |
| CCND1 amplification | None | None | Yes, see clinical trials section |
| CDK4 amplification | None | None | Yes, see clinical trials section |
| MDM2 amplification | None | None | Yes, see clinical trials section |
| MYC amplification | None | None | Yes, see clinical trials section |
| NKX2-1 amplification | None | None | None |

Note: Genomic alterations detected may be associated with activity of certain FDA approved drugs; however, the agents listed in this report may have varied clinical evidence in the patient's tumor type. Neither the therapeutic agents nor the trials identified are ranked in order of potential or predicted efficacy for this patient, nor are they ranked in order of level of evidence for this patient's tumor type.

GENOMIC ALTERATIONS

| GENE Alteration | INTERPRETATION |
|---|---|
| • ERBB3 amplification | ERBB3 encodes Erbb3 ———————————————————————————— ———————————————————— in several cancer types. |
| • CCND1 amplification | CCND1 encodes Cyclin D1 ————————————————————————— ———————————————————————————————————————— |
| • CDK4 amplification | CDK4 encodes cyclin-dependent ————————————————————— ——————————————————————— investigation in clinical trials. |
| • MDM2 amplification | Mdm2 acts to prevent the ———————————————————————— ————————————————————————————— et al., 2011;2173:4724). |
| • MYC amplification | MYC is located on ————————————————————————————— ——————————————————— but more data is required. ————————————————————————— Amplification of MYC has been |

Patient Name: Kell, Jesse
Report Date: 31 December 1969
Diagnosis: Prostate acinar adenocarcinoma

Patient Name　　　　Report Date　　　　Diagnosis
Kell, Jesse　　　　31 December 1969　　Prostate acinar adenocarcinoma

912 →

THERAPIES

There are no therapies FDA approved in this patient's tumor type that are specific to the reported genomic alterations.

ADDITIONAL THERAPIES — FDA APPROVED IN OTHER TUMOR TYPES
THERAPY　　　　RATIONALE

Pertuzumab　　Pertuzumab is a humanized monoclonal antibody that interferes with Erbb2 and Erbb3 heterodimerization. Pertuzumab has been approved in combination with trastuzumab and docetaxel for use in certain patients with metastatic, ERBB2-amplified breast cancer (Baselga et al., 2012;22149875). ERBB3 amplification may predict sensitivity to pertuzumab. A Phase 2 study of pertuzumab in men with castration-resistant prostate cancer resulted in prolonged survival (Agus et al., 2007; 17308272). Clinical trials are ongoing multiple tumor types.

Genomic alterations detected may be associated with activity of certain FDA approved drugs, however the agents listed in this report may have little or no evidence in the patient's tumor type.

*FIG. 9E*

Patient Name  Report Date  Diagnosis
Kell, Jesse  31 December 1969  Prostate acinar adenocarcinoma

914 →

CLINICAL TRIALS TO CONSIDER

IMPORTANT: While every effort is made to ensure the accuracy of the information contained below, the information available in the public domain is continuously updated and should be investigated by the physician or research staff. This is not meant to be a complete list of available trials. In order to conduct a more thorough search, please go to www.clinicaltrials.gov and use the search terms provided below. For more information about a specific clinical trial, type the NCT ID of the trial indicated below into the search bar.

GENE  RATIONALE FOR POTENTIAL CLINICAL TRIALS

ERBB3  Mutation or amplification of ERBB3 may be associated with response to therapies targeting Erbb3.
amplification  A search of the trial website clinicaltrials.gov, using terms such as "ERBB3", "MM-121", "prostate" and/or "solid tumor" retrieves at least 5 trials that may be relevant for this patient's tumor.

Two of these trials are shown below.

| TITLE | PHASE | TARGETS | LOCATIONS | NCT ID |
|---|---|---|---|---|
| A phase 1, Pharmacologic and Pharmacodynamic Study of MM-121 in Combination With Multiple Anticancer Therapies in Patients With Advanced Solid Tumors | Phase 1 | ERBB3 | Indiana, New York, Ohio, Pennsylvania | NCT01447225 |
| A Phase 1 Open-label, Multiple Dose, Dose Escalation Study of Monoclonal Antibody AV-203 Administered in Subjects With Metastatic or Advanced Solid Tumors | Phase 1 | ERBB3 | Arizona, Texas | NCT01603979 |

FIG. 9F

Patient Name: Kell, Jesse
Report Date: 31 December 1969
Diagnosis: Prostate acinar adenocarcinoma

CLINICAL TRIALS TO CONSIDER (CONT.)

GENE

RATIONALE FOR POTENTIAL CLINICAL TRIALS

CCND1 encodes the cell-cycle regulator Cyclin D1, which interacts with Cdk4 and Cdk6 to inactivate Rb and activate the cell cycle. Inhibition of Cdk4 and Cdk6 may therefore be relevant in tumors with elevated levels of Cyclin D1 due to CCND1 amplification.

CCND1 amplification

A search of the trial website clinicaltrials.gov, using terms such as "CDK", "PD0332991", "BAY1000394", "LEE011", "LY2835219" and/or "solid tumor" and/or "prostate" retrieves at least 3 trials that may be relevant for this patient's tumor.

These three trails are shown below.

| TITLE | PHASE | TARGETS | LOCATIONS | NCT ID |
|---|---|---|---|---|
| An Open-label, Phase 1, Dose-escalation Study to Characterize the Safety, Tolerability, Pharmacokinetics, and Maximum Tolerated Dose of BAY 1000394 Given Twice Daily in a 3 Days on / 4 days Off Schedule in Subjects With Advanced Malignancies | Phase 1 | CDK1, CDK2, CDK4, CDK9 | Missouri, New York, Ohio, Baden-W (Germany), Nordrhein-Westfalen (Germany), Caen Cedex (France), Lyon Cedex (France), Marsellie Cedex 20 (France), Villejuif Cedex (France) | NCT01188252 |
| A Phase 1 Multi-center, Open Label, Dose-escalation Study of Oral LEE011 in Patients With Advanced Solid Tumors or Lymphoma | Phase 1 | CDK4, CDK6 | Massachusetts, New York, Tennessee, Lyon (France), Utrecht (Netherlands), Villejuif (France) | NCT01237236 |
| A Phase 1 Study of a CDK 4/6 Dual Inhibitor in Patients With Advanced Cancer | Phase 1 | CDK4, CDK6 | California, Massachussetts, Texas | NCT01394016 |

Patient Name: Keil, Jesse
Report Date: 31 December 1969
Diagnosis: Prostate acinar adenocarcinoma

914 →

CLINICAL TRIALS TO CONSIDER (CONT.)

| GENE | RATIONALE FOR POTENTIAL CLINICAL TRIALS |
|---|---|
| CDK4 amplification | Amplification of CDK4 may lead to excessive Cdk4 protein expression and activity, resulting in unrestricted cell cycle progression. Cdk4 inhibitors may therefore be relevant in a tumor with CDK4 amplification.<br><br>A search of the trial website clinicaltrials.gov using terms such as "CDK4" and/or "CDK" and/or "PD-0332991" and/or "BAY1000394" and/or "LEE011" and/or "LY2835219" and/or "prostate" and/or "solid tumor" retrieves at least 3 trials that may be relevant for this patient's tumor.<br><br>These three trials are shown below. |

| TITLE | PHASE | TARGETS | LOCATIONS | NCT ID |
|---|---|---|---|---|
| An Open-label, Phase 1, Dose-escalation Study to Characterize the Safety, Tolerability, Pharmacokinetics, and Maximum Tolerated Dose of BAY 1000394 Given Twice Daily in a 3 Days on / 4 days Off Schedule in Subjects With Advanced Malignancies | Phase 1 | CDK1, CDK2, CDK4, CDK9 | Missouri, New York, Ohio, Baden-W (Germany), Nordrhein-Westfalen (Germany), Caen Cedex (France), Lyon Cedex (France), Marseille Cedex 20 (France), Villejuif Cedex (France) | NCT01188252 |
| A Phase 1 Multi-center, Open Label, Dose-escalation Study of Oral LEE011 in Patients With Advanced Solid Tumors or Lymphoma | Phase 1 | CDK4, CDK6 | Massachusetts, New York, Tennessee, Lyon (France), Utrecht (Netherlands), Villejuif (France) | NCT01237236 |
| A Phase 1 Study of a CDK 4/6 Dual Inhibitor in Patients With Advanced Cancer | Phase 1 | CDK4, CDK6 | California, Massachussetts, Texas | NCT01394016 |

*FIG. 9H*

Patient Name: Kell, Jesse
Report Date: 31 December 1969
Diagnosis: Prostate acinar adenocarcinoma

914 →

CLINICAL TRIALS TO CONSIDER (CONT.)

| GENE | RATIONALE FOR POTENTIAL CLINICAL TRIALS |
|------|------------------------------------------|
| | Inhibitors of the Mdm2-p53 interaction are being tested in clinical trials. Overexpression or amplifiction of MDM2 may increase sensitivity to these agents, but more data is required. |
| MDM2 amplification | A search of the trial website clinicaltrials.gov, using terms such as "MDM2", "RO5045337", "R7112", "RO5503781", "nutlin", "benzodiasepine", "melanoma", "solid tumor", and/or "advanced malignancies" retrieves at least 2 trials that may be relevant for this patient's tumor. |

These two trails are shown below.

| TITLE | PHASE | TARGETS | LOCATIONS | NCT ID |
|-------|-------|---------|-----------|--------|
| A Multi-center, Open Label, First in Human Phase 1 Dose Escalation Study of Single Agent RO5503781, a Small Molecule MDM2 Antagonist, Administered Orally in Patients With Advanced Malignancies, Except Leukemia | Phase 1 | MDM2 | Ontario (Canada), Quebec (Canada), Bordeaux (France), Groningen (Netherlands), Lyon (France), Melbourne (Australia), Seoul (Korea, Republic of) | NCT01462175 |
| A Phase 1, Open-Label, Dose-Escalation, Safety, Pharmacokinetic and Pharmacodynamic Study of Kevetrin (Thioureidobutyronitrile) Adminstered Intravenously, in Patients With Advanced Solid Tumors | Phase 1 | p53 | Massachusetts | NCT01664000 |

FIG. 9I

Patient Name: Kell, Jesse
Report Date: 31 December 1969
Diagnosis: Prostate acinar adenocarcinoma

914 →

CLINICAL TRIALS TO CONSIDER (CONT.)

| GENE | RATIONALE FOR POTENTIAL CLINICAL TRIALS |
|---|---|
| MYC amplification | Several strategies are under investigation to address amplification or overexpression of MYC in human cancer. One such strategy involves inhibition of Myc. Another strategy is inhibition of Aurora kinases.<br><br>A search of the trial website clinicaltrials.gov using terms such as "Myc", "Aurora", "prostate" and/or "solid tumor" retrieves 6 trials that may be relevant for this patient's tumor.<br><br>Two of these trials are shown below. |

| TITLE | PHASE | TARGETS | LOCATIONS | NCT ID |
|---|---|---|---|---|
| A Phase 1, First-in-Human Study Evaluating the Safety, Tolerability, Pharmacokinetics and Pharmacodynamics of Orally Administered AMG 900 in Adult Subjects With Advanced Solid Tumors | Phase 1 | Aurora kinase | Maryland, New Mexico | NCT00858377 |
| A Phase 1 Dose Escalation Study of MLN8237, an Aurora A Kinase inhibitor, In Adult Patients With Nonhematological Malignancies, Followed by a Phase 2 of MLN8237 in Lung, Breast, Head and Neck, or Gastroesophageal Malignancies | Phase 1/2 | Aurora kinase | Connecticut, Texas, Utah | NCT01045421 |

Patient Name: Kell, Jesse
Report Date: 31 December 1969
Diagnosis: Prostate acinar adenocarcinoma

APPENDIX
REFERENCES

Agus DB, Sweeney CJ, Morris MJ, et al. (2007) — J Clin Oncol 25 (6):675-81

Arango D, Corner GA, Wadler S, et al, (2001) c-myc/p53 — Cancer Res 61(12):4910-5

Barietta JA, Perner S, Iafrata AJ, et al. (2009) — J Cell Mol Med 13(8B):1977-86

Baselga J, Cortes J. Kim SB, et al. (2012) — N Engl J Med 3˜6(2): 109-19

Beltran E, Fresquet V, Martinez-Useros J, et al. (2011) — Proc Natl Acad Sci USA 108(30):12461-6

Ben Sahra I, Laurent K, Loubat A, et al. (2008) — Oncogene 27(25):3576-86

Beroukhim R, Mermel Ch, Porter D, eet al. (2010) — Nature 463(7283):899-905

Blancato J, Singh B, Liu A, et al. (2004) — Br J Cancer 90(8):1612-9

Bottone MG, Soldani C, Tognon G, et al. (2003) — Exp Cell Rs 290(1):49-59

Brown CJ, Lain S, Verma CS, et al. (2009) — Nat. Rev Cancer 9(12):862-73

Bubendorf L, Kononen J, Koivisto P, et al. (1999) — Cancer Res 59(4):803-6

Chen JP, Lin C, Xu CP, et al. (2001) — J. Gastroenterol Hepatol 16(1):22-8

Clegg NJ, Couto SS, Wongvipat J, et al. (2011) — PLoS ONE 6(3):e17449

Cordon-Cardo C, Latres E, Drobnjak M, et al. (1994) — Cancer Res 54(3):794-9

Dang CV, O'Donnell KA, Zeller KI, et al. (2006) — Semin Cancer Biol 16(4):253-64 den Hollander J, Rimpi S, Doherty JR, et al. (2010) — Blood 116(9):1498-505

Elsheikh S, Green AR, Aleskandarany MA, et al. (2008) — Breast Cancer Rest Treat 109(2):325-35

Fox KE, Fankell DM, Erickson PF, et al. (2006) — J. Biol Chem 281(52):40341-53

Fu M, Wang C, Li Z, et al. (2004) — Endocrinology 145(12):5439-47

Gautschi O, Ratschiller D, Gugger M, et al. (2007) — Lung Cancer 55(1):1-14

Patient Name: Kell, Jesse
Report Date: 31 December 1969
Diagnosis: Prostate acinar adenocarcinoma

APPENDIX

REFERENCES

Glinsky GV, Ivanova YA, Gilinskii AB (2003) — Cancer Lett 201(1):67-77

Goldstein NS (2002) Immunophenotypic — Am J Clin Pathol 117(3):471-7

Gupta VK, Feber A, XI L, et al. (2008) — Clin Cancer Res 1 (23):7804-12

Hamdan H, Liu H, Li C, et al. (1998) — Biochim Biophys Acta 1396(3):336-48

Han EK, Lim JT, Arber N, et al. (1998) — Prostate 35(2):95-101

Hawksworth D, Ravindranath L, Chen Y, et al. (2010) — Prostate Cancer Prostatic Dis 13(4):311-5

Homminga I, Pieters R, Langerak AW, et al. (2011) — Cancer Cell 19(4):484-97

Hook KE, Garza SJ, Lira ME, et al. (2012) — Mol Cancer Ther 11(3):710-9

Horiuchi D, Kusdra L, Huskey NE, et al. (2012) — J Exp Med 209(4):679-96

Hsu DS, Acharya CR, Balakumaran BS, et al. (2009) — Proc Natl Acad Sci USA 106(13):5312-7

Ismail A, Bandla S, Reveiller M, et al. (2011) — Clin Cancer Res 17(13):4513-22

Italiano A, Bianchini L, Gjernes E, eet al. (2009) — Clin Cancer Res 15(18):5696-703

Iwakawa R, Kohno T, Kato M, et al. (2011) — Clin Cancer Res 17(6):1481-9

Kaltz-Wittmer C, Kienk U, Gloessgen A, et al. (2000) — Lab Invest 80(9):1455-64

Kamijo T, Weber JD, Zambetti G, et al. (1998) — Proc Natl Acad Sci USA 95(14):8292-7

Kaminagakura E, Werneck da Cunha I, Soares FA, et al. (2011) — Head Neck 33(10):1413-9

Kendall J, Liu Q, Bakieh A, et al. (2007) — Proc Natl Acad Sci USA 104(42):16663-8

Kwei KA, Kim YH, Girard L, et al. (2008) — Oncogene 27(25):3635-40

Lapenna S, Giordano A (2009) — Nat Rev Drug Discov 8(7):547-66

Leite KR, Franco MF, Srougi M, et al. (2001) — Mod Pathol 14(5):428-36

Leite KR, Mitteldorf CA, Srougi M, et al. (2008) — Ann Diagn Pathol 12(4):260-6

*FIG. 9L*

| | Patient Name<br>Kell, Jesse | Report Date<br>31 December 1969 | Diagnosis<br>Prostate acinar<br>adenocarcinoma |
|---|---|---|---|

916

APPENDIX
REFERENCES

Liles JS, Amaletti JP, Kossenkov AV, et al. (2011) — Br J Cancer 105(4):523-33

Lin CP, Liu CR, Lee CN, et al. (2010) — World J Hepatol 2(1):16-20

Lu W, Chen L, Peng Y, et al. (2001) — Oncogene 20(25):3206-16

Mejia-Guerrero S, Quejada M, Gokgoz N, et al. (2010) — Cancer 49(6):518-25

Mohamed AM, Elwakil TF, Taher IM, et al. (2009) — Cell Tissue Res 338(1):107-15

Mu K, Li L, Yang Q, et al. (2011) — Histopathology 58(4):601-7

Musgrove EA, Caldon CE, Barraclough J, et al. (2011) — Nat Rev Cancer 11(8):588-72

Nai G, Marques M (2011) Role of ROC1 — Pathol Res Pract 207(3):174-81

Nesbit CE, Tersak JM, Prochownik EV (1999) — Oncogene 18(19):3004-16

Ngan ES, Lang BH, Liu T, et al. (2009) — J Natl Cancer Inst 101(3):162-75

Nord H, Segersten U, Sandgren J, et al. (2010) — Int J Cancer 126(6):1390-402

Oliner JD, Kinzler KW, Meltzer PS, et al. (1992) — Nature 358(6381):80-3

Rao SK, Edwards J, Joshi AD, eet al. (2010) — J Neurooncol 98(2):169-79

Sato H, Minei S, Hachiya T, et al. (2006) — Int J Urol 13(6):761-6

Sattler HP, Rohde V, Bonkhoff H, et al. (1999) — Prostate 39(2):79-86

Schuuring E. (1995) The involvement of the — Gene 159(1):83-96

Schwartz GK, LoRusso PM, Dickson MA, et al. (2011) — Br J Cancer 104(12):1862-8

Sheng Q, Liu J (2011) The therapeutic — Br J Cancer 104(8):1241-5

Sheng Q, Liu X, Fleming E, et al. (2010) — Cancer Cell 17(3):298-310

Shi F, Telesco SE, Liu Y, et al. (2010) — Proc Natl Acad Sci USA 107(17):7692-7

Takahashi-Yanaga F, Sasaguri T (2008) — Cell Signal 20(4):581-9

Tsuda H, Birrer MJ, Ito YM, et al. (2004) — Cancer Genet Cytogenet 155(2):97-107

Patient Name: Kell, Jesse
Report Date: 31 December 1969
Diagnosis: Prostate acinar adenocarcinoma

APPENDIX

REFERENCES

Weir BA, Woo MS, Getz G, et al. (2007) — Nature 450(717):893-8

Wilkman H, Nymark P, Vayrynen A, et al. (2005) — Genes Chromosomes Cancer 42(2):193-9

Wu A, Wu B, Guo J, et al. (2011) — J Transl Med 9:38

Zafarana G, Ishkanian AS, Malloff CA, et al. (2012) — Cancer 118(16):4053-62

Zaharieva BM, Simon R, Diener PA, et al. (2003) — J. Pathol 201(4):603-8

Zeller KI, Jegga AG, Aronow BJ, et al. (2003) — Genome Biol 4(10):R69

| Patient Name | Report Date | Diagnosis |
|---|---|---|
| Kell, Jesse | 31 December 1969 | Prostate acinar adenocarcinoma |

APPENDIX

ABOUT THE TEST

Foundation Medicine Test: _____
_____
_____
_____
_____ complexity clinical testing.

Diagnostic Significance/Lock _____
_____
_____ in this report (Report).

Associated Publicly Available _____
_____
_____
_____
_____
_____ www.N-of-One.com Alterations and Drugs Not _____
_____ or predicted efficacy.

Level of Evidence Not Provided: _____
_____ of published evidence.

No Guarantee of Clinical _____
_____ provide no clinical benefit.

No Guarantee of Reimbursement: _____
_____ patient for the cost of the Test.

Treatment Decisions are Responsibility _____
_____
_____
_____ treatment.

Decisions on patient care and _____
_____
_____ contained in this Report.

FIG. 90

THERAPEUTIC IMPLICATIONS

— 906

| Genomic Alterations Detected | FDA Approved Therapies (in patient tumor type) | FDA Approved Therapies (in another tumor type) | Potential Clinical Trials |
|---|---|---|---|
| ERBB3 amplification | None | Pertuzumab | Yes, see clinical trials section |
| CCND1 amplification | None | None | Yes, see clinical trials section |
| CDK4 amplification | None | None | Yes, see clinical trials section |
| MDM2 amplification | None | None | Yes, see clinical trials section |
| MYC amplification | None | None | Yes, see clinical trials section |
| NKX2-1 amplification | None | None | None |

Note: Genomic alterations detected may be associated with activity of certain FDA approved drugs; however, the agents listed in this report may have varied clinical evidence in the patient's tumor type. Neither the therapeutic agents nor the trials identified are ranked in order of potential or predicted efficacy for this patient, nor are they ranked in order of level of evidence for this patient's tumor type.

FIG. 9P

My Patients | All Patients

- Erik Fairbairn
  Report sent 1 week ago
- Ted Hullinger
  Updated 12 weeks ago
- Elsa Bowne
  Updated 12 weeks ago Mindy Barning
Updated 3 weeks ago
Randall Stidham
Updated 3 weeks ago
Marcus Lindner
Updated 2 weeks ago
Clifford Shih
Updated 2 weeks ago
Tom Branum
Updated 2 weeks ago
Tammie Cowley
Updated 2 weeks ago Stan Welle    Support    Feedback Erik Fairbairn
Colorectal cancer
Born May 1, 1955
Archive patient Report Aug 24, 2012

14 similar patients
Treatment and outcome

What is Erik Fairbairn's current treatment?

Add treatment — 1902
Therapeutic agent or regimen — 1904
Radiation — 1906
Surgery — 1908

1900

Save Updates    Skip for now

Patient has consented to share information about treatments and outcomes. See approval.

FIG. 19

My Patients | All Patients

- Erik Fairbairn
  Report sent 1 week ago
- Ted Hullinger
  Updated 12 weeks ago
- Elsa Bowne
  Updated 12 weeks ago Mindy Banning
Updated 3 weeks ago Randall Stidham
Updated 3 weeks ago Marcus Lindner
Updated 2 weeks ago Clifford Shih
Updated 2 weeks ago Tom Branum
Updated 2 weeks ago Tammie Cowley
Updated 2 weeks ago Stan Welle    Support    Feedback Erik Fairbairn
Colorectal cancer
Born May 1, 1955
Archive patient Report
Aug 24, 2012

14 similar patients
Treatment and outcome

What is Erik Fairbairn's current treatment?

1. Therapeutic agent or regimen

Er| — 2104
  Erbitux — 2106
  Erlotinib — 2108
  Erwinia L-asparaginase — 2110

Add another treatment ▼

X Delete treatment — 2112

2100

2102

Save Updates    Skip for now

Patient has consented to share information about treatments and outcomes. See approval.

◇ Stan Welle    Support    Feedback    ☆ ≫ ✈

| My Patients | All Patients |

Erik Fairbairn
Colorectal cancer
Born May 1, 1955
Archive patient

▦ Report
Aug 24, 2012

👥 14 similar patients
Treatment and outcome

• Erik Fairbairn
   Report sent 1 week ago

• Ted Hullinger
   Updated 12 weeks ago

• Elsa Bowne
   Updated 12 weeks ago

What is Erik Fairbairn's current treatment?

Mindy Banning
Updated 3 weeks ago

1. Therapeutic agent or regimen

Randall Stidham
Updated 3 weeks ago

[ Erbitux ▦ ] — 2202

Marcus Lindner
Updated 2 weeks ago

☐ Provide start date for treatment

Clifford Shih
Updated 2 weeks ago

☐ Treatment is part of a clinical trial

Tom Branum
Updated 2 weeks ago

[ Add another treatment ▶ ] — 2204

Tammie Cowley
Updated 2 weeks ago

[ Save updates ]    [ Skip for now ]

✕ Delete treatment

Patient has consented to share information about treatments and outcomes. See approval.

| My Patients | All Patients |
|---|---|

◇ Stan Welle   Support   Feedback

○ Erik Fairbairn — 2502
Updated today

● Ted Hullinger
Updated 12 weeks ago

● Elsa Bowne
Updated 12 weeks ago

Mindy Banning
Updated 3 weeks ago

Randall Stidham
Updated 3 weeks ago

Marcus Lindner
Updated 2 weeks ago

Clifford Shih
Updated 2 weeks ago

Tom Branum
Updated 2 weeks ago

Tammie Cowley
Updated 2 weeks ago

Ted Hullinger
Colorectal cancer
Born December 7, 1962
Archive patient

[Report icon] Report
January 15, 2012 — 2503

37 similar patients
Treatment and outcome

2500

What is Ted Hullinger's current treatment?

1. Therapeutic agent or regimen
   Vandetanib
   Start date: July 2, 2012          X Delete treatment — 2504

Add another treatment ▼

How is the patient's tumor responding?
○ Progressive disease — 2506
● Stable disease (answer 12 weeks ago) — 2508
○ Partial response — 2510
○ Complete response — 2512

[Save updates] ◀ [Skip for now]
         ↑
         2514

Patient has consented to share information about treatments and outcomes. See approval.

Foundation Medicine MVP | Trial Summary Page: Report View

| Foundation | Client Name FM Test Portal | | J Thomas ▼ Alerts (2) Support Feedback |
|---|---|---|---|

(A) ▶ Patient Michael Thomas Report > Trial NCT01306543     (F)    (G)    (H) Print (B) NCT01306543
Molecular Profiling and Targeted Therapy for
Advanced Non-Small Cell Lung Cancer, Small
Cell Lung Cancer, and Thymic Malignancies (C) As presented in 06.15.11 report (D) Phase III, Recruiting
Trial Contact Information
NCI Referral Office 1-888-NCI-1937
Mark Jones, PI: mjones@nci.org, 303-235-9425
Trial Locations
National Institutes of Health Clinical Center
9000 Rockville Pike
Bethesda, Maryland, United States, 20892

Oregon Health Sciences University Cancer Center
Portland, Oregon, United States, 97239

Targets
GENE, GENE, GENE, GENE, GENE, GENE, GENE

Conditions
NSCLC, SCLC, Thyroid

Eligibility
Individuals at least 18 ———— surgery or radiation therapy.

Summary
The current standard of ———————— provide personalized treatment (E) ▶ Relevant Patient Alterations
EGFR, L858R
2 Related Therapies (2) ▶
Therapy (Therapy)
Therapy (Therapy)
19 Related References (6) ▶
Bell et al., 2005
Engelmen et al, 2007;
Greulich et al, 2005
Hirsch et al, 2008
Hirsch et al, 2008

FIG. 33

Foundation Medicine MVP | Trial Summary Page: Report View

Foundation | Client Name FM Test Portal | J Thomas ▼ Alerts (2) Support Feedback Ⓗ Print Ⓐ Patient Michael Thomas Report > (Naiate, et al)

Ⓑ Phase III of Vandetanib compared with Erlotinib in Patients with previously treated advanced non-small-cell lung cancer Ⓒ As presented in 06.15.11 report Ⓓ Authors
Natale, R. B., Thongpresent, S., Greco, F.A., Thomas, M. Tsai, C. M., Sunpeweragong, P., Ferry, D., Mulatero, C., Whart, R., Thompson, J., et al. (2011)

Publication
Journal of clinical oncology: official journal of the American Society of Clinical Oncology 29, 1059-1066.

Abstract
Viducillis aut audaero repudae ─────────────────────────
───── eaque ent adis qui ant.

Vilitis exeaqu isitati optial ─────────────
───────────────── simenditas dus, sunt.v.

Ⓔ
| Relevant Patient Alterations ▶ |
| EGFR, L858R |
| Related Therapies (1) ▶ |
| Erlotinib (Capelea) |
| Related Therapies (1) ▶ |
| NCT01306543 |

FOUNDATIONMEDICINE.COM

*FIG. 34*

Foundation Medicine MVP | Account Settings

Foundation | Client Name FM Test Portal

Settings
General

| | | |
|---|---|---|
| Name | Jonathan Thomas | Edit |
| Email | JThomas@hospital.org | Edit |
| Password | Updated over a year ago | Edit |
| Account | Beth Israel Desconess Medical Center | Edit |

Alerts

Foundation Medicine sends alerts related to report information.
You may set preferences for the types, frequency, and delivery methods of alerts.
Choose which types of alerts you want to receive.

We provide updates about our test and information related to patient reports.
You may choose which types of alerts you wish to receive.

| | | |
|---|---|---|
| Interpretation Alerts | Subscribed | Edit |
| Therapy Alerts | Subscribed | Edit |
| Trial Alerts | Subscribed | Edit |
| Reference Alerts | Subscribed | Edit |

Set your email delivery preferences.
We send a weekly email alert update for all patients.

You may opt out of this email delivery or change your small preferences.

Send alerts via email

*FIG. 35*

MVP System Pages | Account: Settings

Send daily alert summary ☐
Send weekly alert summary ☑
Send monthly alert summary ☐

Ⓐ Set customized patient alert options

The above settings are global and apply to all patients.
You may override these settings on a per-patient basis to customize the
type, frequency, and delivery of alerts for individual patients.

Ⓑ Thomas, Michael ▼

Ⓒ Customize the types of alerts you want to receive for this patient.

We provide updates about our test and information related to patient reports.
You may choose which types of alerts you wish to receive.

| | Global Setting | Patient Setting |
|---|---|---|
| Interpretation Alerts | Subscribed | Receive alerts ▶ |
| Therapy Alerts | Subscribed | Receive alerts ▶ |
| Trial Alerts | Subscribed (customized) | Do not receive alerts ▶ |
| Reference Alerts | Not subscribed (customized) | Receive alerts ▶ |

Ⓓ Customize your email delivery preferences for this patient.
You may customize delivery preferences for this patient.

| | Global Setting | Patient Setting |
|---|---|---|
| Email Alerts | Subscribed | Receive alerts ▶ |
| Real Time Alerts | Subscribed | Do not receive alerts ▶ |
| Daily alert summary | Not subscribed (customized) | Receive alerts ▶ |
| Weekly alert summary | Subscribed (customized) | Do not receive alerts ▶ |
| Monthly alert summary | Not subscribed | Do not receive alerts ▶ |

FOUNDATIONMEDICINE.COM

*FIG. 36*

Frameworks | Data Tables

Patient Index

| All Patients > Patients to Research | | | | | |
|---|---|---|---|---|---|
| Name | Diagnosis | Case No. | Physician | Reported | Updated |
| Lastname, Firstname | Diagnosis | FM-004578 | Thomas, Jonathan | 11.12.11 | |
| Lastname, Firstname | Diagnosis | FM-004578 | Thomas, J | 11.12.11 | |
| Lastname, Firstname | Diagnosis | FM-004578 | Thomas, J | 11.12.11 | |
| Lastname, Firstname | Diagnosis | FM-004578 | Thomas, J | 11.12.11 | |
| Lastname, Firstname | Diagnosis | FM-004578 | Thomas, J | 11.12.11 | |
| Lastname, Firstname | Diagnosis | FM-004578 | Thomas, J | 11.10.11 | |
| Lastname, Firstname | Diagnosis | FM-004578 | Thomas, J | 11.09.11 | |
| Lastname, Firstname | Diagnosis | FM-004578 | Thomas, J | 11.09.11 | 10.03.11 |
| Lastname, Firstname | Diagnosis | FM-004578 | Thomas, J | 11.01.11 | 10.03.11 |
| Lastname, Firstname | Diagnosis | FM-004578 | Thomas, J | 10.28.11 | |

Updates Timeline

Updates timeline
Show Updates For: [ Interpretations ] [ Therapies ] [ Trials ] [ References ]
　　　　　　　　　　　3806　　　　　　3808　　　　3810　　　3812

○ Interpretation for Alteration X in GENE has been added as new therapies, trials, and and references have been added to associated information tests.　　11.12.11
xxxxxxxxxxxxxxxxx ☐ The reference "Minyeran perrum sineips aopudionsed que venocaborepe consed volorest quato quam ot vei Imi, vellet" supporting evidence of clinical benefit has been added for Suntinib(Sufent).　　11.12.11
Show Interpretations △ Interpretation for Alteration X in GENE has been edited.　　11.10.11

△ NCT ID: NCT00940228 (Study of Gabozantinib (XL184) has been added as trial with associated benefit for Alteration X in GENE　　11.06.11

| NCT01306543 | | | | | |
|---|---|---|---|---|---|
| Cutris, Documulus hue confecote atom huois clost Amquam con lecicardt vicce pairc cent eloris | GENE, GENE, GENE, GENE, GENE, GENE, GENE, GENE, GENE, GENE, | Phase III | Recruiting | Therapy (Therapy) Therapy (Therapy) | LOC LOC LOC |

11.09.11　1

Hide Trial Listing

△ Interpretation for Alteration X in GENE has been edited to include addition for new reference.　　11.06.11

◯ 8 Trials (Updated 11.10.11) ⟵ 3826

| Trial A | B Targets | C Phase | D Status | E Therapies | F Locations | G Updates |
|---|---|---|---|---|---|---|
| NCT01306543 Cutris, Documulus hue confecote atom huois clost Amquam con lecicardt vicce pairc cent eloris xxxxxxxxxx | GENE, GENE, GENE, GENE, GENE, GENE, GENE, GENE, GENE, | Phase III | Recruiting | Therapy (Therapy) Therapy (Therapy) | LOC LOC LOC | 1   11.09.11 |

Trials Header and Row Module (Updates View) ⟵ 3820

◯ 32 References ⟵ 3828

| Reference A | B | Report Citations |
|---|---|---|
| Nulpa veide soquibus nein pedi conpention pere sunj audi dis mormin quam quo die penni volupium es et oui uipe elli ——————————————— ui ent questi urenum. |  | 4 |
| Reference Dates |  |  |

References Header and Row Module (Report View)

FIG. 38D

Frameworks | View Filters (Updates Timeline)

Foundation    Client Name FM Test Portal      J. Thomas   Alerts (2)   Support   Feedback   Print Patients > Michael Thomas Report — 3902

Michael Thomas      Report 06.15.11 | Updates

Updates timeline

Show Updates For: [ Interpretations ] [ Therapies ] [ Trials ] [ References ] ← 3904

○   Interpretation for Alteration X in GENE has been added as new therapies, trials, and and references have been added to associated information tests.    11.12.11
     Show Interpretation ☐   The reference "Minyeran perrum sineips aopudionsed que venocaborepe consed volorest quato quam ot vei lmi, vellet" supporting evidence of clinical benefit has been added for Sunitinib (Sutent).    11.12.11
     Show Reference Listing △   Interpretation for Alteration X in GENE has been edited.    11.10.11

△   NCT ID: NCT00940228 (Study of Cabozantinib (XL184)) has been added as trial with associated benefit for Alteration X in GENE    11.06.11
     Hide Trial Listing

| NCT01306543 | GENE, GENE, | Phase III | Recruiting | Therapy (Therapy) | LOC 1 | 11.09.11 |
| Cutris, Documulus hue confecote atom | GENE, GENE, | | | Therapy (Therapy) | LOC | |
| huois clost Amquam con lecicardt | GENE, GENE, | | | | LOC | |
| vicce pairc cent eloris | GENE, GENE, | | | | | |

Trial Updates ☑

More Updates

△   Interpretations ▶

△   5 Therapies (Updated 11.09.11) ▶

△   8 Trials (Updated 11.10.11) ▶

△   32 References (Updated 11.12.11) ▶

FOUNDATIONMEDICINE.COM

Report of Record View
Includes an "Associated Information" section with 4 information categories To Fig. 40B

Foundation | Client Name FM Test Portal | J. Thomas | Alerts (2) | Support | Feedback
Print Patients > Michael Thomas Report
Michael Thomas Report 06.15.11 | Updated 11.12.11

Trial Information xxx xx xxxxx xxxxx xxxxx xxxxx xxxx xxxx

Trial Updates xxx xx xxxxx xxxxx xxxxx xxxxx xxxx xxxx

| EGFR | STK11 | TP53 |
|---|---|---|
| L858R Mutation | Whole Gene Deletion | R248L |

| GENE | GENE | GENE |
|---|---|---|
| Pes eribus nenum pubicdost abom o elrum | Pes eribus nenum pubicdost abom o elrum | Pes eribus nenum pubicdost abom o elrum | xxx xxxxx xxxxx xxxx x xxxx xxxxxx xxx
xxx xxx xxxx xxxx xxx
xxx xxxxx xxxx xxxx xxx x xxxx xxxxx xxx
xxx xxxxx xxxxx xxxxx xxxxx xxxxxx xxx
xxx xxxxx xxxx xxxxx x xxxx xxxxxx xxx Associated Information Xxxxxxxxx Xxxxxxx

| Xxxxxxxx Xxxxxxx | Xxxx Xxxxxx |
|---|---|
| | Xxxx Xxxxxx |
| | Xxxxxxxx |
| Interpretations | Xxxx Xxxxxx |
| Therapies (3) | Xxxx Xxxxxx |
| Trials (7) | Xxxx Xxxxxx |
| References (32) | |

Ⓑ

FOUNDATIONMEDICINE.COM

Report of Record View with Updates Available
Includes notification bar with a link to an updates timeline

FIG. 40C

Information Updates View
includes the timeline category, plus 4 information categories

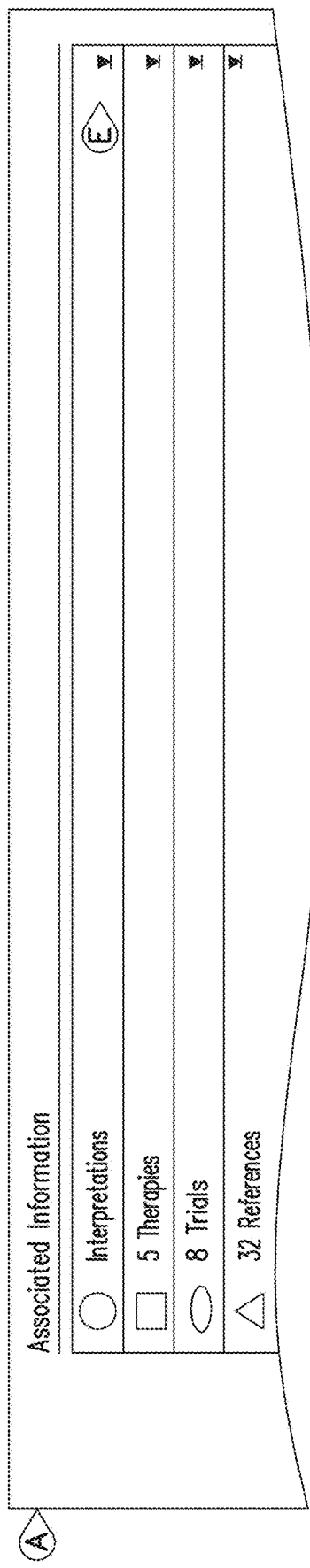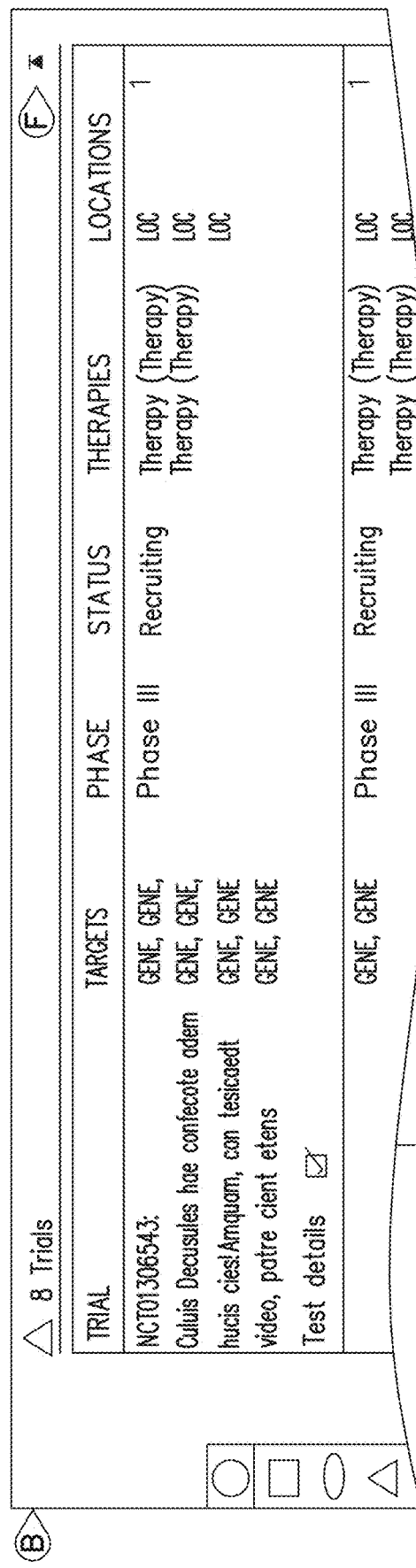
FIG. 41A

Associated Information Updated 11.09.11

Therapies Associated with Clinical Benefits

○ Recent Updates
○ Interpretations
□ Therapies (5)     xxxx (EGFR)
◯ Trials (7)    xxxx (STK11)
△ References (30)    xxxx (STK11)

*FDA approved for NSCLC

Ⓖ Xxxxxxxxx Xxxxxxx

Ⓗ

Ⓘ

△ 8 Trials (Updated 11.10.11)    Ⓗ

| TRIAL | TARGETS | PHASE | STATUS | THERAPIES | LOCATIONS | UPDATES |
|---|---|---|---|---|---|---|
| NCT01306543: Culuis Decusules hoe confecote adem hucis ciesl Amquam, con tesicaedt video, patre cient etens | GENE, GENE, GENE, GENE, GENE, GENE, GENE, GENE | Phase III | Recruiting | Therapy (Therapy) Therapy (Therapy) | LOC LOC LOC | 1   11.09.11 |
| Test details ☑ | | | | | | |
| | GENE, GENE | Phase III | Recruiting | Therapy (Therapy) Therapy (Therapy) | LOC LOC | 1 |

Frameworks | Update Indicators

| Lastname, Firstname | Diagnosis | FM-004578 | Thomas, J | A) 10.01.11 |

*4202*

Associated Information

| Recent Updates | | |
|---|---|---|
| Interpretations | Xxxx Xxxxxxxxxxx | C) View Updates |
| 5 Therapies | | View Updates |
| 8 Trials | | View Updates |
| 32 References | | View Updates |

*4204* B)     *4206*

| △ 8 Trials | | | | | | |
|---|---|---|---|---|---|---|
| TRIAL | TARGETS | PHASE | STATUS | THERAPIES | LOCATIONS | UPDATES |
| NCT01306543:<br>Quluis Decusales hae confecate adem hucis ciesiAmquam, con tesicaedt video, patre cient etens | GENE, GENE<br>GENE, GENE<br>GENE, GENE<br>GENE, GENE | Phase III | Recruiting | Therapy (Therapy)<br>Therapy (Therapy) | LOC<br>LOC  1<br>LOC | D) 11.08.11 |
| Test details ☑ | | | | | | *4208* |

△ NCT ID: NCT00940225 (Study of Cabozantinib (XL184) has been added as trial with associated benefit for Alteration X in GENE.

Hide trial testing

| NCT01306543: | GENE, GENE | Phase III | Recruiting | Therapy (Therapy) | LOC 1 | Ⓔ 11.08.11 |
| Cuiuis Decusuies hae confecote adem | GENE, GENE | | | Therapy (Therapy) | LOC | |
| hucis cies!Amquam, con tesicaedt | GENE, GENE | | | | LOC | |
| video, patre cient etens | GENE, GENE | | | | | |

11.08.11

↙ 4210

Test details ☑

Ⓕ New updated page ↺
↖ 4212

Ⓖ ↺ Page updated November 12, 2011
↖ 4214

Additional Page Types and Alternates | Report: Expanded State (view by alteration alternate) (continued)

| Associated Information | | View by Category | View by Alteration |
|---|---|---|---|
| EGFR L858R Mutation | ○ Therapy | △ 2 Trials | ☐ 3 References |

(A) ○ Interpretation

In the metastatic setting, EGFR mutations are strong predictors of efficacy for the EGFR tyrosine kinase inhibitors (TKI, erlotinib (Tarceva).

View summary page (B) ○ 1 Therapy associated with clinical benefit

| Therapy | GENE | Alteration | | | | |
|---|---|---|---|---|---|---|
| Erlotinib (Capreisa) | EGFR | L858R | NCSLC Stage ▼ | FDA-Approved | FDA-Approved Uses | ☐ 6 |
| | | | | | NSCL | 1 |

Therapy dates ☑

△ 2 Trials associated with clinical benefit

| Trial | Targets | Phase | Status | Therapies | Locations | ☐ |

*FIG. 46A*

| NCT01306543: Culuis Decusules hae confecote adem hucis cieslAmquam, con tesicaedt video, patre cient etens Test details ☑ | GENE, GENE, GENE, GENE, GENE, GENE GENE, GENE | Phase III | Recruiting | Therapy (Therapy) Therapy (Therapy) | LOC LOC LOC | 1 |
| NCT01306543: Culuis Decusules hae confecote adem hucis cieslAmquam, con tesicaedt video, patre cient etens Test details ☑ | GENE, GENE, GENE, GENE, GENE, GENE GENE, GENE | Phase III | Recruiting | Therapy (Therapy) Therapy (Therapy) | LOC LOC | 1 |
| ○ 3 References | | | | | | |
| STK11 | Whole Gene Deletion | | | ○ 2 Therapies | △ 3 Trials | □ 9 References ▶ |
| TP53 | R2248L | | | ○ 2 Therapies | △ 3 Trials | □ 9 References ▶ |
| GENE | Pae eribus nonum pubicael abem o atrum | | | ○ 2 Therapies | △ 3 Trials | □ 9 References ▶ |
| GENE | Pae eribus nonum pubicael | | | ○ 2 Therapies | △ 3 Trials | □ 9 References ▶ |
| GENE | Pae eribus nonum pubicael abem o atrum | | | ○ 2 Therapies | △ 3 Trials | □ 9 References ▶ |

FOUNDATIONMEDICINE.COM

*FIG. 46B*

| Foundation Medicine Logo | Patients Knowledge | 🔍 J Thomas ▼ \| Feedback \| Contact Us |

Knowledge — 5002

1243 Patient Cases    8 cancer types researched    1249 Trials
324 Oncologists    301 Genes tested    809 Therapies
562 Medical Professionals    987 Identifiable alterations    12437 References

— 5000 —    5008

Explore case studies
View patient xxxxx xxxxx xxx conditions
Condition — 5004
[All xxxxxxx ▶]
[All therapies ▶]
[All alterations ▶]
Treatment
[All xxxxxx ▶]
[All xxxx ▶]
Patient Characteristics
[Age ▶]
[Sex ▶]
[Exxxxxxx Xxxx ▶]
[Search by Keyword 🔍]

| Topic of Discussion | Type | Notes | Last Post |
|---|---|---|---|
| Name of a therapy | Therapy | 5 | 10/23/11 |
| Name of a gene mutation | Gene mutation | 4 | 10/14/11 |
| Name of a clinical trial | Clinical Trial | 2 | 09/20/11 |
| Name of a reference | Reference | 5 | 05/14/11 |
| Name of a Cancer type | Cancer type | 7 | 05/14/11 |
| Name of a conference | Conference | 8 | 05/14/11 |
| Name of a publication | Publication | 9 | 05/14/11 |
| Name of a therapy | Therapy | 1 | 05/14/11 |
| Name of a gene mutation | Gene mutation | 3 | 05/14/11 |
| Name of a clinical trial | Clinical trial | 5 | 05/14/11 |
| | | | VIEW ALL |

| Fig. 50A |
| Fig. 50B |
| Fig. 50C |

*FIG. 50A*

Learn more about cancer genomics

Research alterations, genes and cancer types

All xxxxx ▸
All genes ▸
All alterations ▸
Search by Keyword 🔍

*5006*

*5010* — Most Discussed

Cryogungery and Dysplasia
Latest Note
_____

Pulmonary
Latest Note
_____

FDA Approves Cervical
Latest Note
_____

View All

*5012* — Most Viewed Case Studies

A 33 year old with a _____

Rxxxxxx Xxxxx Cell
_____

Herididary Colon Cancer
Dr. Richard Lie

Lung Cancer A Case Study
Dr. Richard Lie

A 2 year cell _____

Dr. Dan Smith

A 22 year old with an _____
Dr. Dan Smith

A 20 month old with _____
Dr. Andrea Smith

View All

| Fig. 50B |
| Fig. 50C |

5014 — Recently Open Trials
- A Dave Fielding Study
- Massachusetts, Tennessee
- Trial of MEX
- Maryland
- Study of Hefatic
- New Jersey, New York
- View All 5016 — Most Recent Publications
- Relationship between
- Publication Home
- Source:
- Article Title.
- Avoiding the zone
- Source:
- View All

FOUNDATIONMEDICINE.COM    PATIENTS    KNOWLEDGE | CONTACT US    FEEDBACK

| | | |
|---|---|---|
| Evaluation of the Setting | Prostate Cancer; Breast Cancer; Colorectal Cancer; Thoracic Cancer | Other: CKS<br>Facing Forward booklet | Recruiting |
| MKC2208 and Breast Cancer | Breast Cancer Unspecified Adult Solid Tumor, Protocol Specific | Drug, ASE<br>pharmacological study | Recruiting |
| Reducing Cancer West | Prostrate Cancer Colorectal Cancer, Breast Cancer; Cervical Cancer, Lung Cancer | Behavioral Navigation Services; Behavioral Cancer education | Completed |

| Fig. 51B |
|---|
| Fig. 51C |

*FIG. 51B*

| Genomic Testing for Cancer | Breast Caner | Procedure: Tumor Biopsy, Registry | Recruiting |
|---|---|---|---|
| Evaluating an Interactive Cancer | Lung Cancer, Stage | Other: Chess success if needed | Recruiting |
| Order Patients Colon Cancer | Cancer, Psychsocial medical chart review. | Conditions: Breast Cancer, Corrected | Completed |

1 2 3 4 5 6 7 >

FOUNDATIONMEDICINE.COM   PATIENTS   KNOWLEDGE | CONTACT US   FEEDBACK

*FIG. 51C*

Treatment Notes ⎯ 5208

| Treatment | Date | Status | Open |
|---|---|---|---|
| Name of treatment course | 00.00.00–00.00.00 | Inaffective ○ | Title of the Clinical Trial, Date of Completion |
| Name of treatment course | 00.00.00–00.00.00 | Inaffective | Title of the Clinical Trial, Date of Completion |
| Name of treatment course | 00.00.00–00.00.00 | Inaffective ○ | Related References ⎯ 5218 |
| Name of treatment course | 00.00.00–00.00.00 | Inaffective ○ | Publication Title, Reference, Date of Publishing |
| Name of treatment course | 00.00.00–00.00.00 | Ongoing | Publication Title, Reference, Date of Publishing |
|  |  |  | Publication Title, Reference, Date of Publishing |
|  |  |  | Publication Title, Reference, Date of Publishing |

Last updated 00.00.00 automatically via Xxxx xxxxxxxx ⎯ 5210

Treatment change due to report results? ⎯ 5210
Yes

| Fig. 52B |
|---|
| Fig. 52C |

*FIG. 52B*

Community Comments —— 5212

Member Name     Tern fagit quno tend
10.20.11
10:53AM
                                        (View More *)

Member Name     Alternate results for similiar patient.
10.20.11        Tern fagit quno tend
10:53AM
                                        Cape abo.

5220 —— Related Therapies
Therapy
Therapy
Therapy
Therapy

*FIG. 52C*

Activity —5308

Shared Samantha Reed's Patient Report with Dr. Sanders
5:35pm Today

Submitted a note to the
6:30pm Friday

Submitted Tom Smiths Patients Report

5:30pm Oct. 22nd, 2011

Saved
1:30pm Oct 22nd, 2011

Shared Samantha Reed's Patient Report with Dr. Sanders
5:01pm Today

Submitted a note to the
5:30pm Friday

| Fig. 53B |
|----------|
| Fig. 53C |

*FIG. 53B*

Submitted Tom Smiths Patients Report for the ___
5:30pm Oct 22nd, 2011

Saved ___
1:30pm Oct 22nd, 2011

Shared Samantha Reed's Patient Report with Dr. Sanders
5:01pm Today

Submitted a note to the ___
5:30pm Friday

Submitted Tom Smiths Patients Report for the ___
5:30pm Oct 22nd, 2011

Saved ___
1:30pm Oct 22nd, 2011

VIEW MORE —— 5310

*FIG. 53C*

SYSTEM AND METHOD FOR OUTCOME TRACKING AND ANALYSIS

CROSS-REFERENCE TO RELATED APPLICATIONS

This application is a continuation of U.S. application Ser. No. 16/579,496, filed Sep. 23, 2019, which is a continuation of U.S. application Ser. No. 14/146,742-14/146,782, filed Jan. 3, 2014, now abandoned, which claims benefit of U.S. Provisional App. No. 61/749,291, filed Jan. 5, 2013, and U.S. Provisional App. No. 61/749,288, filed Jan. 5, 2013, the contents of each of which are incorporated by reference herein in their entirety.

BACKGROUND

Many conventional resources exist for accessing outcome information associated with patient populations and medical treatments. For example, cancer treatment information may be available through various resources. Notably, ClinicalTrials.gov provides public access to clinical trials through search interfaces. The website and interfaces enable searching through registered trials based on keywords that can be input by a user.

SUMMARY

It is realized that conventional approaches and publically available information sources fail to capture a large portion of outcome information associated with medical treatments, including, for example, cancer treatment. Further, some conventional approaches fail to provide valuable information on the progression of treatment. In one example, some conventional approaches can fail to present changes in therapy over time and the response of the disease over the various stages of treatment. In other settings, conventional approaches can fail to distill treatment and outcome information into useable and/or actionable information that a physician can apply in daily practice or, in another example, use to inform the physician's decision on potential treatment options. In other instances, physicians and other health professionals need prior knowledge of multiple systems and knowledge of cancer treatments to obtain the necessary information to make an informed treatment decision.

Accordingly, provided are systems and methods for capturing outcome information associated with various cancer treatments. According to one aspect, a system is provided that facilitates capture and analysis of cancer treatment information and associated outcome information. According to one embodiment, cancer treatment information and outcome information can include information relating to genetic analysis and treatment of different cancers. In one embodiment, a system may be provided that stores and analyzes a group of information including tumor type, genomic alterations (e.g., genes and associated alterations, gene sequence mutations, alterations, amplifications, deletions, etc.), and treatment (including, for example, treatments targeted to specific genes and/or genomic alterations). Users of the outcome system can supply and use the treatment and outcome information to facilitate diagnosis and therapy decisions. Such an outcome system may be accessed by users through a user-facing application referred to herein as an outcome application. Further, user interfaces of the outcome application may be provided to easily allow users to locate outcome information associated with particular treatments of tumors having certain genomic alterations.

According to another embodiment of the present invention, genomic alteration data is correlated with outcome data, and tools are provided to allow users to easily locate such correlations. For instance, it may be useful to have a tool that allows a physician to locate treatment and outcome information for patients with the same or similar genomic alterations occurring in different tumor types to inform decision-making for off-label uses of a particular treatment. In another embodiment, contact information for treating physicians associated with particular treatment/outcomes may be stored, and this contact information may be used by physicians or other personnel to contact such treating physicians for questions regarding their cases. This feature may permit, for example, socialization among physicians resulting in improved patient outcomes. In further embodiments, genomic testing information can be developed on the system, accessed, or requested. Genomic tests can be used to analyze a patient's cancer, specific cells, tumor types, etc., to facilitate the development of actionable information.

According to some aspects, the treatment and outcome information provided can be of limited value unless the information facilitates treatment decisions, without unduly impacting the amount of time the user (e.g., physician) spends to utilize that information. In some embodiments, the outcome system can be configured to limit data input for a single patient to a matter of minutes and provide resulting summary information responsive to any submission. In one embodiment, physicians and other users provide outcome data for particular patients in an interface that permits simple classification of outcome data. Outcome data that is normalized from multiple sources (e.g., patient data, references, trials, etc.) may be presented to the physician and may lead to more effective treatments.

According to one embodiment, the outcome system can be configured to aggregate collected outcome data and associated therapy information into a central database. Other sources of outcome data (e.g., formal registry studies and outcome data from academic medical center partnerships) can be combined with a central database to create a large and rich outcome data source that can be accessed by users of an outcome system. According to one embodiment, a global data model for cancer treatment outcomes can enable the integration of the variety of data sources into a consistent and easily navigated information source. For example, the central database organized under the global model can be used to provide the cancer treatment outcome information according to specific visualizations presented to end users. In various embodiments, the outcome system is configured to provide functions as a mechanism to gather outcome data and to visualize the outcome data. This contrasts with conventional approaches that do not aggregate various sources of information, and do not distill the information into an actionable form based on, for example, a patient's analyzed tumor.

According to another aspect, it is realized that physicians and other medical personnel would benefit by having a tool that would allow them to locate more quickly appropriate treatment and outcome information. Further, adoption and use of, for example, the outcome system can be directly impacted by how much time it takes to provide information and/or view valuable information in return. According to various embodiments, the outcome system can be specially configured to minimize the time to input useful information. For example, the system can be configured to categorize complex treatments and outcomes into intuitive and visually selectable categories. The categorizations and visualizations enable quick and easy entry of sophisticated and voluminous data, while preserving the value represented by the input treatment and outcome information.

Some embodiments relate to an outcome system that is capable of generating in real-time treatment and outcome time line displays, as it is appreciated that treatment is a process and can be analyzed as a function of time. For example, time line displays may be provided that summarize treatment and display any associated outcome of the treatment for each patient over time. In some embodiments, input treatment and outcome information can also be used to provide information associated with similar patients having similar timeline information. For example, the outcome system can identify similar patients based on matching patient condition and treatment information (including e.g., genomic alteration test results, tumor type, affected gene, treatment, etc.) over time. The outcome system can identify those similar patients and display their information such that valuable treatment and outcome information for other patients can be easily navigated to obtain relevant and related treatment/outcome information.

According to one example, the outcome system can provide for selections in a user interface to navigate to information on system identified similar patients. Further, navigation options can be generated to direct the user to valuable information contained in public information sources (e.g., clinicaltrials.gov). In other embodiments, proprietary information sources can also be accessed via system generated navigation links to provide such similar patient information and genomic testing information.

According to one aspect, a system for tracking and analysis of cancer treatment and outcome information is provided. The system comprises at least one processor operatively connected to a memory, the at least one processor when executing is configured to receive treatment and outcome information associated with a patient from at least one user, organize the treatment and the outcome information according to one or more of alteration, affected gene, affected pathway, tumor type, and treatment, generate outcome summary information including course of treatment displays over time, and communicate the outcome summary information to the at least one user.

In one embodiment, the treatment information includes any one or more of drugs, therapeutics, named drugs, named therapeutics, drug cocktails, drug combinations, radiation, and surgery. In one embodiment, the outcome information includes information regarding a status of a patient's cancer. In one embodiment, the status of the patient's cancer includes one or more of complete response, partial response, stable disease, and progressive disease. In one embodiment, the course of treatment includes information regarding how patient is responding to treatment over time.

In one embodiment, the system further comprises an analysis component executed by the at least one processor configured to identify similar patients based on information related to genomic alteration. In one embodiment, the system further comprises an analysis component executed by the at least one processor configured to identify similar patients based on information related to affected gene identified in a cancer. In one embodiment, the system further comprises an analysis component executed by the at least one processor configured to identify similar patients based on information related to treatment. In one embodiment, the system further comprises an analysis component executed by the at least one processor configured to identify similar patients based on related to tumor type. In one embodiment, the system further comprises an analysis component executed by the at least one processor configured to identify similar patients based on information relating to a combination of at least two or more of a group comprising alteration, affected gene, affected pathway, tumor type, and treatment.

In one embodiment, the system further comprises an analysis component executed by the at least one processor configured to identify similar patients based on information related to at least one of alteration, affected gene, affected pathway, tumor type, and treatment for a patient's cancer, wherein the analysis component is configured to aggregate responsive information according to one or more of alteration, affected gene, affected pathway, tumor type, and treatment. In one embodiment, the analysis component is configured to aggregate similar patients within classes of alterations. In one embodiment, the classes of alteration include alterations in a specified domain of a gene. In one embodiment, the domain includes at least a kinase domain of the gene.

In one embodiment, the gene includes BRAF, and the specific domains include at least one of kinase, BRAF V600E, and BRAF V600K. In one embodiment, analysis component can aggregate alteration on all BRAF V600 mutations together or all of the mutations in the kinase domain of BRAF. In one embodiment, the analysis component is configured to aggregate alteration information according to pathways affected by respective alterations. In one embodiment, the analysis component is configured to aggregate similar patient information based on functional similarity of identified alterations, which can be determined for distinct mutations having functionally similar characteristics in the cancer cells.

In one embodiment, the system further comprises a reminder component executed by the at least one processor configured to communicate an update request to the at least one user. In one embodiment, the reminder component is configured to determine a scheduled period for a patient update has expired. In one embodiment, the reminder component is configured to communicate an estimated time to complete the update request.

In one embodiment, the system further comprises an input component executed by the at least one processor configured to determine a type of information required for a patient. In one embodiment, the input component is configured to determine the type of information required is one of treatment and outcome information based on analysis of a patient record. In one embodiment, the input component is configured to generate an update request according to the type of information required. In one embodiment, the input component is configured to analyze the patient record to determine if treatment information has been input. In one embodiment, the input component is configured to determine an estimated time to input information based on the update request and the type of information.

In one embodiment, the system further comprises an analysis component executed by the at least one processor configured to compare a current patient record to existing treatment information. In one embodiment, the existing treatment information includes at least one of alteration, affected gene, affected pathway, tumor type, and one or more treatments. In one embodiment, the analysis component is configured to identify similar patients based on information in the current patient record, wherein identifying the similar patients includes determining a match between the current patient record and at least one of alteration, affected gene, affected pathway, tumor type, and treatment. In one embodiment, the analysis component is configured to identify similar patients based on user selection of at least one of tumor type, alteration, gene, and treatment. In one embodiment, the analysis component is configured to filter a grouping of similar patients based on additional specification of at least one of alteration, affected gene, affected pathway, tumor type, and treatment.

In one embodiment, the system further comprises a connection component executed by the at least one processor configured to provide connection information associated with care providers for respective patients within a group of similar patients. In one embodiment, the connection component is configured to provide contact information based on user selection of permission options.

In one embodiment, the system further comprises a UI component executed by the at least one processor configured to display treatment and outcome information for a patient within a history timeline. In one embodiment, the UI component is configured to enable navigation within treatment and outcome information based on selection of alteration, affected gene, affected pathway, tumor type, and treatment. In one embodiment, the UI component is configured to present selection elements for one of more of alteration, affected gene, affected pathway, tumor type, and treatment. In one embodiment, the selection elements are configured to cause the system to identify a subset of matching patient records according to specification of one or matching criteria with the selection elements.

In one embodiment, the UI component is configured to present a general treatment display configured to group a plurality of matching patients according to a common treatment. In one embodiment, the UI component is configured to present a similar patient view of a plurality of matching patients, wherein the similar patient view is configured to display groupings of patient records matching information in a current patient record. In one embodiment, the UI component is configured to determine the matching information based on one or more of alteration, affected gene, affected pathway, tumor type, and treatment. In one embodiment, the UI component is further configured to display filter options within the selection elements based on one or more of the alteration, affected gene, affected pathway, tumor type, and treatment information for the current patient record.

In one embodiment, the UI component is configured to transition from the similar patient view to a detailed view of outcome information for a group of patients based on selection of filter data presented in the similar patient view. In one embodiment, selection of the filter data includes specification of filter data for alteration, affected gene, affected pathway, tumor type, and treatment associated with a plurality of patients' cancers. In one embodiment, the detailed view of the outcome information is configured to display a respective outcome for each respective patient within the group of patients. In one embodiment, the UI component is configured to transition to a view of the respective patient's information based on selection of the respective patient display in the detailed view of the outcome information.

In one embodiment, the UI component is configured to accept specification of filter data for one or more of alteration, affected gene, affected pathway, tumor type, and treatment associated with a plurality of patients to display treatment and outcome information. In one embodiment, the UI component is configured to display a detailed view of treatment and outcome information for a patient population based on specifying filter data for alteration, affected gene, affected pathway, tumor type, and treatment.

In one embodiment, the system further comprises a storage component executed by the at least one processor configured to manage cancer treatment and outcome information according to a data model. In one embodiment, the data model comprises a data structure associated with patient records, and wherein the data structure includes data records for specification of alteration, affected gene, affected pathway, tumor type, and treatment.

According to one aspect, a computer implemented method for tracking and analysis of cancer treatment and outcome information is provided. The method comprises receiving, by a computer system, treatment and outcome information associated with a patient from at least one user, organizing, by the computer system, the treatment and the outcome information according to one or more of alteration, affected gene, affected pathway, tumor type, and treatment, generating, by the computer system, outcome summary information including course of treatment displays over time, and communicating, by the computer system, the outcome summary information to the at least one user.

According to one embodiment, the treatment information includes any one or more of drugs, therapeutics, named drugs, named therapeutics, drug cocktails, drug combinations, radiation, and surgery. According to one embodiment, the outcome information includes information regarding a status of a patient's cancer. According to one embodiment, the status of the patient's cancer includes one or more of complete response, partial response, stable disease, and progressive disease. According to one embodiment, the course of treatment includes information regarding how patient is responding to treatment.

According to one embodiment, the method further comprises identifying, by the computer system, similar patients based on information related to genomic alteration. According to one embodiment, the method further comprises identifying, by the computer system, similar patients based on information related to affected gene identified in a cancer. According to one embodiment, the method further comprises identifying, by the computer system, similar patients based on information related to treatment. According to one embodiment, the method further comprises identifying, by the computer system, similar patients based on related to tumor type. According to one embodiment, the method further comprises identifying, by the computer system, similar patients based on information relating to a combination of at least two or more of a group comprising alteration, affected gene, affected pathway, tumor type, and treatment. According to one embodiment, the method further comprises identifying, by the computer system, similar patients based on information related to at least one of alteration, affected gene, affected pathway, tumor type, and treatment for a patient's cancer, and aggregating, by the computer system, responsive information according to one or more of alteration, affected gene, affected pathway, tumor type, and treatment.

According to one embodiment, the method further comprises aggregating, by the computer system, similar patients within classes of alterations. According to one embodiment, the classes of alteration include alterations in a specified domain of a gene. According to one embodiment, the domain includes at least a kinase domain of the gene. According to one embodiment, the gene includes BRAF, and the specific domains include at least one of kinase, BRAF V600E, and BRAF V600K. According to one embodiment, the method further comprises aggregating, by the computer system, alteration information according to pathways affected by respective alterations. According to one embodiment, the method further comprises aggregating, by the computer system, similar patient information based on functional similarity of identified alterations, which can be determined for distinct mutations having functionally similar characteristics in the cancer cells.

According to one embodiment, the method further comprises communicating, by the computer system, an update request to the at least one user. According to one embodiment, the method further comprises determining, by the computer system, a scheduled period for a patient update has expired. According to one embodiment, communicating the update request includes communicating an estimated time to complete the update request. According to one embodiment, the method further comprises determining, by the computer system, a type of information required for a patient. According to one embodiment, the method further comprises determining, by the computer system, the type of information required is one of treatment and outcome information based on analysis of a patient record. According to one embodiment, the method further comprises generating, by the computer system, an update request according to the type of information required.

According to one embodiment, the method further comprises analyzing, by the computer system, the patient record to determine if treatment information has been input. According to one embodiment, the method further comprises determining, by the computer system, an estimated time to input information based on the update request and the type of information. According to one embodiment, the method further comprises comparing, by the computer system, a current patient record to existing treatment information. According to one embodiment, the existing treatment information includes at least one of alteration, affected gene, affected pathway, tumor type, and one or more treatments.

According to one embodiment, the method further comprises identifying, by the computer system, similar patients based on information in the current patient record, wherein identifying the similar patients includes determining a match between the current patient record and at least one of alteration, affected gene, affected pathway, tumor type, and treatment. According to one embodiment, the method further comprises identifying, by the computer system, similar patients based on user selection of at least one of tumor type, alteration, genes, and treatment. According to one embodiment, the method further comprises filtering, by the computer system, a grouping of similar patients based on additional specification of at least one of alteration, affected gene, affected pathway, tumor type, and treatment. According to one embodiment, the method further comprises providing, by the computer system, connection information associated with care providers for respective patients within a group of similar patients.

According to one embodiment, the method further comprises providing, by the computer system, contact information based on user selection of permission options. According to one embodiment, the method further comprises displaying, by the computer system, treatment and outcome information for a patient within a history timeline. According to one embodiment, the method further comprises navigating, by the computer system, within treatment and outcome information display in a user interface based on selection of alteration, affected gene, affected pathway, tumor type, and treatment. According to one embodiment, the method further comprises displaying, by the computer system, selection elements for one of more of alteration, affected gene, affected pathway, tumor type, and treatment. According to one embodiment, the selection elements are configured to cause the system to identify a subset of matching patient records according to specification of one or matching criteria with the selection elements. According to one embodiment, the method further comprises displaying, by the computer system, a general treatment display configured to group a plurality of matching patients according to a common treatment.

According to one embodiment, the method further comprises displaying, by the computer system, a similar patient view of a plurality of matching patients, wherein the similar patient view is configured to display groupings of patient records matching information in a current patient record. According to one embodiment, the method further comprises determining, by the computer system, the matching information based on one or more of an alteration, affected gene, affected pathway, tumor type, and treatment. According to one embodiment, the method further comprises displaying, by the computer system, filter options within the selection elements based on one or more of the alteration, affected gene, affected pathway, tumor type, and treatment information for the current patient record.

According to one embodiment, the method further comprises transitioning, by the computer system, from the similar patient view in a user interface to a detailed view of outcome information for a group of patients based on selection of filter data presented in the similar patient view. According to one embodiment, selection of the filter data includes specification of filter data for alteration, affected gene, affected pathway, tumor type, and treatment associated with a plurality of patients' cancers. According to one embodiment, the detailed view of the outcome information is configured to display a respective outcome for each respective patient within the group of patients. According to one embodiment, the method further comprises comprising transitioning, by the computer system, to a view of the respective patient's information based on selection of the respective patient display in the detailed view of the outcome information.

According to one embodiment, the method further comprises accepting, by the computer system, specification of filter data for one or more of alteration, affected gene, affected pathway, tumor type, and treatment associated with a plurality of patients to display treatment and outcome information. According to one embodiment, the method further comprises displaying, by the computer system, a detailed view of treatment and outcome information for a patient population based on specifying filter data for alteration, affected gene, affected pathway, tumor type, and treatment. According to one embodiment, the method further comprises managing, by the computer system, cancer treatment and outcome information according to a data model. According to one embodiment, the data model comprises a data structure associated with patient records, and wherein the data structure includes data records for specification of alteration, affected gene, affected pathway, tumor type, and treatment.

According to one aspect, a computer-readable medium having computer-readable signals stored thereon that define instructions that, as a result of being executed by a computer, instruct the computer to perform a method for tracking and analysis of cancer treatment and outcome information is provided. The method comprises receiving treatment and outcome information associated with a patient from at least one user, organizing the treatment and the outcome information according to one or more of alteration, affected gene, affected pathway, tumor type, and treatment, generating outcome summary information including course of treatment displays over time, and communicating the outcome summary information to the at least one user.

According to one embodiment, the treatment information includes any one or more of drugs, therapeutics, named drugs, named therapeutics, drug cocktails, drug combinations, radiation, and surgery. According to one embodiment, the outcome information includes information regarding a status of a patient's cancer. According to one embodiment, the status of the patient's cancer includes one or more of complete response, partial response, stable disease, and progressive disease. According to one embodiment, the course of treatment includes information regarding how patient is responding to treatment.

According to one embodiment, the method further comprises identifying similar patients based on information related to genomic alteration. According to one embodiment, the method further comprises identifying similar patients based on information related to affected gene identified in a cancer. According to one embodiment, the method further comprises identifying similar patients based on information related to treatment. According to one embodiment, the method further comprises identifying similar patients based on related to tumor type. According to one embodiment, the method further comprises identifying similar patients based on information relating to a combination of at least two or more of a group comprising alteration, affected gene, affected pathway, tumor type, and treatment. According to one embodiment, the method further comprises identifying similar patients based on information related to at least one of alteration, affected gene, affected pathway, tumor type, and treatment for a patient's cancer, and aggregating responsive information according to one or more of alteration, affected gene, affected pathway, tumor type, and treatment.

According to one embodiment, the method further comprises aggregating similar patients within classes of alterations. According to one embodiment, the classes of alteration include alterations in a specified domain of a gene. According to one embodiment, the domain includes at least a kinase domain of the gene. According to one embodiment, the gene includes BRAF, and the specific domains include at least one of kinase, BRAF V600E, and BRAF V600K. According to one embodiment, the method further comprises aggregating alteration information according to pathways affected by respective alterations. According to one embodiment, the method further comprises aggregating similar patient information based on functional similarity of identified alterations, which can be determined for distinct mutations having functionally similar characteristics in the cancer cells.

According to one embodiment, the method further comprises communicating an update request to the at least one user. According to one embodiment, the method further comprises determining a scheduled period for a patient update has expired. According to one embodiment, communicating the update request includes communicating an estimated time to complete the update request. According to one embodiment, the method further comprises determining a type of information required for a patient. According to one embodiment, the method further comprises determining the type of information required is one of treatment and outcome information based on analysis of a patient record. According to one embodiment, the method further comprises generating an update request according to the type of information required.

According to one embodiment, the method further comprises analyzing the patient record to determine if treatment information has been input. According to one embodiment, the method further comprises determining an estimated time to input information based on the update request and the type of information. According to one embodiment, the method further comprises comparing a current patient record to existing treatment information. According to one embodiment, the existing treatment information includes at least one of alteration, affected gene, affected pathway, tumor type, and one or more treatments.

According to one embodiment, the method further comprises identifying similar patients based on information in the current patient record, wherein identifying the similar patients includes determining a match between the current patient record and at least one of alteration, affected gene, affected pathway, tumor type, and treatment. According to one embodiment, the method further comprises identifying similar patients based on user selection of at least one of tumor type, alteration, genes, and treatment. According to one embodiment, the method further comprises filtering a grouping of similar patients based on additional specification of at least one of alteration, affected gene, affected pathway, tumor type, and treatment. According to one embodiment, the method further comprises providing connection information associated with care providers for respective patients within a group of similar patients.

According to one embodiment, the method further comprises providing contact information based on user selection of permission options.

According to one embodiment, the method further comprises displaying treatment and outcome information for a patient within a history timeline. According to one embodiment, the method further comprises navigating within treatment and outcome information display in a user interface based on selection of alteration, affected gene, affected pathway, tumor type, and treatment. According to one embodiment, the method further comprises displaying selection elements for one of more of alteration, affected gene, affected pathway, tumor type, and treatment. According to one embodiment, the selection elements are configured to cause the system to identify a subset of matching patient records according to specification of one or matching criteria with the selection elements. According to one embodiment, the method further comprises displaying a general treatment display configured to group a plurality of matching patients according to a common treatment.

According to one embodiment, the method further comprises displaying a similar patient view of a plurality of matching patients, wherein the similar patient view is configured to display groupings of patient records matching information in a current patient record. According to one embodiment, the method further comprises determining the matching information based on one or more of an alteration, affected gene, affected pathway, tumor type, and treatment. According to one embodiment, the method further comprises displaying filter options within the selection elements based on one or more of the alteration, affected gene, affected pathway, tumor type, and treatment information for the current patient record.

According to one embodiment, the method further comprises transitioning from the similar patient view in a user interface to a detailed view of outcome information for a group of patients based on selection of filter data presented in the similar patient view. According to one embodiment, selection of the filter data includes specification of filter data for alteration, affected gene, affected pathway, tumor type, and treatment associated with a plurality of patients' cancers. According to one embodiment, the detailed view of the outcome information is configured to display a respective outcome for each respective patient within the group of patients. According to one embodiment, the method further comprises comprising transitioning to a view of the respective patient's information based on selection of the respective patient display in the detailed view of the outcome information.

According to one embodiment, the method further comprises accepting specification of filter data for one or more of alteration, affected gene, affected pathway, tumor type, and treatment associated with a plurality of patients to display treatment and outcome information. According to one embodiment, the method further comprises displaying a detailed view of treatment and outcome information for a patient population based on specifying filter data for alteration, affected gene, affected pathway, tumor type, and treatment. According to one embodiment, the method further comprises managing cancer treatment and outcome information according to a data model. According to one embodiment, the data model comprises a data structure associated with patient records, and wherein the data structure includes data records for specification of alteration, affected gene, affected pathway, tumor type, and treatment.

Still other aspects, embodiments, and advantages of these exemplary aspects and embodiments, are discussed in detail below. Any embodiment disclosed herein may be combined with any other embodiment in any manner consistent with at least one of the objects, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment. The accompanying drawings are included to provide illustration and a further understanding of the various aspects and embodiments, and are incorporated in and constitute a part of this specification. The drawings, together with the remainder of the specification, serve to explain principles and operations of the described and claimed aspects and embodiments.

BRIEF DESCRIPTION OF THE DRAWINGS

Various aspects of at least one embodiment are discussed below with reference to the accompanying figures, which are not intended to be drawn to scale. Where technical features in the figures, detailed description or any claim are followed by reference signs, the reference signs have been included for the sole purpose of increasing the intelligibility of the figures, detailed description, and claims. Accordingly, neither the reference signs nor their absence, are intended to have any limiting effect on the scope of any claim elements. In the figures, each identical or nearly identical component that is illustrated in various figures is represented by a like numeral. For purposes of clarity, not every component may be labeled in every figure. The figures are provided for the purposes of illustration and explanation and are not intended as a definition of the limits of the invention. In the figures:

FIGS. 7A-K are example user interface screen captures, according to one embodiment;

FIGS. 8A-8B are an example user interface screen captures, according to one embodiment;

FIGS. 8C-8F are example user interface screen captures, according to one embodiment;

FIGS. 9A-9B and 9P illustrate an example of a static genomic alteration report, according to one embodiment;

FIGS. 9C-9O illustrate an example of a static genomic alteration report, according to one embodiment;

FIG. 19 is an example user interface, according to one embodiment;

FIG. 21 is an example user interface, according to one embodiment;

FIG. 22 is an example user interface, according to one embodiment;

FIG. 23 is an example user interface, according to one embodiment;

FIG. 25 is an example user interface, according to one embodiment;

FIG. 28 is an example user interface, according to one embodiment;

FIG. 29 is a screen capture of an example interface including displays for similar patients, according to one embodiment;

FIG. 33 illustrates an example trial summary page, according to one embodiment;

FIG. 34 illustrates an example reference summary view, according to one embodiment;

FIG. 35 illustrates an example user interface for defining system alert preferences, according to one embodiment;

FIG. 36 illustrates an example user interface for defining alerts, according to one embodiment;

FIG. 38A-D illustrate example content items, according to one embodiment;

FIG. 39 illustrates an example page accessible via as part of a genomic report, according to one embodiment;

FIG. 40A-C illustrate information in example views shown in an unexpanded or collapsed state, according to one embodiment;

FIG. 41A-B illustrate information in example views shown in an expanded state, according to one embodiment;

FIGS. 42A-B illustrate example update indicators, according to one embodiment;

FIG. 43 illustrates example alert indicators, according to one embodiment;

FIG. 45 illustrates an example test report view including information in a collapsed state;

FIG. 46A-B illustrate an example test report view including information in an expanded state;

FIG. 50A-C illustrate an example knowledge base page, according to one embodiment;

FIG. 51A-C illustrate an example trial index page, according to one embodiment;

FIG. 52A-C illustrates an example patient case study, according to one embodiment; and FIG. 53A-C shows an example user profile page, according to one embodiment.

DETAILED DESCRIPTION

Figure 1:
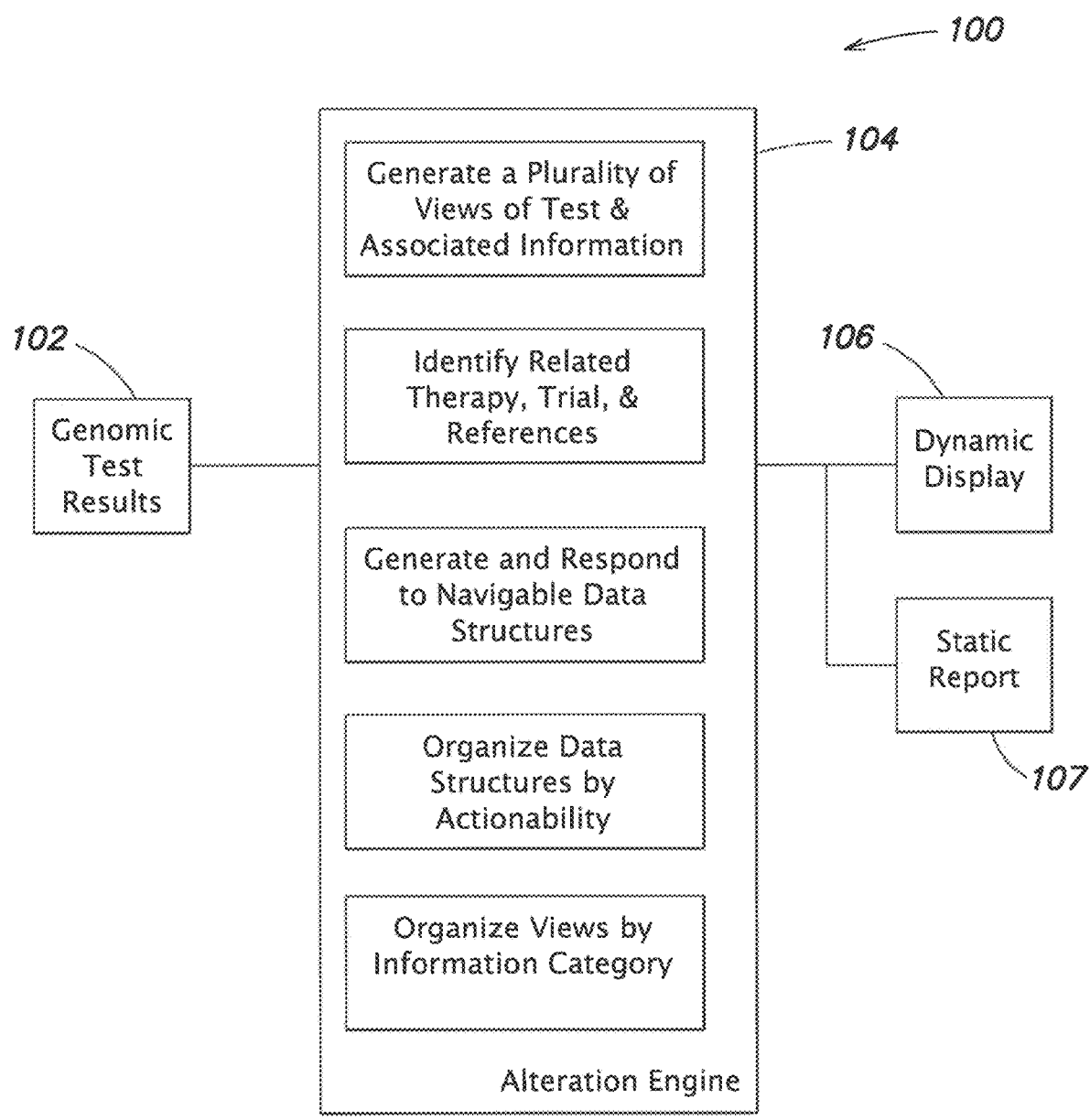
FIG. 1 is a diagram of a system for managing genomic testing information using an alteration engine, according to one embodiment.

As described above, conventional knowledge bases (e.g., ClinicalTrials.gov) are insufficient to capture large portions of treatment and outcome information from physicians and their patients. Further, conventional aggregations of treatment and outcome information fail to provide actionable and/or usable data in a manner that would allow a physician to assimilate that information into their daily practice and treatment decision making in a timely manner.

According to one embodiment, an outcome system is provided that includes an outcome engine configured to generate requests for physicians to provide treatment and outcome information specific to their patients. The outcome engine generates a user interface presented to the physician for inputting treatment and outcome information such that the time required for a physician to input data is minimized (e.g., using intuitive user interfaces). In one embodiment, the outcome engine is configured to categorize complex treatment and outcome information into simple visual selections that convey valuable information to physicians for use in treatment decision-making. According to another embodiment, treatment and outcome information is focused on cancer therapies and can be organized based on genomic alteration, tumor type, and therapy being applied. Various embodiments can facilitate user entry and display of patient outcome information within the organizations of genomic alteration, tumor type, and therapy.

Further embodiments can incorporate genomic testing information on a patient's cancer to develop actionable information. In one example, testing performed on patient cancer tissue can be included as part of a patient. In further examples, information on the tumor type, genomic alterations found, candidate treatment options, etc., can be used to match a current patient to other treatment and outcome information on the system.

Responsive to treatment and outcome information input, the outcome engine can be configured to generate outcome information for one or more patients carrying a particular genomic alteration, carrying alterations to genes implicated in a particular pathway, having a particular tumor type, or having received a particular therapy, as a function of time (e.g., within a timeline display). In one embodiment, such interfaces can be presented immediately in response to user input. According to some embodiments, the timeline displays visually summarize course of treatment data from patients sharing given characteristics in an intuitive format configured to provide actionable or advisory information for treatment decision making. In one embodiment, outcome data is normalized in one or more categories that may be easily interpreted by a physician or other user.

In some embodiments, the outcome engine facilitates data navigation by the user. For example, the outcome engine can identify and provide navigation options to information on similar patients (e.g., using genomic alteration, treatment, and/or tumor information to match related and/or similar information). The patient information can be correlated by the engine within treatment and outcomes to enable the system to convey valuable information on populations of similar patients, their treatments, and their outcomes.

Figure 10:
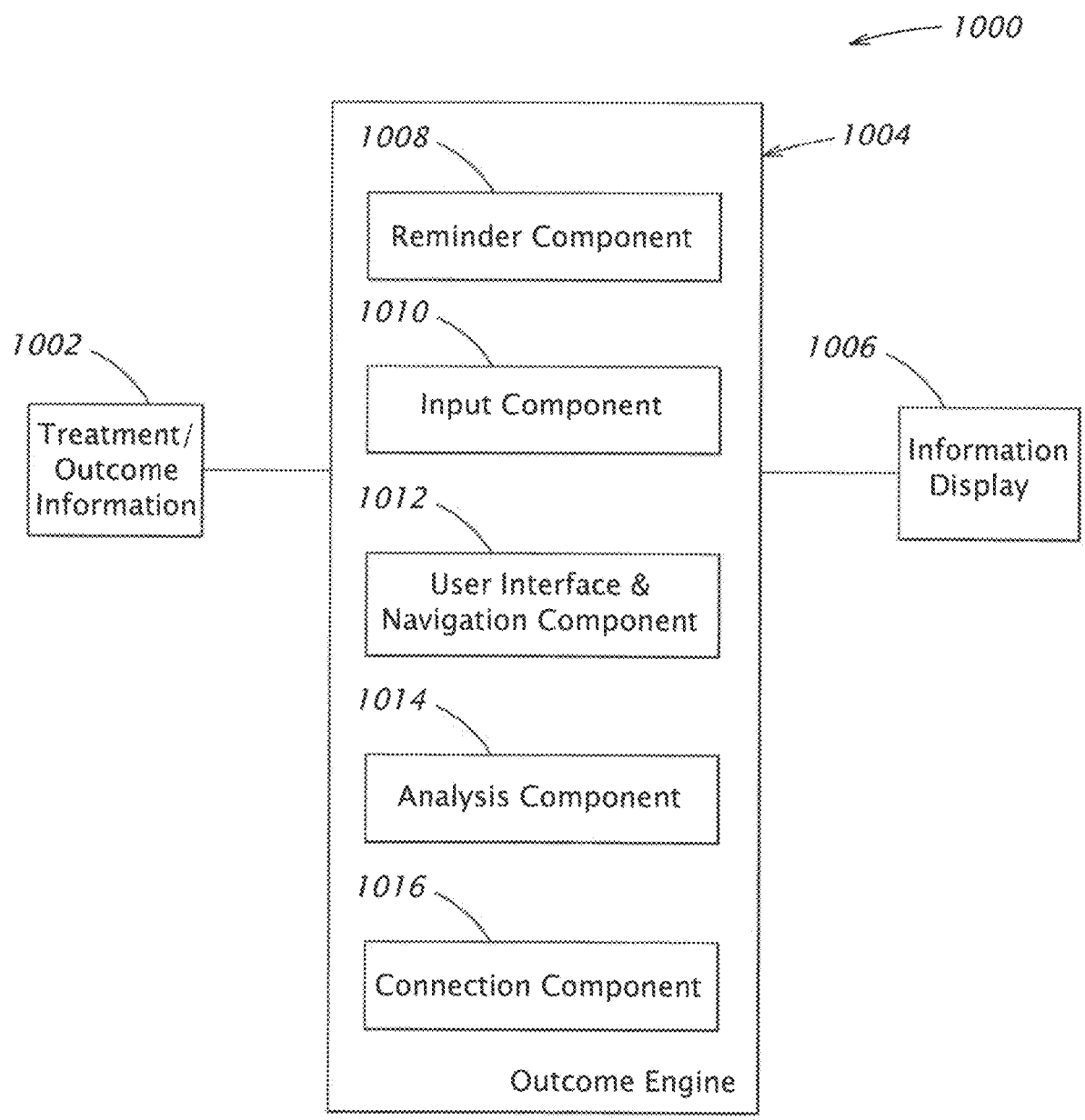
FIG. 10 is a diagram of a system for capturing and processing treatment and outcome information using an outcome engine.

Referring to FIG. 10, there is illustrated one example of a system 1000 for processing treatment and outcome information using an outcome engine 1004. Elements of the system 1000 can be provided using a computing system such as the computer system 1400 and/or 1402 described with reference to FIG. 14. For example, the outcome engine 1004 can be executed on the computer system 1400 and/or 1402 to provide the functions and operations discussed herein. In other embodiments, the outcome engine 1004 can include additional components executed on the computer system to perform specific operations.

As shown in FIG. 10, various embodiments of the outcome engine 1004 are configured to receive input from a remote system operated by a user. For example, the user can access the system 1000 to input treatment and outcome information 1002 (e.g., treatment and outcome information specific to the user's patients). Responsive to entry of the treatment and outcome information 1002, the outcome engine 1004 can be configured to generate and display diagnostic information to the user at 1006. For example, treatment and outcome information can be displayed based on query criteria (e.g., alteration, affected gene or pathway, tumor type, treatment) as an information display 1006, as soon as the treatment and outcome information is saved on system 1000. In some examples, the information display 1006 is designed to facilitate treatment for a given patient by providing treatment and outcome information for patients with similar characteristics (e.g., genomic alterations, alterations to given gene(s) or pathway(s), tumor types, etc.). In one embodiment, patients having similar characteristics can also be identified based on alterations in a level of expression of a gene and/or associated protein. In one example, testing can identify alterations in expression through analysis of suitable vectors for determining expression. Various embodiments are configured to enable a user to review any characteristics available (e.g., genomic alterations, alterations to given gene(s) or pathway(s), tumor types, expression level, etc.) to facilitate treatment.

Figure 23:
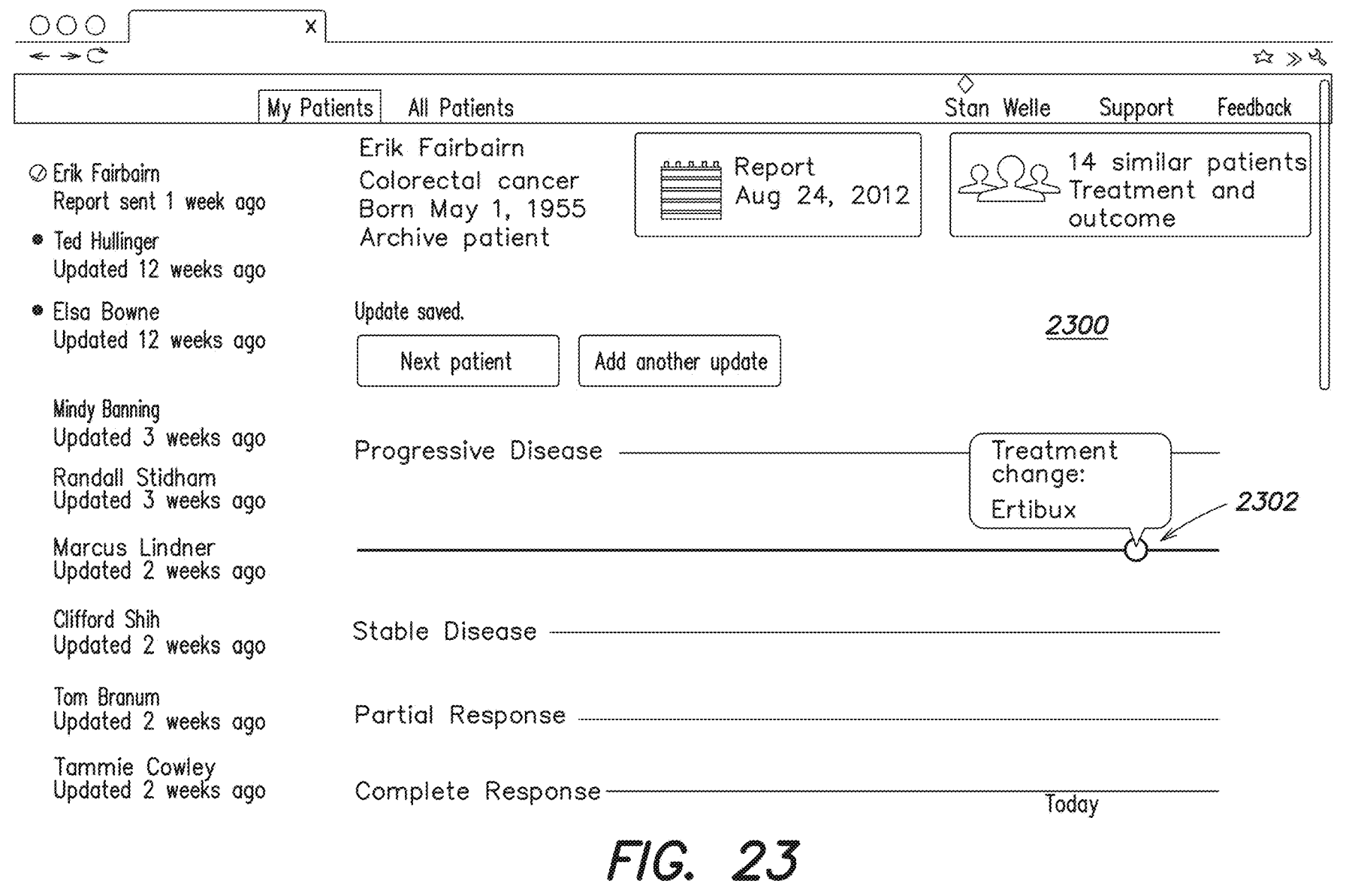
Figure 24:
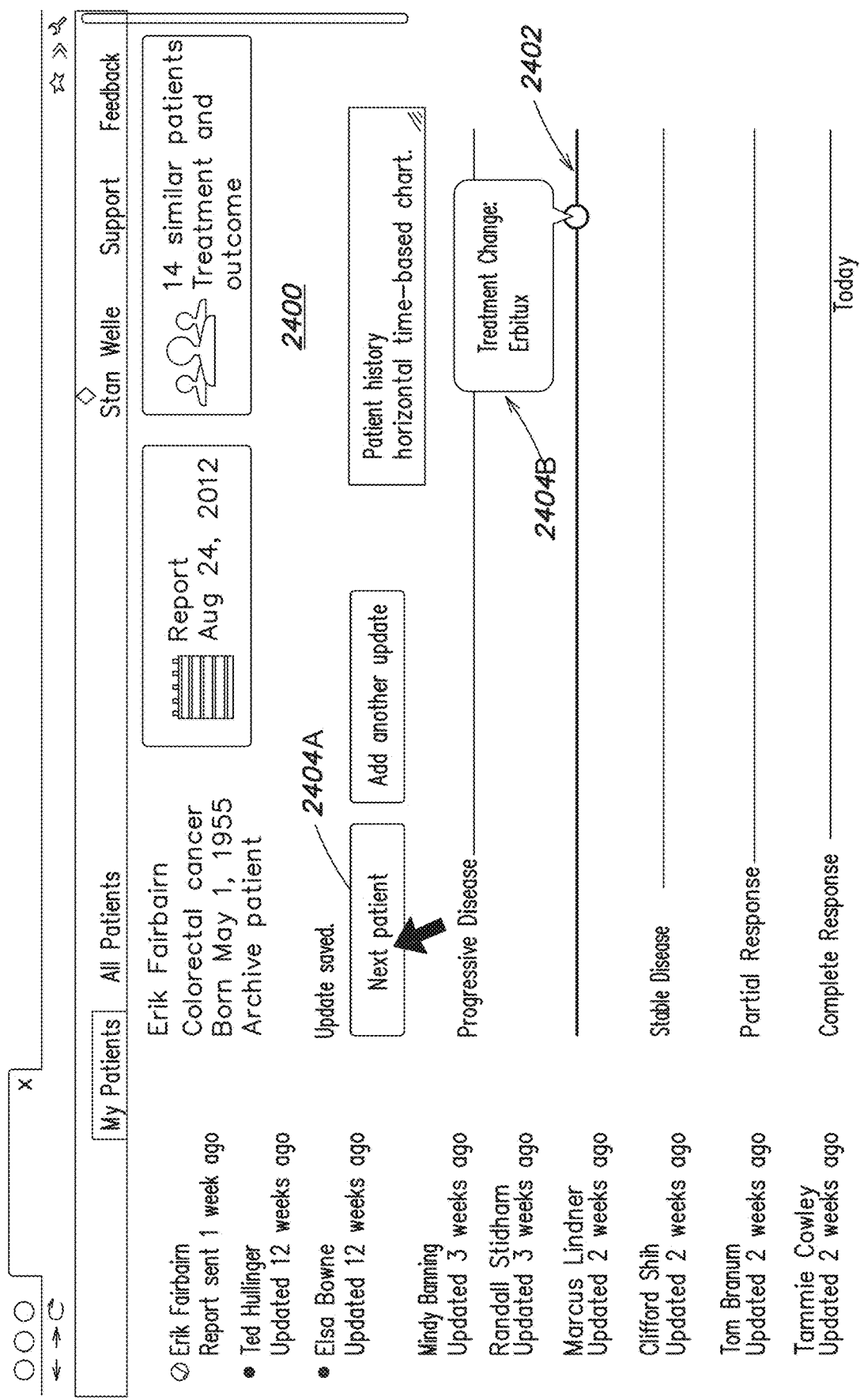
FIG. 24 is a user selection within an example user interface to transition to a next patient from a timeline display, according to one embodiment.
Figure 26:
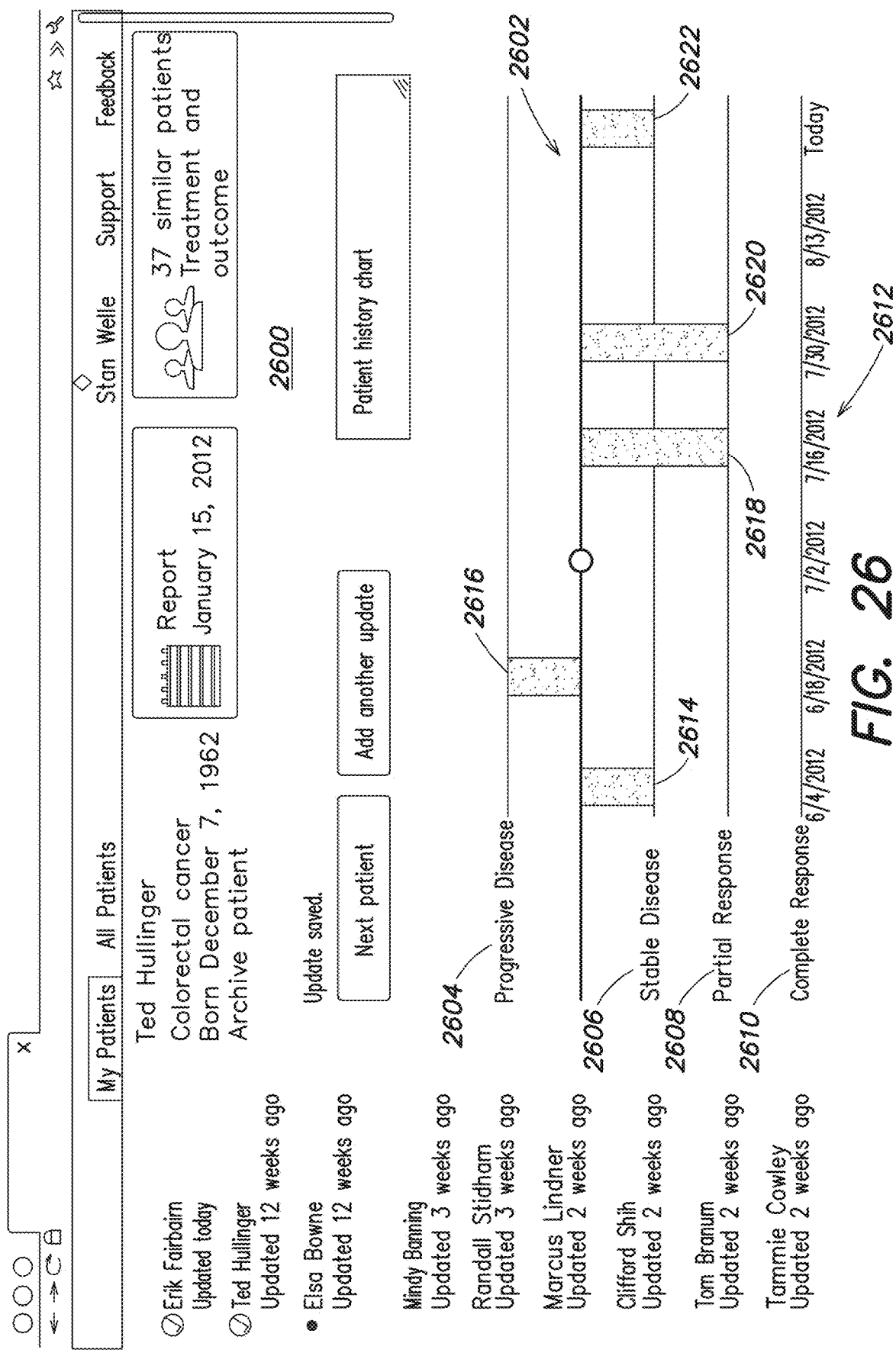
FIG. 26 is an example user interface, according to one embodiment.
Figure 27:
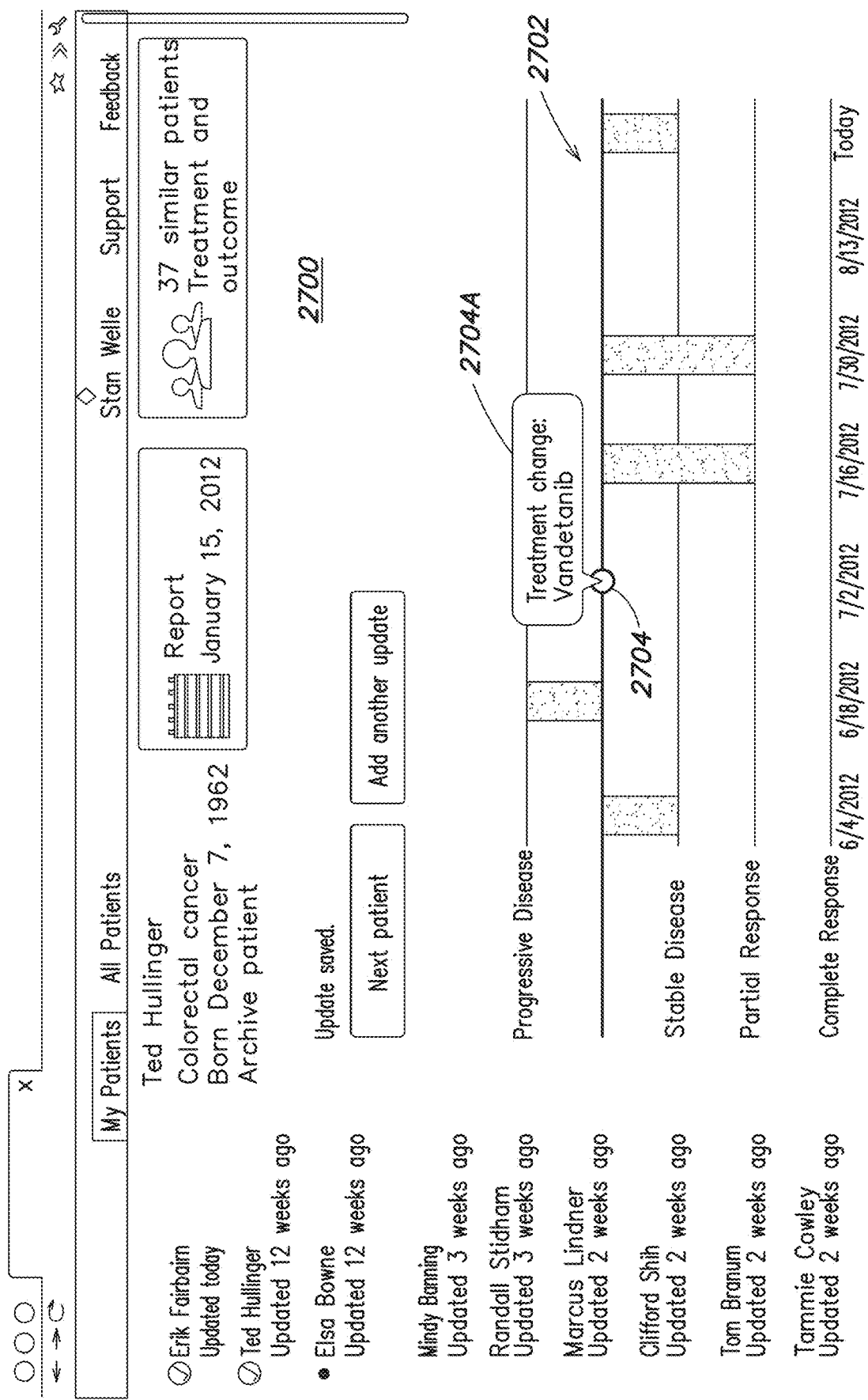
FIG. 27 is an example user interface displaying additional detail, according to one embodiment.

For example, the information display 1006 is generated such that the user (e.g., a physician) can understand and interpret the information readily from the display (e.g., see patient history timelines shown in FIG. 23, FIG. 24 and FIG. 26). In a cancer treatment setting, various ones of the displays can be organized based on a tumor type identified for the patient and a genomic alteration associated with the patient (e.g., see FIG. 30 and FIG. 31 discussed in greater detail below). Additional information regarding treatment can also be provided where available.

According to one embodiment, the outcome engine 1004 facilitates collection and analysis of the treatment and outcome information by simplifying the input of sophisticated and extensive treatment and outcome information. For example, the outcome engine 1004 can include an input component 1100 configured to organize data being entered into tumor type (if not already known), genomic alteration (if not already known), and treatment options. In some embodiments, an affected gene or genes can also be specified in the patient record. The input component can be configured to allow the user to enter specific information within any of the preceding options and narrow the data entry based on any known information (e.g., genomic alteration, affected gene or pathway, tumor type, expression etc.). Once input, the combined information can be used by the system 1000 and/or outcome engine 1004 to provide information on outcomes associated with patients within any one or more tumor type, genomic alteration, and treatment.

Further, the input component 1010 can be configured to present treatment information based on system categorizations. In the cancer treatment setting, the outcome engine 1004 accepts treatment information by presenting treatment categories defined by the input component 1010 for selection by the user. In one example, a user interface can be generated by the system 1000 and displayed on a respective computer system of the user (e.g., example user interface displays are shown in FIGS. 15-31). Further, the outcome engine 1004 can include a user interface ("UI") component 1012 configured to generate user interfaces displayed by the system. The UI component 1012 accesses categories defined on the system, for example, by the input component 1010 and generate user interface displays to accept input treatment and/or outcome information accordingly.

In the cancer treatment example, the displayed categories for treatment can include therapeutic agent or regimen, radiation, and/or surgery, among other options. As discussed, the organization on tumor type, alteration, and therapy facilitates ease and speed of data access. For example, using categorizations of therapy and outcome information, within one or two clicks of a mouse, cancer treatment information can be submitted to the system for a specific patient (e.g., surgery—2 clicks (click "add treatment," click "surgery," radiation—2 clicks, click "add treatment," click "radiation" as shown in FIG. 19). Example user interface displays are shown in FIG. 15-31, which include displays and functionality for entering treatment information. In further examples, the system 1000 can be configured to default to adding treatment information upon accessing a patient record without treatment data reducing the number of clicks for selecting a treatment (e.g., surgery or radiation) to 1 click each.

Figure 18:
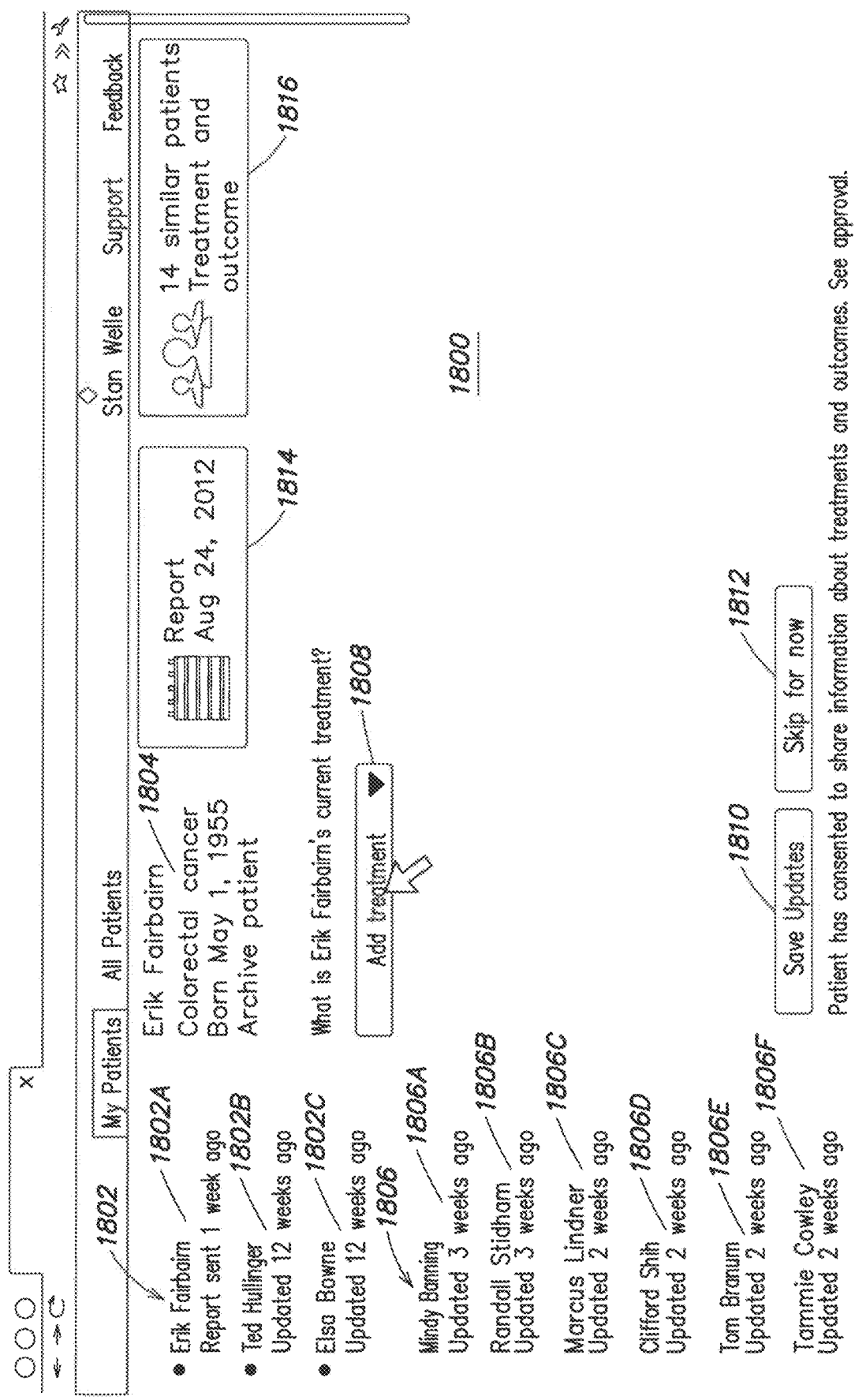
FIG. 18 is an example user interface, according to one embodiment.

FIG. 18 shows a user interface 1800 for inputting treatment information. At 1804, a currently selected patient's information is displayed. At 1802, a user can navigate between displayed patients including patients listed at 1802A-C. At 1806, a recently updated menu can be displayed to provide access to recently updated patient information (e.g., at 1806A-F). For the currently selected patient "Erik Fairbairn," the user provided options to add treatment information associated with the current patient, for example, at 1808. In one embodiment, treatment information can be added by selecting a drop down menu 1808. Once treatment information has been defined, the input information can be saved, by selecting 1810. If the user does not wish to add treatment information, the user can select "skip for now" at 1812.

In one embodiment, the patient treatment user interface 1800 can provide access to any genomic testing reports associated with the selected patient. For example, the user can select display 1814 to access genomic reports for the patient (discussed in greater detail herein). Additionally, similar patients can also be accessed through displays on page 1800, at 1816. For example, the system can identify similar patients based on matches between any one or more of: genomic alterations, affected genes or pathways, treatments, and/or tumor types. The system identified similar patients can then be accessed by selecting display 1816. In some embodiments, the system can be configured to dynamically identify similar patients to a current patient record. In one example, responsive to entry of new treatment information, system determined similar patients can be updated. For example, if new treatment information is entered at 1808, display 1816 can change according to new matches against, for example, specified treatment information.

FIG. 19 is an example user interface 1900. Interface 1900 includes a drop down menu at 1902 for selecting from types of treatment for a patient. At 1902, a user has selected "Add treatment," and the user may select from pre-defined options at 1904—therapeutic agent or regimen, 1906—radiation, and 1908—surgery. Once a particular treatment option has been entered, that treatment can be saved by the system.

Figure 20:
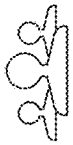
FIG. 20 is an example user interface, according to one embodiment.

For therapeutic agent or regimen as a treatment option, the outcome engine 1004 and/or input component 1010 can also be configured to accept text input to specify a particular agent or regimen (e.g., as shown in FIG. 20 at 2002 and FIG. 21 at 2102). In some embodiments, the outcome engine 1004 can be configured to present a search interface for identifying a therapeutic agent or regimen. Optionally, the outcome engine provides a user interface element through the UI component 1012 for accepting search criteria.

FIG. 20 illustrates an example user interface 2000. Interface 2000 displays options for entering specific treatment information at 2002. Responsive to selecting therapeutic agent or regimen (e.g., at 1904 of FIG. 19), the user interface can display a text input box at 2002. The text input box allows users to search agents and regimens to facilitate user selection. At 2006, the user interface provides options for entering a start date associated with the treatment. At 2008, the user interface can also provide options for entering additional detail regarding the treatment. For example, at

2008 the user can specify that the treatment information being entered is part of a clinical trial. The clinical trial indicator can be used to match similar patients, identify and/or link to the clinical trial, etc. Interface 2000 can also be configured to accept multiple treatment options. For example, selection of 2010 enables entry of multiple treatments, and even multiple treatments of the same kind.

FIG. 21 is an example user interface 2100. Interface 2100 illustrates search functionality provided as part of entering treatment information. At 2102, a text search box displays potential matches to the user responsive to their input. For example, "Er" entered at 2104 is matched by the system to candidate treatments "Erbitux" at 2106, "Erlotinib" at 2108, and "*Erwinia* L-asparaginese" at 2110. The user can select from displayed options or finish typing in treatment information. Additionally, the user may delete a treatment responsive to selecting 2112 "Delete treatment." FIG. 22 shows an example user interface where the user has selected or input a specific treatment ("Erbitux" at 2202). Once any treatment information is input, the user can save that information. For example, treatment information can be saved responsive to selection of 2204. According to one embodiment, the user can enter a variety of treatment information prior to saving the data entered for that patient.

In another embodiment, the outcome engine 1004 and/or UI component 1012 can also be configured to accept date information associated with a given treatment. In some embodiments, the date information is optional, as the outcome engine 1004 is configured to use a current date absent other specification by the user. Other additional data fields can be provided. In one example, the user can specify if a treatment is being administered as part of a clinical trial. The outcome engine 1004 can be configured to use the clinical trial flag to capture additional information and/or generate navigable user interface displays to direct a user to associated clinical trial information.

Once the treatment information has been defined on the system, the outcome engine 1004 and/or UI component 1012 can be configured to generate and display a patient history timeline (e.g., FIG. 23 at 2302, FIG. 24 at 2402, and FIG. 26 at 2602). In one embodiment, the patient history timeline presents treatment and outcome in a visual summary display. The visual summary display can be configured based on system defined categories for outcomes. According to some embodiments, users can readily appreciate a course of a patient's treatment based on the displayed treatment and the temporal display of that treatment's outcome over time. Additionally, the user can readily gain insight into the effect a change in treatment may yield in a similar situation.

FIG. 26 shows four categories describing outcome information: 2604 progressive disease, 2606 stable disease, 2608 partial response, and 2610 complete response are shown with respect to a period of time shown at horizontal display bar 2612. Outcome information can be displayed graphically as vertical bars reaching the outcome category for a respective time (e.g., at 2614-2622). The categories can be configured to simplify data capture and/or entry by a user (e.g., a physician), similar to categorization of treatments. If no outcome information is available or outcome information has not been input, the patient history chart is configured to display the input treatment information as a start point on a timeline display without outcome information (e.g., 2402, FIG. 24).

FIG. 23 illustrates one example of a timeline display 2300. Timeline display 2300 can be organized as a horizontal time-based chart of patient history. If the treatment information is the only information entered the timeline display can illustrate the new information as a treatment change at 2302. FIG. 24 shows a user selection to transition to a next patient from a timeline display. As shown, the current patient's treatment information is displayed as a treatment change 2404 on timeline 2402. By selecting 2404, the user can quickly transition to another patient, for example, to add and/or update treatment information.

Upon selection of next patient, user interface 2500 of FIG. 25 can be displayed. The next patient displayed can reflect a list of patients identified by the system needing updates (e.g., shown at 2502). Current treatment information for a selected patient can be displayed at 2503. The user can update information on that treatment at 2504. For example, the user can select any one of 2506-2512, and save that information by selecting 2514. Upon saving the treatment information, the user interface can transition to a timeline display, for example, 2600 of FIG. 26.

If a prior date is supplied with the input treatment information the outcome engine 1004 can also be configured to request outcome information associated with the prior treatment. For example, the outcome engine 1004 can be configured to display the input treatment information (e.g., any specific agent or regimen), and display outcome categories or classifications (e.g., progressive disease, stable disease, partial response, and complete response) for user selection. Optionally, the outcome engine can also accept date information that can be associated with an input outcome. In some examples, the system and/or outcome engine can display radio buttons associated with each outcome category for selection in a user interface. In further examples, users can also select date information based system specified time periods (weekly, bi-weekly, monthly, etc.), for example, as radio buttons displayed in the user interface.

In some examples, user interface displays can be responsive to selection to provide further detail entered by the user, in summary views. For example, user interface 2700 of FIG. 27 can provide additional detail on a display item shown on a timeline 2702. At 2704, a treatment change icon is shown. Responsive to selection a dialogue box may be displayed to provide additional detail associated with the point on the timeline display.

According to one embodiment, outcome information is provided as an update to existing patient records. For example, the outcome engine 1004 can include a reminder component 1008 configured to deliver a request to a physician to update a patient record by inputting treatment information. The reminder component 1008 can be configured to deliver the update request via e-mail, text, etc. In some embodiments, the reminder component can be configured to estimate a length of time required by the user to submit requested information. In one example, the estimated time can be specified in an update request (e.g., FIG. 16).

Figure 15:
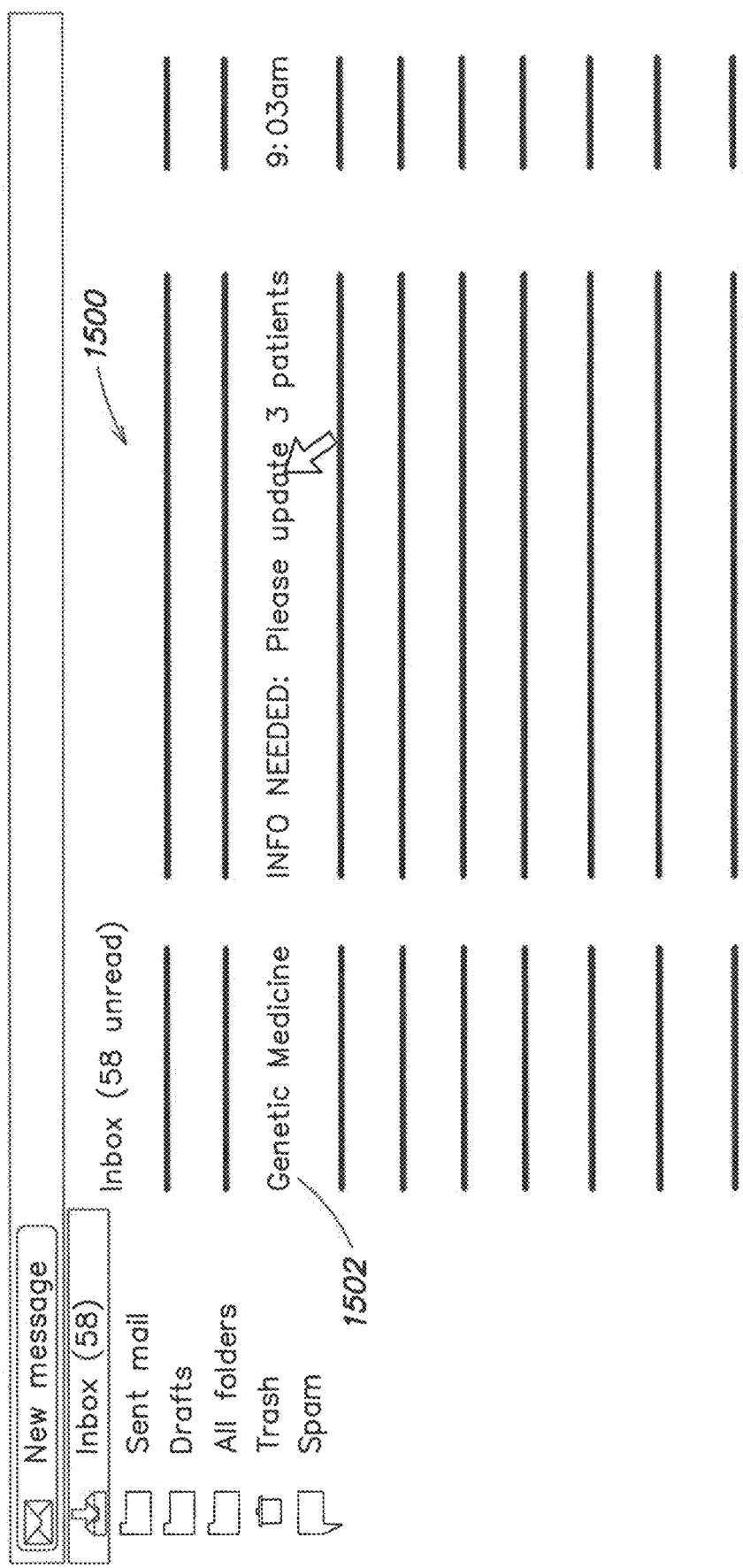
FIG. 15 is a screen capture of an update request message, according to one embodiment.
Figure 16:
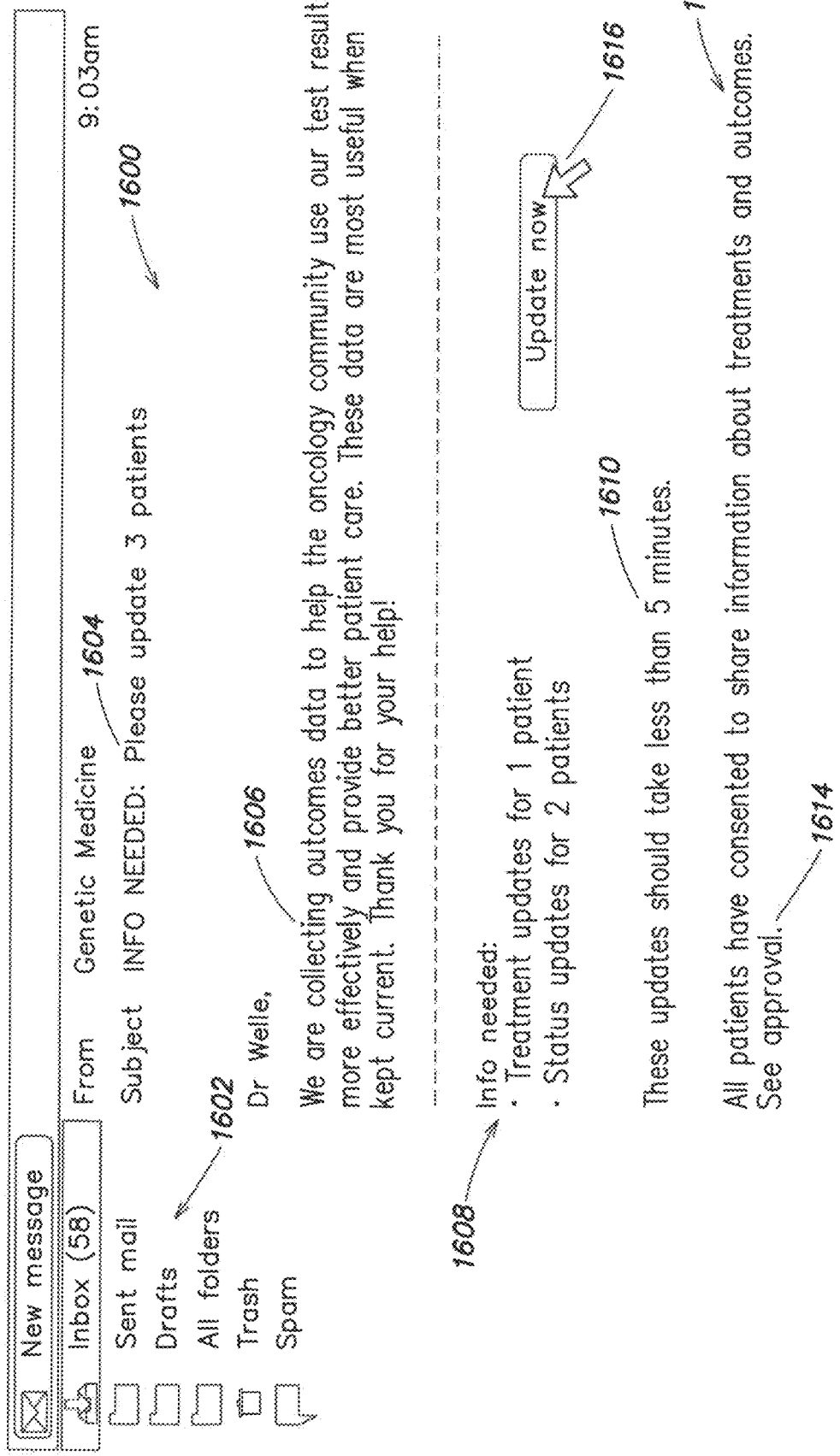
FIG. 16 is a screen capture of an electronic message, according to one embodiment.

FIG. 15 is a screen capture 1500 of an update request message 1502 communicated by the outcome system. FIG. 16 is a screen capture 1600 of an electronic message (e.g., e-mail) to a user of the outcome system. Various messaging functions can be provided by the e-mail service to which the user subscribes. For example, conventional e-mail menus are shown at 1602. Messaging window 1604 provides access to the update request sent to the user. The update request sent by the system can specify what updates are requested "Please update 3 patients," as well as an invitation message regarding participation in the outcome community at 1606.

Figure 17:
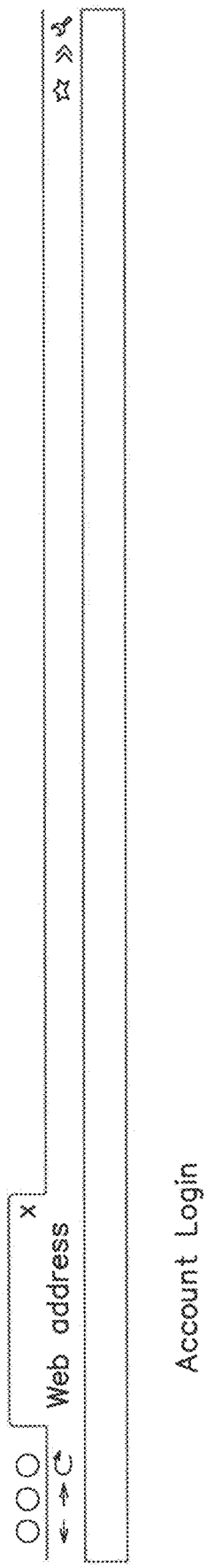
FIG. 17 is an example account login page, according to one embodiment.

In one embodiment, based on analysis of the user's account and patient information, the system identifies what information should be updated. For example, the system can determine that treatment information is needed for 1 patient, and status updates needed for 2 of the user's patients (e.g., at 1608). In some examples, the system estimates an amount of time to complete the update request (e.g., at 1610). In further embodiments, the system can provide information on the user's patients, and in particular, the message can include information regarding patient consent status relating to sharing treatment and outcome information (e.g., at 1612). The message can also include links to information sharing authorizations at 1614. At 1616, the user can select a link to access the outcome system and update information. If the user has not logged into the outcome system, selection of "update now" at 1616 can bring the user to a login window. FIG. 17 shows an example account login page.

In some embodiments, the user can identify one or more preferred methods of contact when registering for a user account. In other embodiments, the user can also specify an order for contact methodologies, where subsequent contact methods are only used if no response is received to prior update requests. The reminder component 1008 can be configured to request updated patient information on a periodic basis, according to schedule, among other options. The update request can include links that direct the user to specific patient records to update on system 1000 (e.g., as shown in FIGS. 15-16). For example, the update request can specify a request for updates regarding treatment being undertaken by the patient.

Once the user accesses a patient record to provide updated information, the outcome engine 1004 can be configured to automatically associate any treatment input with a current date (i.e., the date and/or time the outcome information is input into the system). Further, the system can also be configured to associate the current date to an outcome when entered as an update to an existing patient record.

Figure 28:
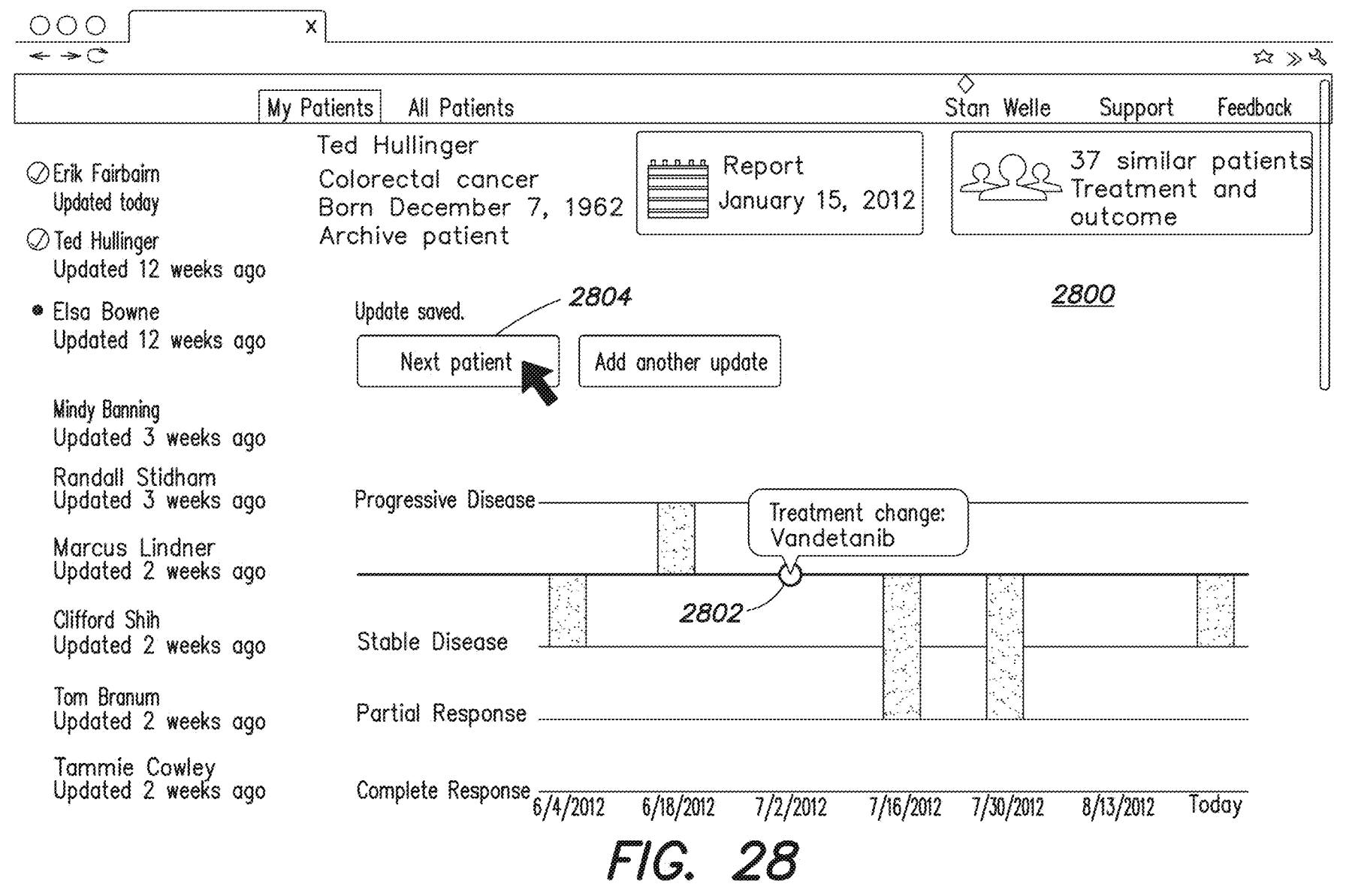

Once treatment and/or outcome information is entered on the system, the UI component 1004 can be configured to generate and display a patient history timeline including any outcome information provided for the patient (e.g., FIGS. 26-29). According to one embodiment, the patient history timeline displays outcome categories on a y-axis and time information on the x-axis. Treatment changes (e.g., start of regimen, new regimen, change in regimen, etc.) are displayed on the timeline, for example, as milestones. In some examples, the outcome associated with each date can be displayed as a vertical bar reaching the point on the y-axis reflective of an outcome category. In some embodiments, a treatment milestone is shown on the history timeline as a visual indicator (e.g., circle, star, flag, etc.) to illustrate the start or the change in treatment being provided. The outcome engine 1004 can be configured to provide additional information on the treatment, for example, in response to hovering pointer on the visual indicator or by clicking on the visual indicator. FIG. 28 shows an example user interface 2800 having an example indicator 2802. Responsive to selection of "Next patient" at 2804, a user may navigate to further timeline displays associated with different patients.

According to another aspect, the outcome engine 1004 can also be configured to integrate with genomic testing services to facilitate cancer diagnosis and treatment. In one setting, a physician can request a genomic test for a patient to determine any genomic alteration that exists in the patient's cancer cells. The information obtained from the genomic testing service can be used to define patient records accessible by the outcome engine 1004. Alternatively, the outcome engine can provide a platform on which to request genomic testing services for a patient. In some embodiments, the outcome engine 1004 can accept electronic or paper based genomic testing information, and associate any such testing information with a patient record. In one embodiment, the outcome engine 1004 can process genomic test information to define a patient record and associate the patient record with the genomic test results.

For users overseeing treatment of large numbers of patients, the outcome engine 1004 can be configured to provide a display of the patients associated with the user as options selectable in a user interface. In one example, a list of patients is displayed vertically along the left edge of a display screen (e.g., FIG. 18 at 1802). Each display of a patient name is selectable to navigate to additional information on the patient (e.g., at 1802A-C). Once a patient is selected for review, the outcome engine 1004 displays any history information for that patient as a patient history timeline in a portion of the user interface display. The user interface display can include a visual indicator associated with any genomic test results for that patient. The test result indicator can be selected in the user interface to provide additional detail on genomic test results.

Figure 29:
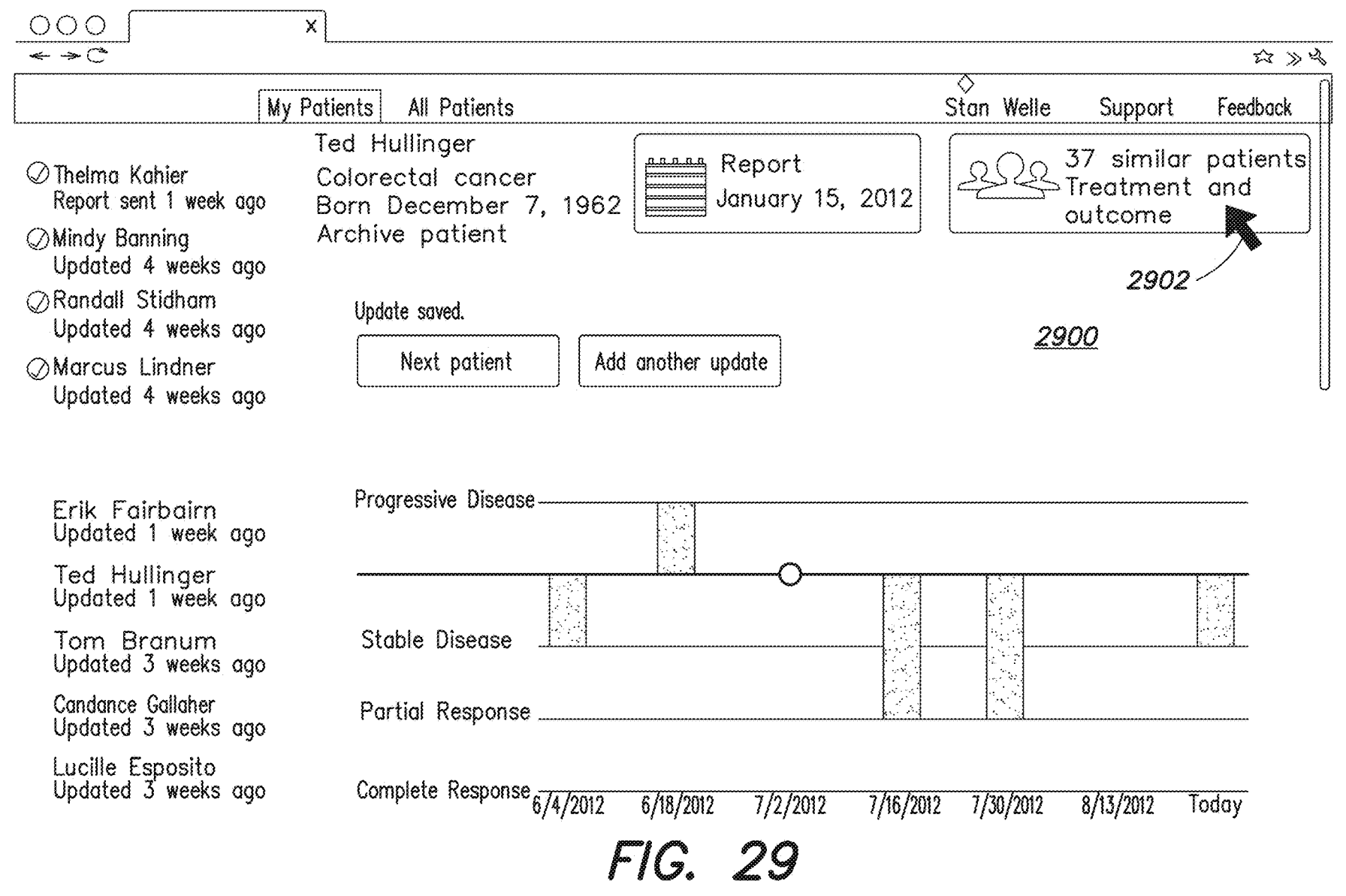

In further embodiments, the outcome engine 1004 can identify and provide navigation options for transitioning to patient who share or have diagnostic information in common with the user's patient (e.g., FIG. 29 "37 similar patients" at 2902). According to one embodiment, the outcome engine 1004 can include an analysis component 1014 configured to identify patients similar to a current patient based on common genomic alterations, affected genes or pathways, disease characteristics, ailment characteristics, treatment characteristics, etc. The analysis component 1014 can be configured to analyze all patient information available on system 1000 to determine matching characteristics, and to provide the information the UI component 1012 for display to the user. In the cancer setting, similar patients can be identified based on matches between any one or more of: genomic alterations, affected genes or pathways, treatments, and/or tumor types.

Any identified similar patients can be made accessible by the UI component 1012 through a selectable visual display (e.g., 2902 of FIG. 29). For example, a patient information screen can also include a visual indicator for any similar patients identified by the system. FIG. 29 is a screen capture of an example interface 2900. Interface 2900 includes a display for "similar patients" 2902 identified by the system. Selection of the similar patients display can transition the system to treatment information summary displays associated with the similar patients (e.g., shown in FIG. 30).

As discussed, similar patients can be dynamically determined by the outcome engine 1004 and/or analysis component 1014. The UI component 1012 can generate a visual indicator for the similar patients, which can also include information on a number of matches identified. Thus, a determination of similar patients and/or number of matching patients can be dynamically determined and updated any time the user inputs additional information regarding treatment and/or outcome.

According to one embodiment, the similar patients indicator is selectable to provide additional detail on similar patient populations. In one example, the UI component 1012 is configured to transition the user interface to a similar patient display in response to selection of the similar patient indicator (e.g., shown in FIGS. 29-30). The similar patient display can provide additional detail on the similar patient population identified by the outcome engine 1004 and/or analysis component 1014.

Figure 30:
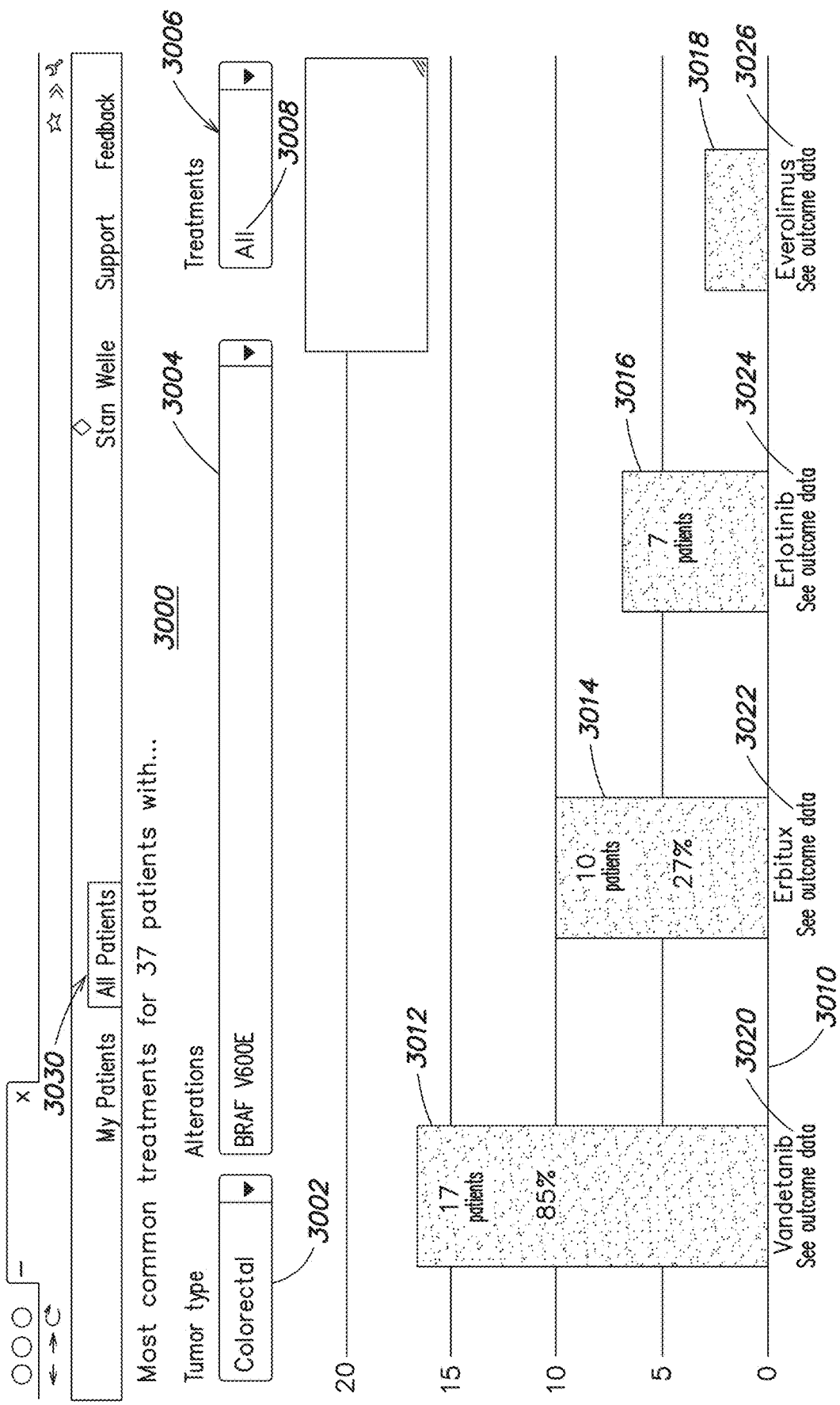
FIG. 30 shows an example user interface including drop-down menus for specifying filter criteria on a patient population, according to one embodiment.

According to one embodiment, the similar patient display can include options to filter the similar patient population (e.g., as shown in FIG. 30). In one example, the analysis component 1014 is configured to perform filter operations (i.e., reduce the number of matching similar patients) on the group of similar patients based on user input of filter criteria. The analysis component 1014 can be configured to match characteristics of a currently viewed patient to any patient sharing the same characteristics for disease and/or treatment. The characteristics used to identify similar patients can also be presented by the UI component 1012 as options for further filtering of the similar patient populations.

For example, in a cancer treatment setting, the UI component 1012 can be configured to display the similar patients with options for filtering on alteration, affected gene or pathway, tumor type, and treatment provided, among other options (e.g., see FIG. 30). According to one embodiment, the system can be configured to present patient populations and/or outcome information responsive to the specification of various combinations of alteration, affected gene or pathway, tumor type, and treatment. The system can be configured to navigate between different groups of patients and respective treatment and outcome data based on user specification of one or more of alteration, affected gene or pathway, tumor type, and treatment. Navigation can occur between different views of treatment and outcome data as well as between different groups of patients that match filter criteria.

According to one embodiment, the user interface includes display options for filtering that provide an intuitive approach for users (e.g., physicians) to access relevant treatment information, to specify more detailed filters on the displayed information, generalize or expand treatment and outcome information, or to include more specific filter criteria. For example, the user can select specific tumor types that they are interested in seeing. In some embodiments, the UI component 1012 displays a list of tumor types that appears in the similar patient population and presents those tumor types as options to select in a drop down list. In one example, the list of tumor types may be determined by the analysis component 1014 and provided to the UI component 1012 for display.

In other embodiments, genomic alterations in the similar patient population are identified and presented as a selectable drop down list. In yet others, treatments within the similar patient populations are identified and presented for possible selection as options in a selectable drop down list. In further implementations, genomic alterations, affected genes or pathways, tumor types, and treatment options can be identified from a larger patient population (rather than limited to the population of similar patients). In one example, the options presented in the user interface for selection can be displayed to include a visual indication reflective that a particular selection is from the larger population (i.e., not from the similar patient population).

The similar patient display can include groupings within the similar patient population, for example, based on the criteria used to identify the similar patient population. In one example, the patients are grouped by commonality of their respective treatment. Each such group can be presented in the similar patient display, for example, ordered based on the number of patients within each group. The group display can also identify the respective treatment common to the group members.

In some embodiments, the UI component 1012 is also configured to respond to selection of the patient groups or the identified treatment associated with each group. In response to selection of a group, the UI component 1012 is configured to display additional information regarding the selected group. For example, the additional information can include outcome information associated with the group of patients. Shown in FIGS. 15-31 is a collection of user interface captures including a similar patient display and a patient group outcome display that can be presented responsive to selection within a similar patient display of a group of patients. The patient group outcome view can also be presented responsive to selection of a filter, for example, on treatment, where a tumor type and genomic alteration type has already been selected.

More generally, the UI component 1012 can be configured to enable searching within the system to provide access to outcome information. The user can search on one or more of alteration, affected gene or pathway, tumor types, treatment, etc. to identify patient populations the user wished to view. In some embodiments, the UI component 1012 provides summary displays based on what filter criteria (e.g., search terms) is defined on the system. In one setting, the filter criteria can be captured from a currently viewed patient record, and, for example, identification of similar patients can be determined by the system using characteristics of the patient record being viewed. According to some embodiments, the user can also specify the filter criteria for a patient population and outcome/treatment information the user wishes to view. In other embodiments, the user can also generalize the filter settings on the system to broaden the view of treatment and outcome data in, for example, the similar patient display.

In some embodiments, the UI component 1012 presents a plurality of filter criteria as drop down selections (e.g., 3002, 3004, and 3006 of FIG. 30). Each drop down selection can include an "ALL" setting, which reflects no filtering on that basis. In some embodiments, the UI component 1012 can also be configured to require that only one of the filter criteria selections be generalized in order to simplify the visual display of information.

FIG. 30 is an example user interface 3000 having drop-down menus (e.g., 3002, 3004, and 3006) for specifying filter criteria on a patient population. The patient population display can be accessed via a similar patient link, where filter criteria can be pre-specified based on the similar patient analysis. In another example, the patient population display can be accessed via selection of an "all patients" tab, and the population specified by selection within any one or more of: 3002-3006. In one example, a generalized selection within a filter can reflect "ALL" when displayed under treatment (e.g., 3008, FIG. 30). The generalized filter criteria can be used by the UI component 1012 to generate an x-axis of a graphical display, where the y-axis reflects the number of patients within each group displayed on the x-axis (e.g., 3010, FIG. 30). The x-axis can be ordered based on a number of patients and the graphic display sized to fit the number of groups having members. At 3012, the group having the largest number of members "17 patients" treated by "vandetanib" is displayed first, at 3014 the group having the next largest membership is displayed "erbitux" "10 patients," at 3016 the next largest group "erlotinib" "7 patients," and at 3018 "everolimus" with four patients last. Each group can be associated with a link to the group's respective outcome data at 3020-3026. According to one embodiment, the UI component 1012 can also be configured to prevent changing of any other filter criteria to a generalized selection as long as one of the other filter criteria is generalized (e.g., the treatment criteria indicates "ALL").

Figure 31:
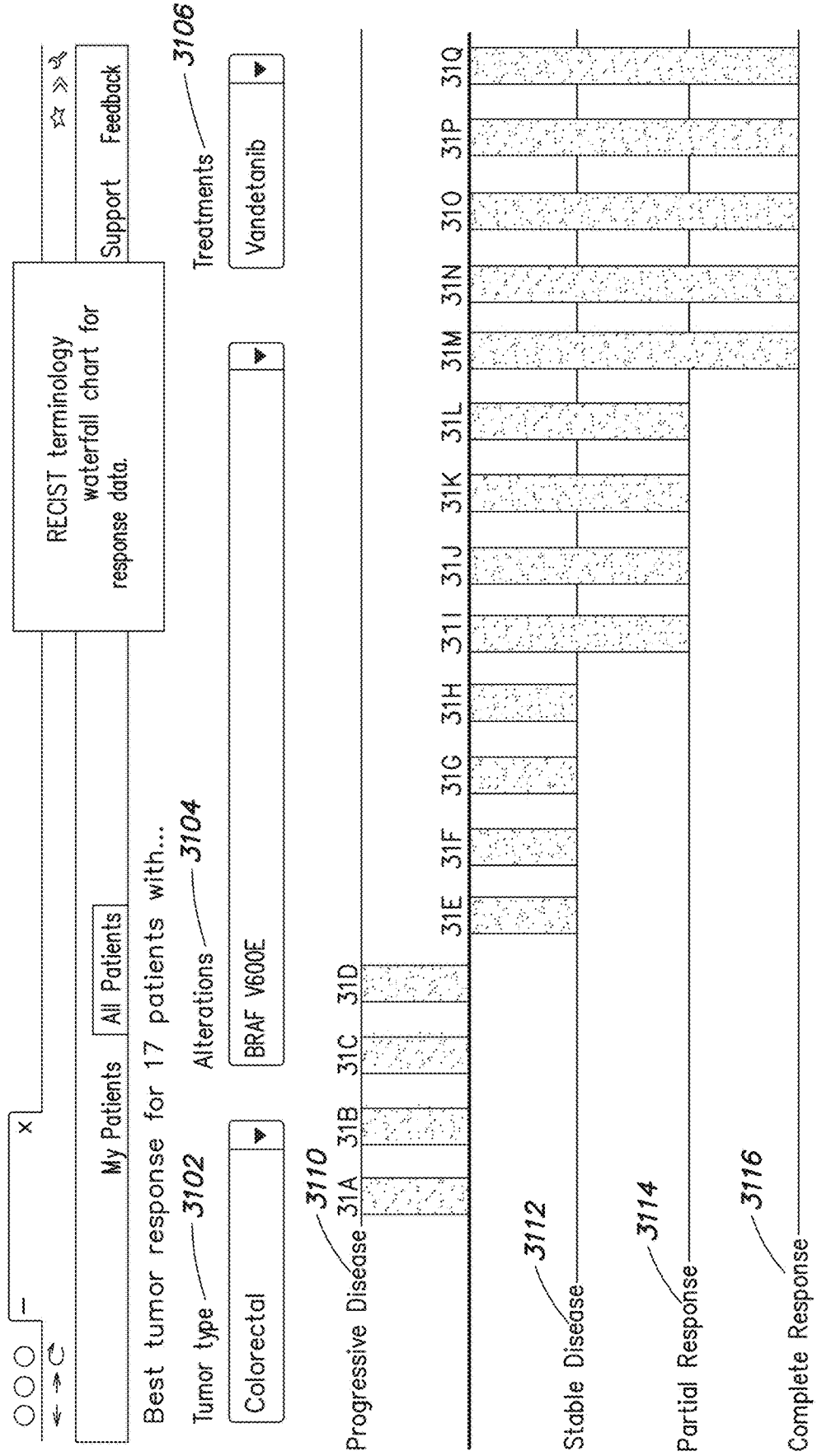
FIG. 31 is an example user interface showing a detailed view of patient outcomes within a patient group.

By specifying a filter selection within a generalized filter category (e.g., FIG. 30 at 3008) the UI component 1012 can be configured to transition to a detail view of outcomes information associated with a fully specified group of patients (e.g., view 3100 of FIG. 31 where fully specified indicates that a specific filter criteria has been input for each displayed filter category, for example, at 3102, 3104, and 3106). According to some embodiments, the system is configured to fully specify the patient group based on specifying alteration, affected gene or pathway, tumor type, and treatment. Within the cancer treatment setting, the UI component 1012 can transition to a detailed view of the outcomes associated with a fully specified treatment group (e.g., tumor type specified, alteration type specified, and treatment type specified).

In some examples, the detailed view of the outcomes within a treatment group is referred to as an outcome waterfall display. In the outcome waterfall display (e.g., 3100), each category of outcome available is displayed on the y-axis (e.g., 3110— progressive disease, 3112 stable disease, 3114 partial response, and 3116 complete response), and on the x-axis a vertical bar for each patient (i.e., member of the filtered group) is displayed (e.g., at 31A-31Q), where the length of bar on the y-axis is configured to show a specific outcome associated with each patient. According to some embodiments, the specific outcome shown for each patient in the waterfall display can be generated based on any one or more of: the last outcome entered for that patient and that treatment, an average of the outcomes entered for that patient on that treatment, a weighted average of outcomes for each patient (e.g., excluding first and last outcome entries where a change in treatment is indicated), a best outcome entry for the displayed patient, and an outcome having the longest time period for the patient, among other options.

According to some embodiments, each bar displayed for each patient can be selected to navigate to additional detail on that patient. In one example, selection of a bar in 3100 causes the UI component 1012 to transition to a patient history timeline. The patient history timeline may be displayed with all of the patient's detail if the selected bar and associated patient is one of the user's patients. If the selected patient is not one of the user's patients, an anonymized view of that patient's treatment over time can be displayed (e.g., as discussed above with respect to the patient history timeline). The anonymized view is configured to exclude any patient identifying information beyond treatment, outcome, and disease characteristic (e.g., genomic alteration, affected gene or pathway, tumor type, expression, etc.).

According to one embodiment, the UI component 1012 is configured to transition between patient group displays and detailed outcome information responsive to fully specifying filter criteria and generalization of filter categories. The examples above and shown in FIGS. 15-31, are discussed with respect to transitioning between patient group displays into detailed outcome information (e.g., outcome waterfall display) based on specification of a treatment option with tumor type and alteration type already specified in the user interface. In other embodiments, transitions can occur responsive to generalization and/or specification of an alteration (e.g., by selecting "ANY" in the user interface) and/or tumor type.

According to some alternatives, generalized patient group views can be generated and displayed where more than one filter category is generalized, or not specified. According to one embodiment, the display of the associated groups of patients can be re-configured such that the groupings of patients can include multiple characteristics (e.g., combinations of specific tumor types and alterations, tumor types and genes, alterations and treatments, alterations and genes, tumor types and treatments, and treatments and genes, among other possible combinations). In other embodiments, visual displays having multiple generalized categories can be generated to illustrated large patient populations and, for example, numbers of patients associated with the multiple generalized categories.

According to other embodiments, similar patient information can be aggregated within patient group views according to any display category. In some embodiments, where the system returns small groups of directly matching patients, the system can aggregate information within the display category to capture further matches. In one example, specific alterations within a patient's cancer are known to be exceeding rare. In some embodiments, the system can aggregate information based on functional similarity, alteration domain, or common pathways to provide meaningful information even for rare alterations.

In one embodiment, patient group views can include information aggregated within the genomic alterations category for a patient group. In one instance, the information can be aggregated based on classes of alterations (e.g., alterations in the kinase domain of a gene (e.g., BRAF) can be grouped separately from BRAF V600E or BRAF V600K alterations). In some embodiments, information can be aggregated on all BRAF V600 mutations together. In others, information can be aggregated within all of the mutations in an alteration domain (e.g., the kinase domain) of a gene (e.g., BRAF).

In some examples, an analysis component can aggregate similar patients within classes of alterations (e.g., alterations in the kinase domain of BRAF can be grouped separately from BRAF V600E or BRAF V600K, or on all BRAF V600 mutations together or all of the mutations in the kinase domain of BRAF). According to another embodiment, the analysis component can aggregate similar patient information based on a functional similarity of identified alterations (e.g., distinct mutations but functionally similar in the cancer). In further embodiments, alterations identified in patient information can be grouped based on a genetic pathway that is implicated by the alteration. For example, alterations that affect the same pathway can be grouped and presented on the system together. Additionally, patients and their associated information can be displayed within groupings based on common pathways and/or associated alterations.

According to one embodiment, the ATP binding pocket domain can include alterations in BRAF G466V and BRAF G469A. The system can use specification of these alterations (e.g., within the ATP binding pocket domain) to aggregate information associated with patients. In some embodiments, the aggregated information can be provided in a user interface display for review and/or comparison.

According to one embodiment, tumor suppressor gene alterations can include splice site mutations, frameshift indels, homozygous deletions, or nonsense mutations. In some examples, these inactivating mutations (tumor suppressor alterations) can be aggregated across patients for a specific tumor suppressor gene or even for tumor suppressor genes in within a same family.

According to one aspect, aggregating responsive information can be implemented to insure that common diagnostic information is available for review and consideration. For example, an alteration in a tumor suppressor gene may be identified for one patient but that specific alteration may not be repeated in another patient. According to one embodiment, by grouping all of the inactivating tumor suppressor mutations/alterations from a specific tumor suppressor (e.g. TP53, BRCA1, BRCA2, etc.) or from tumor suppressors in the same pathway, the system enables the comparison of many more patients having related tumor suppressor alterations. If for example, the data being reviewed was limited only to a matching alteration and gene combination, it may be unlikely that similar patients would ever be identified, as it is highly likely that specific inactivating mutations will not be observed again.

An example of a pathway or family that could be use by the system to aggregate information is the homologous recombination deficiency (HRD) pathway tumor suppressor genes. Various embodiments are configured for aggregating different inactivating mutations in the same gene or inactivating mutations in different genes in the same pathway. The system can present various views of patient information according to any of the information aggregates.

In some embodiments, alterations can be aggregated by genes in the same pathway, including for example, the PI3K/mTOR pathways. The system can be configured to aggregate alterations in PIK3CA, PTEN, PIK3R1, AKT1, AKT2, and other genes in the PI3K/mTOR pathways to increase the number of patients to compare on, for example, respective therapeutic responses.

In further embodiments, alterations can be aggregated by genes in the homologous recombination deficiency (HRD) pathway. The system can identify and aggregate responsive information for inactivating mutations in tumor suppressor genes such as: BRCA1, BRCA2, ATM, ATR, FANCA, FANCE, and others. In one embodiment, the aggregated information can be displayed by the system to a reviewing physician as potentially being biologically and therapeutically equivalent.

According to one embodiment, the outcome engine 1004 can include a connection component 1016 configured to access and display contact information for displayed patients and/or displayed treatment/outcome information. In some embodiments, the contact information provided by the contact component 1016 is configured to connect to the physician caring for a particular patient, or in another example, a manager for a clinical trial.

According to one aspect, the system 1000 and/or the connection component 1016 is configured to facilitate collaboration between medical practitioners to advance the quality of care provided. For example, the connection component 1016 can be configured to provide a communication platform between registered users of system 1000. The connection component 1016 can provide for instant messaging, e-mail, or other chat (video or text) capabilities. In some embodiments, the connection component 1016 can be configured to provide contact information on request. The connection component 1016 can also be configured to allow a user to specify whether their contact information should be provided by the system 1000 when requested.

System 1000 is discussed with respect to example functions and operations that can be performed by specialized components or engines. System components are intended to include computer based instructions that perform operations on a computer system while being executed by one or more processors, for example, as discussed with respect to system 1400 and/or 1402. Various embodiments discussed can include one or more components that provide for the specific functions or operations described herein. In other embodiments, any one or any combination of the functions and/or operations described can be performed more generically by the system alone or the outcome engine itself.

Example System

Figure 11:
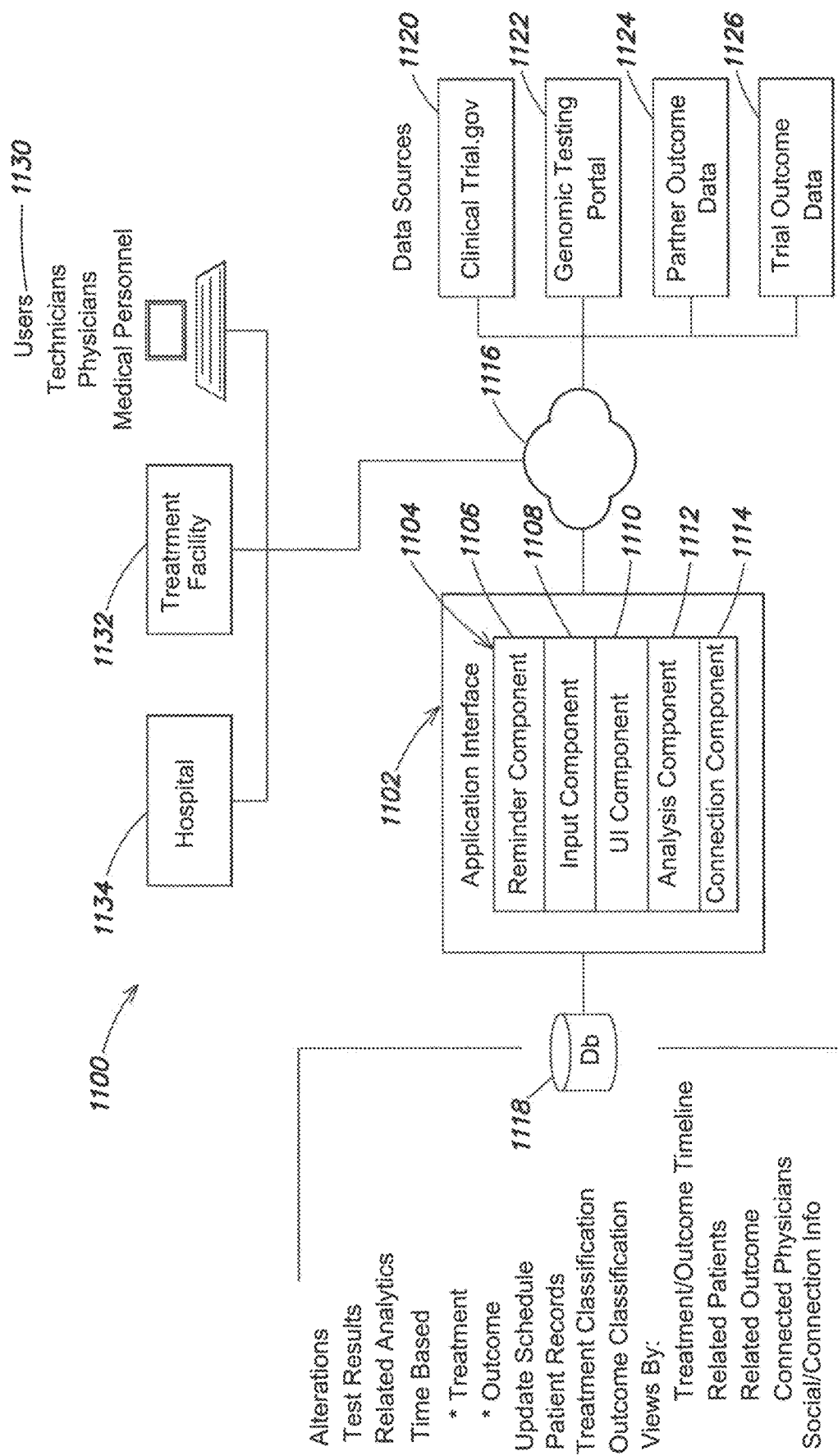
FIG. 11 is a diagram of a system for capturing and processing treatment and outcome information.

FIG. 11 shows an example embodiment of an outcome tracking and analysis system 1100. According to one embodiment, system 1100 can implement an outcome engine 1104 executing on an application interface system 1102 to provide the functions and operations discussed above with respect to system 1000 and/or outcome engine 1004. Outcome engine 1104 can include a plurality of system components. For example, the outcome engine 1104 can include a reminder component 1106 configured to request updates on patient information from associated users. The outcome engine can include an input component 1108 specifying categorizations of treatment and/or outcome information used by the outcome engine 1104 and/or application interface 1102. The outcome engine 1104 can also include a UI component 1110 configured to generate user interface displays rendered by the application interface to end users. The UI component 1110 can be further configured to generate displays including outcome information associated with specific treatments and/or patients and generate visual options for navigating within patient, treatment, and outcome information. The outcome engine 1104 can also include an analysis component 1112 configured to identify relevant treatment/outcome information from known patient populations. In some examples, the analysis component 1112 is configured to capture information on patient populations from external systems.

In one embodiment, the analysis component 1112 can connect to external systems through a communication network 1116. In some embodiments, the analysis component 1112 can be configured to search publically available information sources to capture information on treatment options and any associated outcomes for a given treatment. According to one embodiment, the analysis component 1112 can be configured to search data sources connected to the application interface 1102 via network 1116. The network 1116 can include any one or more of a LAN, WAN, MAN, virtual networks, private network, etc. and may also include, for example, the Internet. For example, the analysis component 1112 can connect to the publically available ClinicalTrials.gov website 1120 and search for disease, treatment, and outcome information available from that site. The analysis component 1112 can be configured to analyze any available information source (e.g., PubMed) and store treatment and outcome data into filterable categories (in one example, tumor type, alteration, and treatment categories).

According to one embodiment, the analysis component 1112 can process the available information into categorized treatment and outcome information and store the information automatically for use by the outcome tracking and analysis system. According to another embodiment, the analysis component 1112 can provide the treatment and outcome information to an administrator for review and acceptance prior to use on the system, for example, prior to storage within database 1118. The analysis component 1112 can also connect to other medical service providers or other medical information sources.

For example, the analysis component can access a genetic testing portal 1122. In some embodiments, the application interface 1102 can be integrated with the genetic testing portal 1122 and can be configured to share information on patients, diseases, treatments, and outcomes. Information on patients, diseases, treatments and outcomes can also be accessed from partner outcome data 1124. Partner outcome data sources 1124 can include other hospitals or treatment facilities that wish to share some level of diagnostic information. In some embodiments, partners can contribute treatment and outcome information, while maintaining the proprietary nature of other data regarding, for example, their own testing and some specific results on treatment and outcomes. In other embodiments, partner information becomes part of the larger database on outcome and treatment information. Other outcome data sources 1126 can include journal publications, study publications, published articles, etc. In some implementations, the analysis component can parse publication data to find and categorize treatment and outcome information for use by the system.

Any such treatment information can be captured and stored for access by the application interface 1102, for example, in database 1118. Database 1118 is illustrated as a single database, but in other embodiments can include any storage medium or organizational unit for storing and accessing treatment and outcome data by a computer system. Further embodiments can include a plurality of databases and can also include distributed data architectures. According to one embodiment, database 1118 can include a variety of information used by the application interface 1102 to track and analyze outcome information.

For example, in a cancer treatment setting, genomic testing information from a genomic testing portal can include genomic analysis of a patient's cancer. Genomic analysis can describe genomic alterations present in the cancer cells, which can be stored in database 1118 and associated with a patient and test results. The alteration information can provide a basis for determining related analytics on other patient cancers, treatment, and outcome information. Any related analytics can also be stored in database 1118.

As discussed above with respect to system 1000, the outcome tracking and analysis system 1100 can facilitate user entry of treatment and outcome information. For example, the outcome engine 1104 can be configured to provide reminders to user to update patient records with treatment and outcome information according to system specified categories. The system specified categories can be configured to minimize the time a user spends inputting information, while preserving the value of the data being input for potential diagnostic uses. According to one implementation, the system is configured to store, access, and enable navigation of outcome and treatment information according to alteration, affected gene or pathway, tumor type, and treatment.

The categorized treatment and outcome data input by users can be stored, for example, in database 1118. The stored treatment and outcome information can be use to generate time based summaries of available treatment and outcome data, for example, by UI component 1110.

According to some embodiments, the application interface 1102 is configured to provide a network accessible portal to medical treatment and outcome information, including, for example, cancer treatment information. Further, the application interface is configured to facilitate entry of treatment and outcome information by end users such that the time to enter information is minimized, maximizing the benefits obtained from the collection and analysis of outcome data. The application interface 1102 is configured to accept a variety of end users. Typically, a user 1130 is a medical professional, including for example, physicians, physician's assistant, nurses, technicians, etc. The end users can access the application 1102 from a variety of locations, including, for example, a treatment facility 1132 and a hospital 1134.

In some embodiments, the application interface 1102 can include a connection component 1114. The connection component 1114 can be configured to provide contact information between a plurality of users located at disparate hospitals, treatment facilities, etc. In some environments, the connection component 1114 can also be configured to manage communication between users (e.g., provide video chat services, instant message services, e-mail services, etc.). According to one embodiment, an example goal in providing the connection component 1114 includes connecting a physician with another care provider who has already pursued one or more courses of treatment with a patient having a similar tumor, a similar alteration, similar affected gene or pathway, or a similar treatment. In one alternative, the physician can be connected to a manager of a clinical trial and receive feedback on course of treatment, candidacy for the trial, suitability for the trial, among other information.

According to one aspect, by providing the application interface 1102 to a variety of users (e.g., 1130) and simplifying the capture of treatment and outcome information, the tracking and analysis system 1100 enables collection of untapped diagnostic information on medical treatment. In one embodiment, the application interface is configured to facilitate collection and analysis of cancer treatment and outcome. The collected information and analysis can facilitate daily practice and decisions making by physicians, whether they are located at major metropolitan hospitals (e.g., 1134), treatment facilities (e.g., 1132), or whether they are solo practitioners.

In some implementations, data aggregation and analysis can be rooted in filterable organization of all treatment and outcome information to enable easy and intuitive navigation within the treatment and outcome data. Various embodiments include organization of treatment and outcome information based, at least in part, on alteration information. Alteration information can be provided as a result of genomic testing relating to a medical condition. In the cancer treatment setting, frequently a multitude of genetic mutations or alterations are present in cancer cells and will be discerned as results from cancer genomic analysis. Within the multitude of alterations, one or more alterations can be associated with a specific patient, tumor type, treatment, and/or treatment outcome. In some embodiments, the outcome tracking analysis systems can implement a data model organizing all treatment and outcome data so that all the data is accessible and navigable based on specification of one or more of alteration, affected gene or pathway, tumor type, and treatment.

In some embodiments, genomic alteration, tumor type, and treatment can be stored as a tuple in a database. The tuple can be associated with information on the affected gene. In some examples, the database can include records for tumor type, treatment, and gene/alteration combinations, stored as a data unit. In other embodiments, the database can be indexed on any one or more of alteration, affected gene or pathway, tumor type, and treatment to speed retrieval of outcome data associated with those data records. In further embodiments, an outcome tracking and analysis system can include a data model based, at least in part, on organizing patient, outcome, and treatment data using alteration or affected gene or pathway information.

In some embodiments, the data model can reduce such treatment information to system specified categories for one or more therapies applied. For example, data input by a user can exclude dosing information, patient demographic information, etc. In other examples, the system can include user interface elements for inputting dosing information, patient specific information, etc., as optional information. In further embodiments, the system can request and/or require more specific information regarding treatment (dose, frequency, duration, patient weight, height, age, or any other patient factor that impacts a dosing regimen).

According to another embodiment, the data model is configured to simplify outcome information inputs. In one example, the data model defines outcome information as one of progressive, stable, partial response, and complete response. The user can input outcome information based on selection of the defined outcomes, simplifying any data entry by users. Further, treatment and outcome information can be captured from third-party information sources and stored according to the data model. According to some embodiments, any data source for treatment and outcome information can be converted into information retrievable on any one or more of alteration, affected gene or pathway, tumor type, and a specified treatment. In further embodiments, additional information on treatment, outcomes, tumor type, affected gene or pathway, genomic alterations can be stored according to the data model. The additional information can be associated with patients, and accessed from any defined patient group. In one example, a patient group can be selected according to user input of any one or more of alteration, affected gene or pathway, tumor type, and treatment. The system can enable selection within any specified patient group to access any additional detail information associated with any patient with the patient group.

In some embodiments, the system can generate and display outcome and treatment information according to the data model. For example, visual displays organizing treatment and outcome information according to genomic alternation, affected gene or pathway, tumor type and treatment can be generated and displayed by the system. The system can be configured to respond to selection within of any of the visual display categories to navigate or filter within the treatment and outcome information. Selection within patient groups can also trigger transitions to detailed views of treatment and outcome information associated with specific patients. (e.g., as shown in FIGS. 29-31).

Figure 12:
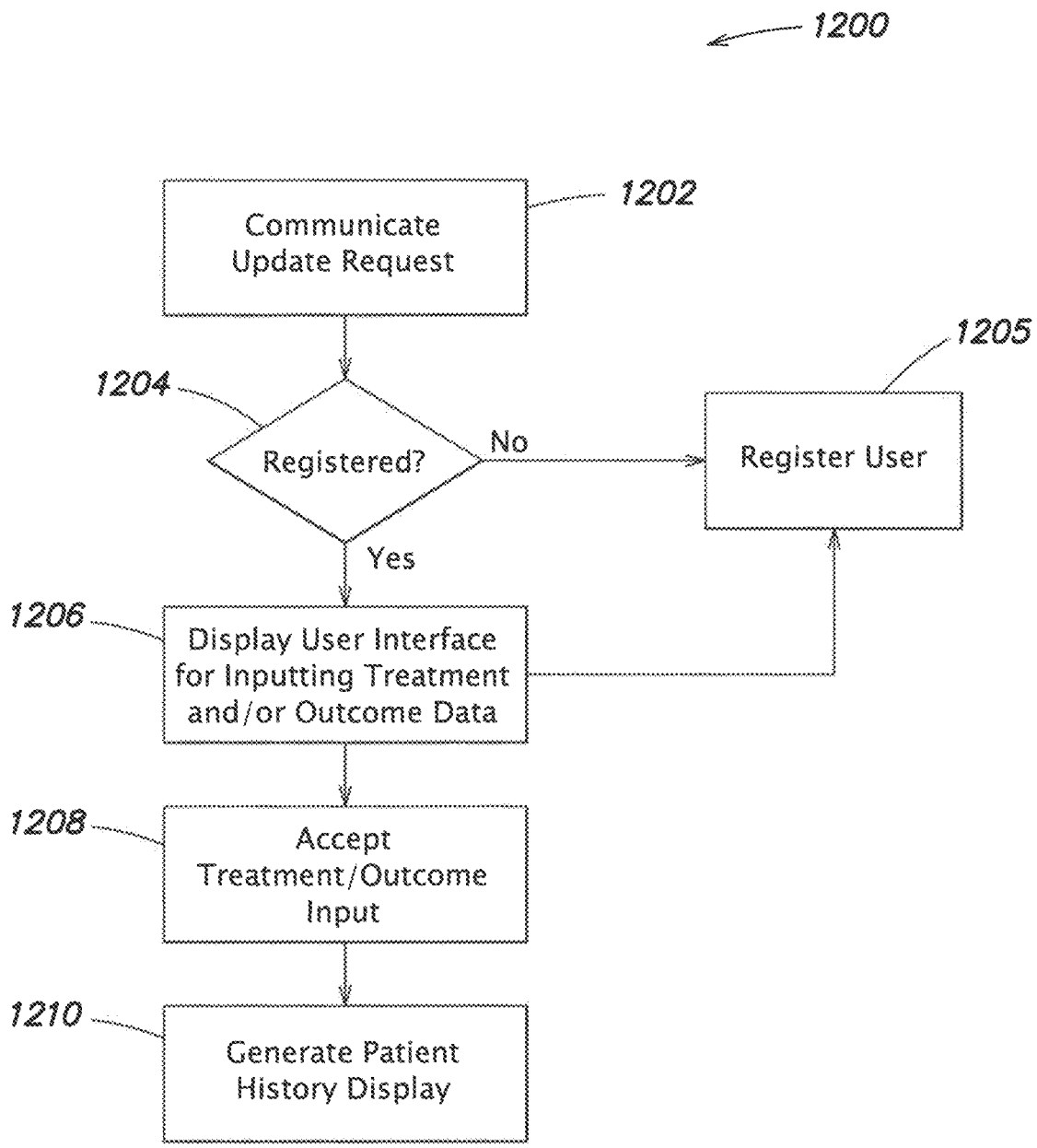
FIG. 12 is an example process flow for a method of capturing and processing treatment and outcome information, according to one embodiment.
Figure 13:
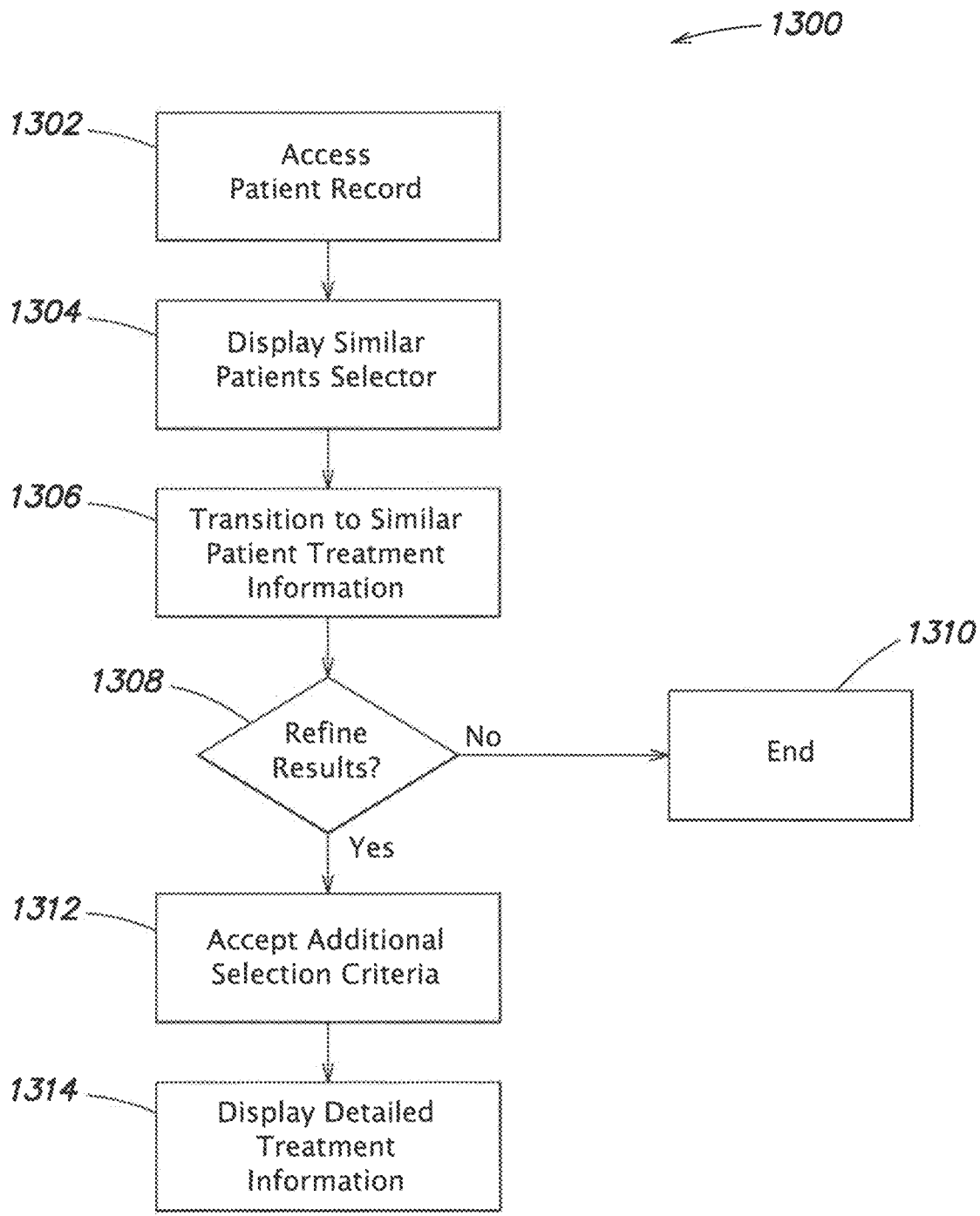
FIG. 13 is an example process flow for a method of navigating treatment and outcome information, according to one embodiment.

According to one embodiment, the system 1100 and/or application interface 1102 can execute a variety of processes to capture treatment and outcome data. FIG. 12 shows an example process 1200 for requesting and capturing treatment and/or outcome information. According to one embodiment, the process 1200 begins at 1202 with communication of an update request at 1202. The update request can specify what information a user is expected to enter on the system. For example, the request can specify that treatment information is requested for a patient who has undergone genetic testing for cancer treatment. The update request can also specify a request for outcome information associated with patients of the user. Regardless of the type of request, the update request can include links to take the recipient to a web portal for accessing/inputting such treatment and outcome information.

Process 1200 continues at 1204 with a determination of whether the current user is registered. If user is registered 1204 (YES), the user can be shown a display at 1206 for inputting treatment and/or outcome data responsive to entering their user name and password. The display can be presented based on any patient requiring an update (e.g., as shown in FIG. 18). If a user is not yet registered 1204 (NO), the user can be registered at 1205, for example, by providing authentication information to validate the user as a health care provider responsible for a patient associated with the update request.

At 1208, the user interface is configured to accept input of treatment and/or outcome data, for example, entered by a user. Once treatment and/or outcome data is entered, a patient history display can be generated at 1210. The patient history display can include treatment information displayed a start point on a treatment timeline. In one example, the treatment timeline displays information on a course of treatment for a cancer and the outcome associated with the course of treatment over time.

According to some embodiments, input treatment and outcome information can be accessed by an outcome engine (e.g., 1004 and 1104) to enable searching or navigation with patient populations associated with the treatment and outcome data. For example, the outcome engine can execute an example process 1300 for navigating treatment and outcome information. The process 1300 can begin with access to a patient record at 1302. In some embodiments, information on a currently viewed patient (e.g., alteration, affected gene or pathway, tumor type, and/or treatment) is used to identify any patients similar to the currently viewed patient. At 1304, a similar patient selector can be displayed, for example, in a user interface. Responsive to execution of the similar patient selector, the currently viewed patient record can be transitioned to similar patient treatment and outcome information. For example, the current patient record can be transitioned to a similar patient population displayed according to any match on genomic alternation, affected gene or pathway, tumor type, or treatment at 1306.

A system executing process 1300 can be responsive to further refinements or navigation within a set of similar patient results. For example, the similar patient population display can include UI elements for further refining the displayed information. If, for example, a user selects additional refinements 1308 (YES), any additional specification is accepted at 1312 and a treatment. Once any new specification of navigation criteria have been accepted at 1312, a new set of similar patients can be generated matching the new criteria. The matching patient population can then be displayed at 1314, for example, as a detailed view of treatment and outcome information associated with individual patients (e.g., FIG. 31).

If no further refinements are desired or specified 1308 (NO) process 1300 can terminate at 1310. Process 1300 is shown by way of example, and in different embodiments, can be executed with other orderings or can combine various steps discussed separately. Further, processes 1300 and 1200 can be executed by various computer systems, which can include outcome engines and/or the components discussed above with respect to some embodiments of an outcome engine. In some embodiments, processes 1300 and 1200 can be executed by the outcome engine, the outcome engine components, or any combination thereof.

Example Computer Systems

Various aspects, functions, components, and/or processes described herein may be implemented as hardware, software, or a combination of hardware and software on one or more computer systems. There are many examples of computer systems currently in use. Some examples include, among others, network appliances, personal computers, workstations, mainframes, networked clients, servers, media servers, application servers, database servers, web servers, and virtual servers. Other examples of computer systems may include mobile computing devices, such as cellular phones, laptops, tablets, and personal digital assistants, and network equipment, such as load balancers, routers and switches. Additionally, aspects in accord with the present invention may be located on a single computer system or may be distributed among one or more computer systems connected to one or more communication networks.

For example, various aspects and functions may be distributed among one or more computer systems configured to provide a service to one or more client computers, or to perform an overall task as part of a distributed system. Additionally, aspects may be performed on a client-server or multi-tier system that includes components distributed among one or more server systems that perform various functions. Thus, the invention is not limited to executing on any particular system or group of systems. Further, aspects may be implemented in software, hardware or firmware, or any combination thereof. Thus, aspects in accord with the present invention may be implemented within methods, acts, systems, system placements and components using a variety of hardware and software configurations, and the implementation is not limited to any particular distributed architecture, network, or communication protocol. Furthermore, aspects in accord with the present invention may be implemented as specially-programmed hardware and/or software.

Figure 14:
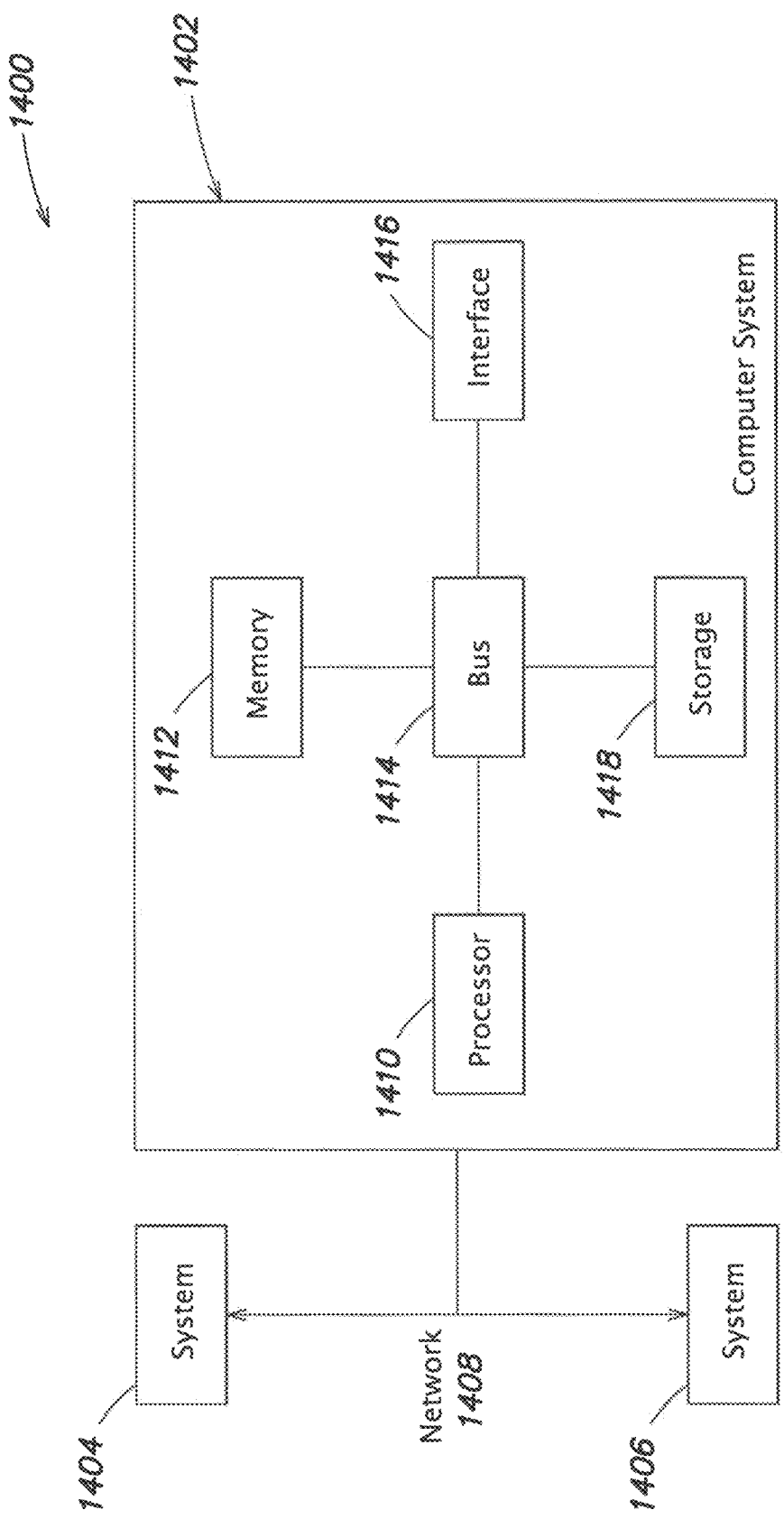
FIG. 14 is a block diagram of one example of a computer system that may be used to perform processes and functions disclosed herein.

FIG. 14 shows a block diagram of a distributed computer system 1400, in which various aspects and functions in accord with the present invention may be practiced. The distributed computer system 1400 may include one or more computer systems. For example, as illustrated, the distributed computer system 1400 includes three computer systems 1402, 1404 and 1406. As shown, the computer systems 1402, 1404 and 1406 are interconnected by, and may exchange data through, a communication network 1408. The network 1408 may include any communication network through which computer systems may exchange data. To exchange data via the network 1408, the computer systems 1402, 1404, and 1406 and the network 1408 may use various methods, protocols and standards including, among others, token ring, Ethernet, Wireless Ethernet, Bluetooth, TCP/IP, UDP, HTTP, FTP, SNMP, SMS, MMS, SS7, JSON, XML, REST, SOAP, CORBA HOP, RMI, DCOM and Web Services.

Computer systems 1402, 1404 and 1406 may include mobile devices such as cellular telephones. The communication network may further employ one or more mobile access technologies including 2nd (2G), 3rd (3G), 4th (4G or LTE) generation radio access for cellular systems, WLAN, Wireless Router (WR) mesh, and other communication technologies. Access technologies such as 2G, 3G, 4G and LTE and future access networks may enable wide area coverage for mobile devices. For example, the network may enable a radio connection through a radio network access such as Global System for Mobil communication (GSM), General Packet Radio Services (GPRS), Enhanced Data GSM Environment (EDGE), Wideband Code Division Multiple Access (WCDMA), among other communication standards. Network may include any wireless communication mechanism by which information may travel between the devices 1404 and other computing devices in the network.

To ensure data transfer is secure, the computer systems 1402, 1404 and 1406 may transmit data via the network 1408 using a variety of security measures including TSL, SSL or VPN, among other security techniques. While the distributed computer system 1400 illustrates three networked computer systems, the distributed computer system 1400 may include any number of computer systems, networked using any medium and communication protocol.

Various aspects and functions in accord with the present invention may be implemented as specialized hardware or software executing in one or more computer systems including the computer system 1402 shown in FIG. 14. As depicted, the computer system 1402 includes a processor 1410, a memory 1412, a bus 1414, an interface 1416 and a storage system 1418. The processor 510, which may include one or more microprocessors or other types of controllers, can perform a series of instructions that manipulate data. The processor 1410 may be a well-known, commercially available processor such as an Intel Pentium, Intel Atom, ARM Processor, Motorola PowerPC, SGI MIPS, Sun Ultra-SPARC, or Hewlett-Packard PA-RISC processor, or may be any other type of processor or controller as many other processors and controllers are available. As shown, the processor 1410 is connected to other system placements, including a memory 1412, by the bus 1414.

The memory 1412 may be used for storing programs and data during operation of the computer system 1402. Thus, the memory 1412 may be a relatively high performance, volatile, random access memory such as a dynamic random access memory (DRAM) or static memory (SRAM). However, the memory 1412 may include any device for storing data, such as a disk drive or other non-volatile storage device, such as flash memory or phase-change memory (PCM). Various embodiments in accord with the present invention can organize the memory 1412 into particularized and, in some cases, unique structures to perform the aspects and functions disclosed herein.

Components of the computer system 1402 may be coupled by an interconnection element such as the bus 1414. The bus 1414 may include one or more physical busses (for example, busses between components that are integrated within a same machine), and may include any communication coupling between system placements including specialized or standard computing bus technologies such as IDE, SCSI, PCI and InfiniBand. Thus, the bus 1414 enables communications (for example, data and instructions) to be exchanged between system components of the computer system 1402.

Computer system 1402 also includes one or more interfaces 1416 such as input devices, output devices and combination input/output devices. The interface devices 1416 may receive input, provide output, or both. For example, output devices may render information for external presentation. Input devices may accept information from external sources. Examples of interface devices include, among others, keyboards, mouse devices, trackballs, microphones, touch screens, printing devices, display screens, speakers, network interface cards, etc. The interface devices 1416 allow the computer system 1402 to exchange information and communicate with external entities, such as users and other systems.

Storage system 1418 may include a computer-readable and computer-writeable nonvolatile storage medium in which instructions are stored that define a program to be executed by the processor. The storage system 1418 also may include information that is recorded, on or in, the medium, and this information may be processed by the program. More specifically, the information may be stored in one or more data structures specifically configured to conserve storage space or increase data exchange performance. The instructions may be persistently stored as encoded signals, and the instructions may cause a processor to perform any of the functions described herein. A medium that can be used with various embodiments may include, for example, optical disk, magnetic disk or flash memory, among others. In operation, the processor 1410 or some other controller may cause data to be read from the non-volatile recording medium into another memory, such as the memory 1412, that allows for faster access to the information by the processor 1410 than does the storage medium included in the storage system 1418. The memory may be located in the storage system 1418 or in the memory 1412. The processor 1410 may manipulate the data within the memory 1412, and then copy the data to the medium associated with the storage system 1418 after processing is completed. A variety of components may manage data movement between the medium and the memory 1412, and the invention is not limited thereto.

Further, the invention is not limited to a particular memory system or storage system. Although the computer system 1402 is shown by way of example as one type of computer system upon which various aspects and functions in accord with the present invention may be practiced, aspects of the invention are not limited to being implemented on the computer system, shown in FIG. 14. Various aspects and functions in accord with the present invention may be practiced on one or more computers having different architectures or components than that shown in FIG. 14. For instance, the computer system 1402 may include specially-programmed, special-purpose hardware, such as for example, an application-specific integrated circuit (ASIC) tailored to perform a particular operation disclosed herein. Another embodiment may perform the same function using several general-purpose computing devices running MAC OS System X with Motorola PowerPC processors and several specialized computing devices running proprietary hardware and operating systems.

The computer system 1402 may include an operating system that manages at least a portion of the hardware placements included in computer system 1402. A processor or controller, such as processor 1410, may execute an operating system which may be, among others, a Windows-based operating system (for example, Windows NT, Windows 2000/ME, Windows XP, Windows 7, or Windows Vista) available from the Microsoft Corporation, a MAC OS System X operating system available from Apple Computer, one of many Linux-based operating system distributions (for example, the Enterprise Linux operating system available from Red Hat Inc.), a Solaris operating system available from Sun Microsystems, or a UNIX operating systems available from various sources. Many other operating systems may be used, and embodiments are not limited to any particular operating system.

The processor and operating system together define a computing platform for which application programs in high-level programming languages may be written. These component applications may be executable, intermediate (for example, C# or JAVA bytecode) or interpreted code which communicate over a communication network (for example, the Internet) using a communication protocol (for example, TCP/IP). Similarly, functions in accord with aspects of the present invention may be implemented using an object-oriented programming language, such as JAVA, C++, Ada, or C# (C-Sharp). Other object-oriented programming languages may also be used. Alternatively, procedural, scripting, or logical programming languages may be used.

Additionally, various functions in accord with aspects of the present invention may be implemented in a non-programmed environment (for example, documents created in HTML, XML or other format that, when viewed in a window of a browser program, render aspects of a graphical-user interface or perform other functions). Further, various embodiments in accord with aspects of the present invention may be implemented as programmed or non-programmed placements, or any combination thereof. For example, a web page may be implemented using HTML while a data object called from within the web page may be written in C++. Thus, the invention is not limited to a specific programming language and any suitable programming language could also be used.

Examples and Embodiments of a Genomic Portal

It is realized that the adoption and integration of genomic testing into daily practice faces significant hurdles, in part, based on the ability to access and the volume of the information that needs to be reviewed and understood in order to facilitate treatment decisions. Further, the complexity of the genomic analysis has also limited its potential and some cases implementation. It is also realized that conventional approaches for providing genomic alteration information are not readily appreciated by the majority of practitioners for their diagnostic value. Nor can the majority of practitioners incorporate such information into actionable steps to be taken with a given patient.

According to one aspect, it is realized that in order to effectively incorporate genomic testing information into daily physician practice, genomic alteration data must be simplified and/or coupled with contextual applications of the genomic alteration data. In some embodiments, volumes of genomic alterations and associated information (e.g., journal articles, clinical trial information, therapies, etc.) are analyzed and synthesized into actionable information items viewable on an alteration system. According to one embodiment, the system can be configured to focus practitioners on discrete portions of the alteration information on which they can act.

According to other aspects, curated information is provided on the system to enable practitioners to make informed decisions regarding the implications of the presence of specific genomic alterations. Curated information includes interpretations of available information (e.g., existing therapies, clinical trials, journals, and publications) for genomic alterations that may be found in a patient's tumor as a result of the genomic analysis. The genomic analysis can identify, for example, a tumor type, an affected gene, and an alteration type specific to a given patient and their cancer. The available information that can be curated can be associated with, and organized by, any of the information provided in the genomic analysis (e.g., specific to tumor type, gene, and alteration).

According to one embodiment, the interpretations present contextual information regarding the gene implicated in a patient's cancer, including, for example, the expression of the gene, related genes, and can provide information on related therapies or clinical trials. In some embodiments, the curated information can also include interpretive statements that summarize and/or apply current analysis of any available information associated with genomic alterations (including, for example, information on an identified gene, information on an identified alteration, and information on the patient's tumor). Further, the curated information can be integrated into a display with genomic test results, providing intuitive and easy access information sources for understanding implication of the test results.

Additionally, the curated information can include references to an information source from which the curated information is derived. In some embodiments, the system can provide direct access to a source of the curated information. For example, the system can provide for direct navigation to a relevant clinical trial while in context of reviewing information on a specific genomic alteration. The curated information can also include direct links to the source information hosted at external information sites.

(e.g., ClinicalTrials.gov, PubMed, etc.). The information sources can also be reviewed by the user to further describe or validate the curated information being provided.

By providing such curated information with an easily navigable interface, a physician or other health care provider may locate the best treatment information in a timely manner. In some embodiments, the interface can be organized and navigated based on specific alterations found in a patient's cancer. In such settings, the user can navigate to information matching the patient's cancer (e.g., tumor type, gene, and alteration) to find directly relevant treatment information. Additionally, the user can navigate to related information matching one or more of a patient's tumor type, gene, and alteration to inform the user of potential off-label treatment options.

Genomic testing provides unique opportunities to make more informed treatment decisions, especially in the field of cancer diagnosis and therapy development. Some conventional approaches can fail to provide useable information within the volumes of information provided as results of genomic testing. Further, it is appreciated that some conventional approaches fail to focus practitioners on actionable information within the genomic testing information and any associated treatment information.

Accordingly, provided are systems and methods for managing genomic testing information that provide a single reporting source for accessing and applying available information on a patient's cancer. According to some embodiments, genomic testing on the patient's cancer provides specific information on the tumor, one or more genes implicated by the tumor, and one or more alterations within the genes. The testing information on tumor, gene, and alteration can be used by the system to manage delivery of curated information that focuses users (e.g., physicians) on actionable information within the genomic test results and associated information. For example, publically available data (e.g., therapy data, clinical trial data, and journal publications) can be interpreted to provide the curated information based on its relationship to one or more of the tumor, gene, and alteration for a patient. The publically available information can be processed on the system to provide navigable data structures informing the user of available actionable information associated with a patient's cancer.

According to one embodiment, by providing users an indicator of actionable information, information within genomic testing reports can be provided succinctly and enable the users to select the indicator to access more detailed information as needed. Further, genomic test results (e.g., listings of alterations) can be ordered based on the presence or absence of actionable information items. In one example, actionability of the navigable data structures can be defined on available information for an FDA approved agent in the patient's tumor type, available information for an FDA approved agent in another tumor type, and/or available information for a mechanistically driven or biologically relevant clinical trial based on the alteration(s) found.

The ordering can be configured to focus the user on the actionable information to facilitate review of a plurality of alterations and their associated information. Indicators of actionable items can be displayed based on an information source (e.g., a therapy indicator/tag references available therapy information items related to a genomic alteration, a trial tag references available clinical trial information items, and a reference tag for reference information items). The indicator can be associated with a respective alteration in the plurality of alterations resulting from genomic testing.

In some embodiments, the system facilitates successive selection of alterations and associated information within the plurality of alteration results, for example, using the indicators. By enabling successive selections, the system facilitates better understanding of a patient's cancer and enables more informed treatment decisions.

According to some embodiments, the actionable information includes identification of FDA approved therapies for a tumor, gene, and alteration combination. Actionable information can also include identification of related therapies that are implicated by any one or more of the tumor, gene, and alteration characteristic of a patient's cancer. According to some embodiments, related therapies can be determined by the system and displayed to users to facilitate treatment decisions. For example, indicators regarding the related therapies can be displayed as part of the navigable data structures within user interface displays generated by the system.

Referring to FIG. 1, there is illustrated an example of a system 100 for managing genomic testing information using an alteration engine 104. Elements of the system 100 can be provided using a computing system such as the computer system 500 and/or 502 described with reference to FIG. 5. For example, the alteration engine 104 can be executed on the computer system 500 and/or 502 to provide the functions and operations discussed herein. In other embodiments, the alteration engine 104 can include additional components executed on the computer system to perform specific operations.

As shown in FIG. 1, various embodiments of the alteration engine 104 are configured to accept genomic test results 102 and associate the genomic test results with curated information. The curated informing can include detailed analysis or additional information tailored to the characteristic of the test results. For example, the test results generated for a specific patient can specify a plurality of genes and alterations found within the patient's cancer. The alteration engine 104 can be configured to associate curated information tailored to the specific genes/alteration identified for the patient.

In some embodiments, the alteration engine 104 can be configured to generate a single source display of the test results, curated information, and any additional information as a dynamic display 106. The dynamic display 106 can include and organize the test results, the curated information, and the additional information to minimize the volume of data displayed to the user at any one time. According to one embodiment, the dynamic display 106 can include a plurality of views of the test results, the curated information, and the additional information. In one example, the test, curated, and additional information can be organized into categories for display in a user interface. In some embodiments, the user interface can be specially configured for navigation with mobile devices.

The user interfaces generated by the system can also be configured to include gene and alteration information specific to a current patient being viewed. The user interfaces are configured to present categorized information to facilitate understanding of the gene and alteration information for the current patient. In one example, the dynamic display is presented for a specific patient selected by the user from a patient listing (e.g. FIG. 6—which can include options for filtering the patient listing at 650). Once selected, the current patient's information (e.g., name, date of birth, height, weight, sex, patient id, case id, etc.) can be provided along with information regarding the genetic testing conducted (e.g., specimen receipt date, report generation date, diagnosis (type of tumor), collection date for specimen, collection method, specimen type, etc.) as a first portion of a dynamic display 106.

A second portion of the dynamic display 106 generated by the system and/or alteration engine 104 can include the results of the genetic testing organized by gene and alteration. In some embodiments, the alteration engine 104 can include a user interface ("UI") component configured to generate and to provide for navigation within the dynamic display 106. For example, each gene and alteration result generated from genomic testing of the current patient's cancer can be displayed as its own data structure. The data structure can contain selectable indicators of actionable information specific to each of the gene/alteration results. In one embodiment, the UI component is configured to transition the dynamic display 106 to the actionable information in response to selection of the indicators.

According to one embodiment, each gene/alteration data structure is referred to as a brick. Each brick includes a display title or name for an associated gene and alteration. Shown by way of example in FIG. 7, is a section of dynamic display containing a first and second portion (702 and 704). The second portion (704) of the display includes the gene/alteration data structures ("bricks") at 706. Highlighted at 708 is an example brick, which includes a title for a gene/alteration identified by the genomic testing. The alteration engine 104 and/or UI component can be configured to arrange the bricks responsive to actionable information associated with each brick. For example, bricks having associated therapy information can be given precedence in a display of the test results at 704 over bricks without associated therapy information. Further bricks having associated clinical trials can be given precedence in the display at 704 over bricks without associated trial information. In further examples, the number of information items within each category can be used to establish a display precedence based on the categories of actionable information (e.g., therapy, trial, reference). In some embodiments, indicators are generated specific to the category of actionable information.

According to some embodiments, actionable information refers to the presence of information diagnostically relevant to a gene or alteration. For example, actionable information can be reviewed by the user (e.g., a physician) to inform treatment decisions for that patient, to facilitate the physician's determinations regarding the patient's cancer, or to educate the physician on the gene/alteration, among other options. The actionable information can also be relevant to patient's tumor type as well as the gene and alteration. As shown, each brick includes a navigable indicator reflecting available actionable information (e.g., at 712 Therapy indicator and 714 Trial indicator). In one embodiment, the display of bricks can be ordered based on actionability, wherein actionability can be defined on available information for an FDA approved agent in the patient's tumor type, available information for an FDA approved agent in another tumor type, and/or available information for a mechanistically driven or biologically relevant clinical trial based on the alteration(s) found. In addition, each brick can include a title display reflecting a specific gene and alteration associated with each brick (e.g., at 716-717) that can be navigated to additional, and/or actionable information regarding the gene and alteration.

In some embodiments, the brick of information for each gene alteration can include information on the gene and the alteration, where additional information is visualized responsive to a hover action. In one example, the number of therapies trials and references can be visualized responsive to user interface pointer hovering over the gene/alteration brick.

In some embodiments, actionable information can be grouped by the system based on categories or source, and indicators can be generated according to any such groupings. For example, the system can group information on available therapies (e.g., 712 therapy indicator or tag), clinical trials (e.g., 714 trial indictor or tag), and in further examples, publications referencing the gene and/or alteration can also be grouped by the system in the dynamic display. Each indicator can be displayed separately for each brick associated with a gene and alteration. The indicators are configured to transition the user to one or more information items associated with the displayed gene/alteration. By selecting the therapy indicator, the user transitions the system to matching therapy information items. In some embodiments, the brick can also include an indicator or tag reflecting that updated information is available in any one or more of the associated therapy, trial, and reference information items.

According to one embodiment, selection of the indicators (e.g., 712-717) can be configured to cause the alteration engine 104 and/or UI component to transition the system to additional information specified by the respective indicator. For example, selection of any of 712-717 causes the system to transition to a third portion of the dynamic display 106 (e.g., FIG. 7B (710)). The system can also transition to new portions/pages using jump menu 711. Shown at 710 is an example of the third portion of the dynamic display 106. As shown, the third portion includes categorization of the information items associated with the tumor, gene, and alteration information relevant to the currently viewed patient (including, for example, the genes/alterations shown at 704). According to some embodiments, the information displayed in the third portion can be grouped based on system categories for the related information. In one example, the system categories can include: Genomic Alteration Interpretations (718); Therapy (720); Clinical Trial (722); and References (724). In some embodiments, each drawer can be responsive to hover, displaying additional information for the drawer being hovered on.

Shown at 710 are the information categories arranged by associated data structures. Each data structure in the third portion 710 of the dynamic display 106 can be configured to expand or open upon selection. Further, the data structures displayed can be accessed through the actionable information indicators at 712-714 or the gene/alteration indicators at 716-717. Common to the data structures in the third portion of the dynamic display 710 is a selectable expansion element (e.g., 726) that expands to show the information items contained within the associated category or group. The data structures in the group can be referred to as drawers, where the drawers are configured to open or expand in a user interface display to provide additional information (e.g., responsive to selection of 726 or actionable information indicators 712-717). Each drawer can include an indication of a number of information items organized within the drawer (e.g., at 728).

Figure 7B:
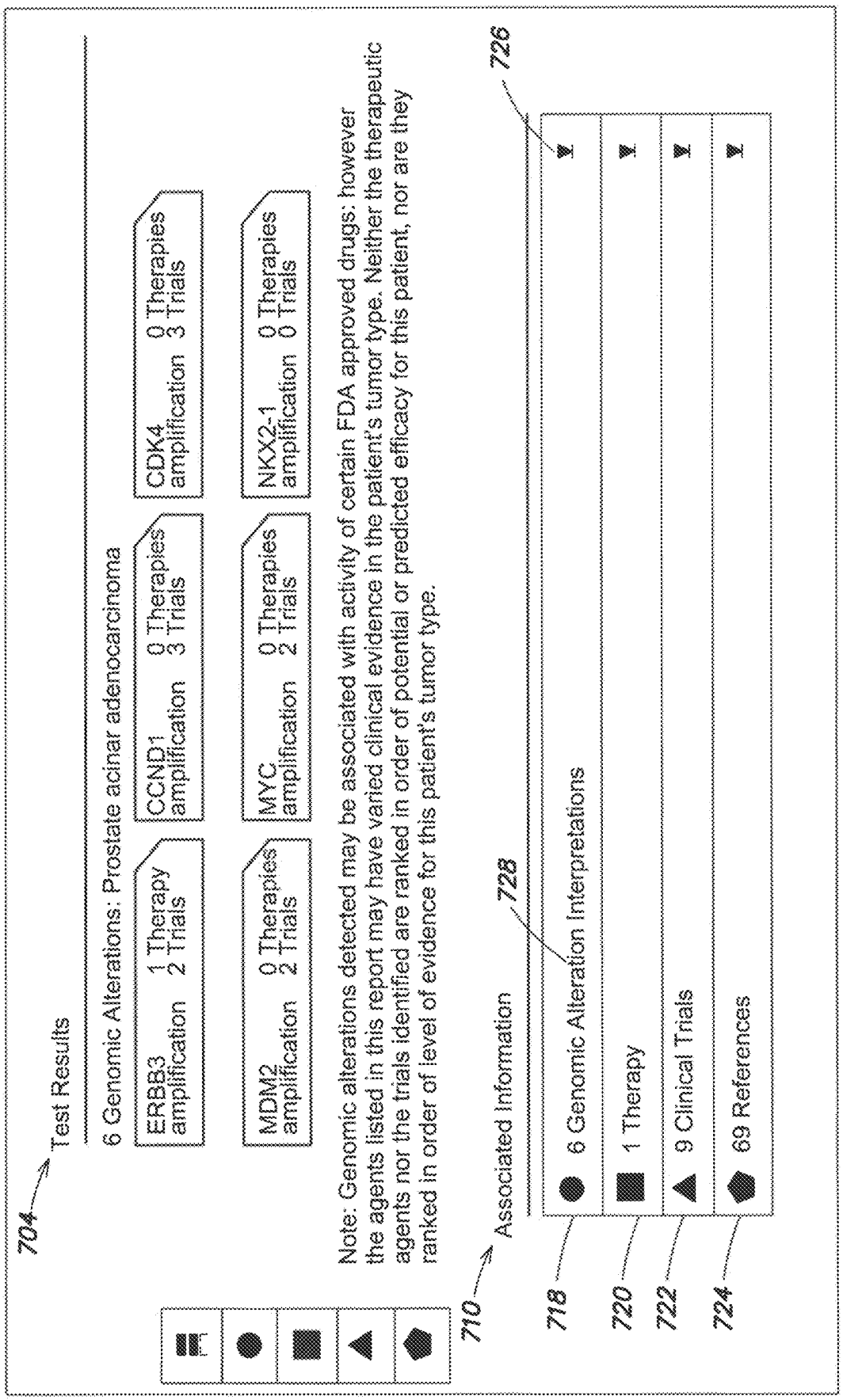
Figure 7D:
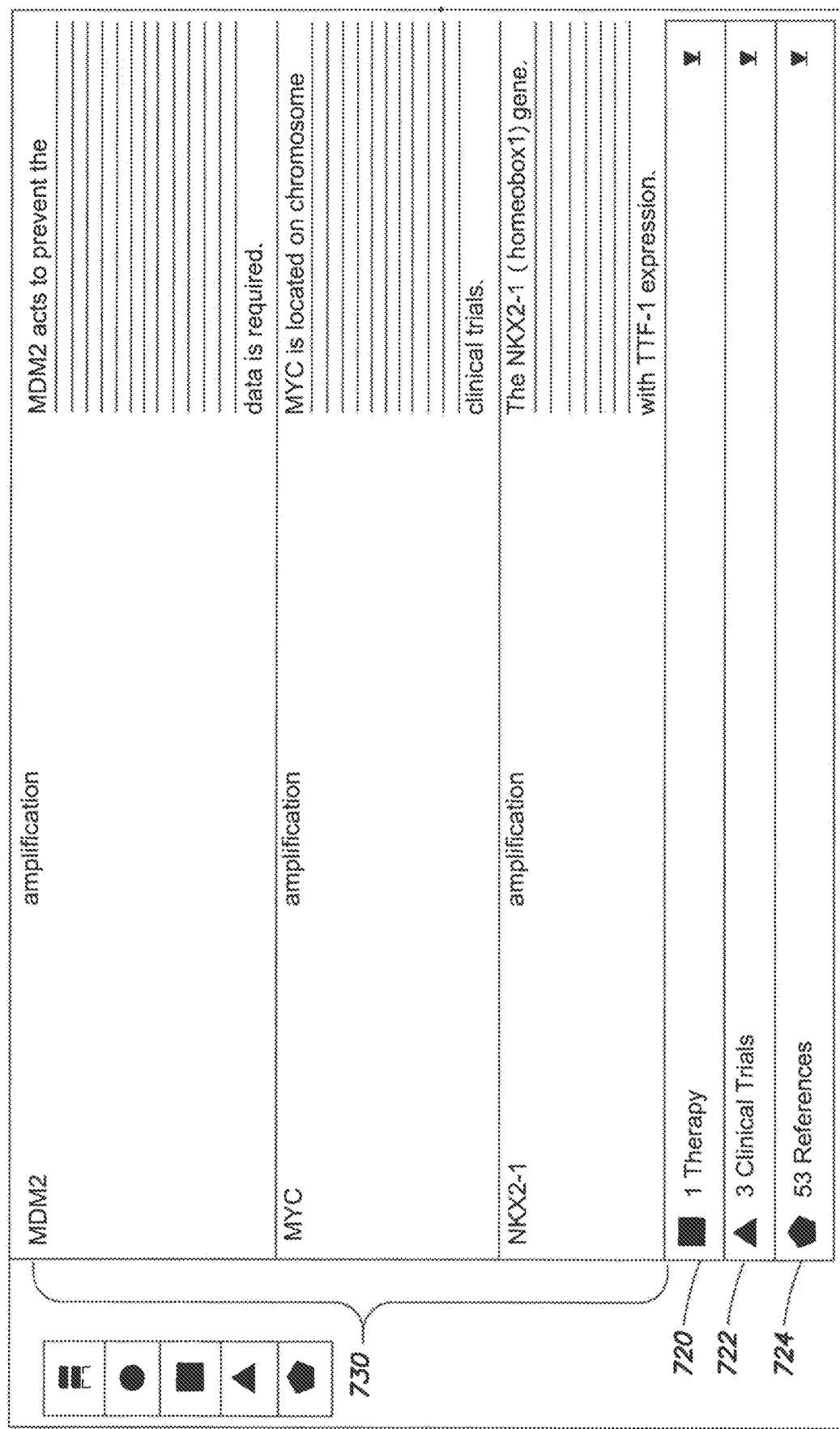

Shown in FIGS. 7C-D is an expanded view of the Genomic Alteration Interpretation Drawer 718. In the example display, each gene and alteration is associated with interpreted statements that provide contextual information regarding the gene/alteration. The contextual information can include, for example, the expression of the gene (e.g., a resulting protein), related genes, genomic family, etc. The interpreted statements can also provide information on frequency of the alteration (e.g., in the general population or a study population), information on related genes/alterations, related therapies, or related clinical trials. In some embodiments, the interpreted statements are included as "curated" information that summarizes and/or provides current medical knowledge and/or analysis of the gene and alteration, whether the knowledge matches the specific tumor type for the patient or not. The curated information can be generated and stored on the system for access by the alteration engine 104 and/or the UI component.

In some embodiments, the alteration engine 104 is configured to generate curated information from various knowledge bases (e.g., ClinicalTrials.gov, PubMed, journal publications, etc.). In one embodiment, the alteration engine 104 can include a curation component configured to capture genomic information for curation. In some embodiments, the alteration engine 104 captures online resources (e.g., clinical studies, journal publications, research documents, academic articles/resource, etc.) pertaining to any one or more of tumor, gene, and alteration. The alteration engine 104 and/or curation component can be configured to present the captured information to a human curator, who creates interpreted statements from the available information. In some embodiments, the alteration engine 104 can be configured to summarize or synthesize online resources into automatically generated interpreted statements. In one embodiment, the alteration engine 104 and/or curation component can be configured to present such interpreted statements to human curators for approval or editing prior to use on the system. In one embodiment, the curation component can automatically identify information items for curation based on keywords (e.g., keywords for tumor type, gene, alteration, and/or therapy). In some implementations, the curation component can parse and capture content from the identified information items. The captured content can be presented to, for example, the human curators for revision and/or approval.

According to one embodiment, each information item within the drawer (e.g., 718) can include a navigation option to provide further detail on a selected information item. For example, row 730A for ERBB3/amplification can be selected in the user interface to transition the system to a detailed view of information on the ERBB3 gene and amplification alteration for the patient's tumor type. In another example, the alteration engine 104 and/or UI component can generate a hyperlink or other navigable element provided in the dynamic display (e.g., at 732) to transition the system to the detailed view. Shown in FIG. 7E is an example detailed view of the gene/alteration/tumor combination. The detailed view can include the interpreted statements shown for the gene and alteration. Further, the detailed view can also include navigation options for transitioning the system to related genomic information. Shown at 734-738 are expandable display elements. Responsive to selection, the expandable display elements can each be independently expanded to provide navigation options. Each navigation option can be grouped according to a respective information source. In some embodiments, the expandable display elements 734-738 can include an indicator of a number of information items within each group (e.g., at 740).

Shown in FIG. 7F is an expanded view of each expansion element 734-738. Each expansion element provides access to a related information source based on the respective grouping (e.g., 734, related therapy, 736, related trial, and 738, related references). In some embodiments, the related therapy group 734 can include therapies that match the patient's tumor type, gene, and alteration as well as therapies that match with any one or more of the three options. In other embodiments, related information can be included in any of the displayed groups 734-738, for example, when the information source matches any one or more of the tumor, gene, and alteration of the current patient.

According to some embodiments, the alteration engine 104 is configured to identify related information for inclusion in the dynamic display 106 and associated views. In one example, the alteration engine 104 can include an analytic subsystem configured to identify matches between tumor type, gene, and/or alteration and includes the matching information items according to display drawers (e.g., at 710). Identification of related information by the analytic subsystem can be employed by the alteration engine 104 and/or the UI component to generate the indication of the number of information items associated with each display drawer (e.g., at 728) and/or in the detailed view expandable elements (e.g., at 740). In some examples, the analytic subsystem and/or alteration engine 104 can maintain counts for each information item within system categories (e.g., therapy, trial, references) and store that information for access within each patient's genomic test report or in a detailed information screen (e.g., at 740).

As discussed, once expanded the expansion elements 734-738 provide navigable links to further detailed information. At 742, provided is a navigable link to a detailed therapy view. In response to selection of 742, for example, in a user interface, the alteration engine 104 and/or UI component causes the system to transition to a detailed view of the Perjeta related therapy. The related trials links at 744-746 and the related references links at 748 are configured to transition the user to external information sources. For example, the related trials links at 744 and 746 are directed to respective clinical trial information sources maintained on the ClinicalTrials.gov website. In another example, the related references links at 748 are configured to transition the user to respective publications maintained at PubMed.gov. In some embodiments, the transition to the external information sources is executed by causing a browser to open a new window or a new tab. The alteration engine 104 and/or UI component can be configured to maintain an active session, for example, in a browser while the user is reviewing external information sources in the new window or tab.

Figure 7G:
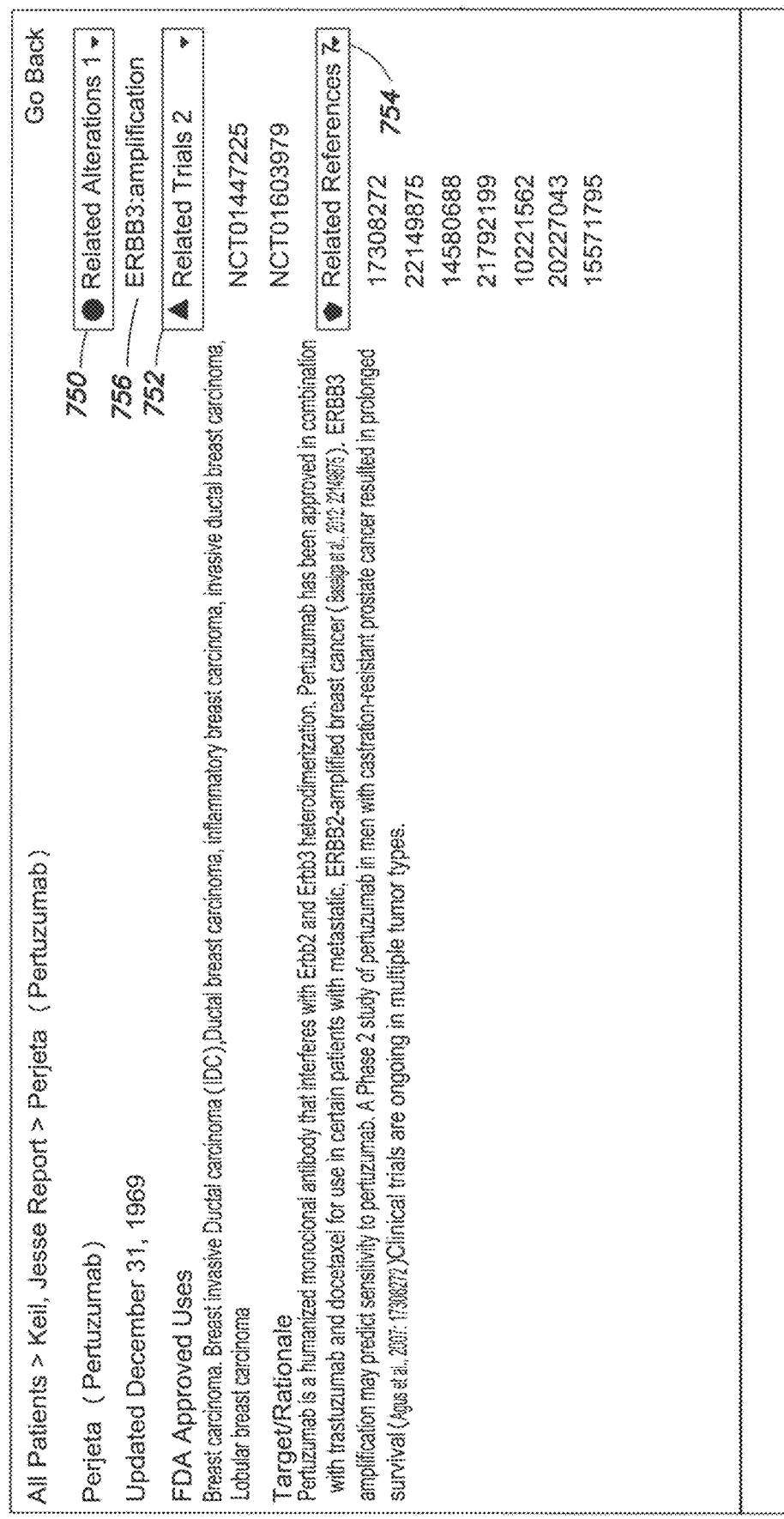

Shown in FIG. 7G is an example detailed therapy view. As discussed above, the detail therapy view can be accessed responsive to selection of 742. The detailed therapy view can also be accessed from an information item display provided with in the therapy drawer 720 (discussed in greater detail below). According to some embodiments, the detailed therapy view describes the details of the therapy, for example, the drug perjeta. The details for the therapy can also include information on the timeframe associated with the descriptive information (e.g., last updated information), which be used by the system to track updates to therapy information. In some embodiments, detailed information for a therapy can include description of any FDA approved uses of the therapy ("on-label" uses). In further embodiments, approved uses can be accompanied by therapy target information and/or rational for applying the therapy to a tumor, gene, and/or alteration. The target/rational information can include interpretive statements, which provide insight into how the therapy is related to a patient, and more specifically to the patient's tumor, gene, and/or alteration.

In the example display of FIG. 7G, illustrated are expansion elements similar to the expansion element of the detailed view of a gene/alteration/tumor combination. According to some embodiments, the expansion elements for Related Trials and Related References (e.g., 752 and 754) can overlap or include the same information sources. In other embodiments, additional information sources can appear as links in either category relative to the detailed view of the gene/alteration/tumor combination. At 750, Related Alterations are displayed as part of the detailed treatment view. Once expanded, the related alterations can include a navigable link 756 directed back to the detailed view of the gene/alteration/tumor of FIG. 7F. In other embodiments, if more than one alteration is matched to perjeta (for example, by the analytic subsystem) additional navigable links would be displayed under 750. As discussed, the user can navigate through a patient's test results and the associated information through a variety of paths.

Figure 7H:
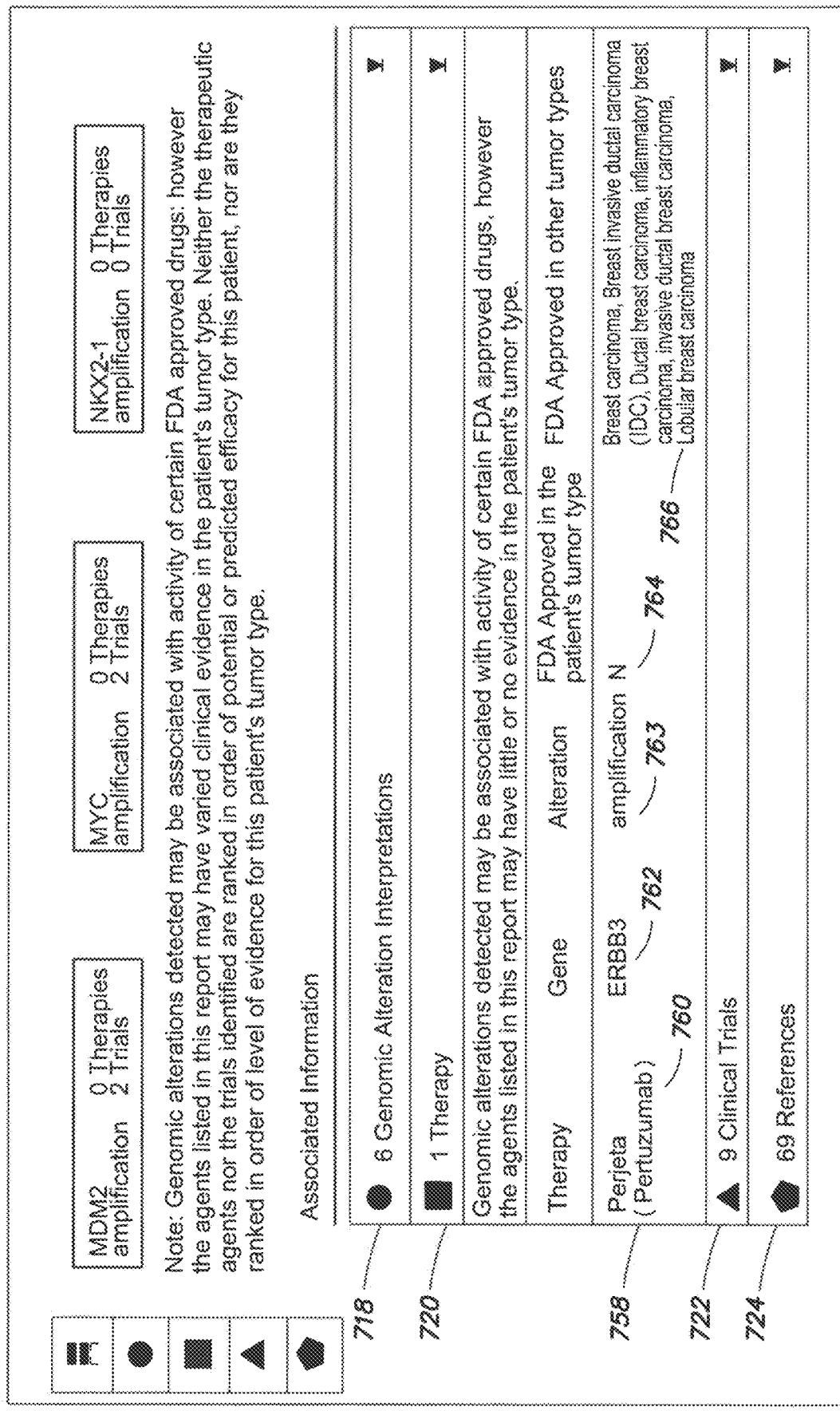
Figure 71:
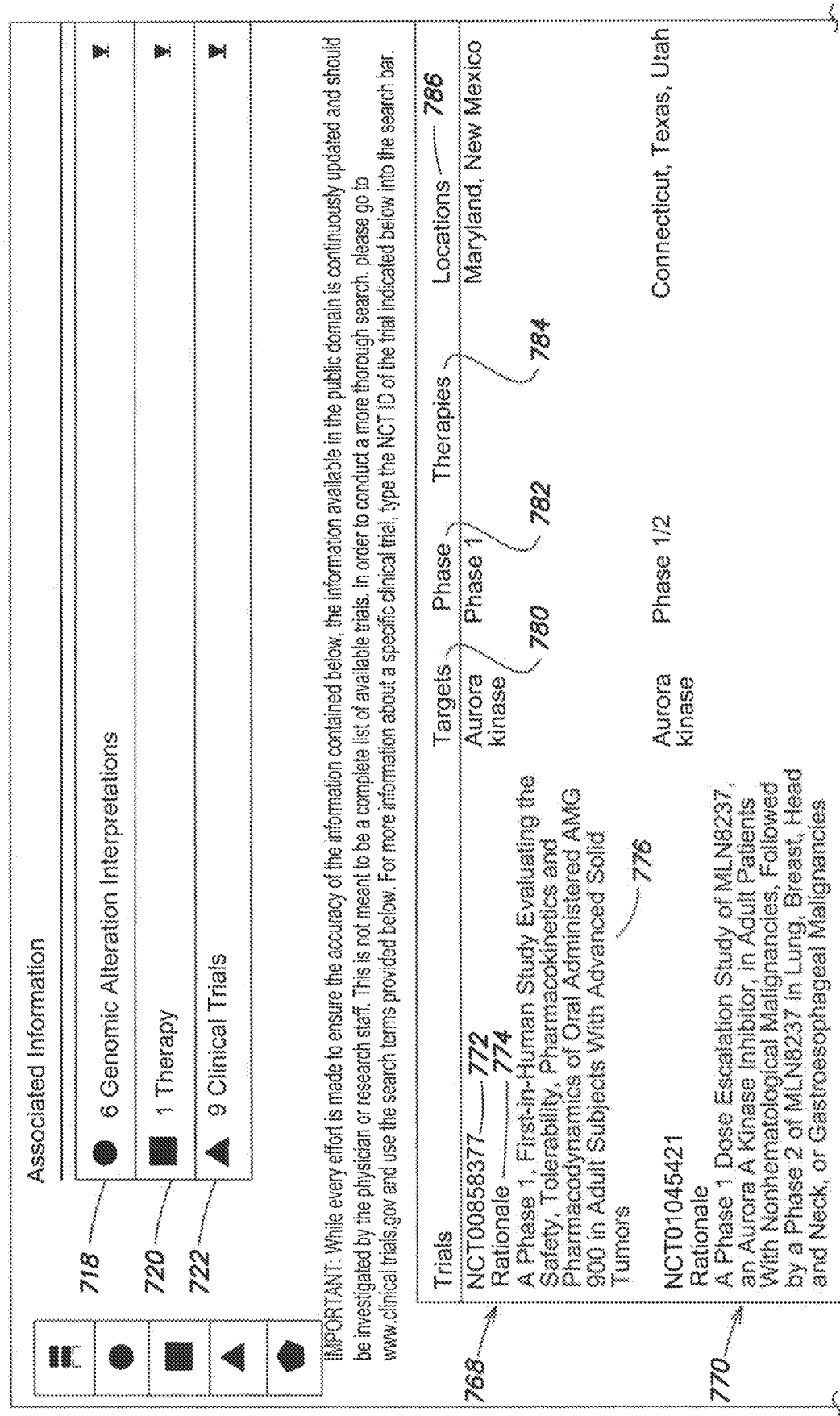

For example, returning to FIG. 7B, drawer 720 can be selected to transition the dynamic display to an expanded view of Therapy drawer 720. Shown in FIG. 7H is an example view of an expanded Therapy drawer. According to one embodiment, within the therapy drawer are all available therapies associated with a patient's cancer. The associated therapies can be identified, for example, by the alteration engine 104 and/or the analytic subsystem based on matching a gene or alteration within the patient's tumor type or in other tumor types. The therapy information item display within the drawer (e.g., at 756) can include an identification for the therapy (e.g., drug name, name of a treatment procedure, combination of drugs, etc.) at 760, the gene (e.g., from the patient's test results) associated with the therapy at 762, the alteration type for the gene at 763, and indicators for whether the therapy has been approved by the FDA within the patient's tumor type at 764, and identification of any tumor types for which the therapy has FDA approval (if any) at 766.

In some embodiments, the gene name and the alteration type identified can also be used to access detailed information views for either the gene or alteration type. For example, 762 and 764 can be selected in a user interface to transition the system to detailed view of the gene/alteration/ tumor combination show in FIG. 7E and to the detailed therapy view shown in FIG. 7G, respectively. According to some embodiments, providing information on FDA approved therapies within a patient's tumor type facilitates on-label uses of approved therapies. In further embodiments, providing information on FDA approved therapies outside of the patient's tumor type provides valuable insight into potential off-label uses, and can facilitate the user's decision making on related but not labeled use of a therapy.

According to some embodiments, the dynamic display is configured for successive navigation through the patient's genomic alterations and the information associated with the patient's genomic alterations. In one example, the user can expand the clinical trial drawer 722 to navigate within the clinical trial information related to the patient's cancer. The user can expand the drawer 722 as an initial selection, or, for example, after viewing information in other drawers. Responsive to selection of the drawer 722, the alteration engine 104 and/or UI component causes the system to transition the dynamic display to an expanded view of the clinical trial drawer 722 (e.g., shown in FIG. 7I).

FIG. 7I shows a portion of an example view of the clinical trial drawer in an expanded state. As shown, only 2 of 9 matching clinical trials are illustrated in the portion of the example view. Each information item (e.g., 768 and 770) within the clinical trial drawer can include common elements. According to one embodiment, the common elements can include a clinical trial identifier 772, which can be selected in the user interface to transition the user to an external information source, for example, ClinicalTrials.gov. In one example, the alteration engine 104 can be configured to transition the user to the external information source through a new browser window or through a new tab opened in a browser program. By opening new windows and/or tabs the user is readily able to transition back to the dynamic display 106 and any view currently shown.

Figure 7J:

In some embodiments, the common element can also include a rational indicator associated with the clinical trial being display. Responsive to selection of the rational indicator at 774 the rational associated with the clinical trial can be displayed as text in an overlay display (e.g., as shown in FIG. 7J, 777). The rational can include specific identification on how the information was obtained (e.g., keyword searching on clinicaltrials.gov including the keywords searched). In some embodiments, the system can provide a link (not shown) associated with the search terms to take the user to the source and the search results obtained. Selection of a close window indicator (e.g., 778) returns the dynamic display to the expanded view of the clinical trial drawer. Other common elements shown in the information items (e.g., 768) can include one or more of: targets associated with the clinical trials (e.g., "Aurora kinase" at 780, a phase associated with the clinical trial at 781, therapies at 784 (if any), location information for the clinical trial at 786, and status for the clinical trial (e.g., recruiting).

In some embodiments, the clinical trial drawer can include filter option displays. The filter operation displays can be configured to accept patient specific criteria (e.g., height, weight, age, tumor type, gene, alteration, sex, prior treatment, current diagnosis, prior outcome, etc.) to return clinical trial information items that match the input criteria.

Once the user has reviewed any clinical trial information she wishes to see, the user may proceed to review references related to the patient's cancer. According to one embodiment, the user can select the references drawer 724 to cause the system to transition the dynamic display 106 to an expanded view of the reference drawer 724. For example, a portion of an expanded view of the reference drawer 724 is shown in FIG. 7K. Each information item with the reference drawer (e.g., 788-794) can include common elements. According to one embodiment, the common element can include a name for the reference at 796, which can include the authors of the reference, the title of the reference, and associated bibliographic information for citing to the reference. Additional common elements can include a link to the reference, for example, at 798. Selection of the link can cause the system to transition to the reference, which may be hosted at a location external to the system. As discussed above, external transitions can be provided through new browser windows and/or tabs, to allow the user to maintain a session with the system.

As discussed above, the dynamic display 106 is configured to provide multiple paths to genomic alteration information, actionable information, and specific information items or views. In some embodiments, the path taken through the dynamic display 106 can impact how the system displays any information within a given view. For example, expansion of one of the drawers at 718-724 provides access to the information items within each group. According to one embodiment, successive selection of another drawer can be configured to close any open drawer as well as to transition the dynamic display to the expanded view of the selected drawer. Further, responsive to selection of a drawer within the dynamic display, each information item within a specific drawer is presented. If the information items within a drawer are accessed from a link (e.g., 712) displayed in a brick (e.g., at 706) from the second portion of the dynamic display (704), then the information items associated with the link (i.e., therapies associated with the ERBB3 gene are highlighted to facilitate review). The system and/or alteration engine 104 can be configured to highlight such associated information items within any drawer accessed (e.g., 718-724) when shown in their respective expanded views.

According to some embodiments, additional drawers can be provided in the dynamic display 106. In one implementation, the third portion of the dynamic display can include an update drawer 800 shown in FIG. 8A. The update drawer 800 organizes updates to any information item presented in a patient report. In some embodiments, the alteration engine 104 is configured to track updates to any information item (e.g., updates to genomic alteration interpretation, new genomic alteration interpretations, revisions to genomic alteration interpretations, new therapies, new approvals for therapies, revisions to approved therapies, new clinical trials, new results for clinical trials, new publications, references, retractions for references, etc.). In some examples, the tracked updates can be organized and presented in an update drawer (e.g., 800). In additional examples, the tracked updates can be identified with a visual indictor (e.g., 802) for a respective drawer having updated information. Each visual indicator for any updates can include information on a number of respective updates (e.g., 803).

In some embodiments, the alteration engine 104 can include an update component configured to track updates to information items associated with a patient's test report. The update component and/or the alteration engine 104 can also be configured to maintain information on the last time a report was accessed to determine what updates have occurred since a last view. The update component can be configured to present such updates within an update drawer. Further, the update component can generate an indicator for each drawer containing updated information (e.g., 802).

Shown in FIG. 8B is an additional view of updates information tracked by the system. FIG. 8B illustrates an updates timeline view accessed, for example, in response to selection of an updates tab at 806. According to one embodiment, the updates timeline view organizes and displays any updates to information items associated with a patient report according to a date for the respective the update. The updates timeline view can also be configured to organize the update information items responsive to categorization. For example, control element can be displayed as part of the updates timeline view at 808. Responsive to selection of 810 Interpretations, 812 Therapies, 814 Trials, and 816 References, updates for information items in each group will be presented at the top of the updates timeline display. FIG. 8D shows another embodiment of an updates timeline display. Some embodiments of the updates timeline display can include a control 818 configured to cause the system to display or hide filters for narrowing or expanding the number of updated information items in the display. Example filters displayed by the system include: update categories at 820, update types at 822, and a temporal filter on displayed updates at 824. Selection within one or more of the filters can be configured to limit the update information items displayed to only those update items matching the filter criteria.

Figure 9D:
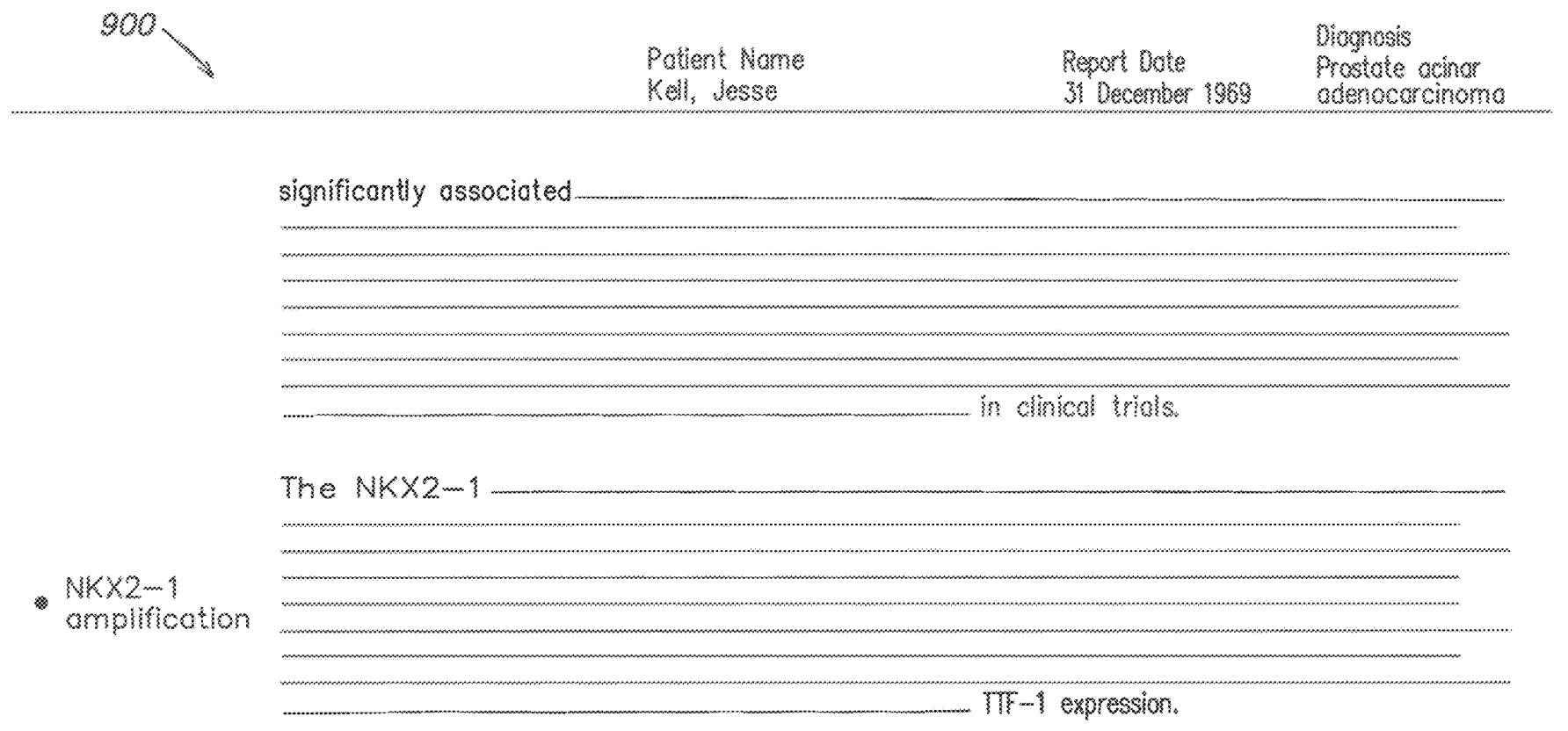

Selection of the displayed updates (e.g. 823 FIG. 9A or 809 FIG. 8C) can be configured to transition the user interface to a detail view of the selected update (e.g., FIG. 8C illustrates a detail view 817 for an EGFR alteration providing information on updates, interpretation, frequency of occurrence, overview information, and relevance to targeted therapies). FIG. 8C can include a selectable option to display an interpretation update history (e.g., 819), where all changes to an interpretation for an alteration can be displayed. Each display drawer (alteration, therapy, trial, and references) can have an updates view for each information item within the respective drawers that provide information on any updates to a respective information item. According to another embodiment, the alteration engine 104 can also be configured to compiled genomic test results and any associated information into static test reports 107. For example, a static test report 107 can be generated by the alteration engine 104 in response to selection of a download control. According to one embodiment, the static report reflect the same organization as the dynamic display 106, however, the static report differs in that all of the associated information reflects the expanded views of each category of associated information (e.g., expanded views of drawers 718-724). An example static report 107 is shown in FIGS. 9A-9N. In further embodiments, users can register to receive static or physical reports that are delivered via mail or fax. In some examples, the user does not access the system to retrieve genomic test results rather the results are delivered as a physical document.

According to one embodiment, the static report can include patient demographic information (e.g., 902—date of birth, gender, case #, medical record #, and id). The static report can also provide summary information on the information contained in the report (e.g., at 904—summary of the genomic alterations found, therapy associated with clinical benefit, therapies associated with lack of response, and clinical trial information, as well as page references for accessing detailed information). In one example, the static report can include summary information on therapies (e.g., at 906—genomic alterations detected, FDA approved therapies (in patient's tumor type), FDA approved therapies (in another tumor type), and potential clinical trials organized by alteration). The static report can include information on genomic alterations at 910 of FIG. 9B-C, detailed information on therapies (e.g., 912), clinical trials to consider at 914 of FIGS. 9E-9I. The static report can also include information on references relied on to generate the report at 916 of FIGS. 9J-9M. In one example, the static report can also include information on the genetic testing performed on the patient and include information on how the report should be utilized (e.g., at 918).

Example Genomic System

Figure 2:
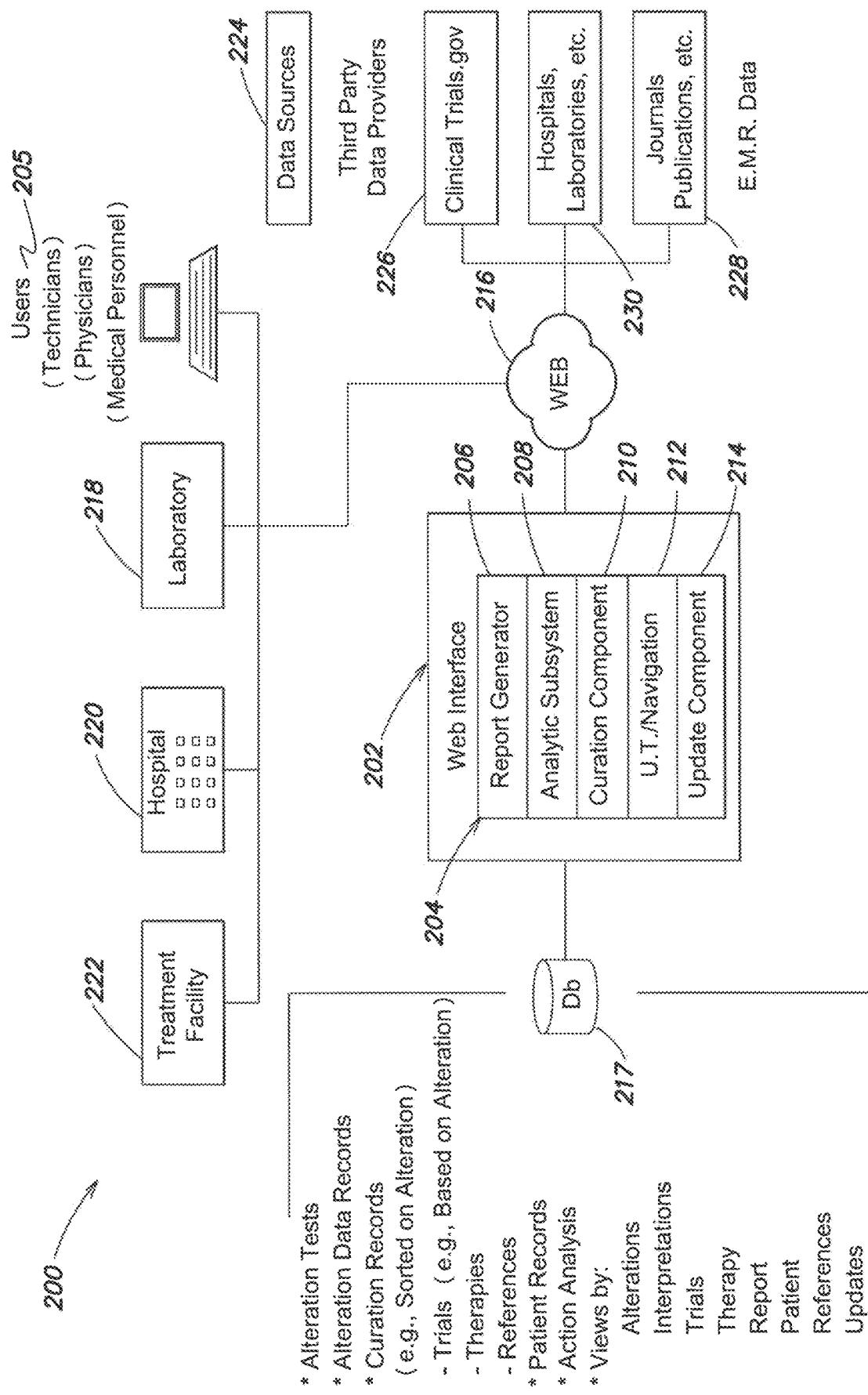
FIG. 2 is a diagram of a system for managing genomic testing information, according to one embodiment.

Show in FIG. 2 is an example embodiment of a system 200 for managing genomic testing information. The system 200 can be configured to provide a single reporting source for accessing and applying available information on a patient's cancer. According to some embodiments, genomic testing on the patient's cancer provides specific information the tumor, one or more genes implicated by the tumor, and one or more alterations within the genes which can be displayed by the system 200 through a web interface 202. In some embodiments, the web interface 202 can include an alteration engine 204 that performs any of the operations discussed above with respect to the alteration engine 104. For example, the web interface and/or alteration engine 204 can be configured to use the testing information on tumor, gene, and alteration for a patient to manage delivery of curated information to end users (e.g., technicians, physicians, medical personal, etc., at 205) over a communication network 216. In one embodiment, the alteration engine 204 can include a UI or navigation component 212 configured to generate displays that focus users (e.g., physicians) on actionable information within the genomic test results and associated information. For example, the UI component 212 can display navigable data structures including information on genes and alterations identified in a genomic test coupled with indicators informing the user of available actionable information associated with a patient's cancer.

According to some embodiments, the alteration engine 204 can include specific component for provide specific functionality on the web interface 202. For example, the alteration engine 204 can also include a report generator component 206 configured to generate physical and/or static report for downloading through the web interface (e.g., shown in FIGS. 9A-9N). The alteration engine 204 can also include an analytic subsystem 208 an analytic subsystem configured to identify matches information between a current patient's tumor type, gene, and/or alteration and include or identify the matching information items for display in the patient's test results.

According another embodiment, the alteration engine can also include a curation component 210 configured to generated curated information for use on the system. The curated information can include interpreted statements regarding any one or more of genomic alterations, an implicated gene, a patient's tumor type, and/or potentially applicable therapies for a patient's cancer. In some examples, the curation component can be accessed by human operators "curators" who generate and/or approve system generated interpreted statement regarding genomic alterations, an implicated gene, a patient's tumor type, and/or potentially applicable therapies.

As discussed, the alteration engine can also include the UI component 212 configured to generate and display navigable data structures (e.g., bricks and drawers) which include information on genes and alterations identified in a genomic test, which can be coupled with indicators for actionable information associated with a patient's cancer. The UI component 212 can transition the system to the actionable information (e.g., therapy information items, trial information items, reference information items) responsive to selection in the user interface.

In further embodiments, the alteration engine can include an update component 214 configured to track any updates to genomic alterations and any information associated with the genomic alterations. In one embodiment, the update component 214 can identify updates information for display by the UI component 212. Various embodiments, of the alteration engine components are configured to perform the function and operations discussed above with respect to the alteration engine 104 and associated components.

According to some embodiments, the web interface 202 can be accessed by users (e.g., 205) over the internet. The user can access the web interface from a variety of location (e.g., laboratory 218, hospital 220, and treatment facility 222). In various embodiments, the users at any one or more of 218-222 can share genomic test reports with each other. For example, the web interface 202 can be configured to provide social functions between users. In some embodiments, the web interface can limit sharing to practice groups, within treatment facilities, or within medical institutions (e.g., hospitals). According to one aspect, sharing of test results and associated genomic information on patients can create a strong community of physicians, and foster discussion about treatment or even specific patients.

According to some embodiments, the web interface 202 stores genomic test information in database 217. Database 217 is illustrated as a single database, but in other embodiments, database 217 can include any storage medium or organizational unit for storing and accessing genomic test results and associated information. Further embodiments can include a plurality of databases and can also include distributed data architectures. According to one embodiment, database 217 can include a variety of data records accessed by the web interface 202 to manage delivery of genomic test results and associated information.

For example, the database can include information on genomic testing. In one example, genomic test results are stored and associated with patient records. The genomic test results can include information on genomic alterations. Specific genomic alterations can be stored in database 217 and access for presenting information within a display of a patient's test report. The database can include curation records stored and associated with any one or more of a tumor type, gene, and/or genomic alteration. Information on clinical trial can likewise be stored as information items associated with any one or more of a tumor type, gene, and/or genomic alteration. The database 217 can also store therapy information and references information and provide associated for either to any one or more of a tumor type, gene, and/or genomic alteration. The database 217 can also be configured to track and store information on updates to any information within the database. In one example, updates can be flagged by other system components and the flags resolved or remove once viewed.

In further embodiments, the database can store information on data views for used by web interface and/or the UI component 212. The views can include, for example, alteration views, genomic interpretation views, clinical trial views, therapy views, static report views, patient record views, references views, and updates views. Each one or more of the views can be accessed and used by the web interface to present information on genomic testing and associated information to a user. In some examples, the system and/or web interface can be configured to capture information from external information sources for storage in database 217. In one example, external data source 224 can contain information related to a patient's tumor type, gene, and/or alteration. The information from the external information can be captured and stored as records in database 217 accessible via the relationship to the tumor type, gene, and/or alteration.

According to some embodiments, the information stored in database 217 can include reference to the external information source. For example, clinical trial information items can include links to clinicaltrials.gov 226, reference information items can include links to PubMed.gov (e.g., 228). In further embodiments, the web interface 202 can be configured to access genomic alteration information for cancer diagnoses made at a hospital or laboratory (e.g., 230). For example, the web interface can capture genomic information from EMR (electronic medical records) to retrieve tumor type, implicated gene, and/or alteration type for storage in database 217. In some implementations, references or links to the specific medical records can also be stored in the database. In one example, the links to the medical records can be presented in a dynamic display generated on system 200.

According to one aspect, the database 217 and all associated information can be organized or accessed based on one or more of tumor type, gene, and alteration. In one embodiment, the tumor type, gene, and alteration data is stored as a data unit (e.g., a tuple). The data unit can be used by the system to identify or display related information based on matching any one or more of the tumor type, gene, and alteration. In further embodiments, each data unit can be linked to actionable information (where it exists). For example, each data unit can be linked to a matching therapy (e.g., a therapy information item describing a specific therapy, application, etc.). In another example, data units can be linked to a matching clinical trial (e.g., stored as a clinical trial information item).

According to one embodiment, associated of all the information in the database according to tumor, gene, or alteration provides insight into prescribed uses of therapies (on-label) and off-label applications for such therapies. In one example, off-label used can be identified based on alteration (e.g., different tumors but same alteration—provides relation information on a potentially effective therapy the current patient's cancer.

According to another embodiment, each record can be associated with a data space for an update flag. Responsive to any update to information on the database 217, the system can enter information in the data space for the update flag. Tracking updates to genomic alteration and associated information facilitates user awareness of potential significant changes in a patient report. Further, tracking of update information in the database 217 enables the system to deliver notification regarding any updates.

In some further embodiment, social functions can have associated records in the database. For example, permission information (e.g., who can share a report and/or who can receive a shared report) can be associated with test reports stored in database 217.

Figure 3:
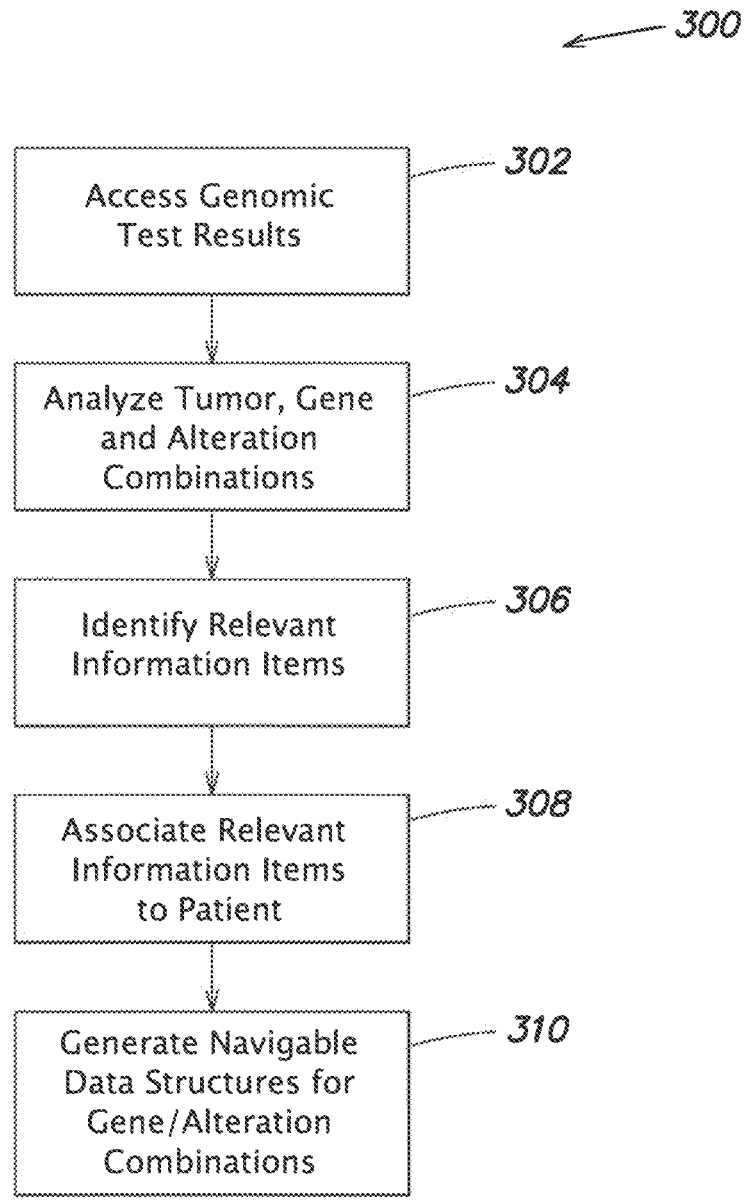
FIG. 3 is an example process flow for a method of managing genomic testing information, according to one embodiment.

According to some embodiments, the web interface 202 can implement a variety of function and processes for managing delivery of genomic test results and any associated information. FIG. 3 shows an example process flow 300 for managing genomic testing information. The process 300 begins at 302 with access to genomic test results. According to one embodiment, genomic test results include information specific to a patient's tumor type, one or more genes implicated by the tumor, and alteration type associated with the one or more gene. At 304, the tumor type, gene, and alteration combinations for the patient's cancer are analyzed, and relevant information items are identified at 306.

In some embodiments, the relevant data items can include clinical trials that match on any one or more of tumor type, gene, and alteration. The relevant data items can also include therapies or references that match on tumor, gene, and/or alteration. In some example, the relevant data items are stored for analysis at 304 based on activity of curators. In one example, human curators can review clinical trial information (e.g., criteria, gene/alteration target, trial therapy, trial drug) and associate that clinical trial information with tumor types, genes, and/or alterations. The human curators can also review and characterize information on therapies and reference for use in, for example, process 300.

Once relevant information is identified, for example, at 306, any relevant information item can be associated with the patient having the matching tumor type, gene, and/or alteration at 308. The association(s) defined at 308 can be used at 310 to generate navigable data structures which can be configured to organize gene and alteration combinations and links to any associated relevant information (e.g., identified at 306 and associated at 308). In some embodiments, the navigable data structures can be presented in user interface display In other embodiments, the relevant information identified at 306 can be associated with patient records and/or specific genomic tests at 308 based on a specified data model. Further, association of the relevant information at 308 can include generation and storage of the associated information a data unit (e.g., information item) and the data unit can then be associated with the patient, and/or a gene or alteration in the patients genomic test results through a navigation link. The navigation link can be used as part of a dynamic display for a specific gene/alteration combination. Responsive to selection of the link, the dynamic display can transition to the relevant information.

Figure 4:
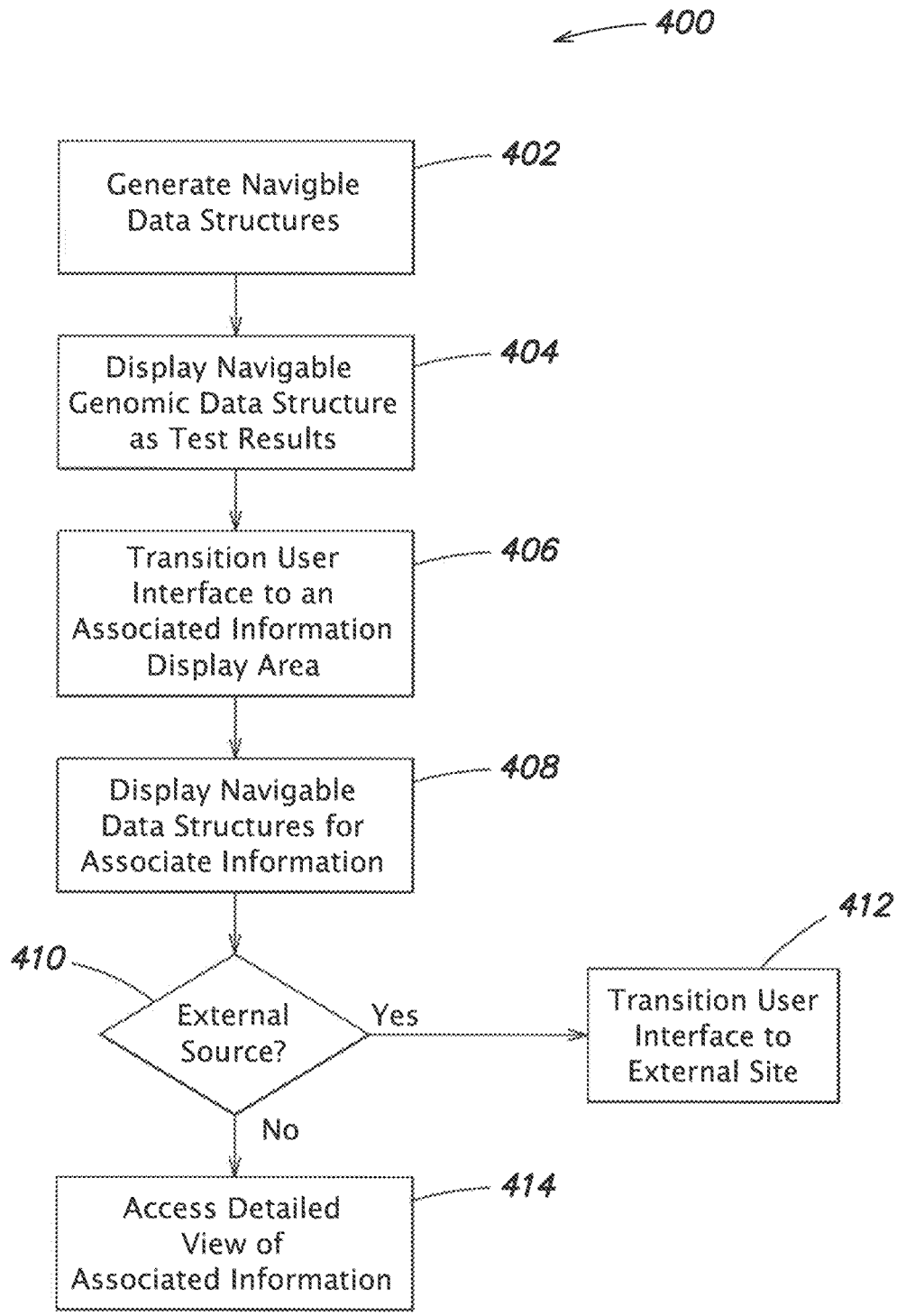
FIG. 4 is an example process flow for a method of navigating genomic testing information, according to one embodiment.

FIG. 4 shows an example process 400 for navigating through genomic testing information. The process 400 begins at 402 with generation of navigable data structures. In some embodiments, the navigable data structures can be generated by other processes (e.g., process 300) and accessed at 402 rather than being generated at 402. The navigable data structures can be generated or accessed based on genomic test results for a current patient. In one embodiment, a genomic data structure is generated or accessed for each genomic alteration identified in the current patient's cancer cells. In other embodiments, navigable data structures can be accessed or generated for any associated information relevant to each genetic alteration at 402. In some examples, the associated information can include relevant therapies, relevant clinical trials, and/or relevant references.

At 404, each genomic data structure is displayed. The genomic data structures can be displayed in a first portion of a user interface. Each of the genomic data structures is configured to access associated information relevant to the genomic alteration stored as part of the genomic data structure. For example, each genomic data structure includes specification of a gene (e.g., by name) and an alteration type for the gene found in the patient's cancer cell. At 406, responsive to selection of one of the genomic data structures, the user interface transitions to an associated information display area. In some embodiments, the associated information display area can include organization of associated information data structures by information type. In some examples, the organization by information type includes drawers for each type configured to expand upon access to the contents (and type) organized within the drawer. Depending on the selection within the genomic data structure, the transition to the associated information display area can include a transition to a specific category of information (e.g., genomic alternation interpretations, therapies, clinical trials, references, and updates). Within the associated information display area, associated information data structures are displayed at 408.

Each of the associated information data structures can also be navigable. Responsive to selection of the associated information data structures, the user interface can transition to additional information on the selected associated information data structure. The transition invoked depends on the source/target of the associated information data structure. If the associated information structure includes an external target, for example, an external website, selection of the external information source at 410 YES, results in a transition of the user interface to the external site at 412. In one example, the external site can include ClinicalTrials.gov or PubMed.gov, among other options.

If the target of the associated information data structure is not external 410 NO, selection of the associated information data structure results in a transition to a detailed view of the associated information at 414. For example, depending on the associated information data structure and/or a target selected within the structure, the transition can be made to a detailed view of therapy information (e.g., FIG. 7G) or a detailed view of a gene/alteration combination (e.g., FIG. 7E).

According to some embodiments, process 400 is intended for successive execution to transition between and within genomic data structures, associated information data structures, detailed views, and external information locations. For example, steps 406-408 can be repetitively executed for each one of a plurality of genomic data structures and/or steps 408-414 can be repetitively executed to access each one or some of a plurality of associated information data structures.

Further, either process 400 or 300 can be executed on various systems or can be executed by various system components.

Example Computer Systems

Various aspects, functions, components, and/or processes described herein may be implemented as hardware, software, or a combination of hardware and software on one or more computer systems. There are many examples of computer systems currently in use. Some examples include, among others, network appliances, personal computers, workstations, mainframes, networked clients, servers, media servers, application servers, database servers, web servers, and virtual servers. Other examples of computer systems may include mobile computing devices, such as cellular phones and personal digital assistants, and network equipment, such as load balancers, routers and switches. Additionally, aspects in accord with the present invention may be located on a single computer system or may be distributed among one or more computer systems connected to one or more communication networks.

For example, various aspects and functions may be distributed among one or more computer systems configured to provide a service to one or more client computers, or to perform an overall task as part of a distributed system. Additionally, aspects may be performed on a client-server or multi-tier system that includes components distributed among one or more server systems that perform various functions. Thus, the invention is not limited to executing on any particular system or group of systems. Further, aspects may be implemented in software, hardware or firmware, or any combination thereof. Thus, aspects in accord with the present invention may be implemented within methods, acts, systems, system placements and components using a variety of hardware and software configurations, and the implementation is not limited to any particular distributed architecture, network, or communication protocol. Furthermore, aspects in accord with the present invention may be implemented as specially-programmed hardware and/or software.

Figure 5:
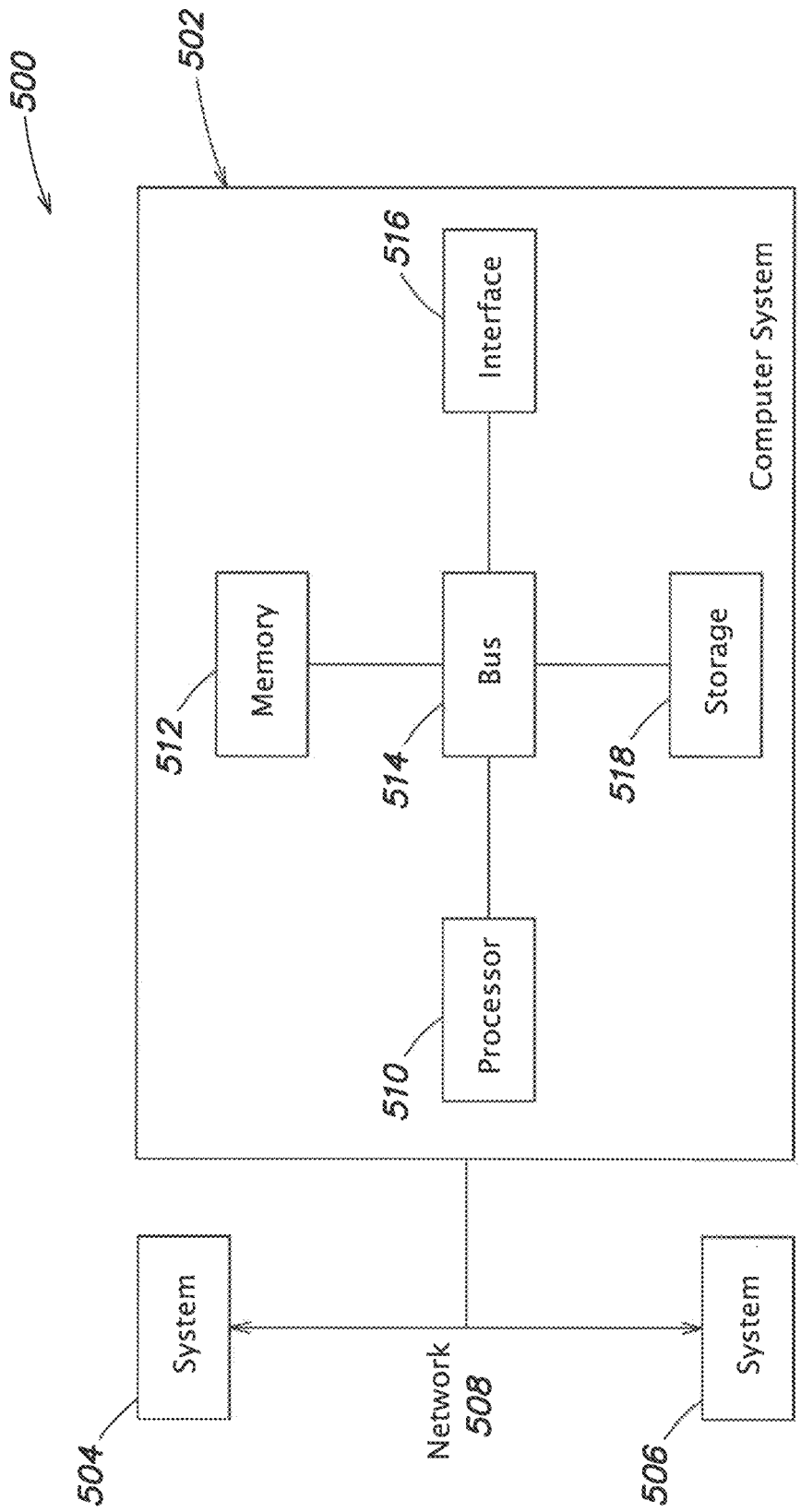
FIG. 5 is a block diagram of one example of a computer system that may be used to perform processes and functions disclosed herein.

FIG. 5 shows a block diagram of a distributed computer system 500, in which various aspects and functions in accord with the present invention may be practiced. The distributed computer system 500 may include one or more computer systems. For example, as illustrated, the distributed computer system 500 includes three computer systems 502, 504 and 506. As shown, the computer systems 502, 504 and 506 are interconnected by, and may exchange data through, a communication network 508. The network 508 may include any communication network through which computer systems may exchange data. To exchange data via the network 508, the computer systems 502, 504, and 506 and the network 508 may use various methods, protocols and standards including, among others, token ring, Ethernet, Wireless Ethernet, Bluetooth, TCP/IP, UDP, HTTP, FTP, SNMP, SMS, MMS, SS7, JSON, XML, REST, SOAP, CORBA HOP, RMI, DCOM and Web Services.

Computer systems 502, 504 and 506 may include mobile devices such as cellular telephones, tablets, touch screen devices, etc. The communication network may further employ one or more mobile access technologies including 2nd (2G), 3rd (3G), 4th (4G or LTE) generation radio access for cellular systems, WLAN, Wireless Router (WR) mesh, and other communication technologies. Access technologies such as 2G, 3G, 4G and LTE and future access networks may enable wide area coverage for mobile devices. For example, the network may enable a radio connection through a radio network access such as Global System for Mobil communication (GSM), General Packet Radio Services (GPRS), Enhanced Data GSM Environment (EDGE), Wideband Code Division Multiple Access (WCDMA), among other communication standards. Network may include any wireless communication mechanism by which information may travel between the devices 504 and other computing devices in the network.

To ensure data transfer is secure, the computer systems 502, 504 and 506 may transmit data via the network 508 using a variety of security measures including TSL, SSL or VPN, among other security techniques. While the distributed computer system 500 illustrates three networked computer systems, the distributed computer system 500 may include any number of computer systems, networked using any medium and communication protocol.

Various aspects and functions in accord with the present invention may be implemented as specialized hardware or software executing in one or more computer systems including the computer system 502 shown in FIG. 5. As depicted, the computer system 502 includes a processor 510, a memory 512, a bus 514, an interface 516 and a storage system 518. The processor 510, which may include one or more microprocessors or other types of controllers, can perform a series of instructions that manipulate data. The processor 510 may be a well-known, commercially available processor such as an Intel Pentium, Intel Atom, ARM Processor, Motorola PowerPC, SGI MIPS, Sun UltraSPARC, or Hewlett-Packard PA-RISC processor, or may be any other type of processor or controller as many other processors and controllers are available. As shown, the processor 510 is connected to other system placements, including a memory 512, by the bus 514.

The memory 512 may be used for storing programs and data during operation of the computer system 502. Thus, the memory 512 may be a relatively high performance, volatile, random access memory such as a dynamic random access memory (DRAM) or static memory (SRAM). However, the memory 512 may include any device for storing data, such as a disk drive or other non-volatile storage device, such as flash memory or phase-change memory (PCM). Various embodiments in accord with the present invention can organize the memory 512 into particularized and, in some cases, unique structures to perform the aspects and functions disclosed herein.

Components of the computer system 502 may be coupled by an interconnection element such as the bus 514. The bus 514 may include one or more physical busses (for example, busses between components that are integrated within a same machine), and may include any communication coupling between system placements including specialized or standard computing bus technologies such as IDE, SCSI, PCI and InfiniBand. Thus, the bus 514 enables communications (for example, data and instructions) to be exchanged between system components of the computer system 502.

Computer system 502 also includes one or more interfaces 516 such as input devices, output devices and combination input/output devices. The interface devices 516 may receive input, provide output, or both. For example, output devices may render information for external presentation. Input devices may accept information from external sources. Examples of interface devices include, among others, keyboards, mouse devices, trackballs, microphones, touch screens, printing devices, display screens, speakers, network interface cards, etc. The interface devices 516 allow the computer system 502 to exchange information and communicate with external entities, such as users and other systems.

Storage system 518 may include a computer-readable and computer-writeable nonvolatile storage medium in which instructions are stored that define a program to be executed by the processor. The storage system 518 also may include information that is recorded, on or in, the medium, and this information may be processed by the program. More specifically, the information may be stored in one or more data structures specifically configured to conserve storage space or increase data exchange performance. The instructions may be persistently stored as encoded signals, and the instructions may cause a processor to perform any of the functions described herein. A medium that can be used with various embodiments may include, for example, optical disk, magnetic disk or flash memory, among others. In operation, the processor 510 or some other controller may cause data to be read from the nonvolatile recording medium into another memory, such as the memory 512, that allows for faster access to the information by the processor 510 than does the storage medium included in the storage system 518. The memory may be located in the storage system 518 or in the memory 512. The processor 510 may manipulate the data within the memory 512, and then copy the data to the medium associated with the storage system 518 after processing is completed. A variety of components may manage data movement between the medium and the memory 512, and the invention is not limited thereto.

Further, the invention is not limited to a particular memory system or storage system. Although the computer system 502 is shown by way of example as one type of computer system upon which various aspects and functions in accord with the present invention may be practiced, aspects of the invention are not limited to being implemented on the computer system, shown in FIG. 5. Various aspects and functions in accord with the present invention may be practiced on one or more computers having different architectures or components than that shown in FIG. 5. For instance, the computer system 502 may include specially-programmed, special-purpose hardware, such as for example, an application-specific integrated circuit (ASIC) tailored to perform a particular operation disclosed herein. Another embodiment may perform the same function using several general-purpose computing devices running MAC OS System X with Motorola PowerPC processors and several specialized computing devices running proprietary hardware and operating systems.

The computer system 502 may include an operating system that manages at least a portion of the hardware placements included in computer system 502. A processor or controller, such as processor 510, may execute an operating system which may be, among others, a Windows-based operating system (for example, Windows NT, Windows 2000/ME, Windows XP, Windows 7, or Windows Vista) available from the Microsoft Corporation, a MAC OS System X operating system available from Apple Computer, one of many Linux-based operating system distributions (for example, the Enterprise Linux operating system available from Red Hat Inc.), a Solaris operating system available from Sun Microsystems, or a UNIX operating systems available from various sources. Many other operating systems may be used, and embodiments are not limited to any particular operating system.

The processor and operating system together define a computing platform for which application programs in high-level programming languages may be written. These component applications may be executable, intermediate (for example, C# or JAVA bytecode) or interpreted code which communicate over a communication network (for example, the Internet) using a communication protocol (for example, TCP/IP). Similarly, functions in accord with aspects of the present invention may be implemented using an object-oriented programming language, such as SmallTalk, JAVA, C++, Ada, or C# (C-Sharp). Other object-oriented programming languages may also be used. Alternatively, procedural, scripting, or logical programming languages may be used.

Additionally, various functions in accord with aspects of the present invention may be implemented in a non-programmed environment (for example, documents created in HTML, XML or other format that, when viewed in a window of a browser program, render aspects of a graphical-user interface or perform other functions). Further, various embodiments in accord with aspects of the present invention may be implemented as programmed or non-programmed placements, or any combination thereof. For example, a web page may be implemented using HTML while a data object called from within the web page may be written in C++. Thus, the invention is not limited to a specific programming language and any suitable programming language could also be used.

It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

Example Web Site for Managing Genomic Testing Results

Figure 6:
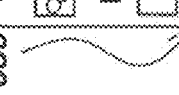
FIG. 6 is an example user interface, according to one embodiment.
Figure 32A:
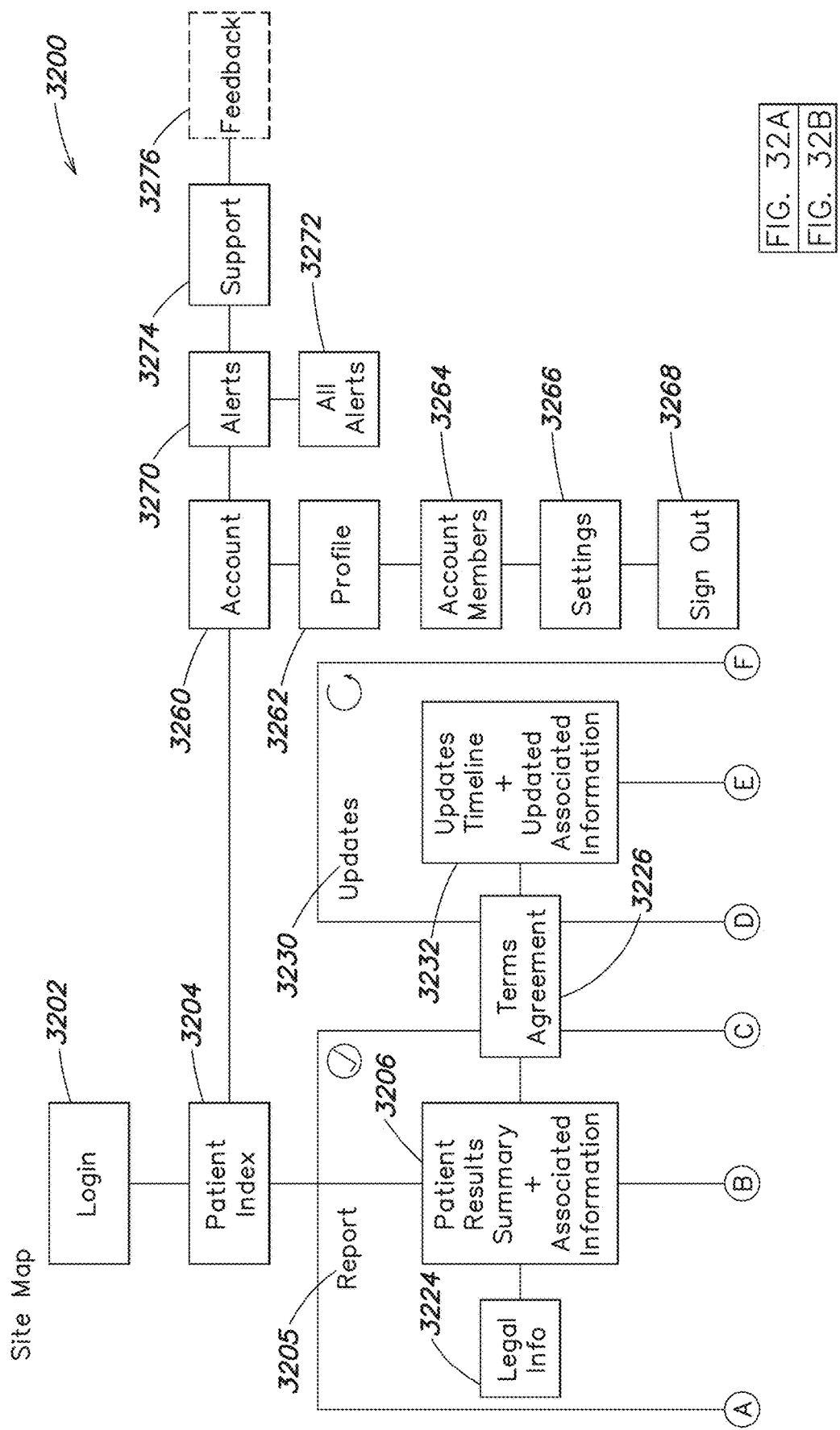
FIG. 32A-B illustrate an example site map, according to one embodiment.
Figure 32B:
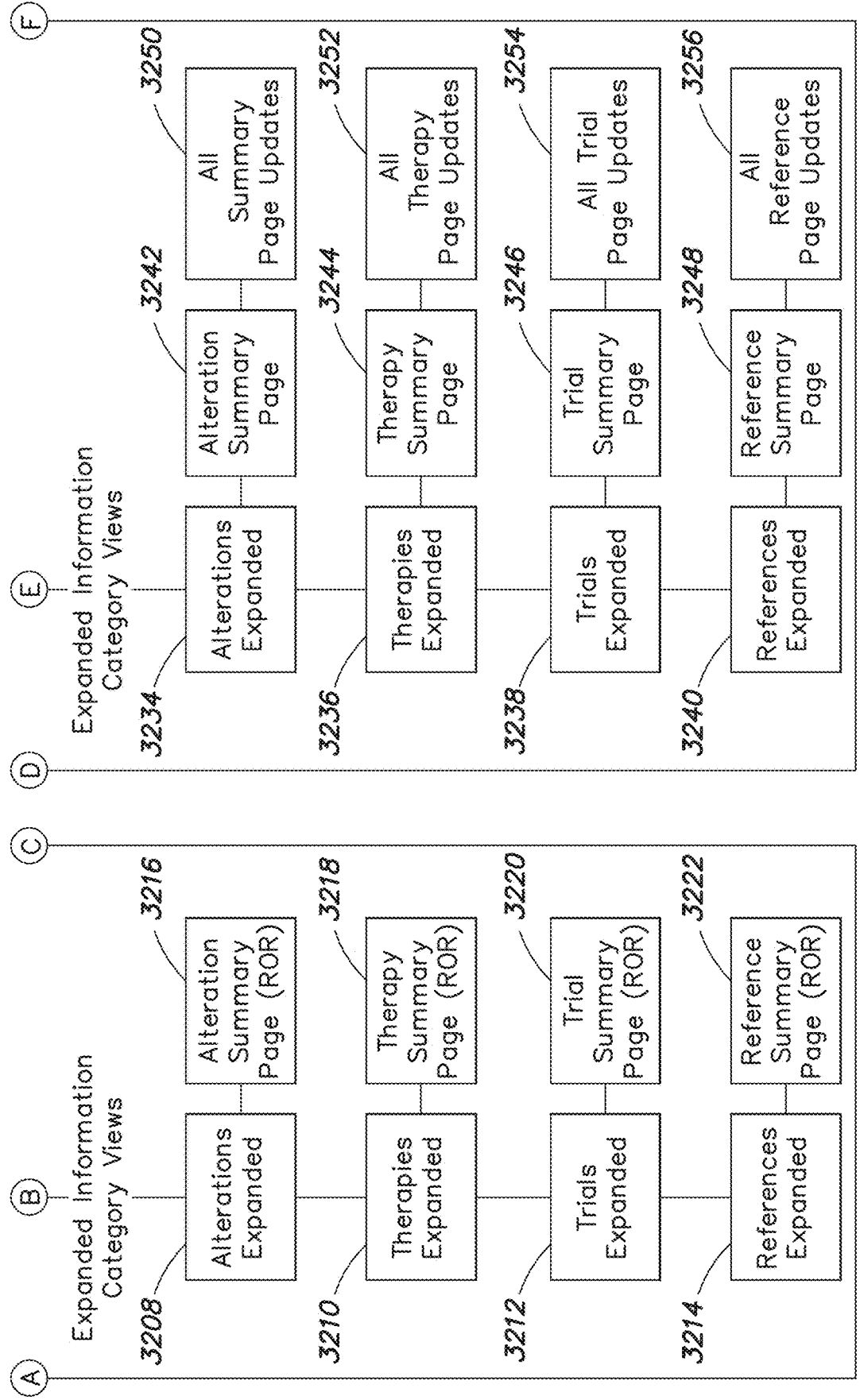

FIG. 32 illustrates an example site map 3200 for a genomic testing website according to one embodiment. Site map 3200 details examples of pages and transitions that are made available by the genomic testing website. According to one embodiment, the website can be accessed via a login page 3202. Once logged into the site, a user is directed to a patient index page 3204 (e.g., FIG. 6 illustrates an example index page). Selecting a patient from the index page directs the user interface into a patient results summary and associated information page 3206 (e.g., FIG. 7A-B illustrate an example results summary page). Selection of an information drawer with the information page allows the user to expand the information displayed for each category. For example, the user can access expanded views for alterations 3208 (e.g., FIG. 7C-D illustrate an expanded view of alterations), therapies 3210 (e.g., FIG. 7I illustrates an example expanded therapy view), trials 3212 (e.g., FIG. 7J illustrates an example trials expanded view), and references 3214 (e.g., FIG. 7L illustrates an example references expanded view).

Selection within the expanded view causes a transition in the user interface to a respective summary page. For example, selection within the alteration expanded view 3208 causes a transition to an alteration summary page 3216 (e.g., FIG. 7E illustrates an example alteration summary page). In another example, selection within the therapies expanded view 3210 causes a transition to a therapy summary page (e.g., FIG. 7H illustrates an example therapy summary page). In another example, selection within the trials expanded view transitions the user interface to a trial summary page for the selected trial (e.g., FIG. 33 illustrates an example trial summary page). In a further example, selection within the references expanded view transitions the user interface to a reference summary view 3222 (e.g., FIG. 34 illustrates an example reference summary view).

Views 3206-3214 are grouped into a patient report 3205. Additional information can be made available in the report. For example, a legal information page 3224 can be accessed from the view of the report 3205. The legal information page 3224 can include information on the diagnostic purposes of the report and the genomic testing process. The user can also access information on terms of use of the site 3226 from the report page 3205.

FIGS. 8A and 8E show another example report page including links to updates associated with the report page 3205. In one embodiment, selection of the updates transitions the user interface to an updates page 3230 and including an updates timeline and associated information view 3232 (e.g. FIG. 8B illustrates an example view of an updates timeline and associated information page). The updates timeline view 3232 can also be associated with expanded views including: alterations expanded view 3234 (e.g., FIG. 8B); therapies expanded view 3236; trials expanded view 3238; and references expanded view 3240. Each expanded view is associated with a respective summary page: alteration summary page 3242; therapy summary page 3244; trial summary page 3246; and reference summary page 3248. Each summary includes links to an all updates view including all summary page updates for a respective category (e.g., 3250—all summary page updates, 3252—all therapy page updates, 3254—all trial page updates, and 3256 all reference page updates).

FIG. 32 shows a site map 3200 which provides access to system pages. The system pages provide user access to account information 3260, user profile information 3262, account members 3264, account settings 3266, and sign-out functions 3268. In addition, the user can access pages for defining general user preferences, e.g., on system alerts (e.g., FIG. 35 shows an example user interface for defining system alert preferences generally and FIG. 36 shows an example user interface for defining alerts on a patient basis). The alerts setting pages can be used to access any alerts (e.g., 3270) for a user account, for example, at 3272. The site can also include pages for support 3274 and user feedback 3276.

Figure 37:
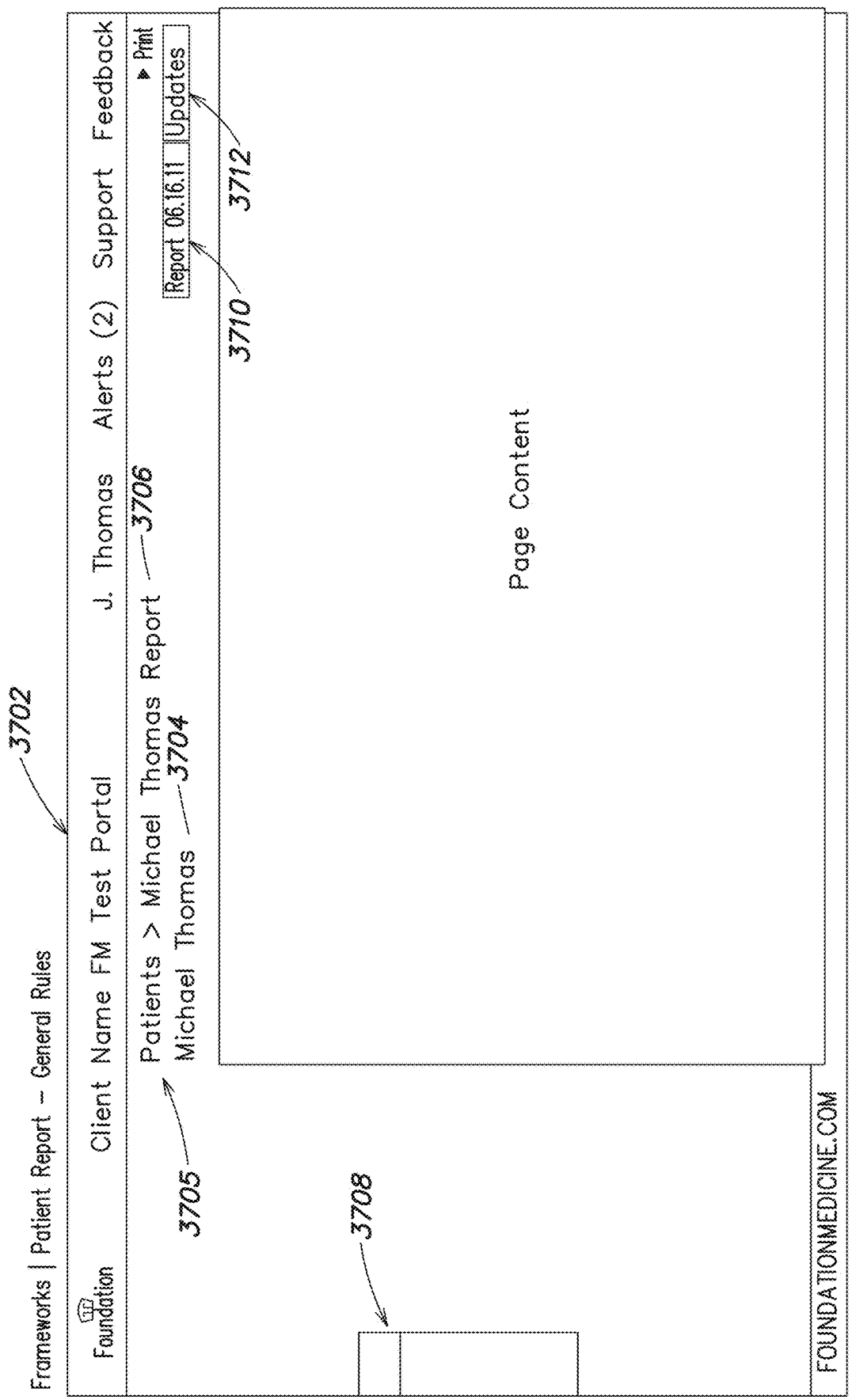
FIG. 37 illustrates an example general framework design for a genomic user interface, according to one embodiment.

FIG. 37 is a general framework design for an example user interface 3700, according to one embodiment. At 3702, the UI can include a global header display. The global elements within the display can include user name, alerts, support, and feedback. The global header can change based on a user state. For example, if the user is logged in, the global header may display in a logged in state. In another example, if a user is not logged in the global header may display in a logged out state (e.g., eliminating the user name, account alerts, support and feedback options). Other global elements can include a page title at 3704 "Michael Thomas" and a breadcrumb trail at 3706 in a page header area 3705. The breadcrumb trail can include links to previous pages traversed to arrive at a current view (e.g., 3700). In some embodiments, global elements can be displayed to filter content view (e.g., shown in FIG. 6) depending on the content displayed. In other embodiments, the global elements can include jump menus for navigating within the content displayed on a page (e.g., at 3708). Upon accessing a specific patient, the patient's information can be displayed in a "report mode" indicated at 3710. The report mode provides access to all information contained in a genomic test report. Where updated information associated with a report is available, an update icon is displayed at 3712.

Figure 38C:
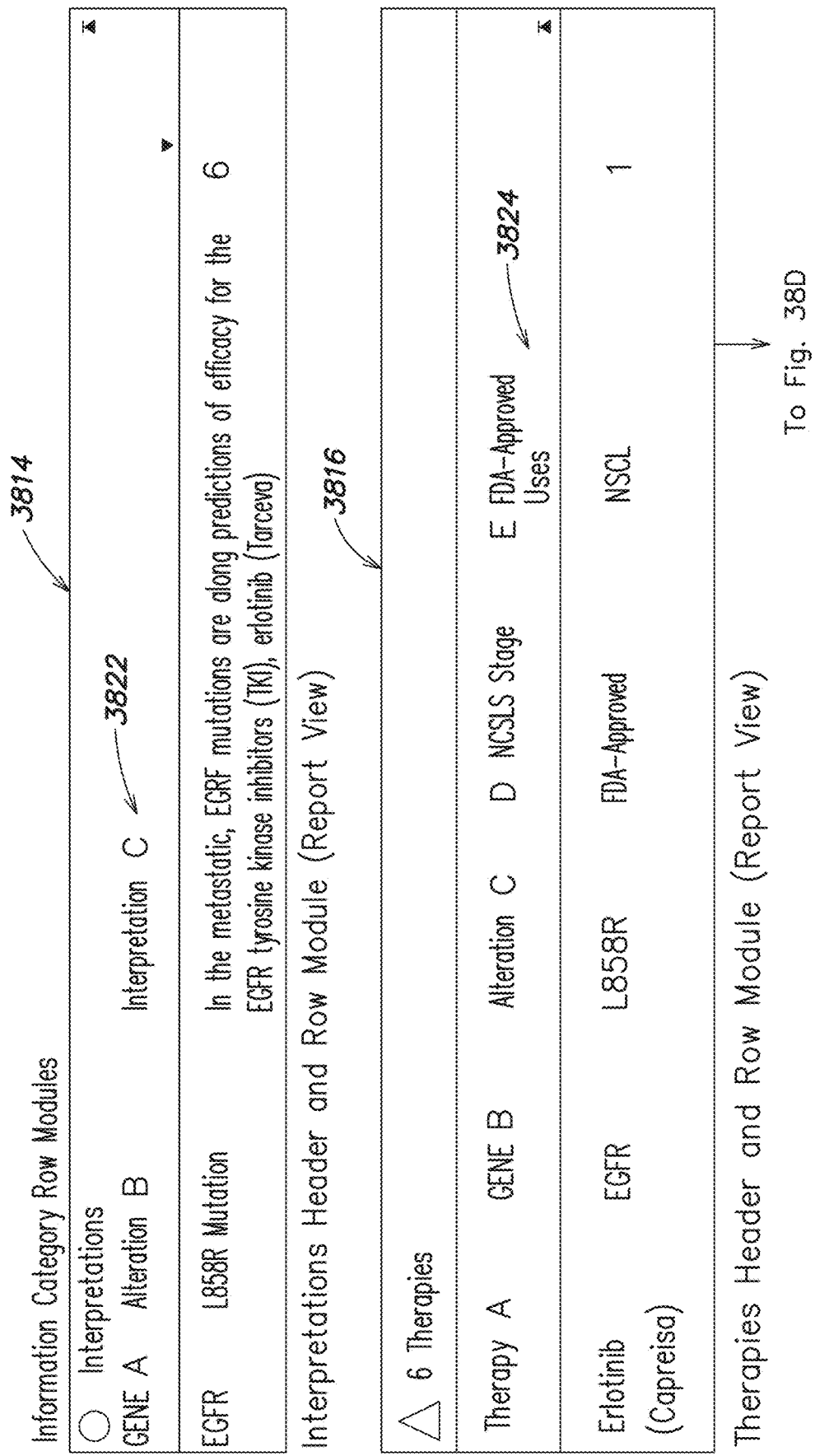

The content that is displayed can be in a variety of formats. Example content items are shown in FIG. 38. A patient index table 3802 can be displayed within a patient index view. In another example, displayed content can include an updates timeline view 3804. The updates timeline view can be organized and/or sorted based on information categories (e.g., interpretations—3806, therapies—3808, trials—3810, and references—3812). Rows within each information category can be displayed in as shown at 3814-3820. Each row can also include sort functionality to enable sorting based on displayed columns (e.g., 3822A-C, 3824A-E, 3826A-G, and 3828A-B).

FIG. 39 illustrates another example page accessible via a genomic report. Page 3900 displays summary content (e.g., 3804 of FIG. 38) associated with an updates timeline 3902. At 3904 information category filters may be engaged by selection within the user interface. Selection of a category changes the display of the filters.

Figure 40A:
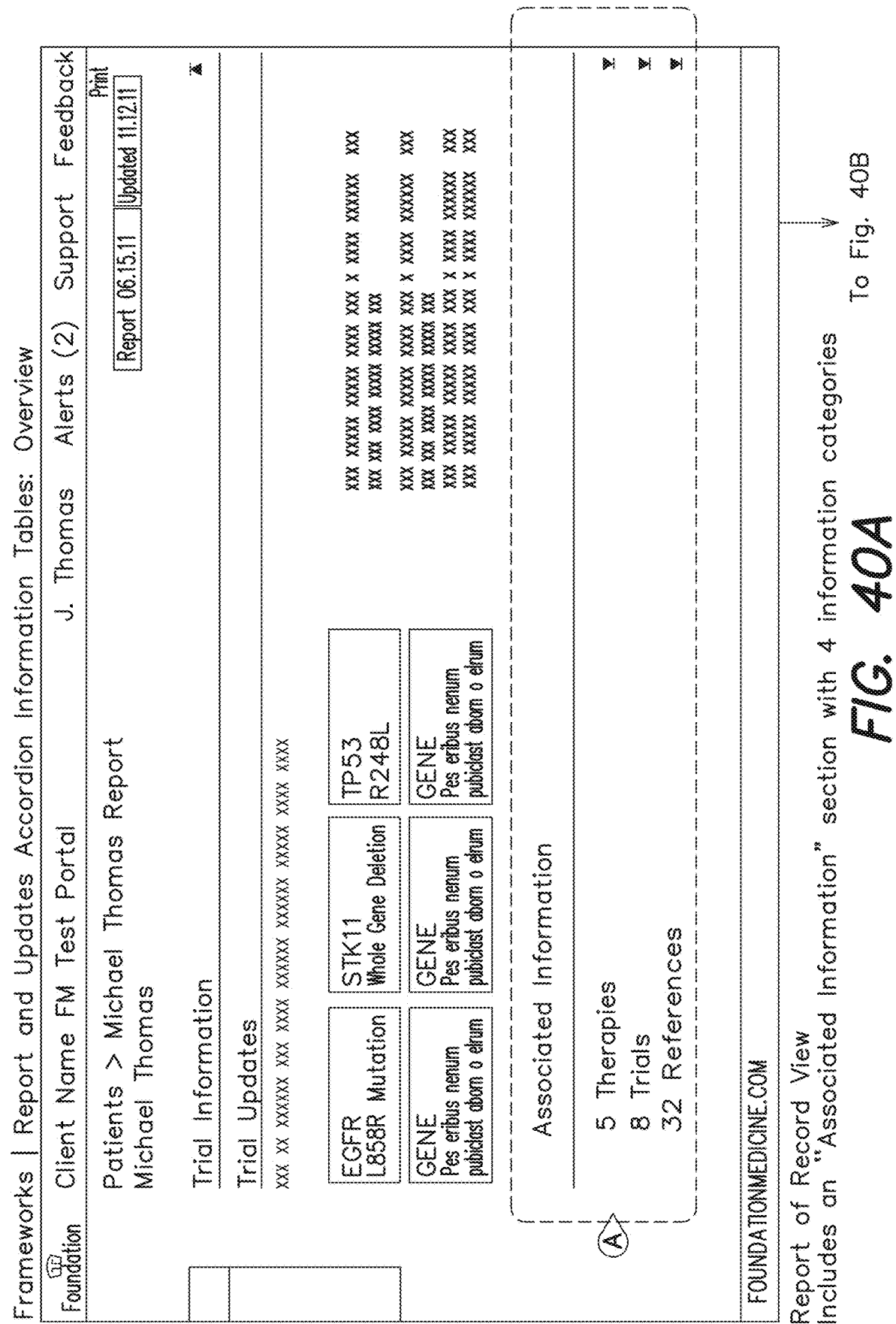

Information view in a report can be configured as accordion information tables, where the accordion tables are responsive to selection to expand and display additional information within the table. FIG. 40 illustrates information in example views shown in an unexpanded or collapsed state. FIG. 41 illustrates information in example views shown in an expanded state.

Figure 43:
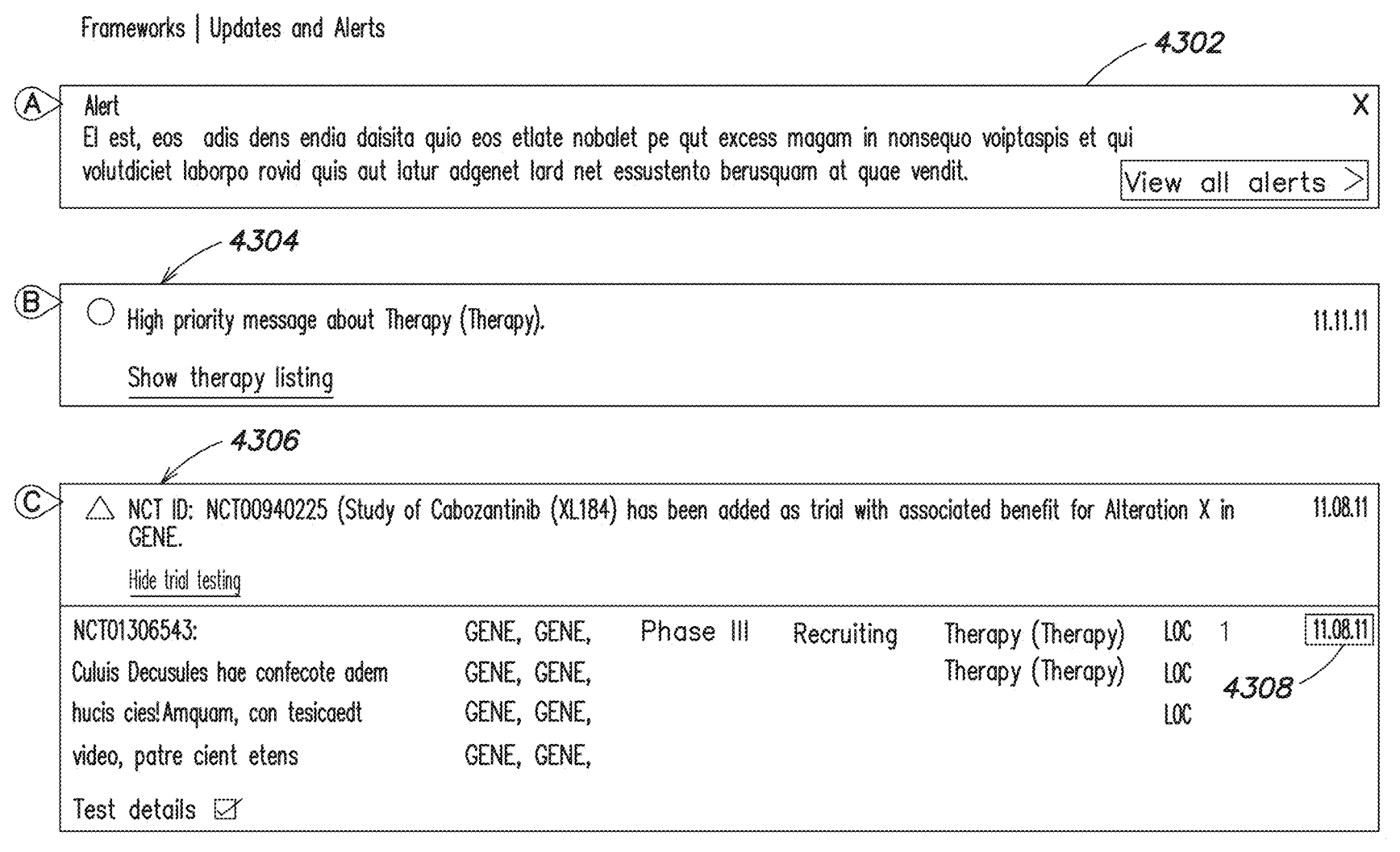

According to one embodiment, information update indicators can be globally provided in views of user interface. FIG. 42 illustrates example update indicators 4202-4214, which can be displayed within respective portions and/or screens of the user interface. Additionally, alert indicators can also be globally provided within views of the user interface. FIG. 43 illustrates example alert indicators 4302-4306, which can be displayed different based on the type of alert. At 4302, a critical alert is displayed as an inline notification for infrequent and high priority alerts. At 4304, a high priority alert can be displayed within an information drawer. At 4306, an alert with a high frequency can be displayed as an indicator within the information that has been updated (e.g., 4308).

Figure 44:
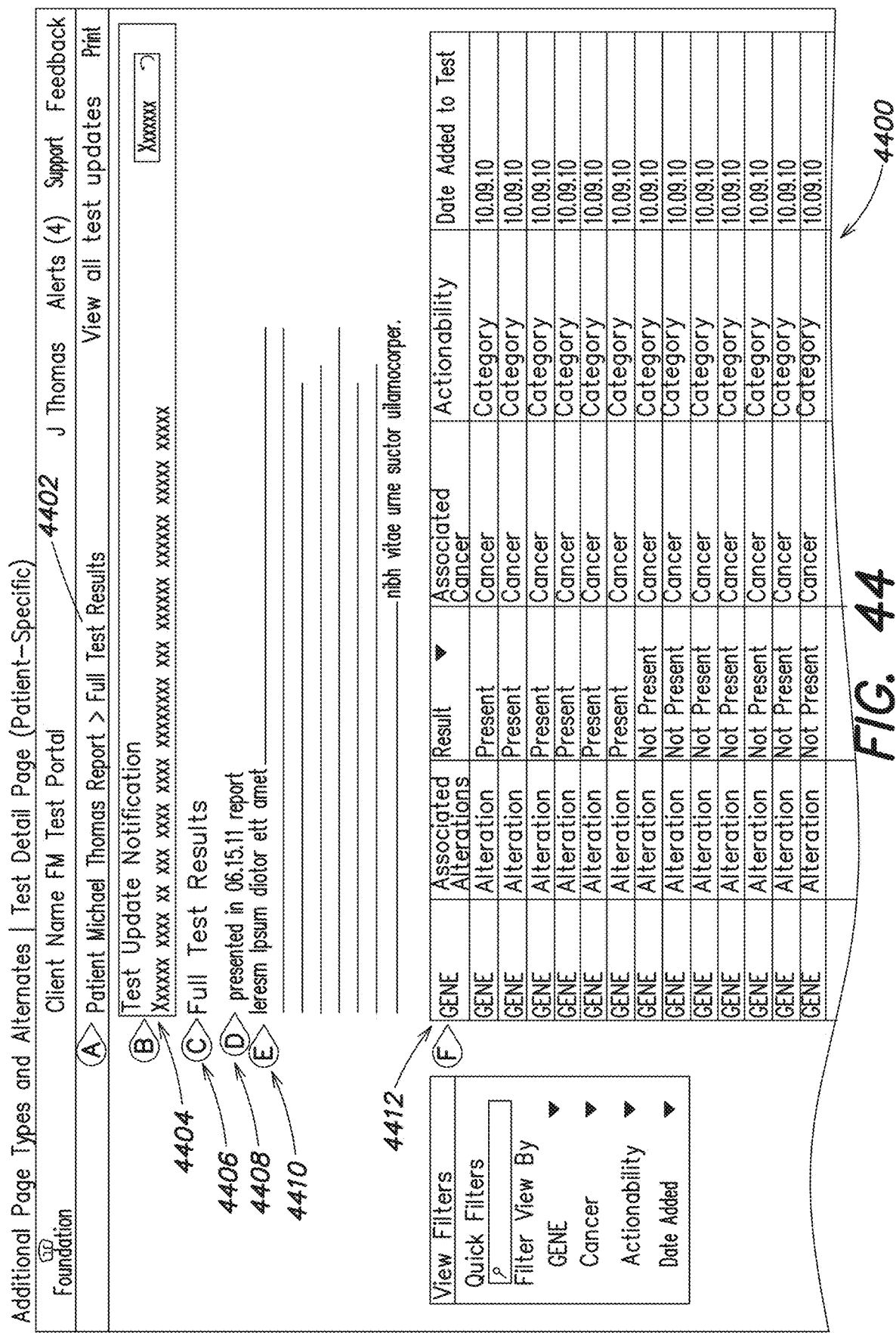
FIG. 44 illustrates another embodiment of a test report view.
Figure 45:
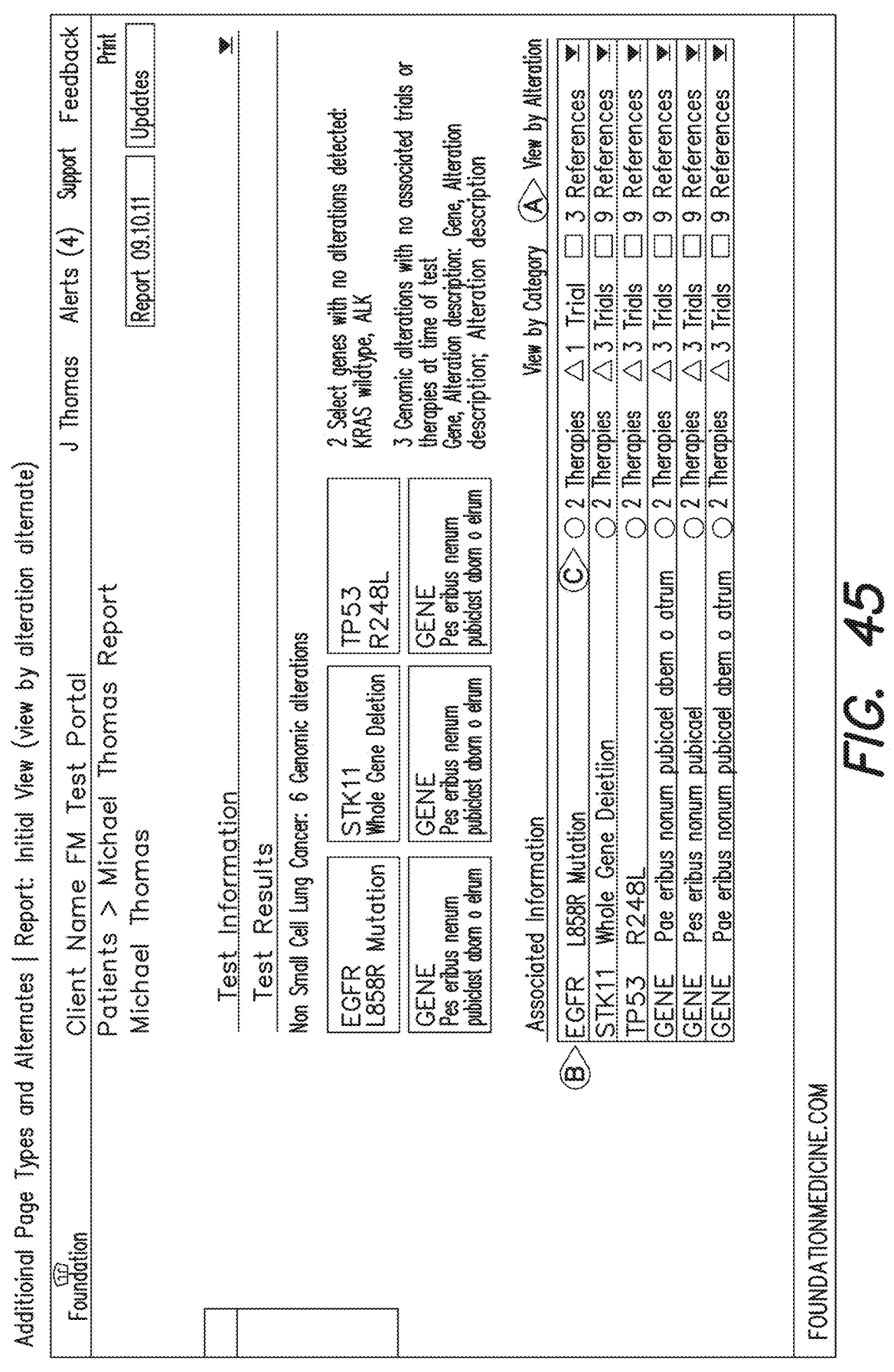

The user interface can include multiple views of genomic information. FIG. 44 shows another embodiment of a test report view 4400. Page 4400 can include a breadcrumb trail at 4402, update notifications 4404, test results content 4406 (e.g., time stamp 4408, test description 4410, gene/alteration list 4412). An alternate initial view of a genomic report is illustrated in FIG. 45, which can display information in a collapsed state as well as an expanded state (e.g., FIG. 46).

Figure 47A:
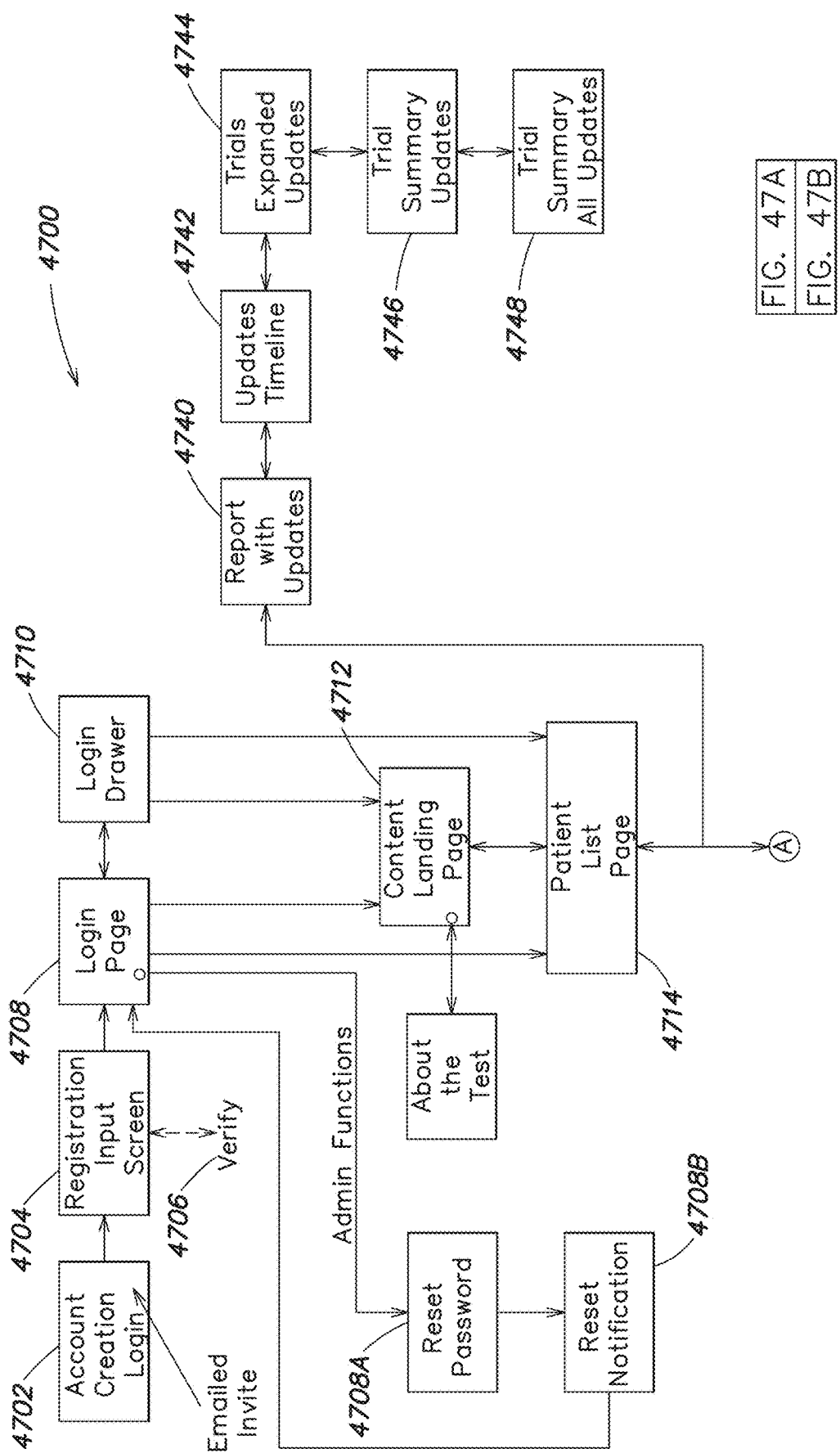
FIG. 47A-B illustrate an example execution flow between respective pages of a genomic testing website, according to one embodiment.
Figure 47B:
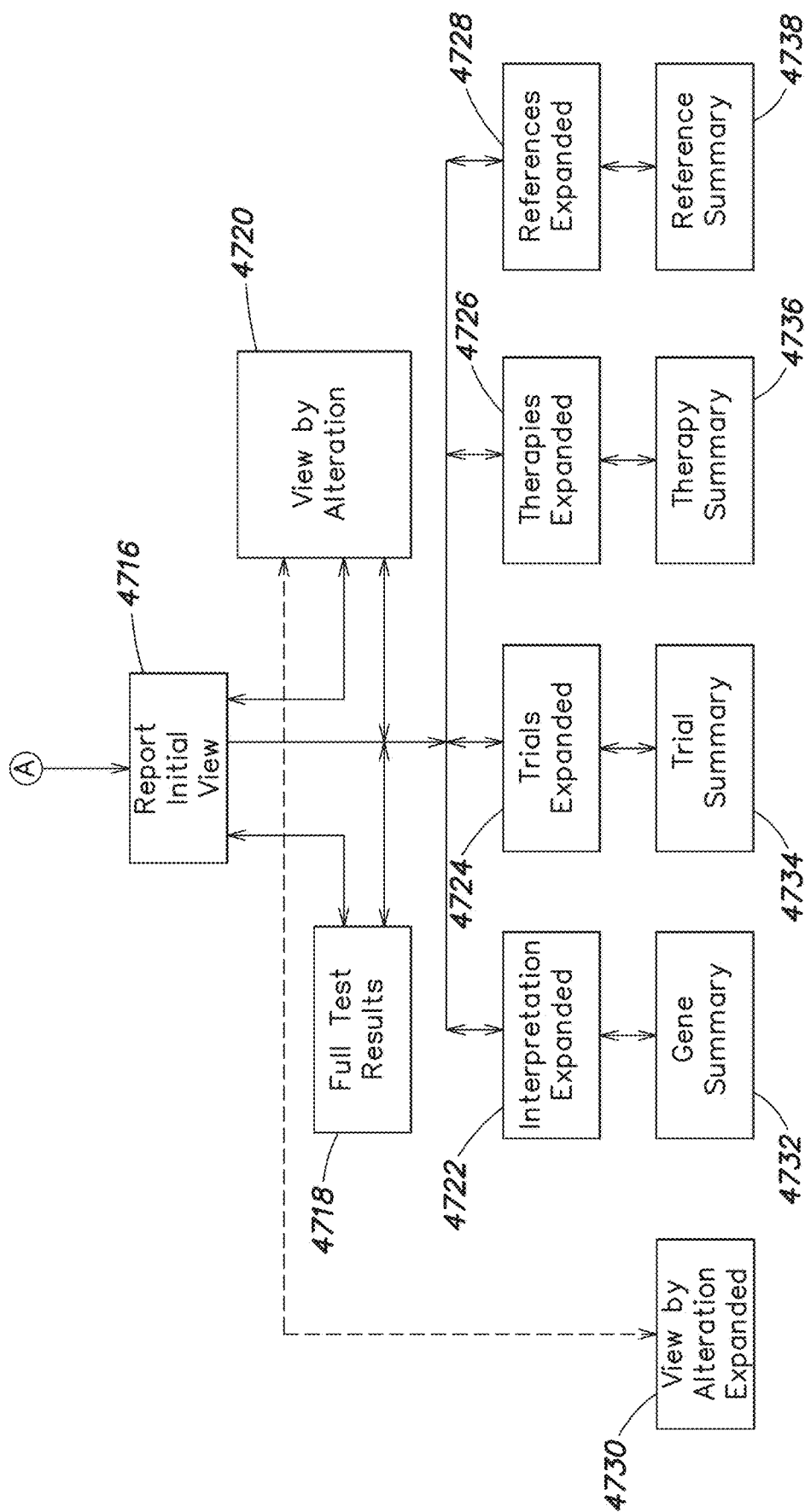

FIG. 47 illustrates an execution flow 4700 between respective pages of a genomic testing website. According to one embodiment, a user is invited to access the genomic testing website at 4702, for example, via an e-mailed invitation. The user is brought to a registration input screen 4704, and the registration information can be verified 4706. Once verified, subsequent access to the genomic testing site allows the now registered user to login. For example, the user may access a login page 4708 or login drawer 4710 to input their access information. Valid access information allows the user to continue to a content landing page 4712 or welcome screen. Alternatively, the user can access administrative functions (e.g., password reset request 4708A and receive a reset notification 4708B). Optionally the welcome screen can be omitted. From the content landing page, the user may access a list of patients 4714 (FIG. 6 illustrates an example patient list page) and associated patient reports at 4716 (FIG. 7A illustrates an example report initial view). In some embodiments, alternative views of genomic test reports are available. For example, a full test results page 4718 and view by alteration page 4720 can be accessed. FIG. 44 is an example of a full test results page. FIG. 45 is an example of a view by alteration page.

The information displayed in the report initial view 4716 provides summary information, for example, grouped by information categories (e.g., interpretations, trials, therapies, and references). Each group of information can be accessed via the report initial view, to provide expanded views of respective information responsive to selection by a user. For example, information in the report can be expanded to provide an interpretation expanded view 4722 (e.g., shown in FIG. 7C); a trials expanded view 4724 (e.g., shown in FIG. 7I); a therapies expanded view 4726 (e.g., shown in FIG. 7I); and a references expanded view 4728 (e.g., shown in FIG. 7K). The alternative page views may also include expanded information views at 4730 (e.g., shown in FIG. 46).

The information displayed can be associated with respective summary pages providing additional information. For example, interpretation information items can be linked to a gene summary page 4732 (e.g., shown in FIG. 7E or 7F), a trial summary page 4734 (e.g., shown in FIG. 33), a therapy summary page 4736 (e.g., shown in FIG. 7G), and a reference summary page 4738 (e.g., shown in FIG. 34). Each of the summary views can link back to their respective expanded view, and expanded views can be collapsed to return to a report initial view 4716.

In some alternatives, upon accessing a report, the user may be directed to a report view with updates 4740. For example, if information contained in a patient report has changed since a last view, the system can provide a view of the patient report with update indicators. FIGS. 8A and 8E illustrate an example interface with update indicators. Responsive to selection of an update indicator, an updates timeline page 4742 can be displayed. FIG. 8B illustrates an example updates timeline page. Like the report page, the update page can include expandable views of the update items. For example, selection of a trial category will expand trial information into a trial expanded update view 4744. In various embodiments, selection of information items within view 4746 transitions to a respective summary view associated with the selected item. For example, selection of specific trial information causes a transition to a display of a trial summary update page 4746.

Additionally, the user may access a summary of all available updates at 4748. According to some embodiments, the site is configured to allow a user to access genomic information easily and interact with the genomic information at whatever level is desired. A quick review can be managed through initial report views and summary pages. Alternatively, detailed review can be managed through the site via the summary pages available on respective information sources and/or interactive access to detailed genomic information. Further, the site facilitates access to new information through update indicators and access to pages specifically organizing updated information (e.g., 4740-4748).

Figure 48:
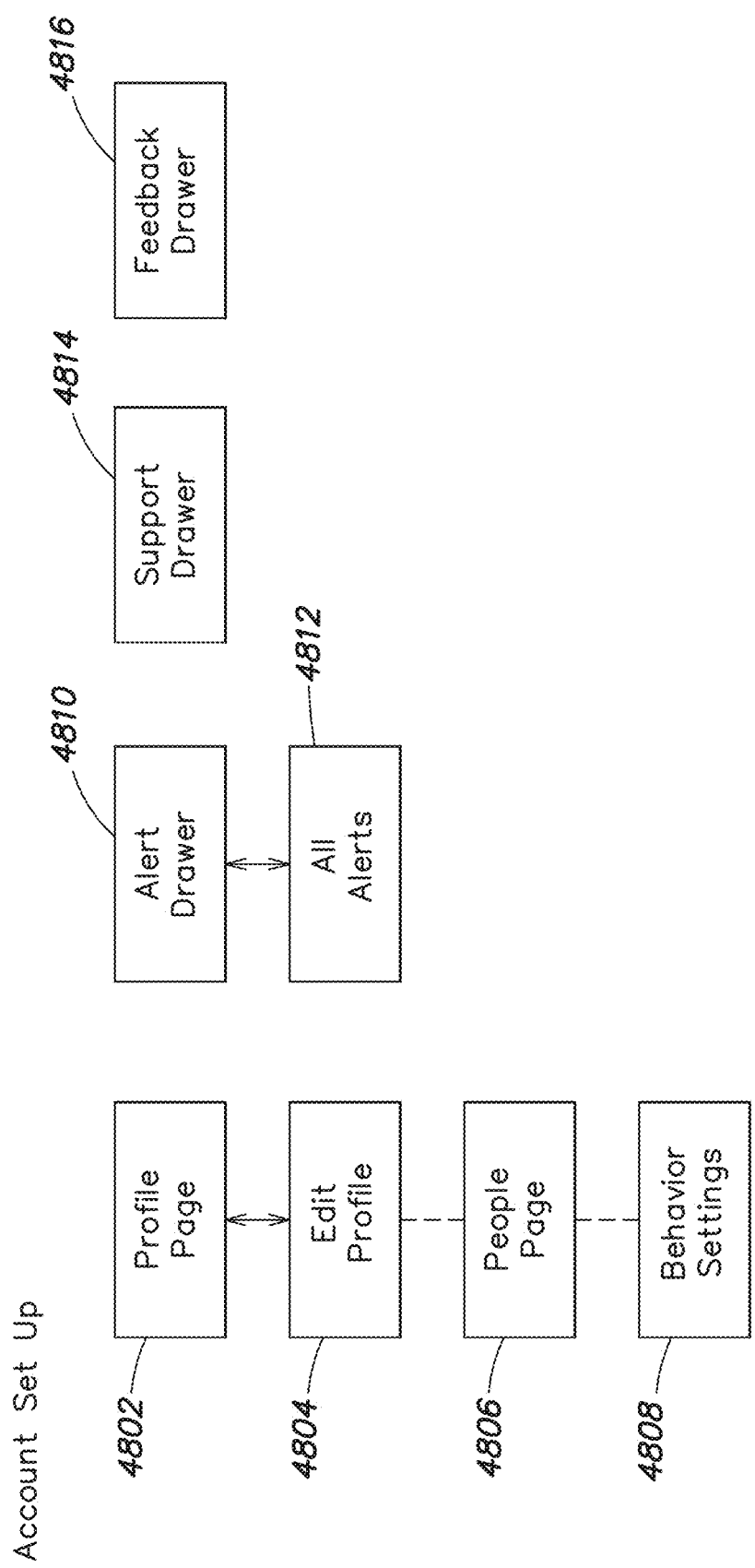
FIG. 48 illustrates an example flow for configuration of system behavior, according to one embodiment.

In some embodiments, the site can also enable configuration of system behavior through account set up pages (e.g., FIG. 48). For example, a user may access a profile page 4802 of FIG. 48 and edit their information via profile editing page 4804 to define or edit profile information (e.g., profile image, contact information, background, etc.). A user can enable other users to access an account, for example, in a group practice setting. The user may access a people page 4806 to define users and access rights (e.g., for accessing patient data associated with a particular practice). Further, the user can define behavior settings for the site at 4808. For example, the user can define when and how the site provides alerts, information updates, etc. A user may also access an alert drawer 4810 configured to provide access to alert information associated with an account. The user can access all available alerts via page 4812 by expanding the alerts drawer. Support is available via page 4814, where the user may access support information. Additionally, the user can provide feedback through a feedback drawer 4816.

Figure 49:
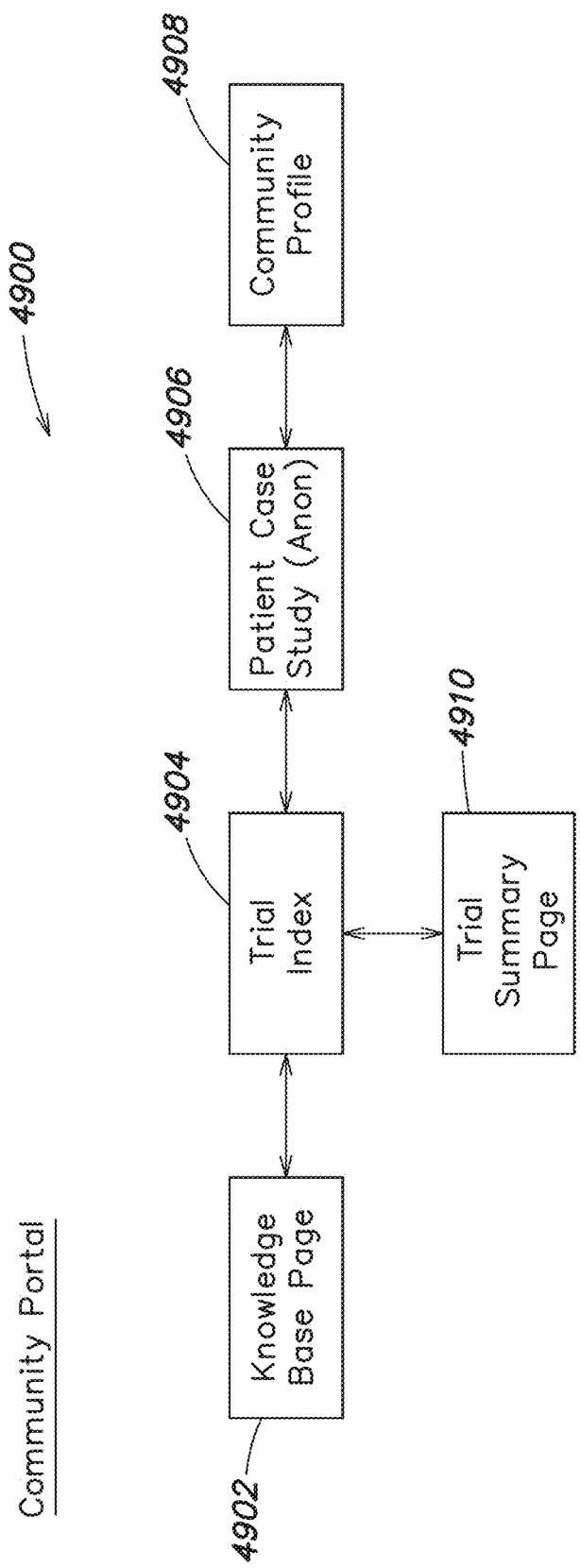
FIG. 49 illustrates an example flow for accessing aggregated genomic testing information in a community portal.
Figure 51A:
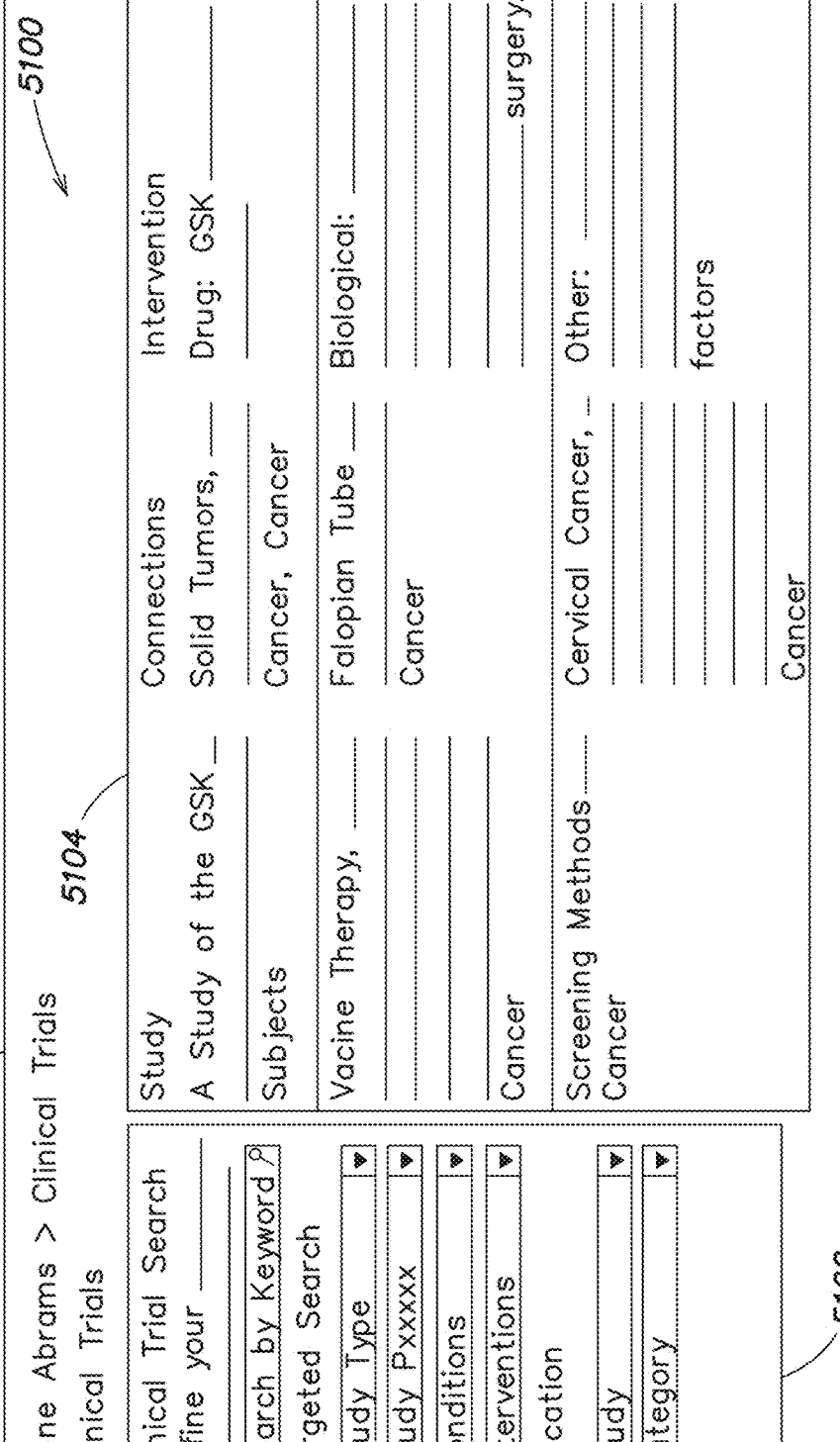

According to some embodiments, the genomic testing site can also provide access to a genomic information community. In one embodiment, the site provides a community portal 4900 of FIG. 49 for accessing aggregated genomic testing information. Access to the community can start at a knowledge base portal page 4902 (FIG. 50 illustrates an example knowledge base page). The knowledge base page provides anonymized information on genomic testing, patient populations, genes/alterations, therapies, trials, and/or reference information. Specific trial information can be accessed and/or searched at 4904 (shown in FIG. 51 is an example trial index page). Additional information on respective trials can be accessed via a trial summary page 4910.

Further, patient case study pages are made available in the community portal. For example, patient case study pages can be accessed at 4906 and reviewed for anonymized information on the patient, a diagnosis, tumor type, gene alteration, treatment notes, status of treatments, related patient case studies, related trials, and related references (discussed in greater detail below in FIG. 52). The community portal 4900 may also provide access to community profiles. For example, participating users can identify their background, specialty, related users (e.g., group practice), and activities within or out of the community. The system can provide access to detailed community profile pages at 4910 (discussed in greater detail below in FIG. 53).

FIG. 50 illustrates an example knowledge base page 5000. The knowledge base page 5000 can include information on aggregated and anonymized genomic test reports, patient populations, cancer diagnoses, etc. For example, at 5002 information can be displayed on: a number of patient cases, participating oncologist, participating medical professionals, cancers types researched, number of genes tested, number of identified alterations (e.g., via genomic testing reports), number of clinical trials, number of therapies, and number of references available to review and/or discuss.

Page 5000 can include a number of options for navigating the information in the community portal. For example, at 5004 a menu for navigating within the available case studies is provided. Users can access case studies based on matching condition information, including any one or more of cancer, diagnosis, and genomic alteration. Further, options can be provided for matching treatment information, or therapy and clinical trial information. In addition, options can be provided for matching patient characteristics, including age, sex, and diagnosis date. Other options for accessing information in the knowledge base can also include keyword search functions. For example, additional menus can provide for navigation within the portal on cancer genomic information generally. Users can access information based on matching cancer type, specified gene, and specified alterations at 5006. Additionally, users can enter keyword searches at 5006 to access matching information.

Page 5000 can also include summary information on discussion topics being developed within the community portal. The information on the discussion topics can be organized by categories, including, topic of discussion, type, a number of notes in the discussion, and last post in the discussion at 5008. A limited number of discussion topics can be shown in the knowledge base page 5000, with access to additional topics provided via links (e.g., "view all").

Page 5000 can also provide information on the most discussed topics within the community. For example, at 5010 the most discussed topics are displayed for review. The most discussed topics can be limited in number on the display at 5010, with access to additional topics available via a "view all" link. Page 5000 can also provide information on most viewed case studies. For example, at 5012 page 5000 displays a list of the most viewed case studies. For case studies that do not fit within the display area of 5012 remaining cased studies can be accessed via a "view all" option.

Other information can be displayed on page 5000 based on tracking user activity within the community. For example, at 5014 displayed is information on recently open clinical trials. The information on the recently open clinical trial can include a description of the trial, diagnosis, and can include location information. In another example, at 5016 a list of most recent publications is displayed. A "view all" option is available to access recent publications that do not fit within the display area of 5016.

The community portal can include additional pages for accessing more detailed information. For example, the community portal can include a clinical trial page 5100, FIG. 51. Page 5100 can include menus for searching available information on clinical trials. For example, at 5102 users can enter keyword search criteria and/or access drop down menus for targeted searching. Users can receive results on matching clinical trials by specifying study type, study result, conditions, and interventions. Users can also filter matching clinical trials based on location, including, state and/or country. Matching trials can be shown in display area 5104. The resulting trials can be organized by study title, study conditions, study interventions, and trial status, for example, within display area 5104. The available information (e.g., matching clinical trials) can also be organized by pages to provide access to large numbers of clinical trials.

Figure 52A:
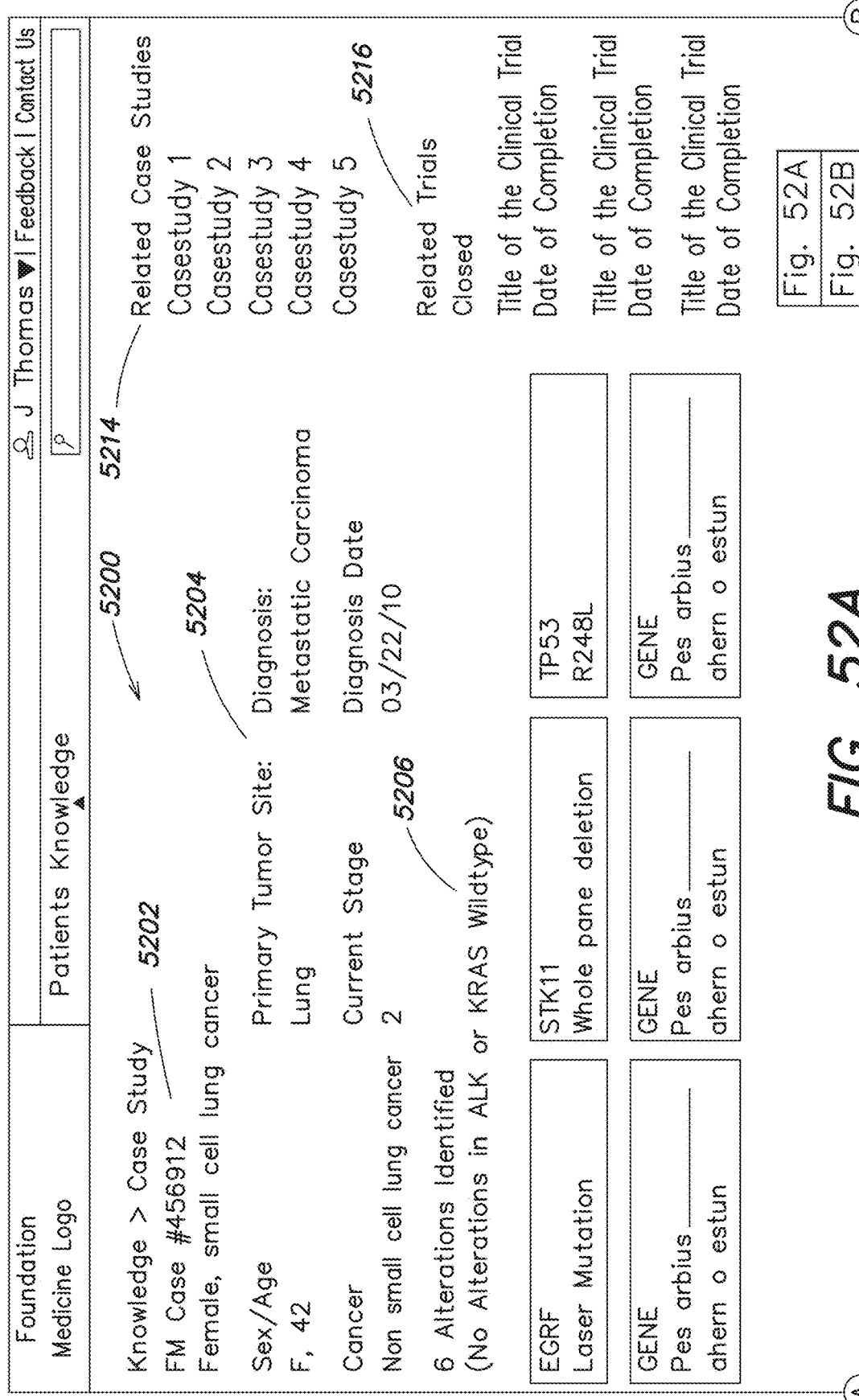

The community portal can also include detailed information on patient case studies that contain anonymized patient outcome information (including, for example, as discussed with respect to systems and methods for outcome tracking and analysis) and provide insight into other oncologists' treatment paths and level of success. Page 5200 of FIG. 52 illustrates an example patient case study made available through the community portal.

Anonymized information on the patent is provided at 5202 (e.g., via a case number) while providing non-identifying descriptive information (e.g., female, small cell lung cancer). The descriptive information provided can include age and sex, cancer type, primary tumor site—lung, current state of the cancer, diagnosis—metastatic carcinoma, and diagnosis date (for example, shown at 5204). Patient case studies can also provide genomic testing information associated with the patient. For example, the genomic testing on the patient's cancer identified six alternations, and the respective alterations can be displayed at 5206.

For patients having treatment information, treatment notes can be displayed at 5208. The treatment information can be displayed at 5208 and organized by attempted treatment, timeline for treatments, and status of treatment. In some examples, additional information can be available with each course of treatment (e.g., shown by an icon displayed next to a treatment record). Additional information can also be displayed for patient treatment, including information on when a last update occurred, and if a treatment change was indicated by the results of genomic testing (e.g., at 5210).

In addition to information on the patient, community comments and/or notes can be displayed as part of a patient case study. For example, user comments can be displayed at 5212, and include any information a respective user wishes to share on the patient case study. Each comment can include information on the posting member, which can be used to access a community profile (e.g., including background information, specialty information, etc.). Some users may suggest alternate treatments and even provide links to other patient case studies exploring the suggested treatments. Other users may post cautions and/or considerations, while other comments may specifically request feedback from the community or request an answer to a question.

Information on the patient in the case study may also be augmented via related information displays. In one embodiment, the system can identify and display related information with respect to the case study. For example, at 5214 links to related case studies can be displayed. At 5216, links to related trials can also be displayed. The display of related trials can be grouped on current status—closed or open. At 5218, related references can be displayed, and at 5220 related therapies can be provided.

Figure 53A:
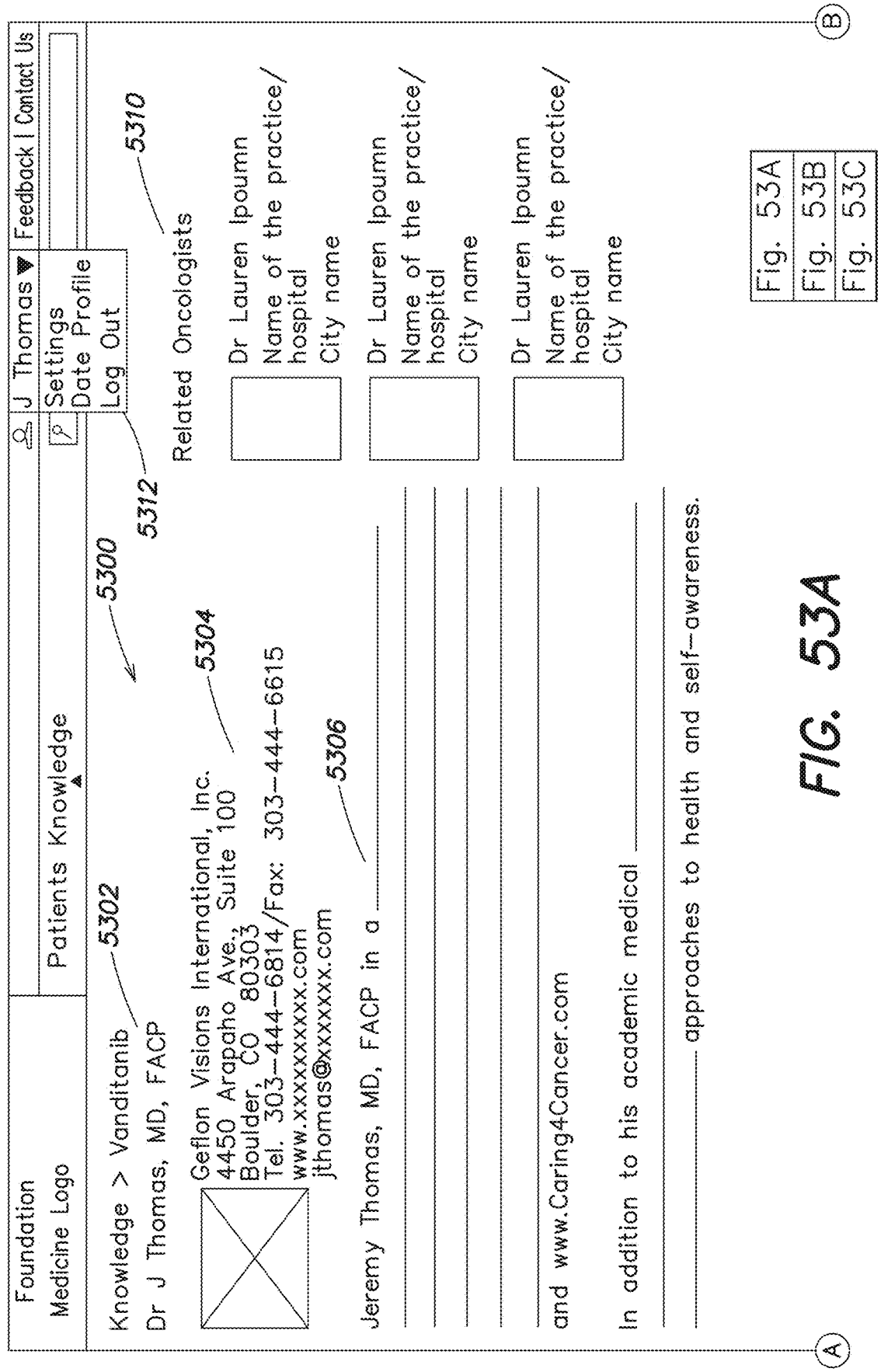

FIG. 53 shows an example user profile page 5300 accessible through the community portal. According to one embodiment, a community participant can define elements of a community profile for display. At 5302, the user is identified, and the user identification can include information on their profession, any specialty, and professional membership(s). Contact information can also be displayed to other community members at 5304, and the user's background can be displayed (e.g., at 5306).

A user's community profile page 5300 can include activity information tracking the user's recent activity within the community. At 5308, a user's recent posts, comments, interactions, shared reports, etc., can be provided. Additional activity can be accessed via a "view more" link. Other physicians related to the user can also be displayed. For example, in a community profile display, members of a practice group can be displayed at 5310 as related members. When accessed by the user, the user may edit their own profile via menu 5312.

According to some embodiments, various user interfaces are provided to enable users to access and comprehend genomic testing information. The user interfaces also make available community tools for collaborating on related cases, identifying relevant information, and enabling the best information to be used by physician users to support their diagnoses. The system can also facilitate access to clinical trials and facilitate communication between clinical researchers and treating physicians. According to various embodiments, systems for managing genomic testing results can be incorporated within systems for outcome tracking and analysis. Additionally, the various embodiments, functions, and methods discussed for outcome tracking and analysis can be incorporated within embodiments of the systems and methods for managing genomic testing results discussed herein. In some examples, genomic testing information (e.g., gene and alteration information) for patients can be associated with specific treatment and outcome information. In some examples, genomic test reports and dynamic displays can organize information on patient outcome and treatment information. For example, a dynamic display of genomic testing information can include references to outcome and treatment information. In one instance, an outcome/treatment drawer is provided to facilitate access to outcome and treatment information. In other examples, the outcome tracking and analysis system can be used to request and provide access to genomic test results and associated information.

According to another aspect, provided are systems and methods for managing genomic testing information that provide a single reporting source for accessing and applying available information on a patient's cancer. According to some embodiments, genomic testing on the patient's cancer provides specific information on the tumor, one or more genes implicated by the tumor, and one or more alterations within the genes. The testing information on tumor, gene, and alteration can be used by the system to manage delivery of curated information that focuses users (e.g., physicians) on actionable information within the genomic testing information. For example, publically available data (e.g., therapy data, clinical trial data, journal publications) can be interpreted to provide the curated information. The curated information can be accessed on the system based on its relationship to one or more of the tumor, gene, and alteration for a patient. The publically available information can also be processed on the system to provide navigable data structures informing the user of available actionable information associated with a patient's cancer.

In further aspects, the practitioner is able to view the single report source for genomic information on the system. The single report source can incorporate tumor information, gene information, and genomic alteration information to review and, potentially, to apply actionable steps towards treating various cancers. According to one embodiment, the single report source is dynamic, incorporating updates to any associated information (e.g., new curated information, updated curated information, a new clinical trial, a new therapy, a new publication associated with any of an alteration, gene, tumor found in a genomic test report) as they become available. The system can deliver update notifications responsive to new information. Further embodiments provide intuitive navigation options within views on the system to expand the information displayed and/or navigate to additional information on a selected information source (e.g., specific information on a tumor, gene, and/or alteration, and external links to available information, among other options).

According to one embodiment, a user interface is provided that allows easy navigation to genomic alteration results and associated information to reduce the amount of time necessary to determine an appropriate treatment for a user. For instance, as a result of genomic testing, of a patient sample, particular genomic alterations may be detected and displayed to a user for a particular patient. The user may be presented, within the display, a collection of information that user would need to access to provide an informed treatment recommendation. For example, with a first level view of identified alterations, the user may be permitted to navigate to other information related to the genomic alterations, such as, therapy information, information on a clinical trial related to the genomic alteration, and any references that might be available to inform or support the application of such therapies. By having such information within an easily navigable interface, users may more quickly identify appropriate treatments.

According to one embodiment, the system may identify and display to the user genomic alterations and associated information arranged based on actionability analysis. The actionability analysis can be configured to display genomic alteration and associated information having the highest degree of actionability. In one embodiment, the actionability analysis can prioritize information on available therapies or related therapies over clinical trial information and available references. Additionally, the clinical trial information can be prioritized over available references. The priority can be used by the system to define display precedence. For example, an order of display for genomic alterations and associated information can reflect the priority and/or actionability analysis.

In some embodiments, the system can provide an indication regarding the number or volume of therapy information items, the number or volume or clinical information items, and the number or volume of available reference information items. The numbers within each group can also be used to establish priority. For example, on genomic alterations having multiple associate therapies, the alteration having the larger number can be displayed first. As updates to genomic alterations and associated information occur, the actionability analysis can change over time to reflect the new information. Further, such updates can be communicated directly to the user and/or highlighted in a test report for the user's review.

According to another aspect, the system can be organized based on a genomic testing data model. In one embodiment, the data model is configured to organize information on tumor type, implicated genes within the tumor, and alteration types for the implicated genes for specific tests and/or by patient. The system is configured to use the data model to facilitate access to genomic alteration test results and all related information for a test and/or patient. In some embodiments, the gene/alteration combination can form at least part of the basis of organization. Each gene/alteration combination can be linked in the data model to actionable information (if any exists). The actionable information can be linked to any of the gene/alteration combinations and can optionally be match to the tumor type for a patient. Categorization of all information in the data model by associating a gene, alteration, and/or tumor type provides insight into prescribed uses of therapies (on-label) and off-label applications based on related alteration information (e.g., information on different tumors but the same alteration—an effective therapy for the alteration in a different tumor type could be relevant to a patient's tumor type).

In some embodiments, users are able to share test reports and associated information between physicians in a practice group or between physicians within an institution (e.g., hospital, treatment facility, etc.) In addition to the dynamic display of the genomic information and associated information, some embodiments, of the system can provide for generation of physical and/or static reports. In one example, a physical report can be generated to include genomic alteration information for a patient and all the associated information organized into display groups for therapy, trial, and reference information.

According to one aspect, a system for managing delivery of genomic testing information is provided. The system comprises at least one processor operatively connected to a memory, the at least one processor when executing is configured to access genomic testing results including at least one gene and alteration combination for a patient's cancer, analyze one or more of a tumor type, gene, and alteration for the patient's cancer, wherein analyzing includes identifying associated information items matching at least one of the tumor type, gene, and alteration for the patient's cancer, and generate at least one genomic data structure including at least one tag, wherein the at least one tag is selectable to transition a user interface from the genomic data structure to an associated information display space including at least one associated information item describing information related to characteristics of the genomic data structure.

In one embodiment, the system further comprises a user interface component, executed by the at least one processor, configured to display the at least one genomic data structure within a user interface accessible over a communication network. In one embodiment, the user interface component is configured to assign associated information items to categories responsive to a type of information for the associated information item. In one embodiment, the user interface component is configured to generate two or more tags displayed within each genomic data structure, wherein the two or more tags are selected from a group of categories including therapy, clinical trial, genomic interpretation, and alteration. In one embodiment, the user interface component is configured to generate at least four tags within each genomic data structure for at least the therapy, clinical trial, genomic interpretation, and alteration categories.

In one embodiment, the user interface component is configured to display a count of associated information items referenced by each tag. In one embodiment, the user interface component is configured to highlight the at least one associated information item within the associated information display space responsive to selection of the at least one tag. In one embodiment, the user interface component is configured to generate at least one data structure in the associated information display space for organizing associated information items.

In one embodiment, the user interface component is configured to display the at least one organizing data structure in the associated information display space in an unexpanded view. In one embodiment, the unexpanded view conceals any associated information items. In one embodiment, the user interface component is configured to display the at least one organizing data structure in an expanded view responsive to at least one of the transition to the associated information space and selection of the at least one organizing data structure. In one embodiment, the expanded view includes a display of the at least one associated information organized by the at least one organizing data structure.

In one embodiment, the user interface component is configured to generate organizing data structures for at least the therapy, clinical trial, genomic interpretation, alteration, and a references category. In one embodiment, one organizing data structure organizes associated information items for both the genomic interpretation and the alteration categories. In one embodiment, the user interface component is configured to limit a number of organizing data structures displayed in the expanded view. In one embodiment, the user interface component is configured to limit the number of organizing data structures displayed in the expanded view to one.

In one embodiment, the user interface component is configured to generate an update organizing data structure for organizing any updated associated information items. In one embodiment, the user interface component is configured to identify updated associated information items responsive to a last view date. In one embodiment, the user interface component is configured to display the at least one associated information items within the associated information space.

In one embodiment, the user interface component is configured to generate in each of the at least one associated information items a selectable display for navigating to at least one of a detailed view of an associated information item and an external source for the at least one information item. In one embodiment, the user interface component is configured to generate for each of the at least one associated information items organized in the genomic interpretation category at least one of: a) interpretive information, e.g., information of the role of the gene in health and disease, e.g., in cancer, e.g., the patient's type of cancer, or another cancer, including curated information e.g., one or more identifiers of sources of primary information, e.g., published journal articles, on the prevalence of the alteration in particular cancers or populations, therapies for the subject genomic alteration, or related genomic alterations, clinical studies of specific therapies for cancers within the current patient's tumor type or otherwise, and genomic alteration, e.g., a type of alteration, e.g., amplification, deletion, translocation, etc.; b) the name of the affected gene; and c) the type of alteration.

In one embodiment, the user interface component is configured to generate for each of the at least one associated information items organized in the therapy category one or more or all of: a) a therapy, e.g., a drug, one or more of all of: an indication of whether the therapy is approved for the patient's tumor type; an indication of whether the therapy is approved for other tumor types (which can be useful in identifying off-label uses); b) an identifier for a therapy; c) the identity of the gene involved in the alteration; and d) the type of alteration. In one embodiment, the user interface component is configured to generate for each of the at least one associated information items organized in the clinical trial category one or more or all of the following (if there is such a clinical trial): a) an identifier for a clinical trial, e.g., one that implicates one or more or all of the patient's tumor type, a gene affected by the patient's alteration, the genetic alteration type; b) rationale for the trial, e.g., a statement of why the therapy is implicated in the patient's tumor type or another tumor type; c) a description of the trial, e.g., an indication of phase, and type of cancer treated; d) a geographic location of trial; e) an identification of the target in clinical trial, e.g., aurora kinase, and wherein in embodiments, one or more or all, of a, b, c and d, are presented concurrently to the user, without need for leaving the screen, e.g., without further computer operation or without more than brief computer operation by the user.

In one embodiment, the user interface component is configured to generate for each of the at least one associated information items organized in the references category one or more or all of the following: a) reference bibliography information e.g., author, title, publisher, location, copyright, journal name, journal title, publication name, publication company, ISBN, etc.; and b) a navigable link to the reference.

In one embodiment, the system further comprises a storage component executed by the at least one processor configured to organize genomic testing results and associated information by patient according to a data model. In one embodiment, the data model comprises a data structure associated with patient records, and wherein the data structure includes data records for specification of tumor type, gene, and alteration. In one embodiment, all genomic testing results and the associated information is accessible by the storage component using gene and alteration records. In one embodiment, each patient record includes gene and alteration data units, and the storage component is configured to associate actionable information (e.g., therapy information items or clinical trial information items) to the gene and alteration date units. In one embodiment, the actionable information includes therapy information items that specify whether an associated therapy is approved by the FDA in the patient's tumor type, and whether the associated therapy is approved by the FDA in another tumor type.

In one embodiment, the data model includes specification of an actionability evaluation for associated information items. In one embodiment, therapy information items are assigned a highest level of actionability. In one embodiment, clinical trial information items are assigned a second level of actionability. In one embodiment, reference information items are assigned a lowest level of actionability. In one embodiment, genomic data structures can be assigned a display precedence responsive to a level of actionability determined from respective associated information items.

In one embodiment, the system further comprises an update component, executed by the at least one processor, configured to track any updates to one or more of genomic test results and any associated information items. In one embodiment, the update component is configured to communicate update notification to users responsive to identification of updated information. In one embodiment, the update component is configured to generate notifications according to user notification preferences.

In one embodiment, the system further comprises a report component configured to generate static reports containing all gene alteration combinations specific to a patient and all associated information items organized into respective display areas on the report, wherein the respective display areas are arranged by information type. In one embodiment, the report component is configured to deliver the static report via a fax.

In one embodiment, the system further comprises a curation component, executed by the at least one processor, configured to identify information sources relevant to any one or more of a patient's tumor type, at least one gene implicated by the tumor, and an alteration type for the at least one gene. In one embodiment, the curation component is configured to generate interpretive statements accessible at least by using a gene and alternation combination. In one embodiment, the interpretive statement include e.g., information of the role of the gene in health and disease, e.g., in cancer, e.g., the patient's type of cancer, or another cancer, including curated information e.g., one or more identifiers of sources of primary information, e.g., published journal articles, on the prevalence of the alteration in particular cancers or populations, therapies for the subject genomic alteration, or related genomic alterations, clinical studies of specific therapies for cancers within the current patient's tumor type or otherwise, and genomic alteration, e.g., a type of alteration, e.g., base substitution, insertion, deletion, amplification, homozygous deletion, rearrangement.

In one embodiment, the curation component is configured to categorize information sources, and store the categorizations at least for use by a user interface component. In one embodiment, the curation component is configured to identify updates to treatment options. In one embodiment, the curation component is configured to identify updates genomic alteration interpretive statements. In one embodiment, the curation component is configured to tag updated records responsive to at least one of timing of a study, approval of a therapy, start of a new trial, and publication of a new reference.

According to one aspect, a computer implemented method for delivering patient information is provided. The method is comprised of: A) optionally, providing reports for a plurality of patients, e.g., a plurality of patients of a user; B) providing, e.g., displaying, e.g., responsive to a selection by a user, a first portion of said report, said first portion comprising, one or more or all of: i) patient information comprising a) Patient Diagnosis; and, optionally, one or more or all of b) Patient identifier; c) other Patient bibliographic information, e.g., age; and ii) a genomic alteration space, e.g., a genomic alteration brick, for each cancer cell genomic alteration, which comprises or provides, e.g., without further computer operation by the user, one or more or all of: a) a first space, or cancer cell genomic alteration space, having, e.g., an indication of a gene involved; b) a second space, or type of alteration space, having, e.g., an indication of alteration type, e.g., an amplification, translocation, or point mutation; c) a third space, or therapy or actionable item space; d) a fourth space, or for clinical trial space; wherein in embodiments, one or more or all, of a, b, c and d, are presented concurrently to the user, without need for leaving the screen, e.g., without further computer operation or without more than brief computer operation by the user; and iii) an associated information space, comprising one or more or all of: a) first associated space, or genomic alteration interpretation space, e.g., a genomic alteration interpretation drawer, b) second associated space, or therapy space, e.g., a therapy drawer, c) third associated space, or clinical trial space, e.g., a clinical trial drawer, d) forth associated space, or references space, e.g., a references drawer, e) an optional fifth associated space, or updates space, e.g., an updates drawer, wherein in embodiments, one or more or all, of a, b, c and d, are presented in an unexpanded or expanded view to the user, without need for leaving the screen, e.g., without further computer operation for the unexpanded view and without more than brief computer operation by the user to transition to the expanded view; and C) providing or displaying, e.g., in response to user input, e.g., a brief computer operation, which selects one of B(2)a-d: i) for B(2) a or b, one or more or all of: a) interpretive information, e.g., information of the role of the gene in health and disease, e.g., in cancer, e.g., the patient's type of cancer, or another cancer, including curated information e.g., one or more identifiers of sources of primary information, e.g., published journal articles, on the prevalence of the alteration in particular cancers or populations, therapies for the subject genomic alteration, or related genomic alterations, clinical studies of specific therapies for cancers within the current patient's tumor type or otherwise, and genomic alteration, e.g., a type of alteration, e.g., amplification, deletion, translocation, etc.; b) the name of the affected gene; and c) the type of alteration; ii) for B(2) c, one or more or all of: a) a therapy, e.g., a drug, one or more of all of: an indication of whether the therapy is approved for the patient's tumor type; an indication of whether the therapy is approved for other tumor types (which can be useful in identifying off-label uses); b) an identifier for a therapy; c) the identity of the gene involved in the alteration; and d) the type of alteration; iii) for B(2) d, one or more or all of one or more of the following (if there is such a clinical trial): a) an identifier for a clinical trial, e.g., one that implicates one or more or all of the patient's tumor type, a gene affected by the patient's alteration, the genomic alteration type; b) rationale for the trial, e.g., a statement of why the therapy is implicated in the patient's tumor type or another tumor type; c) a description of the trial, e.g., an indication of phase, and type of cancer treated; d) geographic location of trial; e) identification of the target in clinical trial, e.g., aurora kinase, wherein in embodiments, one or more or all, of a, b, c and d, are presented concurrently to the user, without need for leaving the screen, e.g., without further computer operation or without more than brief computer operation by the user.

In one embodiment, the method further comprises: D) providing or displaying, e.g., in response to user input, e.g., a brief computer operation, which selects one of B(3)a-e: i) for B(3) a, one or more or all of: a) interpretive information, e.g., information of the role of the gene in health and disease, e.g., in cancer, e.g., the patient's type of cancer, or another cancer, including curated information e.g., one or more identifiers of sources of primary information, e.g., published journal articles, on the prevalence of the alteration in particular cancers or populations, therapies for the subject genomic alteration, or related genomic alterations, clinical studies of specific therapies for cancers within a current patient's tumor type or otherwise, or related, genomic alteration; b) the name of the affected gene; and c) the type of alteration; ii) for B(3) b, one or more or all of: a) a therapy, e.g., a drug, one or more of all of: an indication of whether the therapy is approved for the patient's tumor type; an indication of whether the therapy is approved for other tumor types (which can be useful in identifying off-label uses); b) an identifier for a therapy; c) the identity of the gene involved in the alteration; and d) the type of alteration; iii) for B(3)c, one or more or all of one or more of the following (if there is such a clinical trial): a) an identifier for a clinical trial, e.g., one that implicates one or more or all of the patient's tumor type, a gene affected by the patient's alteration, the genomic alteration type; b) rationale for the trial, e.g., a statement of why the therapy is implicated in the patient's tumor type or another tumor type; c) a description of the trial, e.g., an indication of phase, and type of cancer treated; d) geographic location of trial; e) identification of the target in clinical trial, e.g., aurora kinase, iv) for B(3)d, one or more or all of the following: a) reference bibliography information e.g., author, title, publisher, location, copyright, journal name, journal title, publication name, publication company, ISBN, etc.; and b) a navigable link to the reference; v) for B(3)e, one or more or all of the following: a) an updates time line including updated information for any one or more or all of D(1)-(4); wherein in embodiments, one or more or all, of a, b, c, d, and e, are presented consecutively to the user, without need for leaving the screen, without more than brief computer operation by the user.

In one embodiment, the method includes successive execution of C), e.g. successive access, e.g., by brief computer operation, by a user to a plurality of genomic alteration spaces, e.g., bricks. In one embodiment, the method includes successive accesses, e.g., by brief computer operation, by a user to a plurality of spaces selected within B(2)a-d. In one embodiment, the method includes selection of successive operations described above, by no more than y, wherein y is equal to or less than two, brief computer operations, for each of the plurality of genomic alteration spaces accessed.

In one embodiment, the method further comprises migration from the first portion, through at least one of the genomic alteration spaces, e.g., bricks, to the associated information space (e.g., the clinical trial space, therapy space, interpretation space) by no more than X, wherein X is equal to or less than one, brief computer operations. In one embodiment, the method further comprises migration from the first portion, through at least one of the genomic alteration spaces, e.g., bricks, to the associated information space (e.g., the clinical trial space, therapy space, interpretation space) by no more than X, wherein X is equal to or less than two, brief computer operations.

In one embodiment, the method further comprises successive execution of the act of migrating from the first portion, through at least one of the genomic alteration spaces, e.g., bricks, to the associated information space (e.g., the clinical trial space, therapy space, interpretation space) Z times, wherein Z successive acts of migrating can be performed with no more than z*x brief computer operations, wherein x is equal to one or two, or no more than z*x plus z. In one embodiment, C) is executed successively to access at least 1, 2, 3, 4, 5, 6, 7, 8, 9, or 10, genomic alteration spaces, resulting in 1, 2, 4, 5, 6, 7, 8, 9, or 10 successive transitions to the associated information space.

According to one aspect a computer implemented method for managing delivery of genomic testing information is provided. The method comprises accessing, by a computer system, genomic testing results including at least one gene and alteration combination for a patient's cancer, analyzing, by the computer system, one or more of a tumor type, gene, and alteration for the patient's cancer, wherein analyzing includes identifying associated information items matching at least one of the tumor type, gene, and alteration for the patient's cancer, and generating, by the computer system, at least one genomic data structure including at least one tag for display in a user interface, wherein the at least one tag is selectable to transition the user interface from the genomic data structure to an associated information display space including at least one associated information item describing information related to characteristics of the genomic data structure.

According to one embodiment, the method further comprises displaying, by the computer system, the at least one genomic data structure within the user interface accessible over a communication network. According to one embodiment, the method further comprises assigning, by the computer system, the associated information items to categories responsive to a type of information for a respective associated information item. According to one embodiment, the method further comprises generating, by the computer system, two or more tags displayed within each genomic data structure, wherein the two or more tags are selected from a group of categories including therapy, clinical trial, genomic interpretation, and alteration. According to one embodiment, the method further comprises generating, by the computer system, at least four tags within each genomic data structure for at least the therapy, clinical trial, genomic interpretation, and alteration categories. According to one embodiment, the method further comprises displaying, by the computer system, a count of associated information items referenced by each tag. According to one embodiment, the method further comprises highlighting, by the computer system, the at least one associated information item within the associated information display space responsive to selection of the at least one tag.

According to one embodiment, the method further comprises generating, by the computer system, at least one data structure in the associated information display space for organizing associated information items. According to one embodiment, the method further comprises displaying, by the computer system, the at least one organizing data structure in the associated information display space in an unexpanded view. According to one embodiment, the unexpanded view conceals any associated information items.

According to one embodiment, the method further comprises displaying, by the computer system, the at least one organizing data structure in an expanded view responsive to at least one of the transition to the associated information space and selection of the at least one organizing data structure. According to one embodiment, the expanded view includes a display of the at least one associated information organized by the at least one organizing data structure. According to one embodiment, the method further comprises generating, by the computer system, organizing data structures for at least the therapy, clinical trial, genomic interpretation, alteration, and a references category. According to one embodiment, one organizing data structure organizes associated information items for both the genomic interpretation and the alteration categories. According to one embodiment, the method further comprises limiting, by the computer system, a number of organizing data structures displayed in the expanded view.

According to one embodiment, the method further comprises limiting, by the computer system, the number of organizing data structures displayed in the expanded view to one. According to one embodiment, the method further comprises generating, by the computer system, an update organizing data structure for organizing any updated associated information items. According to one embodiment, the method further comprises identifying, by the computer system, updated associated information items responsive to a last view date. According to one embodiment, the method further comprises displaying, by the computer system, the at least one associated information items within the associated information space. According to one embodiment, the method further comprises generating, by the computer system, in each of the at least one associated information items a selectable display for navigating to at least one of a detailed view of an associated information item and an external source for the at least one information item.

According to one embodiment, the method further comprises generating, by the computer system, for each of the at least one associated information items organized in the genomic interpretation category at least one of: a) interpretive information, e.g., information of the role of the gene in health and disease, e.g., in cancer, e.g., the patient's type of cancer, or another cancer, including curated information e.g., one or more identifiers of sources of primary information, e.g., published journal articles, on the prevalence of the alteration in particular cancers or populations, therapies for the subject genomic alteration, or related genomic alterations, clinical studies of specific therapies for cancers within the current patient's tumor type or otherwise, and genomic alteration, e.g., a type of alteration, e.g., amplification, deletion, translocation, etc.; b) the name of the affected gene; and c) the type of alteration.

According to one embodiment, the method further comprises generating, by the computer system, for each of the at least one associated information items organized in the therapy category one or more or all of: a) a therapy, e.g., a drug, one or more of all of: an indication of whether the therapy is approved for the patient's tumor type; an indication of whether the therapy is approved for other tumor types (which can be useful in identifying off-label uses); b) an identifier for a therapy; c) the identity of the gene involved in the alteration; and d) the type of alteration. According to one embodiment, the method further comprises generating, by the computer system, for each of the at least one associated information items organized in the clinical trial category one or more or all of the following (if there is such a clinical trial): a) an identifier for a clinical trial, e.g., one that implicates one or more or all of the patient's tumor type, a gene affected by the patient's alteration, the genetic alteration type; b) rationale for the trial, e.g., a statement of why the therapy is implicated in the patient's tumor type or another tumor type; c) a description of the trial, e.g., an indication of phase, and type of cancer treated; d) a geographic location of trial; e) an identification of the target in clinical trial, e.g., aurora kinase, and wherein in embodiments, one or more or all, of a, b, c and d, are presented concurrently to the user, without need for leaving the screen, e.g., without further computer operation or without more than brief computer operation by the user.

According to one embodiment, the method further comprises generating, by the computer system, for each of the at least one associated information items organized in the references category one or more or all of the following: a) reference bibliography information e.g., author, title, publisher, location, copyright, journal name, journal title, publication name, publication company, ISBN, etc.; and b) a navigable link to the reference.

According to one embodiment, the method further comprises organizing, by the computer system, genomic testing results and associated information by patient according to a data model. According to one embodiment, the method further comprises storing, by the computer system, a data structure associated with patient records, and wherein the data structure includes data records for specification of tumor type, gene, and alteration. According to one embodiment, all genomic testing results and the associated information is accessible by the computer system using gene or alteration records. According to one embodiment, each patient record includes gene and alteration data units, and the method further comprises associating actionable information (e.g., therapy information items or clinical trial information items) to the gene and alteration date units. According to one embodiment, the actionable information includes therapy information items that specify whether an associated therapy is approved by the FDA in the patient's tumor type, and whether the associated therapy is approved by the FDA in another tumor type.

According to one embodiment, the data model includes specification of an actionability evaluation for associated information items. According to one embodiment, the method further comprises assigning, by the computer system, a highest level of actionability to therapy information items. According to one embodiment, the method further comprises assigning, by the computer system, a second level of actionability to clinical trial information items. According to one embodiment, the method further comprises, by the computer system, a lowest level of actionability to reference information items. According to one embodiment, the method further comprises assigning, by the computer system, a display precedence responsive to a level of actionability determined from respective associated information items.

According to one embodiment, the method further comprises tracking, by the computer system, any updates to one or more of genomic test results and any associated information items. According to one embodiment, the method further comprises communicating, by the computer system, update notification to users responsive to identification of updated information. According to one embodiment, the method further comprises generating, by the computer system, notifications according to user notification preferences.

According to one embodiment, the method further comprises generating, by the computer system, static reports containing all gene alteration combinations specific to a patient and all associated information items organized into respective display areas on the report, wherein the respective display areas are arranged by information type. According to one embodiment, the method further comprises delivering, by the computer system, the static report via a fax.

According to one embodiment, the method further comprises identifying, by the computer system, information sources relevant to any one or more of a patient's tumor type, at least one gene implicated by the tumor, and an alteration type for the at least one gene. According to one embodiment, the method further comprises generating, by the computer system, interpretive statements accessible at least by using a gene and alternation combination. According to one embodiment, wherein interpretive statements include e.g., information of the role of the gene in health and disease, e.g., in cancer, e.g., the patient's type of cancer, or another cancer, including curated information e.g., one or more identifiers of sources of primary information, e.g., published journal articles, on the prevalence of the alteration in particular cancers or populations, therapies for the subject genomic alteration, or related genomic alterations, clinical studies of specific therapies for cancers within the current patient's tumor type or otherwise, and genomic alteration, e.g., a type of alteration, e.g., base substitution, insertion, deletion, amplification, homozygous deletion, rearrangement.

According to one embodiment, the method further comprises categorizing, by the computer system, information sources, and storing the categorizations at least for use by a user interface component. According to one embodiment, the method further comprises identifying, by the computer system, updates to treatment options. According to one embodiment, the method further comprises identifying, by the computer system, updates genomic alteration interpretive statements. According to one embodiment, the method further comprises tagging, by the computer system, updated records responsive to at least one of timing of a study, approval of a therapy, start of a new trial, and publication of a new reference.

According to one aspect, a system for delivering patient information is provided. The system comprises at least one processor operatively connect to a memory, the at least one processor when executing causes the system to perform operations for: A) optionally, providing reports for a plurality of patients, e.g., a plurality of patients of a user; B) providing, e.g., displaying, e.g., responsive to a selection by a user, a first portion of said report, said first portion comprising, one or more or all of: i) patient information comprising a) Patient Diagnosis; and, optionally, one or more or all of b) Patient identifier; c) other Patient bibliographic information, e.g., age; and ii) a genomic alteration space, e.g., a genomic alteration brick, for each cancer cell genomic alteration, which comprises or provides, e.g., without further computer operation by the user, one or more or all of: a) a first space, or cancer cell genomic alteration space, having, e.g., an indication of a gene involved; b) a second space, or type of alteration space, having, e.g., an indication of alteration type, e.g., an amplification, translocation, or point mutation c) a third space, or therapy or actionable item space, d) a fourth space, or for clinical trial space, wherein in embodiments, one or more or all, of a, b, c and d, are presented concurrently to the user, without need for leaving the screen, e.g., without further computer operation or without more than brief computer operation by the user; and iii) an associated information space, comprising one or more or all of: a) first associated space, or genomic alteration interpretation space, e.g., a genomic alteration interpretation drawer, b) second associated space, or therapy space, e.g., a therapy drawer; c) third associated space, or clinical trial space, e.g., a clinical trial drawer, d) forth associated space, or references space, e.g., a references drawer, e) an optional fifth associated space, or updates space, e.g., an updates drawer, wherein in embodiments, one or more or all, of a, b, c and d, are presented in an unexpanded or expanded view to the user, without need for leaving the screen, e.g., without further computer operation for the unexpanded view and without more than brief computer operation by the user to transition to the expanded view; and C) providing or displaying, e.g., in response to user input, e.g., a brief computer operation, which selects one of B(2)a-d: i) for B(2) a or b, one or more or all of: a) interpretive information, e.g., information of the role of the gene in health and disease, e.g., in cancer, e.g., the patient's type of cancer, or another cancer, including curated information e.g., one or more identifiers of sources of primary information, e.g., published journal articles, on the prevalence of the alteration in particular cancers or populations, therapies for the subject genomic alteration, or related genomic alterations, clinical studies of specific therapies for cancers within the current patient's tumor type or otherwise, and genomic alteration, e.g., a type of alteration, e.g., amplification, deletion, translocation, etc.; b) the name of the affected gene; and c) the type of alteration; ii) for B(2) c, one or more or all of: a) a therapy, e.g., a drug, one or more of all of: an indication of whether the therapy is approved for the patient's tumor type; an indication of whether the therapy is approved for other tumor types (which can be useful in identifying off-label uses); b) an identifier for a therapy; c) the identity of the gene involved in the alteration; and d) the type of alteration; iii) for B(2) d, one or more or all of one or more of the following (if there is such a clinical trial): a) an identifier for a clinical trial, e.g., one that implicates one or more or all of the patient's tumor type, a gene affected by the patient's alteration, the genomic alteration type; b) rationale for the trial, e.g., a statement of why the therapy is implicated in the patient's tumor type or another tumor type; c) a description of the trial, e.g., an indication of phase, and type of cancer treated; d) geographic location of trial; e) identification of the target in clinical trial, e.g., aurora kinase, wherein in embodiments, one or more or all, of a, b, c and d, are presented concurrently to the user, without need for leaving the screen, e.g., without further computer operation or without more than brief computer operation by the user.

According to one embodiment, the system is caused to perform operations for: D) providing or displaying, e.g., in response to user input, e.g., a brief computer operation, which selects one of B(3)a-e: i) for B(3) a, one or more or all of: a) interpretive information, e.g., information of the role of the gene in health and disease, e.g., in cancer, e.g., the patient's type of cancer, or another cancer, including curated information e.g., one or more identifiers of sources of primary information, e.g., published journal articles, on the prevalence of the alteration in particular cancers or populations, therapies for the subject genomic alteration, or related genomic alterations, clinical studies of specific therapies for cancers within a current patient's tumor type or otherwise, or related, genomic alteration; b) the name of the affected gene; and c) the type of alteration; ii) for B(3) b, one or more or all of: a) a therapy, e.g., a drug, one or more of all of: an indication of whether the therapy is approved for the patient's tumor type; an indication of whether the therapy is approved for other tumor types (which can be useful in identifying off-label uses); b) an identifier for a therapy; c) the identity of the gene involved in the alteration; and d) the type of alteration; iii) for B(3)c, one or more or all of one or more of the following (if there is such a clinical trial): a) an identifier for a clinical trial, e.g., one that implicates one or more or all of the patient's tumor type, a gene affected by the patient's alteration, the genomic alteration type; b) rationale for the trial, e.g., a statement of why the therapy is implicated in the patient's tumor type or another tumor type; c) a description of the trial, e.g., an indication of phase, and type of cancer treated; d) geographic location of trial; e) identification of the target in clinical trial, e.g., aurora kinase, iv) for B(3)d, one or more or all of the following: a) reference bibliography information e.g., author, title, publisher, location, copyright, journal name, journal title, publication name, publication company, ISBN, etc.; and b) a navigable link to the reference; v) for B(3)e, one or more or all of the following: a) an updates time line including updated information for any one or more or all of D(1)-(4); wherein in embodiments, one or more or all, of a, b, c, d, and e, are presented consecutively to the user, without need for leaving the screen, without more than brief computer operation by the user.

According to one embodiment, the system is caused to perform operations for successive execution of C), e.g. successive access, e.g., by brief computer operation, by a user to a plurality of genomic alteration spaces, e.g., bricks. According to one embodiment, the system is caused to perform operations for successive accesses, e.g., by brief computer operation, by a user to a plurality of spaces selected within B(2)a-d. According to one embodiment, the system is caused to perform operations for selection of successive operations described in above, by no more than y, wherein y is equal to or less than two, brief computer operations, for each of the plurality of genomic alteration spaces accessed. According to one embodiment, the system is caused to perform operations for migration from the first portion, through at least one of the genomic alteration spaces, e.g., bricks, to the associated information space (e.g., the clinical trial space, therapy space, interpretation space) by no more than X, wherein X is equal to or less than one, brief computer operations.

According to one embodiment, the system is caused to perform operations for migration from the first portion, through at least one of the genomic alteration spaces, e.g., bricks, to the associated information space (e.g., the clinical trial space, therapy space, interpretation space) by no more than X, wherein X is equal to or less than two, brief computer operations. According to one embodiment, the system is caused to perform operations for successive execution of the act of migrating from the first portion, through at least one of the genomic alteration spaces, e.g., bricks, to the associated information space (e.g., the clinical trial space, therapy space, interpretation space) Z times, wherein Z successive acts of migrating can be performed with no more than z*x brief computer operations, wherein x is equal to one or two, or no more than z*x plus z. According to one embodiment, C) is executed successively by the system to access at least 56, 57, 58, 59, 60, 61, 62, 63, 64, or 65, genomic alteration spaces, resulting in 56, 57, 59, 60, 61, 62, 63, 64, or 10 successive transitions to the associated information space.

According to one aspect, a computer-readable medium having computer-readable signals stored thereon that define instructions that, as a result of being executed by a computer, instruct the computer to perform a method for managing delivery of genomic testing information is provided. The method comprises accessing genomic testing results including at least one gene and alteration combination for a patient's cancer, analyzing one or more of a tumor type, gene, and alteration for the patient's cancer, wherein analyzing includes identifying associated information items matching at least one of the tumor type, gene, and alteration for the patient's cancer, and generating at least one genomic data structure including at least one tag for display in a user interface, wherein the at least one tag is selectable to transition the user interface from the genomic data structure to an associated information display space including at least one associated information item describing information related to characteristics of the genomic data structure.

According to one embodiment, the method further comprises displaying the at least one genomic data structure within the user interface accessible over a communication network. According to one embodiment, the method further comprises assigning the associated information items to categories responsive to a type of information for a respective associated information item. According to one embodiment, the method further comprises generating two or more tags displayed within each genomic data structure, wherein the two or more tags are selected from a group of categories including therapy, clinical trial, genomic interpretation, and alteration. According to one embodiment, the method further comprises generating at least four tags within each genomic data structure for at least the therapy, clinical trial, genomic interpretation, and alteration categories. According to one embodiment, the method further comprises displaying a count of associated information items referenced by each tag. According to one embodiment, the method further comprises highlighting the at least one associated information item within the associated information display space responsive to selection of the at least one tag.

According to one embodiment, the method further comprises generating at least one data structure in the associated information display space for organizing associated information items. According to one embodiment, the method further comprises displaying the at least one organizing data structure in the associated information display space in an unexpanded view. According to one embodiment, the unexpanded view conceals any associated information items.

According to one embodiment, the method further comprises displaying the at least one organizing data structure in an expanded view responsive to at least one of the transition to the associated information space and selection of the at least one organizing data structure. According to one embodiment, the expanded view includes a display of the at least one associated information organized by the at least one organizing data structure. According to one embodiment, the method further comprises generating organizing data structures for at least the therapy, clinical trial, genomic interpretation, alteration, and a references category. According to one embodiment, one organizing data structure organizes associated information items for both the genomic interpretation and the alteration categories. According to one embodiment, the method further comprises limiting a number of organizing data structures displayed in the expanded view.

According to one embodiment, the method further comprises limiting the number of organizing data structures displayed in the expanded view to one. According to one embodiment, the method further comprises generating an update organizing data structure for organizing any updated associated information items. According to one embodiment, the method further comprises identifying updated associated information items responsive to a last view date. According to one embodiment, the method further comprises displaying the at least one associated information items within the associated information space. According to one embodiment, the method further comprises generating in each of the at least one associated information items a selectable display for navigating to at least one of a detailed view of an associated information item and an external source for the at least one information item.

According to one embodiment, the method further comprises generating for each of the at least one associated information items organized in the genomic interpretation category at least one of: a) interpretive information, e.g., information of the role of the gene in health and disease, e.g., in cancer, e.g., the patient's type of cancer, or another cancer, including curated information e.g., one or more identifiers of sources of primary information, e.g., published journal articles, on the prevalence of the alteration in particular cancers or populations, therapies for the subject genomic alteration, or related genomic alterations, clinical studies of specific therapies for cancers within the current patient's tumor type or otherwise, and genomic alteration, e.g., a type of alteration, e.g., amplification, deletion, translocation, etc.; b) the name of the affected gene; and c) the type of alteration.

According to one embodiment, the method further comprises generating for each of the at least one associated information items organized in the therapy category one or more or all of: a) a therapy, e.g., a drug, one or more of all of: an indication of whether the therapy is approved for the patient's tumor type; an indication of whether the therapy is approved for other tumor types (which can be useful in identifying off-label uses); b) an identifier for a therapy; c) the identity of the gene involved in the alteration; and d) the type of alteration. According to one embodiment, the method further comprises generating for each of the at least one associated information items organized in the clinical trial category one or more or all of the following (if there is such a clinical trial): a) an identifier for a clinical trial, e.g., one that implicates one or more or all of the patient's tumor type, a gene affected by the patient's alteration, the genetic alteration type; b) rationale for the trial, e.g., a statement of why the therapy is implicated in the patient's tumor type or another tumor type; c) a description of the trial, e.g., an indication of phase, and type of cancer treated; d) a geographic location of trial; e) an identification of the target in clinical trial, e.g., aurora kinase, and wherein in embodiments, one or more or all, of a, b, c and d, are presented concurrently to the user, without need for leaving the screen, e.g., without further computer operation or without more than brief computer operation by the user.

According to one embodiment, the method further comprises generating for each of the at least one associated information items organized in the references category one or more or all of the following: a) reference bibliography information e.g., author, title, publisher, location, copyright, journal name, journal title, publication name, publication company, ISBN, etc.; and b) a navigable link to the reference.

According to one embodiment, the method further comprises organizing genomic testing results and associated information by patient according to a data model. According to one embodiment, the method further comprises storing a data structure associated with patient records, and wherein the data structure includes data records for specification of tumor type, gene, and alteration. According to one embodiment, all genomic testing results and the associated information is accessible by the computer system using gene or alteration records. According to one embodiment, each patient record includes gene and alteration data units, and the method further comprises associating actionable information (e.g., therapy information items or clinical trial information items) to the gene and alteration date units. According to one embodiment, the actionable information includes therapy information items that specify whether an associated therapy is approved by the FDA in the patient's tumor type, and whether the associated therapy is approved by the FDA in another tumor type.

According to one embodiment, the data model includes specification of an actionability evaluation for associated information items. According to one embodiment, the method further comprises assigning a highest level of actionability to therapy information items. According to one embodiment, the method further comprises assigning a second level of actionability to clinical trial information items. According to one embodiment, the method further comprises a lowest level of actionability to reference information items. According to one embodiment, the method further comprises assigning a display precedence responsive to a level of actionability determined from respective associated information items.

According to one embodiment, the method further comprises tracking any updates to one or more of genomic test results and any associated information items. According to one embodiment, the method further comprises communicating update notification to users responsive to identification of updated information. According to one embodiment, the method further comprises generating notifications according to user notification preferences.

According to one embodiment, the method further comprises generating static reports containing all gene alteration combinations specific to a patient and all associated information items organized into respective display areas on the report, wherein the respective display areas are arranged by information type. According to one embodiment, the method further comprises delivering the static report via a fax.

According to one embodiment, the method further comprises identifying information sources relevant to any one or more of a patient's tumor type, at least one gene implicated by the tumor, and an alteration type for the at least one gene. According to one embodiment, the method further comprises generating interpretive statements accessible at least by using a gene and alternation combination. According to one embodiment, wherein interpretive statements include e.g., information of the role of the gene in health and disease, e.g., in cancer, e.g., the patient's type of cancer, or another cancer, including curated information e.g., one or more identifiers of sources of primary information, e.g., published journal articles, on the prevalence of the alteration in particular cancers or populations, therapies for the subject genomic alteration, or related genomic alterations, clinical studies of specific therapies for cancers within the current patient's tumor type or otherwise, and genomic alteration, e.g., a type of alteration, e.g., base substitution, insertion, deletion, amplification, homozygous deletion, rearrangement.

According to one embodiment, the method further comprises categorizing information sources, and storing the categorizations at least for use by a user interface component. According to one embodiment, the method further comprises identifying updates to treatment options. According to one embodiment, the method further comprises identifying updates genomic alteration interpretive statements.

According to one embodiment, the method further comprises tagging updated records responsive to at least one of timing of a study, approval of a therapy, start of a new trial, and publication of a new reference.

According to one aspect, a computer-readable medium having computer-readable signals stored thereon that define instructions that, as a result of being executed by a computer, instruct the computer to perform a method for delivering patient information is provided. The method is comprised of: A) optionally, providing reports for a plurality of patients, e.g., a plurality of patients of a user; B) providing, e.g., displaying, e.g., responsive to a selection by a user, a first portion of said report, said first portion comprising, one or more or all of: i) patient information comprising a) Patient Diagnosis; and, optionally, one or more or all of b) Patient identifier; c) other Patient bibliographic information, e.g., age; and ii) a genomic alteration space, e.g., a genomic alteration brick, for each cancer cell genomic alteration, which comprises or provides, e.g., without further computer operation by the user, one or more or all of: a) a first space, or cancer cell genomic alteration space, having, e.g., an indication of a gene involved; b) a second space, or type of alteration space, having, e.g., an indication of alteration type, e.g., an amplification, translocation, or point mutation; c) a third space, or therapy or actionable item space; d) a fourth space, or for clinical trial space; wherein in embodiments, one or more or all, of a, b, c and d, are presented concurrently to the user, without need for leaving the screen, e.g., without further computer operation or without more than brief computer operation by the user; and iii) an associated information space, comprising one or more or all of: a) first associated space, or genomic alteration interpretation space, e.g., a genomic alteration interpretation drawer, b) second associated space, or therapy space, e.g., a therapy drawer, c) third associated space, or clinical trial space, e.g., a clinical trial drawer, d) forth associated space, or references space, e.g., a references drawer, e) an optional fifth associated space, or updates space, e.g., an updates drawer, wherein in embodiments, one or more or all, of a, b, c and d, are presented in an unexpanded or expanded view to the user, without need for leaving the screen, e.g., without further computer operation for the unexpanded view and without more than brief computer operation by the user to transition to the expanded view; and C) providing or displaying, e.g., in response to user input, e.g., a brief computer operation, which selects one of B(2)a-d: i) for B(2) a or b, one or more or all of: a) interpretive information, e.g., information of the role of the gene in health and disease, e.g., in cancer, e.g., the patient's type of cancer, or another cancer, including curated information e.g., one or more identifiers of sources of primary information, e.g., published journal articles, on the prevalence of the alteration in particular cancers or populations, therapies for the subject genomic alteration, or related genomic alterations, clinical studies of specific therapies for cancers within the current patient's tumor type or otherwise, and genomic alteration, e.g., a type of alteration, e.g., amplification, deletion, translocation, etc.; b) the name of the affected gene; and c) the type of alteration; ii) for B(2) c, one or more or all of: a) a therapy, e.g., a drug, one or more of all of: an indication of whether the therapy is approved for the patient's tumor type; an indication of whether the therapy is approved for other tumor types (which can be useful in identifying off-label uses); b) an identifier for a therapy; c) the identity of the gene involved in the alteration; and d) the type of alteration; iii) for B(2) d, one or more or all of one or more of the following (if there is such a clinical trial): a) an identifier for a clinical trial, e.g., one that implicates one or more or all of the patient's tumor type, a gene affected by the patient's alteration, the genomic alteration type; b) rationale for the trial, e.g., a statement of why the therapy is implicated in the patient's tumor type or another tumor type; c) a description of the trial, e.g., an indication of phase, and type of cancer treated; d) geographic location of trial; e) identification of the target in clinical trial, e.g., aurora kinase, wherein in embodiments, one or more or all, of a, b, c and d, are presented concurrently to the user, without need for leaving the screen, e.g., without further computer operation or without more than brief computer operation by the user.

In one embodiment, the method further comprises: D) providing or displaying, e.g., in response to user input, e.g., a brief computer operation, which selects one of B(3)a-e: i) for B(3) a, one or more or all of: a) interpretive information, e.g., information of the role of the gene in health and disease, e.g., in cancer, e.g., the patient's type of cancer, or another cancer, including curated information e.g., one or more identifiers of sources of primary information, e.g., published journal articles, on the prevalence of the alteration in particular cancers or populations, therapies for the subject genomic alteration, or related genomic alterations, clinical studies of specific therapies for cancers within a current patient's tumor type or otherwise, or related, genomic alteration; b) the name of the affected gene; and c) the type of alteration; ii) for B(3) b, one or more or all of: a) a therapy, e.g., a drug, one or more of all of: an indication of whether the therapy is approved for the patient's tumor type; an indication of whether the therapy is approved for other tumor types (which can be useful in identifying off-label uses); b) an identifier for a therapy; c) the identity of the gene involved in the alteration; and d) the type of alteration; iii) for B(3)c, one or more or all of one or more of the following (if there is such a clinical trial): a) an identifier for a clinical trial, e.g., one that implicates one or more or all of the patient's tumor type, a gene affected by the patient's alteration, the genomic alteration type; b) rationale for the trial, e.g., a statement of why the therapy is implicated in the patient's tumor type or another tumor type; c) a description of the trial, e.g., an indication of phase, and type of cancer treated; d) geographic location of trial; e) identification of the target in clinical trial, e.g., aurora kinase, iv) for B(3)d, one or more or all of the following: a) reference bibliography information e.g., author, title, publisher, location, copyright, journal name, journal title, publication name, publication company, ISBN, etc.; and b) a navigable link to the reference; v) for B(3)e, one or more or all of the following: a) an updates time line including updated information for any one or more or all of D(1)-(4); wherein in embodiments, one or more or all, of a, b, c, d, and e, are presented consecutively to the user, without need for leaving the screen, without more than brief computer operation by the user.

In one embodiment, the method includes successive execution of C), e.g. successive access, e.g., by brief computer operation, by a user to a plurality of genomic alteration spaces, e.g., bricks. In one embodiment, the method includes successive accesses, e.g., by brief computer operation, by a user to a plurality of spaces selected within B(2)a-d. In one embodiment, the method includes selection of successive operations described above, by no more than y, wherein y is equal to or less than two, brief computer operations, for each of the plurality of genomic alteration spaces accessed.

In one embodiment, the method further comprises migration from the first portion, through at least one of the genomic alteration spaces, e.g., bricks, to the associated information space (e.g., the clinical trial space, therapy space, interpretation space) by no more than X, wherein X is equal to or less than one, brief computer operations. In one embodiment, the method further comprises migration from the first portion, through at least one of the genomic alteration spaces, e.g., bricks, to the associated information space (e.g., the clinical trial space, therapy space, interpretation space) by no more than X, wherein X is equal to or less than two, brief computer operations.

In one embodiment, the method further comprises successive execution of the act of migrating from the first portion, through at least one of the genomic alteration spaces, e.g., bricks, to the associated information space (e.g., the clinical trial space, therapy space, interpretation space) Z times, wherein Z successive acts of migrating can be performed with no more than z*x brief computer operations, wherein x is equal to one or two, or no more than z*x plus z. In one embodiment, C) is executed successively to access at least 1, 2, 3, 4, 5, 6, 7, 8, 9, or 10, genomic alteration spaces, resulting in 1, 2, 4, 5, 6, 7, 8, 9, or 10 successive transitions to the associated information space. It is to be appreciated that embodiments of the methods and apparatuses discussed herein are not limited in application to the details of construction and the arrangement of components set forth in the following description or illustrated in the accompanying drawings. The methods and apparatuses are capable of implementation in other embodiments and of being practiced or of being carried out in various ways. Examples of specific implementations are provided herein for illustrative purposes only and are not intended to be limiting. In particular, acts, elements and features discussed in connection with any one or more embodiments are not intended to be excluded from a similar role in any other embodiments.

Also, the phraseology and terminology used herein is for the purpose of description and should not be regarded as limiting. Any references to embodiments or elements or acts of the systems and methods herein referred to in the singular may also embrace embodiments including a plurality of these elements, and any references in plural to any embodiment or element or act herein may also embrace embodiments including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for tracking cancer treatment and outcome information, comprising:
generating a model configured to analyze treatment data and outcome data, wherein generating the model includes:
indexing outcome data based on one or more genomic-based indices, and
specifying a data structure that includes the one or more genomic-based indices;
receiving, by one or more processors, a user input indicative of an update to treatment or outcome of a patient via a first user interface having one or more user interface controls categorizing treatment information and outcome information into a plurality of selectable categories to minimize time required by a physician to input data;
processing the user input according to the model;
dynamically identifying, by the one or more processors, a set of patients similar to the patient based on the model;
receiving an instruction for viewing similar patients; and
responsive to receiving the instruction for viewing similar patients, configuring a second user interface based at least partially on the model by generating:
a treatment data structure associated with the set of patients similar to the patient to provide actionable information or advisory information for treatment decision making, wherein the set of patients similar to the patient is dynamically identified based on the model and
wherein the second user interface is configured to allow the physician to locate the treatment information and the outcome information for the set of patients similar to the patient dynamically identified based on the model to inform decision-making for off-label uses of a particular treatment.

2. The method of claim 1, wherein the treatment data includes data representing drugs, therapeutics, named drugs, named therapeutics, drug cocktails, drug combinations, radiation, and surgery.

3. The method of claim 1, wherein the second user interface further comprises a genomic filter configured to filter the set of patients similar to the patient based on selected genomic information associated with each patient, wherein the outcome data includes data representing one or more of complete response, partial response, stable disease, and progressive disease, and wherein the genomic filter specifies one or more genomic alterations.

4. The method of claim 1, wherein the outcome data is associated with a plurality of patients and includes data associated a patient of the plurality of patients, the data based on one or more of a most recent outcome of the patient, an average of outcomes of the patient, a weighted average of outcomes of the patient, or an optimal outcome of the patient.

5. The method of claim 1, further comprising:
responsive to a selection of a filter, displaying a waterfall view of one or more patients.

6. The method of claim 1, wherein the set of patients is identified based on one or more of:
a genomic alteration associated with the patient,
an affected gene identified in a cancer associated with the patient,
an affected pathway associated with the patient,
a treatment associated with the patient, and
a tumor type associated with the patient.

7. The method of claim 6, further comprising:
comparing a first number of patients in the set of patients to a threshold;

if the number of patients in the set of patients is less than the threshold, aggregating information associated with one or more of the genomic alteration, the affected gene, the affected pathway, the treatment, and the tumor type; and identifying a second set of patients based on the aggregated information, wherein a second number of patients in the second set of patients is greater than the first number.

8. The method of claim 1, wherein the set of patients similar to the patient is identified based on a class of genomic alterations associated with the patient, the class of genomic alterations selected from a plurality of classes of genomic alterations.

9. The method of claim 8, wherein the class of genomic alterations include alterations in a specified domain of a gene.

10. The method of claim 9, wherein the domain includes at least a kinase domain of the gene.

11. The method of claim 10, wherein the gene includes BRAF, and the specified domain include at least one of kinase, BRAF V600E, and BRAF V600K.

12. The method of claim 9, wherein the domain includes at least an ATP binding pocket domain.

13. The method of claim 12, further comprising aggregating information associated with patients having at least one alteration within the ATP binding pocket domain.

14. The method of claim 1, further comprising aggregating information based on a specific gene.

15. The method of claim 1, further comprising aggregating information based on at least one gene identified within a pathway.

16. The method of claim 1, wherein the set of patients is identified by one or more of aggregating alteration information according to pathways affected by respective alterations or based on functional similarity of a genomic alteration associated with the patient.

17. An electronic device, comprising:
a display;
one or more processors;
a memory; and
one or more programs, wherein the one or more programs are stored in the memory and configured to be executed by the one or more processors, the one or more programs including instructions for:
generating a model configured to analyze treatment data and outcome data, wherein generating the model includes:
indexing outcome data based on one or more genomic-based indices, and
specifying a data structure that includes the one or more genomic-based indices;
receiving, by one or more processors, a user input indicative of an update to treatment or outcome of a patient via a first user interface having one or more user interface controls categorizing treatment information and outcome information into a plurality of selectable categories to minimize time required by a physician to input data;
processing the user input according to the model;
dynamically identifying, by the one or more processors, a set of patients similar to the patient based on the model; and
receiving an instruction for viewing similar patients; and
responsive to receiving the instruction for viewing similar patients, configuring a second user interface based at least partially on the model by generating:
a treatment data structure associated with the set of patients similar to the patient to provide actionable or advisory information for treatment decision making, wherein the set of patient similar to the patient is dynamically identified based on the model and
wherein the second user interface is configured to allow the physician to locate treatment information and outcome information for the set of patients similar to the patient dynamically identified based on the model to inform decision-making for off-label uses of a particular treatment.

18. The electronic device of claim 17, wherein:
the treatment data includes data representing drugs, therapeutics, named drugs, named therapeutics, drug cocktails, drug combinations, radiation, and surgery, and
the outcome data includes data representing one or more of complete response, partial response, stable disease, and progressive disease.

19. The electronic device of claim 17, wherein the set of patients is identified based on one or more of:
a genomic alteration associated with the patient,
an affected gene identified in a cancer associated with the patient,
an affected pathway associated with the patient,
a treatment associated with the patient, and
a tumor type associated with the patient.

20. A non-transitory computer-readable storage medium storing one or more programs, the one or more programs comprising instructions, which when executed by one or more processors of an electronic device having a display, cause the electronic device to:
generate a model configured to analyze treatment data and outcome data, wherein generating the model includes:
indexing outcome data based on one or more genomic-based indices, and
specifying a data structure that includes the one or more genomic-based indices;
receive, by one or more processors, a user input indicative of an update to treatment or outcome of a patient via a first user interface having one or more user interface controls categorizing treatment information and outcome information into a plurality of selectable categories to minimize time required by a physician to input data;
process the user input according to the model;
dynamically identify, by the one or more processors, a set of patients similar to the patient based on the model;
receiving an instruction for viewing similar patients; and
responsive to receiving the instruction for viewing similar patients, configure a second user interface based at least partially on the model by generating:
a treatment data structure associated with the set of patients similar to the patient to provide actionable or advisory information for treatment decision making, wherein the set of patients similar to the patient is dynamically identified based on the model and
wherein the second user interface is configured to allow the physician to locate treatment information and outcome information for the set of patients similar to the patient dynamically identified based on the model to inform decision-making for off-label uses of a particular treatment.

* * * * *